United States Patent [19]
Paoletti et al.

[11] Patent Number: 6,017,542
[45] Date of Patent: Jan. 25, 2000

[54] NUCLEOTIDE AND AMINO ACID SEQUENCES OF CANINE HERPESVIRUS GD AND USES THEREFOR

[75] Inventors: Enzo Paoletti, Delmar; Keith J. Limbach, Troy, both of N.Y.

[73] Assignee: Virogenetics Corporation, Troy, N.Y.

[21] Appl. No.: 08/473,446

[22] Filed: Jun. 7, 1995

Related U.S. Application Data

[60] Division of application No. 08/413,118, Mar. 29, 1995, Pat. No. 5,688,920, which is a continuation-in-part of application No. 08/220,151, Mar. 30, 1994, Pat. No. 5,529,780.

[51] Int. Cl.⁷ .......................... A61K 39/245; C12P 21/02; C12N 7/01; C12N 15/38
[52] U.S. Cl. ...................................... 424/199.1; 424/184.1; 424/229.1; 424/232.1; 435/69.1; 435/69.3; 435/172.3; 435/235.1; 435/236; 435/237; 435/320.1; 536/23.72; 536/24.1
[58] Field of Search ................................. 435/69.1, 69.3, 435/172.3, 235.1, 236, 237, 240.1, 320.1; 424/184.1, 199.1, 229.1, 232.1, 205.1; 536/23.72, 24.1

[56] References Cited

PUBLICATIONS

Ackerman, M., R. Longnecker, B. Roizman, L. Pereire, Virology 150, 207–220 (1986).
Allen, G.P. and M.R. Yeargen, J. Virol. 61, 2454–2467 (1987).
Allen, G.P. and J.T. Bryans, In: Progress in Veterinary Microbiology and Immunology, vol. 2, ed. R. Pandey (basel), pp. 78–144 (1986).
Allen, G.P., and L.D. Coogle, J. Virol. 62, 2850–2858 (1988).
Altenburger, W., C–P. Suter and J. Altenburger, Archives Virol. 105, 15–27 (1989).
Appel, M., In Virus Infections of Vertebrates, vol.1, pp. 5–15. Edited by M. Appel. Amsterdam–Oxford–New York–Toyko: Elsevier Science Publishers (1987).
Audonnet, J.–C., Winslow, J., Allen, G. & Paoletti, E., Journal of General Virology 71, 2969–2978 (1990).
Avery, R.J., and J. Wiven, Infect. and Immun. 26, 795–801 (1979).
Babluk, L.A., J. L'Italian, S. vanDrunen Littel–van den Hurk, T. Zemb. M.J.P Lawman, G. Hughes , and G.A. Gifford, J. Virol. 159, 576–66 (1987).
Baet, R., A.T. Benkier, M.D. Biggin, P.L. Deininger, P.J. Farrell, t.J. Gisbon, G. Hartfurll, G.S. Hudan, S.C. Satchwell, C. Seguin, P.S. Tuffnell, and B.G. Barrell, Nature 310, 207–211 (1984).
Bairnes, J., and B. Roizman, J. Viol. 67, 1441–1452 (1993).
Balachandran, W., S. Bacchetti, and W.E. Rawia, Infect. Immun. 37, 1132–1137 (1982).
Baum, E., Biochemical Journal 209, 331–336 (1983).
Behbahonf, A.M., Microbiological Reviews 47, 455–509 (1983).
Ben–Porst, R., J. Demerchi, J. Pendrya, R.A. Vaach, and A.S. Kaplan, J. Virol. 57, 191–196 (1986).
Ben–Porst, T. and A.S. Kaplan, In: The Herpesvirsues, vol. 3, ed. B. Roizman (Plenum Publishing Corp., New York) pp. 103–173 (1985).
Ben–Porst, T., F.J. Rixon, and M.L. Blankenship, Virology 95, 285–294 (1979).
Bergoin, M., and Dolas, S., In Comparative Virology, eds. K. Maramorach and E. Kurstak, (Academic Press, NY) pp. 169–205 (1971).
Berman, P.W., D. Dowbenko, L.A. Laskey, and C.C. Simonsen, Science 222, 524–527 (1983).
Bertholet, C., Drillien, R., and Wittek, R., Proc. Natl. Acad. Sci. USA 82, 2096–2100 (1985).
Blawett, E. & Miara, V., Journal of General Virology 72, 2083–2090 (1991).
Blobal, G., Proceedings of the National Academy of Sciences, U.S.A. 77, 1496–1500 (1980).
Boursnell, M.E.G., P.F. Green, J.I.A. Campbell, A. Deuter, R.W. Peters, F.M. Tomely, A.C.R. Sesson, P. Chambers, P.T. Emeresson, M.M. Birna, J. gen. Virol. 71, 621–628 (1990a).
Boursnell, M.E.G., P.F. Green, J.I.A. Campbell, A. Deuter, R.W. Peters, F.M. Tomley, A.C.R. Sesson, P. Emmerson, and M.M. Birna, Verterinary Microbiology 23, 305–316 (1990b).
Boursnell, M.E.G., P.F. Green, A.C.R. Samson, J.I.A. Campbell, A. Deuter, R.W. Peters, M.S. Millar, P.T. Emerson, and M.M. Birna, Virology 178, 297–300 (1990c).
Broclamier, S., Lagar, K., Tartagalia, J., Riviera, M., Paoletti, E. & Mengeling, W., Veterinary Microbiology 38, 41–58 (1993).
Buller, R.M.L., G.L. Smith, Cremer, K., Notkins, A.L., and Moss, B., Nature 317, 813–815 (1985).
Buller, R.M.L., Chakrabarti, S., Cooper, J.A., Twardzik, D.R., and Moss, B., J.Virol. 62, 866–874 (1988).

(List continued on next page.)

*Primary Examiner*—Christine M. Nucker
*Assistant Examiner*—Laurie Scheiner
*Attorney, Agent, or Firm*—Frommer, Lawrence & Hung LLP; William S. Frommer; Thomas J. Kowalski

[57] ABSTRACT

Disclosed and claimed are nucleotides for genes encoding the canine herpesvirus (CHV) gB, gC and gD homologues. These genes encode polypeptides of 879, 459 and 345 amino acids, respectively, which are also disclosed and claimed. The genes are useful as DNA probes or, for preparing PCR primers. The polypeptides are useful in antigenic, immunological or vaccine compositions. The nucleotides can be expressed in any suitable vector system, allowing for production of the polypeptides. Additionally, the vector system containing any or any combination of the nucleotides can be employed in an antigenic, immunological or vaccine composition, such as a poxvirus vector system, e.g., a CHV-vaccinia or avipox virus recombinant, as can the products from expression, i.e., the gB, gC and gD glycoproteins. Antibodies elicited by the glycoproteins or from expression of the vector containing the nucleotide(s) are also useful. Methods for making and using the composition are also disclosed and claimed. Also, specific canarypox-CHV gB, gC and gD recombinants vCP 320, vCP322 and vCP294 and methods for making and using them are also disclosed and claimed.

16 Claims, 85 Drawing Sheets

OTHER PUBLICATIONS

Bzik, D.J., B.A. Fox, M.A. DeLuca, and S. Person, Virology 133, 301–307 (1984).
Cadoz, M., A. Strady, B. Meignier, J. Taylor, J. Tartaglia, E. Peoletti and S. Plotkin, The Lancet, 339, 1429 (1992).
Cantin, R.M., R. Eberle, J.L. Baldick, B. Moss, D.E. Willey, A.L. Notkins, and H. Openshaw, Proc. Natl. Acad. Sci. USA 86, 5908–5912 (1987).
Carmichael, L., Stransberg, J. & Barnes, F., Proceedings of the Society for Experimental Biology and Medicine 120, 644–650 (1965).
Carmichael, L., Journal of the American Veterinary Medical Association 156, 1714–1721 (1970).
Chambers, P., N.S. Millar, and P.T. Emmerson, J. Gen. Virol. 67, 2685–2694 (1986).
Chan, W., Immunol. 49, 343–352 (1983).
Child, S.J., Palumbo, G.J., Buller, R.M.L., and Hruby, D.E. Virology 174, 625–629 (1990).
Clewell, D.B., J. Bacteriol. 110, 667–676 (1972).
Clewell, D.B. and D.R. Helinski, Proc. Natl. Acad. Sci. USA 62, 1159–1160 (1969).
Colines, R.J., R.C. Condit and E. Peoletti, Virus Research 18, 49–70 (1990).
Compton, T., In: Cell Biology of Virus Entry, Replication, and Pathogenesis, eds. Compens, R.W., A Helenius, and M.B.A. Oldstone (Alan R. Liss, Inc.) pp. 45–56 (1989).
Cooney, B.L., Corrier, A.C., Greenberg, P.D., et al., Lancet 337, 567–572 (1991).
Cordan, J., Wasylyk, B., Buchwalder, A. Sassone–Corsi, P., Kedinger, C. & Chambon, P., Science 209, 1406–1414 (1980).
Cranage, M.P., T. Kouzardies, A.T. Bankier, S. Satchwell, K. Weston, P. Tomlinsom, B. Barrell, N. Hart, S.E. Bell, A.C. Minson, and G.L. Smith, EMBO J. 5, 3057–3063 (1986).
Cremer, K.J., M. Hackett, C. Wohlenber, A.L. Notkins, and B. Moss, Science 228, 737–740 (1985).
Davis, W.B., J.A. Taylor, and J.E. Oakes, J. Infect. DIs. 140, 534–540 (1979).
Davison, A.J., and J.E. Scott, J. Gen. Virol. 67, 1759–1816 (1986).
Drillien, R., F. Koehren and A. Kirn, Virology 111, 488–499 (1981).
Eberle, R., and R.J. Courtney, J. Virol. 33, 902–917 (1980).
Edbauer, C., R. Weinberg, J. Taylor, A. Rey–Senelonge, J.F. Bouquet, P. Dsmetter, and E. Paoletti, Virology 179, 901–904 (1990).
Engelke, D.R., Homer, P.A., and Collins, F.S., Proc. Natl. Acad. Sci. USA 85, 544–548 (1988).
Espion, D., S. de Menau, C. Letellier, C.–D. Wemers, R. Brasseir. R. Brasseur, J.F. Toung, M. Gross, M. Rosenberg, G. Meulemens and A. Burry, Arch. Virol. 95, 79–95 (1987).
Etinger, H.M., Altenburger, W., Vaccine 9, 470–472 (1991).
Fergeaud, D., C. Benoit Jeamin, F. Kato, and G. Chappuis, Arch. Virol. 80, 69–82 (1984).
Fenner, F., Virology 5, 502–529 (1958).
Fitzpatrick, D. R., Babiuk, L. A. Zamb, T. J., Virology 173, 46–57 (1989).
Flexner, C., Hugen, A., and Moss, B., Nature 330, 259–262 (1987).
Flowers, C., Eastman, E. & O'Callaghan, D., Virology 180, 175–184 (1991).
Framn, H.C., H.S., Hersdan, and D.J. McGeoch, J. Gen. Virol. 67, 745–751 (1986).

Fries et al., 32nd Interscience Conference on Antimicrobial Agents and Chemotherapy, Anaheim, CA (Oct. 1992).
Frink, R.J., M.R. Eisenberg, G. Cohen, and E.K. Wagner, J. Virol. 45, 634–647 (1983).
Funahashi, S., T. Sato and H. Shida, J. Gen Virol. 69, 35–47 (1988).
Garten, W., Kohman, T., and H–D. Klenk. J. Gen. Virol. 51, 207–211 (1980).
Ghendon, Y.Z., and Chernos, V.I., Acta Virol. 8, 359–368 (1964).
Gillard, S., Dpehner, D., Drillien, R., and Kirn, A., Proc. Natl. Acad. Sci. USA 83, 5573–557 (1986).
Glorioso, J., C.H. Schroder, G. Kumel, M. Szczesiul, and M. Levine, J. Virol. 50, 805–812 (1884).
Glorioso, J., U. Krees, G. Kumel, H. Kirchner, and P. Kramer, J. Immunol. 135, 575–582 (1985).
Goebel, S.J., Johnson, G.P., Perkus, M.E., Davis, S.W., Winslow, and E. Paoletti, Virology 179, 517–563 (1990b).
Goldstein, D.J. and S.K. Weller, Virology 166, 41–51 (1988).
Gretch, D.R., B. Kari, L. Rasmusson, R.C. Gehrz, and M.F. Stinski, J. Birol. 62, 875–881 (1988).
Guo, P., Goedel, S., Davis, S., Perkus, M.E., Languet, B., Desmettre, P., Allen, G., and Paoletti, E., J. Virol. 63, 4189–4198 (1989).
Hampl. H., T. Ben–Prost, L. Ehrlicher, K–O. Habermehl, and A.S. Kaplan, J. Virol. 52. 583–590 (1984).
Homma, H., and M. Chuchi, J. Virol. 12, 1457–1465 (1973).
Honess, R. W., Journal of General Virology 65, 2077–2107 (1984).
Honess, R. W., Bodemer, W., Cameron, K.R., Miller, H.–H. & Fleckerstein, B., Proceedings of the National Academy of Sciences, U.S.A. 83, 3604–3608 (1986).
Hruby, D.E., R.A. Maki, D.B. Miller and L.A. Ball, Proc. Natl. Acad. Sci. USA 80, 3411–3415 (1983).
Hutchinson, L., Browne, H., Wergents, V., Doris–Poynter, H., Primorac, S., Goldsmith, K.,, Minson, A., and D.T. Johnson. J. Virol. 66, 2240–2250 (1992).
Hutchinson, L., Goldsmith, K., Snoddy, A., Ghash, M., Graham, F.. and D. Johnson. J. Virol. 66, 5603–5609 (1992b).
Hruby, D.E. and L.A. Bell, J. Virol. 43, 403–409 (1982).
Ichihashi, Y. and Dales, S., Virology 46, 533–543 (1971).
Ihara, T., Kato, A., Ueda, S., Ishihama, A. & Hirai, K., Virus Genes 3, 127–140 (1989).
Ishii, H., Y. Kobsyashi, M. Kuroki and Y. Koama, J. Gen. Virol. 69, 1411–1414 (1988).
Jacobson, J.G., D.A. Leib, D.–J. Goldstein, C.L. Bogard, P.A. Schaffer, S.K. Weller, and D.M. Comm, Virology 173, 276–283 (1989).
Jamisson, A.T., G.A. Gentry and J.H. Subak–Sharpe, J. Gen. Virol. 24, 465–480 (1974).
Kato, A., Sato, I., Ihara, T., Ueda, S., Ishihama, A. & Hirai, K., Gene 84, 399–405 (1989).
Kato, S., M. Takaashi, S. Kamoyama and J. Kamhora, Biken's 2, 353–363 (1959).
Keller, P.M., A.J. Davison, R.S. Lwe, C.D. Bennett, and R.W. Ellis, Virology 152, 181–191 (1986).
Kieff, E., and D. Kiebowitz, In: Virology, Second Edition, eds. Fields, B.M. et al. (Raven Press, Ltd., New York) pp. 1889–1920 (1990).
Kieny, M. P., Lathe, R. Drillien, R., Spahner, D., Skory, S., Schmitt, D., Wiktor, T., Koprowski, H., and Lecocq. J.P., Nature (London) 312, 163–166 (1984).

Klein, P., Kanehisa, M. & DeLisi, C., Biochimica Biophysica Acta 815, 468–476 (1985).
Konishi et al., Virology 190, 454–458 (1992).
Kopp, A. & Mettenleiter, T., Journal of Virology 66, 2754–2762 (1992).
Kost, T.A., C.V. Jones, K.M. Smith, A.P Red, A.L. Brown, and T.J. Miller, Virology 171, 365–376 (1989).
Kotwal, G.J., A.W. Hugin and B. Moss, Virology 171, 579–587 (1989a).
Kotwel, G.J. and B. Moss, J. Virol. 63, 600–606 (1989b).
Kotwel, G.J., S.M. Isaacs, R. McKenzie, M.M. Frank and B. Moss, Science 250, 827–830 (1990).
Kotwel, G.J., and Moss, B., Nature (Lond.) 335, 176–178 (1988).
Kougaridem, T., Bankier, A. T., Satchwell, S. C., Weston, K., Tomlinson, P. & Barrell, B. G., Virology 157, 397–413 (1987).
Kozak, M., Cell 44, 283–292 (1986).
Kuhn, J., Eing, B., Brossmer, R., Munk, K. & Braun, R., Journal of General Virology 69, 2847–2858 (1988).
Lai, A. C.–K. and B. G.–T. Pogo, Virus Res. 12, 239–250 (1989).
Lasky, L.A., D. Dowbenko, C.C. Simonsen, and P.W. Berman, Bio–Technology 2, 527–532 (1984).
Lawrence, W.C., R.C. D'Urso, C.A. Kundel, J.C. Whitebeck and L.J. Bello, J. Virol. 60, 405–414 (1986).
Le, L., R. Brasseur, C. Wemers, G. Meulemans, and A. Burny, Virus Genes 1, 333–350 (1988).
Long, D., Cohen, G., Muggeridge, M. & Eisenberg, R., Journal of Virology 64, 5542–5552 (1990).
Long, D., Wilcox, W., Abrams, W., Cohen, G. & Eisenberg, R., Journal of Virology 66, 6668–6685 (1992).
Longnecker, R., S. Chaterjee, R. Whitley, and B. Roizman, Proc. Natl. Acad. Sci. USA 84, 4303–4307 (1987).
Maeda, K., Morimoto, T., Morimina, J., Kawaguchi, Y., Tomonaga, K., Wilkura, M., Kai, C., Takahashi, E. &n Mikami, T., Archives of Virology 127, 387–397.
Mandecki, W., Proc. Natl. Acad. Sci. USA 83, 7177–7182 (1986).
Maniatis, T., E.F. Fritach, and J. Sambrook, Molecular Cloning: A Laboratory Manual, (Cold Spring Harbor Laboratory, New York) (1982).
Marchioli, C.C., R.J. Yancey, Jr., R.C. Wardley, D.R. Thomsen and L.E. Post, Am. J. Vet. Res. 48, 1577–1583 (1987).
Marchioli, C., R.J. Yancey, Jr., J.G. Timira, L.E. Post, B.R. Yours, and D.A. Povendo, Am. J. Vet. Res. 49, 860–864 (1988).
Marchioli, C.C., R.J. Yancey, Jr., E.A. Petrovakis, J.G. Timins, and L.E. Post, J. Virol. 61, 3977–3982 (1987).
Matthews, R.E.F., Intervirology 17, 42–44 (1982).
McGench, D.J., M.A. Dairymple, A.J. Davison, A. Dolan, M.C. Frame, D. McNab, L.J. Perry, J.E. Scott, and P. Taylor, J. gen. Virol.. 69, 1531–1574 (1988).
McGinnis, L.W., and T.G. Morrison, Virus Research 5, 343–356 (1986).
McLaughlin–Taylor, E., D.E. Willey, E.M. Cantin, R. Eberle, G. Moss, and H. Openshaw, J. Gen. Virol. 69, 1731–1734 (1988).
Moos, R.K., S. L. Fritsch, L.L. Herr, and P.A. Rota, J. Virol. 51, 259–26 2(1984).
Merz, D.C., A. Scheid, and P. Choppin, J. Exper. Med. 151, 275–288 (1980).
Miara, V., R.M. Blumental and L.A. Babiuk, J. Virol. 40, 367–378 (1981).

Morgan, A.J., m. Mackett, S. Finerty, J.R. Arrand, F.T. Scullion and M.A. Epstein, J. Med. Virol. 23, 189–195 (1988).
Moss, B., E. Winters and J. A. Cooper, J. Virol. 40, 387–395 (1981).
Nagai, Y., M.B. Klenk, and R. Rott, Virology 72, 494–508 (1976).
Nagai, Y., To Yoshida, M. Hamguchi, H. Narusce, Mi. Linuma, K. Maeno, and T. Matsumoto, Microbiol. Immunol. 24, 173–177 (1980).
Mazerian, K., Lee, L., Tanagida, H. & Ogawa, R., Journal of Virology 66, 1409–1413 (1992).
Nicolson, L. & Onions, D. E., Virology 179, 378–387 (1990).
Oakes, J.E., and H. Rosemond–Hornbeak, Infect. Immun. 21, 489–495 (1978).
Ogawa, R., M. Tanagid,a S. Saeki, S. Saito, S. Ohkawa, H. Gotch, K. Kodama, K. Kamogawa, K. Sawaguchi and Y. Iritani, Vaccine 8, 486–490 (1990).
Peez, E., S. Dallo and M. Estenban, Proc. Natl. Acad. Sci. USA 82, 3365–3369 (1985).
Palumbo, G.J., Pickup, D.J., Fredrickson, T.H., Mcintyre, L.J., and Buller, R.M.L., Virology 172, 262–273 (1989).
Panicali, D., S.W. Davis, S.R. Mercer, and E. Paoletti, J. Vriol. 37, 1000–1010 (1981).
Panicali, D., and E. Paoletti, Proc. Natl. Acad. Sci. USA 79, 4927–4931 (1982).
Paoletti, E., B.R. Lipinskas, C. Sasmsonoff, S. Mercer, and D. Panicali, Proc. Natl. Acad. Sci. USA 81, 193–197 (1984).
Pappvid, G., and J.B. Derbyshire, Can. J. Comp. Med. 43, 231–233 (1979).
Patel, D.D. and Pickup, D.J., EMBO 6, 3787–3794 (1987).
Patel, D.D., Rey, C.A., Drucker, R.P., and Pickup, D.J., Proc. Natl Acad. Sci. USA 85, 9431–9435 (1988).
Pearson, W. R. & Lipman, D. J., Proceedings of the National Academy of Sciences 85, 2444–2448 (1988).
Pellett, P.E., M.D. Higgin, B.L. Barrell, and B. Roizman, J. Virol. 56, 807–813 (1985).
Perkus, M.E., K. Limbach, and E. Paoletti, J. Virol. 63, 3829–3836 (1989).
Perkus, M.E., A. Piccini, B.R. Lipinskas, and E. Paoletti, Science 229, 981–984 (1989).
Perkus, M.E., Goebel, S.J., Davis, S.W., Johnson, G.P., Limbach, K., Norton, E.K., and Paoletti, E., Virology 179, 276–286 (1990).
Perkus, M.E., D. Panicali, S. Mercer and E. Paoletti, Virology 152, 285–297 (1986).
Perkus, M.E., S.J. Goebel, S.W. Davis, G.P. Johnson, E.–K. Norton and E. Paoletti, Virology 180, 406–410 (1991).
Petrovskis, E.A., J.G. Timirs, M.A. Amentrout, C.C. Marchioli, R.J. Trancey, Jr., and L.E. Post, J. Virol. 59, 216–223 (1986).
Petrovskis, E.A., J.G. Timins, and L.E. Post, J. Virol. 60, 185–193 (1986).
Piccini, A., M.E. Perkus, and E. Paoletti, Methods in Enzymology 153, 545–563 (1987).
Pickup, D.J., B.S. Ink, B.L. Parsons, W. Nu and W.K. Joklik, Proc. Natl. Acad. Sci. USA 83, 7698–7702 (1986).
Pickup, D.J., B.S. Ink, W. Wu, C.A. Ray and W.K. Joklik, Proc. Natl. Acad. Sci. USA 81, 6817–6821 (1984).
Pizer, L., Cohen, G. & Eisenberg, R., Journal of Virology 34, 142–153 (1980).
Plummer, G., Goodheart, C., Henson, D. & Bowling, C., Virology 39, 134–137 (1969).

Proudfoot, M. J. & Brownlee, G. G., Nature 163, 211–214 (1976).

Reed, L.J. and Muench, H., Am. J. Hyg. 27, 493–497 (1938).

Richman, D.D., A. Buckmester, S. Bell, C. Hodhman and A.C. Minson, J. Virol. 57, 647–655 (1986).

Riggio, M.P., A.A. Cullinare, and D.E. Onions, J. Virol. 63, 1123–1133 (1989).

Riviera, R., Tartaglia, J., Perkus, M.E., Morton, E. K., Bongemino, C. M., Lacoste, F., Durst, C., Desmettre, P. & Paoletti, E., Journal of Virology 66, 3424–3434 (1992).

Robbins, A.K., R.J. Watson, M.E. Wathem, M.E. Whealey, C. Gold, R.J. Weston, L.E. Holland, S.D. Weed, Levine, J.C. Glorioss, and L.W. Enquist J. Vriol. 61, 2691–2701 (1987).

Roizman, B. and A.E. Sears, In: Virology, eds. Fields, B.H. and D.M. Knipe (Raven Press, Ltd., New York0 pp.1795–1841 (1990).

Roizman, B., In The Herpesviruses, vol. 1, pp. 1–23, Ed. B. Roizman, New York & London: Plenum Press (1982).

Rodney, J.F., C. Wohlenberg, K.J. Cremer, B. Moss, and A.L. Notkins, J. Virol. 62, 1530–1534 (1988).

Rosenthal, K.L., J.R. Smiley, S. South, and D.C. Johnson, J. Virol. 61, 2438–2447 (1987).

Ross, L., Sanderson, M., Scott, S., Binns, M., Doel, T. & Wilne, B., Journal of General Virology 70, 1789–1804 (1989).

Rots, P.A., R.K. Maes, and W.T. Ryechan, Virology 154, 168–179 (1986).

Rubenstein, A.S. and A.S. Kaplan, Virology 66, 385–392 (1975).

Sanger, F., S. Hicklen, and A. Coulson, Proc. Natl. Acad. Sci. USA 74, 5463–5467 (1977).

Schmidtt, J.F.C. and H.G. Stunnenberg, J. Virol. 62, 1889–1897 (1988).

Seligman, E.H., In Laboratory Techniques in Rabies, Eds. M.M. Kaplan and H. Koprowski. (World Health Organization, Geneva) pp. 279–285 (1973).

Shapira, S.K., Chou, J. Richaud, F.V. and Casdaben, M.J., Gene 25, 71–82 (1983).

Shida, M., Virology 150, 451–462 (1986).

Shida, H., T. Tachikura, T. Sato, T. Konno, K. Hirayoshi, M. Saki, Y. Ito, M. Hatanaka, T. Hiruma, Hm Sugimot, F. Takahashi–Hishimaki, T. Maruyama, K. Miki, K. Swzuki, M. Morita, H. Sashiyama and M. Hayami, EMBO 6, 3379–3384 (1987).

Shida, H., Hirum, Y., Hatanaka, M., Morita, M., Kidokoro, M., Suzuki, K., Maruyzam, T., Takahashi–Hishimaki, F., Sugimoto, M., Kitamura, R., Miyazawa, T., and Hayami, M., J. Virol. 62, 4474–4480 (1988).

Shimizu, M., K. Satou, and M. Wishioka, Arch. Virol. 104, 169–174 (1989).

Sinclair, R., R.F. Cook, and J.A. Mumford, J. gen. Virol. 70, 169–174 (1989).

Slabaugh, H., N. Roseman, R. Davis, and C. Matthews, J. Virol. 62, 519–527 (1988).

Smith, J.S., P.A. Yager, and G.H. Baer, In Laboratory Techniques in Rabies, eds. M. M. Kaplan and H. Koprowski (WHO Geneva) pp. 354–357 (1973).

Sodora, D., COhen, G., Muggeridge, M. & Eisenberg, R., Journal of Virology 65, 4424–4431 (1991).

Spaete, R., Sazena, A., Scott, P., Long, G., Probert, W., Britt, W., Gibson W., Resmussen, L. & Pachi, C., Journal of Virology 64, 2922–2931 (1990).

Spear, P.G., In: The Basis for Serodiagnosis and Vaccines, Immunochemistry of Viruses, vol. 2, eds. M.H.V. Van Regenmortel and A.R. Neurath (New York), pp. 425–443 (1985a).

Spear, P.G., In: The Herpesvirus, vol. 3, ed. B. Roizman (New York), pp. 315–356 (1985b).

Stanberry, L. R., S. Kit and M. G. Myers, J. Birol. 55, 322–328 (1985).

Stevely, W.S., J. Virol. 22, 232–234 (1977).

Stokes, A., G.P. Allen, L.A. Pullen, and P.K. Murray, J. gen. Virol. 70, 1173–1183 (1989).

Sullivan, V. and G.L. Smith, J. gen. Virol. 68, 2587–2598 (1987).

Sullivan, V. and G.L. Smith, J. gen. Virol. 69, 859–867 (1988).

Swain, M.A., R.W. Peet and D.A. Galloway, J. Virol. 53, 561–569 (1985).

Tabor, S., and C.C. Richardson, Proc. Natl. Acad. Sci USA 84, 4767–4771 (1987).

Tartaglia, J. & E. Paoletti, In Immunochemistry of Viruses, II. The Basis for Serodiagnosis and Vaccines. M.H.V. van Regermortel & A.R. Neurath, Eds. 125–151. Elsevier Science Publishers, Amsterdam (1990).

Tartaglia, J., J. Taylor, W.I. Cox, J.–C. Audonnet, M.E. Perkus, A. Radaelli, C. deGiuli Morghen, B.–Meignier, M. Riveria, K. Weinhold, & E. Paoletti, In AIDS Reseach Reviews, W. Koff, F. Wong–Stael & R.C. Kenedy, Eds., Vol. 3, Marcal Dekker, NY (In press) (1993a).

Tartaglia, J., Perkus, M.E., Taylor, J., Norton, E.K., Audonnet, J.–C., Cox, W.I., Davis, S.W., Van Der Hooven, J., Meignier, B., Riviera, M., Languet, B., Paoletti, E., Virology 188, 217–232 (1992).

Tartaglia, J., Jarrett, D., Desmettre, P., Paoletti, E., (1993b) J. Virol., in press.

Taylor, J., C. Trimarchi, R. Weinberg, B. Languet, F. Gwillemin, P. Desmettre and E. Paoletti, Vaccine 9, 190–193 (1991b).

Taylor, J., Weinberg, R., Kawaoka, Y., Webster, R.G., and Paoletti, E., Vaccine 6, 504–508 (1988a).

Taylor, J., R. Weinberg, B. Languet, P. Desmettre, and E. Paoletti, Vaccine 6, 497–503 (1988b).

Taylor, J., R. Weinberg, J. Tartaglia, C. Richardson, G. Alkhatib, D. Briedis, M. Appel, E. Norton & E. Paoletti, Virology 187, 321–328 (1992).

Taylor, G., E. J. Stott, G. Wertz and A. Ball, J. Gen. Virol. 72, 125–130 (1991a).

Taylor, J., Edbauer, C., Rey–Senelonge. A., Bouquet, J.–F., Norton, E., Goebel, S., Desmettre, P., Paoletti. E., J. Virol. 66, 1441–1450 (1990).

Telford, E. A., Watson, M. S., McBride, K. & Davison, A. J. (1992). The DNA Sequences of equine herpavirus–1. Virology 189, 304–316.

Tikoo, S.K., Fitzpatrick, D. R., Babiuk, L. A. & Zamb, T. J., Journal of Virology 64, 5132–5142 (1990).

Toyoda, T., T. Sakaguchi, K. Imai, N. N. Inocencio, B. Gotoh, M. Hamaguchi, and Y. Nagai, Virology 158, 242–247 (1987).

Wachsman, M., L. Aurelian, J.C.R. Hunter, M.E. Perkus, and E. Paoletti, Bioscience Reports 8, 323–334 (1988).

Wachsman, M., J.H. Luo, L.Aurelian, M.E. Perkus, and E. Paoletti, J. gen. Virol. 70, 2513–2520 (1989).

Wachsman, M., L Aurelin, C.C. Smith, B.R. Lipinskes, M.E. Perkus, and E. Paoletti, J. Infect. Dis. 155, 1188–1197 (1987).

Wathen, M.W. and L.M.K. Wathan, J. Virol. 58, 173–178 (1986).

Wathen, M.W. and L.M.K. Wathan, J. Virol. 51, 57–62 (1984).

Wathen, L.M.K., K.B. Platt, M.W. Wathan, R.A. Van Deusen, C.A. Whetstone, and E.C. Pirtle, Virus Res. 4, 19–29 (1985).

Weir, J.P., M. Bennett, E.M. Allen, K.L. Elkins, S. Martin, and B.T. Rouse, J. gen. Virol. 70, 2587–2594 (1989).

Weir, J.P. and B. Moss, J. Virol. 46, 530–537 (1983).

Whailey, J.M., G.R. Robertson, M.A., Scott, G.C. Hudson, C.W. Bell, and L.M. Woodsworth, J. gen. Virol. 70, 383–394 (1989).

Whealy, M.E., A.K. Robbins and L.W. Enquist, J. Virol. 63, 4055–4059 (1989).

Whitbeck, J.C., L.Z. Bello, and W.C. Lawrence, J. Virol 62, 3319–3327 (1988).

Wilcox, W. C., Long, D., Sodora, D. L., Eisenberg, R. J. & Cohen, G. H., Journal of Virology 62, 1941–1947 (1988).

Wittmann, G. and H.–J. Rziha, In: Herpesvirus Diseases of Cattle, Horses and Pigs, ed. G. Wittman (Kluwer Academic Publisher) pp. 230–325 (1989).

Xuan, X., Morimoto, T., Limcumpao, J. A., Takumi, A., Tohya, Y., Takahashi, E. & Mikami, T., Archives of Virology 116, 185–195 (1991).

Zamb, T., Abstract No. 330, 68th Annual Meeting of Conference of Research Workers in Animal Disease, Nov. 16 and 17, 1987, Chicago, IL., USA (1987).

Zarling, J.M., P.A. Moran, R.L. Burke, C. Pachl, P.W. Berman, and L.A. Laskey, J. Immunol. 136, 4669–4673 (1986a).

Zarling, J.M., P.A. Moran, L.A. Lasky, and B. Moss, J. Virol. 59, 506–509 (1986b).

Zezulak, K.M., and P.G. Spear, J. Virol. 49, 741–747 (1984).

Zhou, J., L. Crawford, L. McLean, X. Sun, M. Stanley, M. Almond and G.L. Smith, J. Gen Virol. 71, 2185–2190 (1990).

FIG. IA

| | | | |
|---|---|---|---|
| TTTTCTGGAT | TTCAGCTATG | TCCTTCGGGA | 30 |
| GTTTATATAA | CTTATGAAGA | AAACTGTCCT | 60 |
| TTGGTAGCAG | TTTTACAAAG | CGGTGTAAAT | 90 |
| TGCGAAATTG | GACCAACTAC | AACTGTAATA | 120 |
| TACGACAGTG | ATATTTTTC | TCTTCTTTAT | 150 |
| ACCGTTCTTC | AAAAATTGGC | TCCTGGTGTT | 180 |
| AATATAGAAA | TTTGATAAGT | ATGTTTTCAT<br>  M  F  S> | 210<br>3 |
| TGTATCTATA<br>L  Y  L  Y | TATTTTTTT<br> I  F  F | ATTATTTATA<br> I  I  Y> | 240<br>13 |
| CTTAATAAT<br>T  L  I  I | ATGTGATCCA<br> C  D  P | ACAACACCGG<br> T  T  P> | 270<br>23 |
| AAAGTACTAT<br>E  S  T  I | TAATCCATTA<br> N  P  L | AATCATCACA<br> N  H  H> | 300<br>33 |
| ATTTATCAAC<br>N  L  S  T | ACCTAAACCT<br> P  K  P | ACTTCGGATG<br> T  S  D> | 330<br>43 |
| ATATTCGTGA<br>D  I  R  E | AATTTTACGT<br> I  L  R | GAATCCCAAA<br> E  S  Q> | 360<br>53 |
| TTGAATCTGA<br>I  E  S  D | TGATACATCA<br> D  T  S | ACATTTACA<br> T  F  Y> | 390<br>63 |
| TGTGCCCACC<br>M  C  P  P | ACCATCGGGA<br> P  S  G | TCAACATTGG<br> S  T  L> | 420<br>73 |
| TGCGTTTGGA<br>V  R  L  E | GCCACCTAGA<br> P  P  R | GCATGTCCTA<br> A  C  P> | 450<br>83 |
| ACTATAAACT<br>N  Y  K  L | TGGTAAAAT<br> G  K  N | TTTACAGAAG<br> F  T  E> | 480<br>93 |

| | | | | |
|---|---|---|---|---|
| GAATTGCTGT | AATATTTAAG | GAAAATATTT | 510 | |
| G  I  A  V | I  F  K | E  N  I> | 103 | |
| CTCCTTATAA | ATTTAAAGCT | AATATATACT | 540 | |
| S  P  Y  K | F  K  A | N  I  Y> | 113 | |
| ACAAAAATAT | TATTATCACC | ACTGTATGGT | 570 | |
| Y  K  N  I | I  I  T | T  V  W> | 123 | |
| CTGGAAGCAC | ATATGCAGTA | ATTACTAATA | 600 | |
| S  G  S  T | Y  A  V | I  T  N> | 133 | |
| GATATACAGA | TCGTGTACCT | ATAGGTGTTC | 630 | |
| R  Y  T  D | R  V  P | I  G  V> | 143 | |
| CTGAAATTAC | AGAGTTGATT | GATAGAAGAG | 660 | |
| P  E  I  T | E  L  I | D  R  R> | 153 | |
| GTATGTGTTT | ATCAAAAGCT | GATTATATTC | 690 | |
| G  M  C  L | S  K  A | D  Y  I> | 163 | |
| GTAATAATTA | TGAATTTACC | GCATTTGATA | 720 | |
| R  N  N  Y | E  F  T | A  F  D> | 173 | |
| AGGATGAAGA | CCCCAGAGAA | GTTCATTTAA | 750 | |
| K  D  E  D | P  R  E | V  H  L> | 183 | |
| AGCCTTCAAA | GTTTAATACA | CCAGGATCCC | 780 | |
| K  P  S  K | F  N  T | P  G  S> | 193 | |
| GTGGATGGCA | TACAGTTAAT | GATACTTACA | 810 | |
| R  G  W  H | T  V  N | D  T  Y> | 203 | |
| CAAAAATTGG | GGGTTCTGGA | TTTTATCATT | 840 | |
| T  K  I  G | G  S  G | F  Y  H> | 213 | |
| CTGGAACATC | TGTAAATTGT | ATAGTTGAAG | 870 | |
| S  G  T  S | V  N  C | I  V  E> | 223 | |
| AAGTTGATGC | CAGATCTGTT | TATCCATATG | 900 | |
| E  V  D  A | R  S  V | Y  P  Y> | 233 | |

FIG. 1C

| | | | | |
|---|---|---|---|---|
| ATTCATTTGC | TATCTCCACC | GGGGATATAA | 930 |
| D S F A | I S T | G D I> | 243 |
| TTCATATGTC | CCCTTTTTTT | GGATTACGAG | 960 |
| I H M S | P F F | G L R> | 253 |
| ATGGTGCTCA | TACTGAATAT | ATTAGTTATT | 990 |
| D G A H | T E Y | I S Y> | 263 |
| CAACTGATAG | ATTTCAACAA | ATAGAAGGTT | 1020 |
| S T D R | F Q Q | I E G> | 273 |
| ATTATCCTAT | CGACTTAGAT | ACTAGACTAC | 1050 |
| Y Y P I | D L D | T R L> | 283 |
| AGCTTGGTGC | ACCAGTTTCT | AGGAATTTTT | 1080 |
| Q L G A | P V S | R N F> | 293 |
| TAACAACACA | ACACGTTACT | GTTGCTTGGA | 1110 |
| L T T Q | H V T | V A W> | 303 |
| ATTGGGTTCC | AAAAATTCGT | GAAGTGTGTA | 1140 |
| N W V P | K I R | E V C> | 313 |
| CTTTGGCTAA | ATGGCGTGAA | ATTGATGAAA | 1170 |
| T L A K | W R E | I D E> | 323 |
| TTATTCGTGA | TGAGTATAAG | GGATCTTACA | 1200 |
| I I R D | E Y K | G S Y> | 333 |
| GATTTACAGC | AAAATCAATA | TCTGCAACAT | 1230 |
| R F T A | K S I | S A T> | 343 |
| TTATTTCTGA | TACTACTCAA | TTTGATATTG | 1260 |
| F I S D | T T Q | F D I> | 353 |
| ATCGTGTAAA | GTTAAGTGAT | TGTGCCAAAC | 1290 |
| D R V K | L S D | C A K> | 363 |
| GTGAAGCCAT | AGAAGCTATT | GATAAGATCT | 1320 |
| R E A I | E A I | D K I> | 373 |

FIG. 1D

| | | | |
|---|---|---|---|
| ACAAAAAAAA | ATATAATAAA | ACTCATATTC | 1350 |
| Y K K K | Y N K | T H I> | 383 |
| AAACAGGAGA | ATTGGAAACA | TACTTGGCTA | 1380 |
| Q T G E | L E T | Y L A> | 393 |
| GAGGGGATT | TATTATAGCA | TTTAGACCAA | 1410 |
| R G G F | I I A | F R P> | 403 |
| TGATTAGTAA | TGAGTTAGCA | AAATTGTATA | 1440 |
| M I S N | E L A | K L Y> | 413 |
| TAAATGAGTT | AGTAAGATCT | AATCGTACGG | 1470 |
| I N E L | V R S | N R T> | 423 |
| TTGATTTGAA | ATCTCTTTTA | AATCCATCTG | 1500 |
| V D L K | S L L | N P S> | 433 |
| TAAGAGGGGG | GGCTAGAAAG | AGAAGATCAG | 1530 |
| V R G G | A R K | R R S> | 443 |
| TAGAGGAAAA | TAAAAGATCA | AAACGTAATA | 1560 |
| V E E N | K R S | K R N> | 453 |
| TTGAAGGTGG | TATTGAAAAT | GTAAATAATT | 1590 |
| I E G G | I E N | V N N> | 463 |
| CAACAATAAT | TAAGACAACT | TCATCTGTTC | 1620 |
| S T I I | K T T | S S V> | 473 |
| ATTTTGCTAT | GCTTCAGTTT | GCCTATGATC | 1650 |
| H F A M | L Q F | A Y D> | 483 |
| ATATTCAATC | ACATGTTAAT | GAAATGCTTA | 1680 |
| H I Q S | H V N | E M L> | 493 |
| GTAGAATTGC | AACTGCATGG | TGTAATCTTC | 1710 |
| S R I A | T A W | C N L> | 503 |
| AAAATAAAGA | GAGAACCCTT | TGGAATGAAG | 1740 |
| Q N K E | R T L | W N E> | 513 |

FIG. IE

| | | | |
|---|---|---|---|
| TTATGAAACT<br>V  M  K  L | TAATCCAACT<br>N  P  T | AGTGTGGCTT<br>S  V  A> | 1770<br>523 |
| CGGTTGCTAT<br>S  V  A  M | GGATCAAAGA<br>D  Q  R | GTTTCAGCAC<br>V  S  A> | 1800<br>533 |
| GAATGTTAGG<br>R  M  L  G | GGATGTTCTT<br>D  V  L | GCAGTTACTC<br>A  V  T> | 1830<br>543 |
| AATGTGTTAA<br>Q  C  V  N | TATATCAGGT<br>I  S  G | TCTAGTGTTT<br>S  S  V> | 1860<br>553 |
| TTATTCAAAA<br>F  I  Q  N | TTCCATGCGT<br>S  M  R | GTTTTAGGGT<br>V  L  G> | 1890<br>563 |
| CAACAACTAC<br>S  T  T  T | ATGTTACAGT<br>C  Y  S | CGTCCTCTTA<br>R  P  L> | 1920<br>573 |
| TATCATTTAA<br>I  S  F  K | AGCACTAGAA<br>A  L  E | AACTCAACTA<br>N  S  T> | 1950<br>583 |
| ACTATATTGA<br>N  Y  I  E | AGGACAACTT<br>G  Q  L | GGGGAAAATA<br>G  E  N> | 1980<br>593 |
| ATGAACTATT<br>N  E  L  L | AGTAGAACGA<br>V  E  R | AAGCTAATTG<br>K  L  I> | 2010<br>603 |
| AACCATGTAC<br>E  P  C  T | AGCTAACCAT<br>A  N  H | AAAAGATATT<br>K  R  Y> | 2040<br>613 |
| TTAAATTTGG<br>F  K  F  G | TGCAGATTAT<br>A  D  Y | GTATATTTTG<br>V  Y  F> | 2070<br>623 |
| AAAACTATGC<br>E  N  Y  A | ATATGTTCGA<br>Y  V  R | AAGGTACCTC<br>K  V  P> | 2100<br>633 |
| TTAATGAAAT<br>L  N  E  I | TGAAATGATC<br>E  M  I | AGTGCATATG<br>S  A  Y> | 2130<br>643 |
| TAGATCTTAA<br>V  D  L  N | TATTACATTA<br>I  T  L | CTTGAGGATC<br>L  E  D> | 2160<br>653 |

FIG. 1F

| | | | | |
|---|---|---|---|---|
| GTGAATTTTT | ACCACTAGAG | GTATATACTC | 2190 | |
| R E F L | P L E | V Y T> | 663 | |
| GAGCAGAGTT | AGAAGATACA | GGACTATTGG | 2220 | |
| R A E L | E D T | G L L> | 673 | |
| ACTATAGTGA | GATTCAACGT | AGAAATCAAC | 2250 | |
| D Y S E | I Q R | R N Q> | 683 | |
| TACATGCACT | TAAGTTTTAT | GATATTGACA | 2280 | |
| L H A L | K F Y | D I D> | 693 | |
| GTGTTGTAAA | AGTTGATAAT | AATGTTGTAA | 2310 | |
| S V V K | V D N | N V V> | 703 | |
| TTATGAGGGG | CATTGCAAAT | TTTTTCCAAG | 2340 | |
| I M R G | I A N | F F Q> | 713 | |
| GACTTGGAGA | TGTTGGAGCG | GGATTTGGAA | 2370 | |
| G L G D | V G A | G F G> | 723 | |
| AAGTTGTTTT | GGGTGCTGCA | AATGCTGTTA | 2400 | |
| K <u>V V L</u> | <u>G A A</u> | <u>N A V</u>> | 733 | |
| TTGCAACTGT | TTCTGGAGTG | TCCTCGTTTC | 2430 | |
| <u>I A T V</u> | <u>S G V</u> | <u>S</u> S F> | 743 | |
| TTAATAACCC | ATTTGGGGCG | CTAGCCGTTG | 2460 | |
| L N N P | <u>F G A</u> | <u>L A V</u>> | 753 | |
| GATTGCTGAT | TTTAGCTGGA | CTATTTGCAG | 2490 | |
| <u>G L L I</u> | <u>L A G</u> | <u>L F A</u>> | 763 | |
| CGTTTTTGGC | TTATAGATAT | GTTTCTAAAC | 2520 | |
| <u>A F L A</u> | <u>Y R Y</u> | <u>V</u> S K> | 773 | |
| TTAAGTCAAA | TCCAATGAAA | GCACTATACC | 2550 | |
| L K S N | P M K | A L Y> | 783 | |
| CAGTAACTAC | AAAAAATTTA | AAAGAAAGTG | 2580 | |
| P V T T | K N L | K E S> | 793 | |

FIG. 1G

| | | | |
|---|---|---|---|
| TTAAGAATGG<br>V K N G | TAATTCTGGA<br>N S G | AATAATAGTG<br>N N S> | 2610<br>803 |
| ATGGAGAAGA<br>D G E E | AAATGATGAT<br>N D D | AATATCGATG<br>N I D> | 2640<br>813 |
| AAGAAAAGCT<br>E E K L | TCAACAAGCT<br>Q Q A | AAAGAAATGA<br>K E M> | 2670<br>823 |
| TTAAATATAT<br>I K Y M | GTCTCTAGTT<br>S L V | TCTGCTATGG<br>S A M> | 2700<br>833 |
| AACAGCAGGA<br>E Q Q E | ACATAAAGCT<br>H K A | ATTAAAAAAA<br>I K K> | 2730<br>843 |
| ATAGTGGCCC<br>N S G P | TGCCCTTCTA<br>A L L | GCAAGTCACA<br>A S H> | 2750<br>853 |
| TTACAAACCT<br>I T N L | ATCTCTTAAA<br>S L K | CATCGTGGTC<br>H R G> | 2790<br>863 |
| CAAAATACAA<br>P K Y K | ACGTTTGAAA<br>R L K | AATGTAAATG<br>N V N> | 2820<br>873 |
| AAAATGAAAG<br>E N E S | TAAAGTTTAA<br>K V * | TAAAAAATTT | 2850<br>879 |
| AAATATTACG | TAAAATTTTC | TGACTCTGCC | 2880 |
| CACTTTTTTT | ATAATATAAA | TTTTAGAAAA | 2910 |
| TTTTACTCAT | TTTATTATCT | TTTATAAACC | 2940 |
| TCCAACTATT | TATAAGGAT | AATAAATGGA | 2970 |
| CATTTCTGCG | GTGCCTGTAT | ATCCTACTAA | 3000 |

```
CHV   M------------------------------------------------FSLYL--------------------------------YIFFIIYTLIICDPTTPESTINPLNHHM
FHV   MST--RGDLGKRRRGSRWQHSGYFRQRCFFPSLLGIAATGSRHGNGSSGLTRL----------------ARYVSFIWIVLFLVGPRPVEGQSGSTSEQP
EHV1  MSSGCRS-VGGSTWGN-WRGDGGDLRQRRVLSPVCSAPAAGSWIGSQLGNVGNLLATPHPLGKPASSRVGTIVLACLLLFGSCVVRAVPTTPSPPT
PRV   MPAG--GGLWRGPRGHR-PGHHGGAGLGRLWPA--PHHAAAARGAVALALLLLALAAAPPCGAAAVTRA-------ASASPTPGTATPNDV
VZV   M---------------------------------------------------------------------------FVTAVVSVSPSSFYESL--------
HSV1  MHQG--------APSWGRRW------FVVWALL----------GLTLGVLVASAAPSSP-GTPGVARDPG---GERGPCHSGAAALGAAPTGDPK
HCMV  MES-------------------RIWCLV--------------VCVNLCIVCLGAAVSSSSTSHATS-----------STHNGSHTSR
EBV   MTR-----------------------RR------------VLSVVLLAALACRLGAQ--T-----------------PEQPAPPATT
        *                                                                                                    .                     .

LST---------PKPTSD------D-I--REILRESQIESDDTSTF-Y-M  C  PPPSGSTLVRLEPPRA  C  PNYKLGK-NFTEGIAVIFKENISP
RRTVATPEVGGTPPKPTDPTDMSD-M--REALRASQIEANGPSTF-Y-M  C  PPPSGSTVVRLEPPRA  C  PDYKLGK-NFTEGIAVIFKENIAP
STPTSMSTHSHGTVDPTLLPTETPDPL--RLAVRESGILAED-GDF-Y-T  C  PPPTGSTVVRIEPPRT  C  PKFDLGR-NFTEGIAVIFKENIAP
SAEASLEEIEAFSPGPSEAPDGEYGDLDARTAVRAA--ATERDRF-Y-V  C  PPPSGSTVVRLEPEQA  C  PEYSQGR-NFTEGIAVLFKENIAP
------QVEPTQSEDITRSAHLGDGDEIREAIHKSQ-DAETKPTF-Y-V  C  PPPTGSTIVRLEPTRT  C  PDYHLGK-NFTEGIAVVYKENIAA
PKKNKKPKNPTPPRPAGDNATVAAGHATLREHLRDIKAENTD-ANF-Y-V  C  PPPTGATVQFEQPRR  C  PTRPEGQ-NYTEGIAVVFKENIAP
TTSAQTRSVYSQHVTSSEAVSHRANETIYNITLKYGDVVGVNITKYPYRV  C  SMAQTDLIRFERNII  C  TSMKPINEDLDEGIMVVYKRNIVA
VQPTATR--------------QQTSFPFRV  C  ELSSHGDLFRFSSDIQ  C  PSF-GIRENHTEGLLMVFKDNIIP
                                                    *                                                 *                 *         *      *  *
                                                                                                                            100
```

FIG. 3B

```
YKFKANIYYKNIIITTVWSGSTYAVITNRYTDRVPIGVPEITELIDRRGM C LSKADYIRNNYEFTAFDKDE-DPREVHLKPSKFNTPGSRGWHT
YKFKANIYYKNIIIMTTVWSGSSYAVTTNRYTDRVPVKVQEITDLIDRRGM C LSKADYVRNNYQFTAFDRDE-DPRELPLKPSKFNTPQSRGWHT
YKFRANVYYKDIVVTRVWKGYSHTSLSDRYNDRVPVSVEEIFGLIDSKGK C SSKAEYLRDNIMHHAYHDDE-DEVELDLCRPSLQLRGARAWQT
HKFKAHIYYKNVIVTTVWSGSTYAAITNRFTDRVPVPVQEITDVIDRRGK C VSKAEYVRNNHKVTAFDRDE-NPVEVDLRPSRLNALGTRGWHT
YKFKATVYYKDVIVSTAWAGSSYTQITNRYADRVPIPVSEITDTIDKFGK C SSKATYVRNNHKVEAFNEDK-NPQDMPLIASKYNSVGSKAWHT
YKFKATMYYKDVTVSQWVFGHRYSQFMGIFEDRAPVPFEEVIDKINAKGV C RSTAKYVRNNLETTAFHRDD-HETDMELKPANAATRTSRGWHT
HTFKVRVYQKVLTFRRSYAYIYTYLLGSNTEYVAPPMWEI-HHINKFAQ C YSSYSRVIGGTVFVAYHRDSYENKTMQLIPDDYSNTHSTRYVT
YSFKVRSYTKIVTNLILYNGWYADSVTNRHEEKFSVDSYET-DQMDTIYQ C YNAVKMTKDGLTRVYVDRDGV-NITVNLKPTGGLANGVRRYAS
   *  *   *                    *   *                   *                     *            *

200
NDTYTKIGGSGFYH-SGTSVN C IVEEVDARSVYPYDSFAISTGDIIHMSPFFGLRDGAHTEYISYS--TDRFQQIEGYYPI-DLDTRLQLGAP
NETYTKIGAAGFHH-SGTSVN C IVEEVDARSVYPYDSFAISTGDVIHMSPFFGLRDGAHVEHTSYS--SDRFQQIEGYYPI-DLDTRLQLGAP
NDTSYVGWMPWRHYTSTSVN C IVEEVEARSVYPYDSFALSTGDIVYASPFYGLRAAARIEHNSYA--QERFRQVEGYRPR-DLDSKLQAEEP
INDTYTKIGAAGFYH-TGTSVN C IVEEVEARSVYPYDSFALSTGDIVYMSPFYGLREGAHGEHIGYA--PGRFQQVEHYYPI-DLDSRLRASES
NDTYMVAGTPGTYR-TGTSVN C IIEEVEARSIFPYDSFGLSTGDIIYMSPFFGLRDGAYREHSNYA--MDRFHQFEGYRQR-DLDTR-ALLEP
DLKYNPSRVEAFHRY-GTTVN C IVEEVDARSVYPYDEFVLATGDFVYMSPFYGYREGSHTEHTTYA--ADRFKQVDGFYAR-DLTTKARATAP
KDQWHSRGS-TWLYRETCNLN C MLTITTARSKYPYHFFATSTGDVVYISPFY---NGTNRNASYFGENADKFFIFPNYTIVSDFGRPNAAPET
QTELYDAPGWLIWTYRTRTTVN C LITDMMAKSNSPFDFFVTTGQTVEMSPFY----DGKNKET--FHERADSFHVRTNYKIV-DYDNRGTNPQG
       *     *   *   *                       *       *           *    *         *      *
```

FIG. 3C

```
                300
VS-RNFLTTQHVTVAWNWVPKIREV  C  TLAKWREIDEIIRDEYK-GSYRFTAKSISATFISDTT-QFDIDRVKLSD  C  AKREAIEAIDKIYKK
VS-RNFLETPHVTVAWNWTPKCGRV  C  TLAKWREIDEMLRDEYQ-GSYRFTVKTISATFISNTS-QFEINRIRLGD  C  ATKEAAEAIDRIYKSK
VT-KNFITTPHVTVSWNWTEKKVEA  C  TLTKWKEVDELVRDEFR-GSYRFTIRSISSTFISNTT-QFKLESAPLTE  C  VSKEAKEAIDSIYKKQ
VT-RNFLRTPHFTVAWDWAPKTRRV  C  SLAKWREAEEMTRDETRDGSFRFTSRALGASFVSDVT-QLDLQRVHLGD  C  VLREASEAIDAIYRRR
AA-RNFLVTPHLTVGWNWKPKRTEV  C  SLVKWREVEDVVRDEYAH-NFRFTMKTLSTFISETN-EFNLNQIHLSQ  C  VKEEARAIINRIYTTR
TT-RNLLTTPKFTVAWDWVPKRPSV  C  TMTKWQEVDEMLRSEY-GGSFRFSSDAISTTFTNLI-EYPLSRVDLGD  C  IGKDARDAMDRIFARR
HRLVAFLERADSVISWDIQDEKNVI  C  QLTFWEASERTIRSE-AEDSYHFSSAKMTATFLSKKQ-EVNMSDSAL-D  C  VRDEAINKLQQIFNTS
ER-RAFLDKGTYTLSWKL-ENRTAY  C  PLQHWQTFDSTIATE-TGKSIHFVTDEGTSSFVTNTIVGIELPD-AF-K  C  IEEQVNKTMHEKYEAV
        .  . . .                 .    .     .                  .    .        .
        *  *                     *    *                        *    *        *

400
YNKTHIQTGEL-ETYLARGGFIIAFRPMISNELAKLYINELVRSNRIVDLKSLLNPSVRGGA---RKRRSV-------------EEN-------KRSKRN
YSKTHIQTGIL-ETYLARGGFLIAFRPMISNELAKLYINELARSNRIVDLSALLNPSGETVQ---RTRGSV-------PSNQH-------HRSRRS
ESTHVFSGDV-EYYLARGGFVVAFRPMLSNELARLYLNELVRSNRIYDLKNLLNPNANNNNNTIRRRRSLLSVPEPQPTQDGVHREQILHRLHKR
NSTHVLAGDRPEVYLARGGFVVAFRPLISNELAQLYARELER----LGLAGVVGPAAPAAARRARRSPGPAGTPEPPAVNGTGH-
NSSHVRTGDI-QTYLARGGFVVVFQPLLSNSLARLYLQELVRENTN------HSPQKHPTRNTRSRRSV-------PVELRANRT-
YNATHIKVGQ-PQYYLANGGFLIAYQPLLSNTLAELYVREHLREQS-----------------RKPPNPTPPPPGASANAS-
YNQIYEK-YGNVSVFETSGGLVVFWQGIKQKSLVEL----------------ERLANRSSLNITH-----------------RIRRS
QDRYTKGQEAITYFITSGGLLLAWLPLTPRSLATV-----------------KNLTELTIPTSSPPSSPSPPAPSAARGSTPAAVLRRRRR
        . .   .         *
       **                *
```

FIG. 3D

```
                                                                              500
- IEGGIENVNNSI------IIKTTSSVHFAMLQFAYDHIQSHVNEMLSRIATAW  C  NLQNKERTLWNEVMKLNPTSVASVAMDQRVSARMLGDVL
 TIEGGIETVNNAS------LLKTTSSVEFAMIQFAYDYIQAHVNEMLSRIATAW  C  TLQNREHVLWTETLKLNPGGVVSMALERRVSARLLGDAV
 AVEATAGIDSSNVTAKQLELIKTTSSIEFAMLQFAYDHIQSHVNEMLSRIATAW  C  TLQNKERTLWNEMVKINPSAIVSATLDERVAARVLGDVI
------LRITIGSAEFARLQFTYDHIQAHVNDMLGRIAAAW               C  ELQNKDRTLWSEMSRLNPSAVATAALGQRVSARMLGDVM
------ITTTSSVEFAMLQFTYDHIQEHVNEMLARISSSW                C  QLQNRERALWSGLFPINPSALASTILDQRVKARILGDVI
------VERIKTTSSIEFARLQFTYNHIQRHVNDMLGRVAIAW             C  ELQNHELTLWNEARKLNPNAIASVTVGRRVSARMLGDVM
 TSDNNTTHLS------SMESVH---NLVYAQLQFTYDTLRGYINRALAQIAEAW C  VDQRRTLEVFKELSKINPSAILSAIYNKPIAARFMGDVL
 DAGNATTPVPPTAPGKSLGTLN---NPATVQIQFAYDSLRRQINRMLGDLARAW C  LEQKRQNMVLRELTKINPTTVMSSIYGKAVAAKRLGDVI
      .   .  :.   :     .. *    ** ::  : :..*    :  ** *    *    *.   :.  *:: . *     :     ****

600
 AVTQ  C  VNISGS-SVFIQNSMRVLGSTIT  C  YSRPLISFKALENSTN--YIEGQLGENNELLVERKLIEP  C  TANHKRYFKFGADYVYFENYA
 AVTQ  C  VNISSG-HVYIQNSMRVTGSSIT  C  YSRPLVSFRALNDS-E--YIEGQLGENNDLLVERKLIEP  C  TVNNKRYFKFGADYVYFEDYA
 AITH  C  AKIEG--NVYLQNSMRSMDSNT-  C  YSRPPVTFTITKNANNRGSIEGQLGEENEIFTERKLIEP  C  ALNQKRYFKFGKEYVYENYI
 AISR  C  VEVRGG--VYVQNSMRVPGERGT  C  YSRPLVTF----EHNGTGVIEGQLGDDNELLISRDLIEP  C  TGNHRRYFKLGSGYVYYEDYN
 SVSN  C  PELGSDTRIILQNSMRVSGSTTR  C  YSRPLISIVSLN---GSGTVEGQLGTDNELIMSRDLLEP  C  VANHKRYFLFGHHYVYYEDYR
 AVST  C  VPVAAD-NVIVQNSMRISSRPGA  C  YSRPLVSFRY----EDQGPLVEGQLGENNELRLTRDAIEP C  TVGHRRYFTFGGGYVYFEEYA
 GLAS  C  VTIN-QTSVKVLRDMNVKESPGR  C  YSRPVVIFNFANSSY---VQYGQLGEDNEILLGNHRTEE  C  QLPSLKIFIAGNSAYEYVDYL
 SVSQ  C  VPVN-QATVTLRKSMRVPGSETM  C  YSRPLVSFSFINDTK---TYEGQLGTDNEIFLTKKMTEV  C  QATSQYYFQSGNEIHVYNDYH
         *                         ****                                       *
```

FIG. 3E

```
                                                                          700                                                      800
YVRKVPLNEIEMISAYDVDLNITLLEDREFLPLEVYTRAELEDTGLLDYSEIQRRNQLHALKFYDIDSVVK---VDNNVVIMRGIANFFQGLGDVGA
YVRKVPLSEIELISAYDVDLNLTLLEDREFLPLEVYTRAELEDTGLLDYSEIQRRNQLHALKFYDIDSIVR---VDNNLVIMRGMANFFQGLGDVGA
FVRKVPPTEIEVISTYVELNLNLTLLEDREFLPLEVYTRAELEDTGLLDYSEIQRRNQLHALRFYDIDSVVN---VDNTAVIMQGIASFFKGLGKVGE
YVRMVEVPET--ISTRVTLNLTLLEDREFLPLEVYTREELADTGLLDYSEIQRRNQLHALKFYDIDRVVK---VDHNVVLLRGIANFFQGLGDVGA
YVREIAVHDVGMISTYVDLNLTLKDREFMPLQVYTRDELRDTGLLDYSEIQRRNQMHSLRFYDIDKVVQ---YDSGTAIMQGMAQFFQGLGTAGQ
YSHQLSRADITTVSTFIDLNITMLEDHEFVPLEVYTRHEIKDSGLLDYTEVQRRNQLHDLRFADIDTVIH---ADANAAMFAGLGAFFEGMGDLGR
FKRMIDLSSISTVDSMIALDIDPLENTDFRVLELYSQKELRSSNVFDLEEIMREFNSYKQRV----KYVEDKVVDPLPPYLKGLDDLMSGLGAAGK
HFKTIELDGIATLQTFISLNTSLIENIDFASLELYSRDEQRASNVFDLEGIFREYNFQAQNIAGLRKDLDNAVSNGRNQFVDGLGELMDSLGSVGQ

GFGKVVLGAANAVIATVSGVSSFLNNPFGALAVGLLILAGLFAAFLAYRYVSKLKSNPMKALYP--VTTKNLKE-------SVKNGNSGNNSD
GFGKVVLGAASAVISTVSGVSSFLNNPFGALAVGLLILAGIVAAFLAYFLAYRYISRLRANPMKALYP--VTTRNLKQ-------TAKSPASTAGGD
AVGTLVLGAAGAVVSTVSGIASFLNNPFGGLAIGLLVIAGLVAAFFAYRYVMQIRSNPMKALYP--ITTKALKN-------KAKTS---YGQN
AVGKVVLGATGAVISAVGGMVSFLSNPFGALAIGLLVLAGLVAAFLAYRHISRLRRNPMKALYP--VTIKTLKE--------
AVGHVVLGATGALLSTVHGFTTFLSNPFGALAVGLLVLAGLVAAFFAYRYVLKLKTSPMKALYP--LITKGLKQLPEGMDPFAEKPNATDTPIEEI
AVGKVVMGLVGGVVSAVSGVVSAVSGLVLAGLAAAFFAFRYVMRLQSNPMKALYP--LTTKELKN-------PTNPDASGE
AVGVAIGAVGGAVASVVEGVATFLKNPFGAFTIILVAIAVVIITYLIYTQRRLCTQPLQNLFPYLVSADGTTVTSGSTKDTSLQAPPSYEESVYN
SINLVSTVGGLFSSLVSGFISFFKNPFGGMLILVLVAGVVILVISLTRRTRQMSQQPVQMLYP------GIDELAQQHASG-----
```

FIG. 3F

```
GEENDDN------IDEEKLQQAKEMIKYMSLVSAMEQQEHKAIKKNSGPALLASHITNLSLK----HRGPKYKRLKNVNENESK----V
SDPGVDD------FDEEKLMQAREMIKYMSLVSAMEQQEHKAMKKNKGPAILTSHLTNMALR----RRGPKYQRLNNLDSGDDTETNLV
EEDDGSD------FDEAKLEEAREMIKYMSMVSALEKQEKKAIKKNSGVGLIASNVSKLALR----RRGPKYTRLQQNDTMEN--EKMV
DGVDEGD------VDEAKLDQARDMIRYMSIVSALEQQEHKARKKNSGPALLASRVGAMATR----RR--HYQRL-----ESEDPDAL
GDSQNTEPSVNSGFDPDKFREAQEMIKYMTLVSAAERQESKARKKNKTSALLTSRLTGLALR----NR-RGYSRVR-----TENVTGV
GEEGGD-------FDEAKLAEAREMIRYMALVSAMERTEHKAKKGTSR-LLSAKVTDMVMRK----RRNTNYTQVPNKD--GDADEDDL
SGRKGPGPPSSDASTAAPPYTNEQAYQMLLALARLDAEQR--AQQNGTDSLDGQTGTQDKGQKPNLLDRLRHRKNGYRHLKDSDEEENV
---EGPG---------INPISKTELQAIMLALHEQNQEQKRAAQRAAGPSVASRALQAARDRFPGLRRRRYHDPETAAALLG-EAETEF
```

```
CGAGCCCTAA  TTATTGGTTT  GTATATGACT              30
GTTGGAATTT  GTTACATTTT  TATTAAAACA              60
ATAAATTAAA  TTTTTTAAAC  TATATTACGG              90
TTGTGTGTGT  TTTAAGTTTT  AAATAAAGCA             120
ATATTTCGAA  TTCACATTTA  TCAAAACAT              150
TAAAACCCAA  CACAAAAAAA  TTTCTATAAT             180
CATTAAGGTA  ATAAGTCAAA  ATGAGTTTTA             210
                         M   S   F>              3
AAAATTTTTA  TCTAATATAT  GTAATTATAA             240
 K  N  F Y   L  I  Y     V  I  I>               13
TTTTTATAAA  CTCGATAATA  ACTTCGGCAT             270
 I  F  I N   S  I  I     T  S  A>               23
CTACATCCAA  ACCTTCAACA  CCTACCATAA             300
 S  T  S K   P  S  T     P  T  I>               33
TTCCAACTTC  AGCAAATGAA  TCACCTGCTT             330
 I  P  T S   A  N  E     S  P  A>               43
CCATAGATAC  AACTATAACA  AAACCTATAT             360
 S  I  D T   T  I  T     K  P  I>               53
CTACAGAGGC  AAATAATTTA  AAATCAGTAA             390
 S  T  E A   N  N  L     K  S  V>               63
GTACCTCAAT  TAAACCACCT  AAAAACTTAA             420
 S  T  S I   K  P  P     K  N  L>               73
AAAAAAAATT  ACTTAAATCT  AAATGTAGAG             450
 K  K  K L   L  K  S     K  C  R>               83
ATAATGTTAT  TTATAGGCCA  TATTTTAGTC             480
 D  N  V I   Y  R  P     Y  F  S>               93
AATTAGAAAT  TAACTGTACT  ATAACTAAAA             510
 Q  L  E I   N  C  T     I  T  K>              103
```

FIG. 4B

| | | | | |
|---|---|---|---|---|
| AGCAAAATTT | AAGTAATCCT | TTAATTGAGT | 540 | |
| K  Q  N  L | S  N  P | L  I  E> | 113 | |
| TATGGTTTAA | AGAACTTTCT | ACATATAATA | 570 | |
| L  W  F  K | E  L  S | T  Y  N> | 123 | |
| AAACCAATGA | AAATGTTGAA | AGTTTAAAAA | 600 | |
| K  T  N  E | N  V  E | S  L  K> | 133 | |
| CAGATATATC | AAAAAATATT | TTATTATTTT | 630 | |
| T  D  I  S | K  N  I | L  L  F> | 143 | |
| CGACAAAAAA | TAATAGTGAT | AACTTTTATA | 660 | |
| S  T  K  N | N  S  D | N  F  Y> | 153 | |
| ATGATTTTTT | ATTAGGTATA | CAAAATCAAC | 690 | |
| N  D  F  L | L  G  I | Q  N  Q> | 163 | |
| CAGTAAATTA | TAAACTTTAC | GGTTCCCAAT | 720 | |
| P  V  N  Y | K  L  Y | G  S  Q> | 173 | |
| TTTATGATAA | TGGAAACATA | TTACTAAATA | 750 | |
| F  Y  D  N | G  N  I | L  L  N> | 183 | |
| TAAAGTCGGT | TGACTTTAAA | ACCTCTGGAA | 780 | |
| I  K  S  V | D  F  K | T  S  G> | 193 | |
| TATATACTTG | GAAACTATAT | AATTCAAATA | 810 | |
| I  Y  T  W | K  L  Y | N  S  N> | 203 | |
| ATGAAAGTAT | TTTTGAAACT | TTTAAAATTC | 840 | |
| N  E  S  I | F  E  T | F  K  I> | 213 | |
| AAGTATATGC | ATATCATTCC | CCAAATGTAA | 870 | |
| Q  V  Y  A | Y  H  S | P  N  V> | 223 | |
| ACTTAAAATC | AAACCCAAGT | TTATATAATG | 900 | |
| N  L  K  S | N  P  S | L  Y  N> | 233 | |
| AAAACTACAG | CGCTATTTGT | ACAATAGCAA | 930 | |
| E  N  Y  S | A  I  C | T  I  A> | 243 | |
| ATTACTTTCC | ATTGGAATCT | ACGGAAATAT | 960 | |
| N  Y  F  P | L  E  S | T  E  I> | 253 | |

FIG. 4C

```
TTTGGTTTAA   CGATGGACAA   CCTATTGATA    990
 F  W  F  N   D  G  Q      P  I  D>     263

AAAAATATAT   AGATGAAACT   TATAGTGTAT   1020
 K  K  Y  I   D  E  T      Y  S  V>    273

GGATTGACGG   TCTTATAACA   CGCACTTCAA   1050
 W  I  D      L  I  T      R  T  S>    283

TATTATCCCT   TCCCTTTTCC   GAAGCCATGG   1080
 I  L  S  L   P  F  S      E  A  M>    293

AAAGCCCCCC   CAATTTGCGA   TGTAATGTTG   1110
 E  S  P  P   N  L  R      C  N  V>    303

AATGGTATAA   AAATTCAAAG   GCATCAAAAA   1140
 E  W  Y  K   N  S  K      A  S  K>    313

AATTTTCAAA   TACCGTTATT   CCAAAAGTTT   1170
 K  F  S  N   T  V  I      P  K  V>    323

ACTATAAACC   TTTTATATCT   ATAAATTTG    1200
 Y  Y  K  P   F  I  S      I  K  F>    333

ATAATGGTTT   AGCTATTTGT   GATGCTAAAT   1230
 D  N  G  L   A  I  C      D  A  K>    343

GTGTTTCCCG   TGAAAATAAT   AAATTACAAT   1260
 C  V  S  R   E  N  N      K  L  Q>    353

GGTTAGTTAA   AGATATACCT   ATAAATGGTG   1290
 W  L  V  K   D  I  P      I  N  G>    363

ATGATATTAT   AAGCGGCCCC   TGTTTAAACC   1320
 D  D  I  I   S  G  P      C  L  N>    373

ACCCTGGTTT   GGTCAATATT   CAAAATAAAA   1350
 H  P  G  L   V  N  I      Q  N  K>    383

TAGATATATC   GGATTATGAT   GAACCTGTTA   1380
 I  D  I  S   D  Y  D      E  P  V>    393
```

FIG. 4D

| | | | |
|---|---|---|---|
| CCTATAAATG<br>T Y K C | TTCAATTATT<br>S I I | GGTTATCCAA<br>G Y P> | 1410<br>403 |
| TAATTTTTCC<br>I I F P | CAACTTTTAT<br>N F Y | GATGAAAAGG<br>D E K> | 1440<br>413 |
| TGTTTGATGC<br>V F D A | ATCGGATGAA<br>S D E | AATGTTAGTA<br>N V S> | 1470<br>423 |
| AATCGATGTT<br>K S M L | AATAAGTATT<br>I S I | ACCACAATAA<br>T T I> | 1500<br>433 |
| TTGGTGGAGC<br>I G G A | CATTTTTGTT<br>I F V | ATAGTATTGA<br>I V L> | 1530<br>443 |
| TTTTTATAAC<br>I F I T | AGCTTTATGT<br>A L C | TTTTATTGTT<br>F Y C> | 1560<br>453 |
| CAAAAAATAA<br>S K N N | TAAGATCTAA<br>K I * | TATCAATATT | 1590<br>459 |
| TACGTAAATG | GATTATATAA | TGTTATATTC | 1620 |
| GTGTTATTAT | GATTTATAAG | TTCATCAAAT | 1650 |
| TTAAAAATTT | GTATAGTATT | AAGATTTTTA | 1680 |
| ATAGGGGTAT | CGTTTAATAT<br>M | GGCTCAGTTA<br>A Q L | 1710<br>4 |
| GTTTTAACTG<br>V L T D | ATATTCCCCT<br>I P L | CGAAGATGTG<br>E D V | 1740<br>14 |
| GAAAATAAAA<br>E N K N | ATACTTCATC<br>T S S | CGACGAAGAA<br>D E E | 1770<br>24 |
| ACAACTAACT<br>T T N L | TAAACCAGAA<br>N Q K | AAAATCAACA<br>K S T | 1800<br>34 |
| TGTCAATGTT<br>C Q C L | TATGTGTTAC<br>C V T | CCTTGGATTT<br>L G F | 1830<br>44 |
| TTTGCAGCTG<br>F A A G | GAATTTATT<br>I L L | AACCATAGCT<br>T I A | 1860<br>54 |

FIG. 4E

| | | | |
|---|---|---|---|
| GCAATAATTT | TTACTTTTAT | TTTTACAGTA | 1890 |
| A I I F | T F I | F T V | 64 |
| CCATTAGAAA | TGCTTGGATC | TATTAATTGT | 1920 |
| P L E M | L G S | I N C | 74 |
| CCTCCATCTA | CATTTGGTAT | TGATAATGTT | 1950 |
| P P S T | F G I | D N V | 84 |
| TGTATCGAAC | CAATAAAAAA | ATCTATTAAT | 1980 |
| C I E P | I K K | S I N | 94 |
| TCTTATTCAG | AATTATCTAA | AATATGTTAT | 2010 |
| S Y S E | L S K | I C Y | 104 |
| GATAGATTGT | CAAATCCGAT | AAATCAGAGT | 2040 |
| D R L S | N P I | N Q S | 114 |
| ACTATTAACT | CCTTATTAAC | TGTTTTAAAT | 2070 |
| T I N S | L L T | V L N | 124 |
| ATGTTTGCAG | ATAAAACTA | TGAAAATGTT | 2100 |
| M F A D | K N Y | E N V | 134 |
| TATAATTGTA | ATACAATGAG | TGAAAAAACA | 2130 |
| Y N C N | T M S | E K T | 144 |
| TGTAATTCAT | CAATAGCTAT | TTGTCAAACT | 2160 |
| C N S S | I A I | C Q T | 154 |
| AATCATCCAC | TAAGTTCATT | GGGAAATTTT | 2190 |
| N H P L | S S L | G N F | 164 |
| GTTATTAAAA | TTAGAAAAAT | TTTTGGGTTT | 2220 |
| V I K I | R K I | F G F | 174 |
| AAATAATAAA | TAAAATAAAT | AAACATTACT | 2250 |
| K * | | | 175 |
| TTTTGTTTTT | GTCTTTATTA | AACAGTTGTA | 2280 |

FIG. 6

| FIG. 6A |
|---|
| FIG. 6B |
| FIG. 6C |
| FIG. 6D |

FIG. 6A

```
CHV   MS-FK---NFYLIYVIIIFI--------------------------NSIITSASTSKPSTPTIIPTSANES----
FHV   MRRYRMGRGIYLLYICLLYTYLQFGTSSTTAVSIENSDNSTAEMLSSTSMSATTPISQPTSPFTTPTRRSTNIATS
EHV1  MWLPNLVRFVAVAYLICAGAILTYASG----------------------ASASSSQSTPATPTHTTPNLTTAHG
HSV1  MAPGRVGLAVVLWSLL----WLGAGVSGGSETASTGPTITAGAVTNASEAPTSGSPGSAASPEVTPTSTPNPNNVT
      *          . .                                       . . .    .  ..*

--------PASIDTTITKP----------------ISTEANNLKSVSTSIKPPKNLKKKL----LKSK C R-DNV
      SSTTQASQPTSTLTTLTRSSTTIATSPSTTQAATFIGSSTDSNTTLLKTTKKPKRKKNKNNGARFKLD C GYKGV
      AGSDNTTNANGTESTHSHETT---------------------------------------------IT C T-KSL
      QNKTTPTEPASPPTT-PKPTSTPKSPPTSTP-----DPKPKNNTTPAKSGRPTK--------PPGPVW C DRRDP
              . .  .*                                  .                   *
```

FIG. 6B

```
                          100
IYRPYFSQLEIN-C TITKKQNLSNPL-IELWFKELSTYNKTN-E-NVESLKTDI-SK-NILLFSTKNNSDNFYN-
IYRPYFSPLQLN-C TLPTEPHITNPIDFEIWFKPRTRFGDFL-G-DKEDFVGNH-TRTSILLFSSRNGSVNSMDL
ISVPYYKSVDMN-C TTSVGVNYSE-YRLEIYLNQRTPFSGTPPG-DEENYINHNATKDQTLLLFSTAERKKSRRG
LAR-YGSRVQIR-C RFRNSTRME--FRLQIWRYSMGPSPPIAPAPDLEEVLTNITAPPGGLLVY---DSAPNLTD
 .  :.  *  .    *   :. .    :   : .:    .              *:     **       .
                                              200
-DFLLGI-QNQPVNYKLYGSQFYDNGN--ILLNIKSVDFKTSGIYTWKLYNSN---NESIFETFKIQVYAYHSPNV
GDATLGILQSRIPDYTLYNIPIQHTEA--MSLGIKSVESATSGVYTWRVYGGDG-LNKTVLGQVNSVVAYHPPSV
GQ--LGVIPDRLPKRQLFNLPLHTEGGTKFPLTIKSVDWRTAGIYVWSLYAKNG---TLVNSTSVTVSTYNAPLL
PHVLWAEGAGPGADPPLYSV---TGPLPTQRLIIGEVTPATQGMY----YLAWGRMDSPHEYGTWVRVRMFRPPSL
  .  *  .     *.   .     * *  :  *..  * .   *      *         .*  *    * *
```

FIG. 6C

```
NLKSNPSLYNE NYSAI  C  TIANYFPLESTEIFWFNDGQPID-KKYIDETYSVWIDGLITRTSILSLPFSEAMESP
NLTPRASLF NKT FEAV  C  AVANYFP-RSTKLTWYLDGKPIE-RQYISDTASVWIDGLITRSSVLAIPTTETDSEK
DLSVHPSLKGENYRAT   C  VVASYFPHSSVKLRWYKNAREVDFTKYVT NAS SVWVDGLITRISTVSIPVDPEEEYT
TLQPHAVMEGQPFKAT   C  TAAAYYPRNPVEFVWFEDDHQVFNPGQIDTQTHEHPDGFTTVSTVTSEAVGGQVP-P
  *                *   *   *   **       *    . *   .  **.*   .*. . .  .  .

300
PNLR C  NVEWYKNSKASKKFSNTVIPKVYYKPFISIKFDNGLAI  C  DAK  C  VSRENNKLQWLVKDI---PIN
PDIR C  DLEWHESPVSYKRFTKSVAPDVYYPPTVSVTFADTRAI  C  DVK  C  VPRDGISLMWKIGNYHLPKAMS
PSLR C  SIDWYRDEVSFARIAKAGTPSVFVAPTVSVSVEDGDAV  C  TAK  C  VPSTGVFVSWSVND-HLP-GVP
RTFT C  QMTWHRDSVTFSRR NAT GLALVLPRPTITMEFGVRIVV  C  TAG  C  VP-EGVTFAWFLGDDPSPAAKS
     *     *       *     .     *   *  *      *   *    *    *   .  *
```

FIG. 6D

```
GDDIISGP C LNHPGLVNIQNKIDISDYDEPVTYK C SIIGYPIIFPNFYDEKVFDASD-ENVSKSMLISITTI
ADILITGP C IERPGLVNIQSMCDISETDGPVSYT C QTIGYPPILPGFYDTQVYDASP-EIVSESMLVSVVAV
SQDMTTGV C PSHSGLVNMQSRRPLSEENGEREYS C IIEGYPDGLPMFSDTVVYDASP-IVEDRPVLTSIIAV
A-VTAQES C -DHPGLATVRSTLPIS--YDYSEYI C RLTGYPAGIPVLEHHGSHQPPPRDPTERQVIEAIEWV
         *   ∴**∴ ∴ ∴   ∴    *  ∴    *   ∴∴***       ∴    ∴   ∴    ∴∴    ∴

IGGAIFVIVLIFITALCFYCSKNNK------I
ILGAVLITVFIFITALCLYYSHPRR------L
TCGAAALALVVLITAVCFYCSKPSQAPYKKSDF
GIGIGVLAAGVLVVTAIVYYVVRTSQSR-QRHRR
 *∴        ∴       *  ∴
```

| | | | |
|---|---|---|---|
| GATATTTAAT | AAAACTATTA | TGAAACTTCT | 30 |
| TATAACTTAT | TTGTTTTTAT | TAAATGGGTT | 60 |
| GGGTTGGTTT | TAAAATTACA | TACGTGTATT | 90 |
| AAGAATTAAC | ATCATAAAGG | ACACACCCAT | 120 |
| GAAAACATT | TAAATTCTAT | TAATTTGAAC | 150 |
| GGATTAAACA | TTTTCTCATT | TTAAGAGTTG | 180 |
| CTACGACTTT | TGATAGTAAA | ATGATTAAAC<br>M  I  K> | 210<br>03 |
| TTCTATTTAT<br>L  L  F  I | CTTATTTTAT<br>L  F  Y | TTTAACCCAA<br>F  N  P> | 240<br>13 |
| TAACTGGATA<br>I  T  G  Y | TAAATGGTA<br>K  W  V | GACCCTCCTC<br>D  P  P> | 270<br>23 |
| GTAGGTATAA<br>R  R  Y  N | TTACACCGTT<br>Y  T  V | TTAAGAATGA<br>L  R  M> | 300<br>33 |
| TTCCAGATAT<br>I  P  D  I | TCCAAATCCA<br>P  N  P | ATGGATCCTT<br>M  D  P> | 330<br>43 |
| CTAAAAACGC<br>S  K  N  A | TGAAGTTCGG<br>E  V  R | TATGTAACTT<br>Y  V  T> | 360<br>53 |
| CTACTGACCC<br>S  T  D  P | ATGTGATATG<br>C  D  M | GTTGCTTTGA<br>V  A  L> | 390<br>63 |
| TTTCTAATCC<br>I  S  N  P | AAATATAGAA<br>N  I  E | TCTACAATTA<br>S  T  I> | 420<br>73 |
| AAACGATTCA<br>K  T  I  Q | ATTTGTGCAA<br>F  V  Q | AAGAAAAAAT<br>K  K  K> | 450<br>83 |
| TTTACAATGC<br>F  Y  N  A | ATCTCTTAGT<br>S  L  S | TGGTTTAAAG<br>W  F  K> | 480<br>93 |
| TTGGAGATGA<br>V  G  D  D | TTGTACATAT<br>C  T  Y | CCAATATATT<br>P  I  Y> | 510<br>103 |

FIG. 7B

| | | | |
|---|---|---|---|
| TAATTCAATA | TTTTGATTGT | GATCCTCAAA | 540 |
| L I Q Y | F D C | D P Q> | 113 |
| GAGAATTTGG | CATATGTTTA | AAAAGATCTC | 570 |
| R E F G | I C L | K R S> | 123 |
| CAGATTTTTG | GAAACCATCG | TTAGTTGGTT | 600 |
| P D F W | K P S | L V G> | 133 |
| ACACATTTTT | AACTGATGAT | GAATTGGGAT | 630 |
| Y T F L | T D D | E L G> | 143 |
| TAGTTTTAGC | TGCCCCCGCT | CCATTTAATC | 660 |
| L V L A | A P A | P F N> | 153 |
| AAGGTCAATA | TAGACGGGTT | ATTCAAATTG | 690 |
| Q G Q Y | R R V | I Q I> | 163 |
| AAAATGAAGT | TTTTTATACT | GATTTATGG | 720 |
| E N E V | F Y T | D F M> | 173 |
| TTCAATTACC | ACGAGAAACT | TGTTATTTTT | 750 |
| V Q L P | R E T | C Y F> | 183 |
| CTAAAGAAGA | TAAATTTGAA | CCAACTTTTA | 780 |
| S K E D | K F E | P T F> | 193 |
| TGGAATGGTG | TAAGGAATCT | AGATCTGTAG | 810 |
| M E W C | K E S | R S V> | 203 |
| GAGCATCAAA | AGTTGACGAT | GAACTTTTT | 840 |
| G A S K | V D D | E L F> | 213 |
| ATCTAAATAG | AGCTGGTCCC | CAAACCCTGC | 870 |
| Y L N R | A G P | Q T L> | 223 |
| TTAAATATTA | TGTTATTAAA | GATTTTATA | 900 |
| L K Y Y | V I K | D F Y> | 233 |
| GACTTAACGG | TAGAGAACCT | CCAATAAAAT | 930 |
| R L N G | R E P | P I K> | 243 |
| TTAAAGAAGC | TCTTAGATAC | GATATACCAT | 960 |
| F K E A | L R Y | D I P> | 253 |

FIG. 7C

| | | | |
|---|---|---|---|
| ATAAAGTGAA | TGATAAATTT | GATGATGAAT | 990 |
| Y  K  V  N | D  K  F | D  D  E> | 263 |
| TACCATCGAG | GCCACATATT | AGTAATACTA | 1020 |
| L  P  S  R | P  H  I | S  N  T> | 273 |
| TTAATAAAAC | TATTAAAGAA | ATTGTAAATC | 1050 |
| I  N  K  T | I  K  E | I  V  N> | 283 |
| TTGAAGATTA | TTTTAAAAAT | ACAAATGTTA | 1080 |
| L  E  D  Y | F  K  N | T  N  V> | 293 |
| TAGATACTAC | TACCCCAACA | CCAATAAATA | 1090 |
| I  D  T  T | T  P  T | P  I  N> | 303 |
| ATACCCCAAA | AAATATAACC | GTGGGAATTG | 1140 |
| N  T  P  K | N  I  T | V  G  I> | 313 |
| TTATAATTAT | ATTAATAATA | CTATTTATAA | 1170 |
| V  I  I  I | L  I  I | L  F  I> | 323 |
| TTGGATTTTT | TGTTTATAAA | AGACAAAAAA | 1200 |
| I  G  F  F | V  Y  K | R  Q  K> | 333 |
| TATATAATAA | TTATAAAAAA | TTAACAACAA | 1230 |
| I  Y  N  N | Y  K  K | L  T  T> | 343 |
| ATGTTTAGCC | TTTATAAATT | AATTTACAGA | 1260 |
| N  V  * | | | 345 |
| ATAAACAACT | GGGCGGTCTT | TTGTTTAATA | 1290 |
| AAAATTCATG | TACCTACAAC | TTTTATTCAC | 1320 |

```
CHV   MI-KLLF------------------------------------------------------ILF-----------YF-----
FHV   MMTRLHF------------------------WW--C----------------------------------------YLVCTS
EH'/1 MPAVLLVLYVNPPPSVCILTQKLSLGLYNQWWRVCRSVPPPWYVFFNKRSMSTFKLMMDGRLVFAMAIAILSVVLSCGT
HSV1  MGGA---------------------------------ILF------VVIVGLHGVRGKYALADASLKM---AD
            ------AARLGAV---
       *

-----NPITGYK--WVDPPRRYNYTVLRMIPDIPNPM----DPSKNAEVRYYTSTDP  C  DMVALISNPNIESTIKTI
      SLTTPKTTTVYVKGFNIPPLRYNYTQARIVPKIPQAM----DPKITAEVRYVTSMDS  C  GMVALISEPDIDATIRTI
      CEKAKRAVRGRQDRPKEFPPPRYNYTILTRYNATALASPFINDQVKNVDLRIVTATRP C  EMIALIAKTNIDSILKEL
      PNRFRGKDLPVLDQLTDPPGVRRVYHI----QAGLPNPF--QPPSLPITVYRRVERA  C  RSVLLNAPSEAPQIVRGA
              *. *  *                   . *.*                 *    ..:.*
```

FIG. 9B

```
QFVQKKFYNASLSWFKVGDD C TYPIYLIQYFD C DPQREFGI C LKRSPDFWKPSLVGYTFLTDDELGLVLAAP
QLSQKKT-YNATISWFKVTQG C EYPMFLMDMRL C DPKREFGI C ALRSPSYWLEPLTKYMFLTDDELGLIMMAP
AAAQKT--YSARLTWFKIMPT C ATPIHDVSYMK C NPKLSFAM C DERSDILWQASLITMAAETDDELGLVLAAP
SEDVRKQPYNLTIAWFRMGGN C AIPITVMEYTE C SYNKSLGA C PIRTQPRWN-YDSFSAVSEDNLGFLMHAP
 .: .*        *             *              *         *             .. .** .. **

200
APFNQGQYRRVIQIENEVFYTDFMVQL-PRET C YFSKEDKFEPTFMEW C KESRSVGASKVDDELFYLNRAGPQT
AQFNQGQYRRVITIDGSMFYTDFMVQL-SPTP C WFAKPDRYEEILHEW C RNVKTIGLDGARDYHYYWPYNPQP
AHSASGLYRRVIEIDGRRIYTDFSVTI-PSER C PIAFELNFGN--PDR C KTPEQYSRGEVFTRRFLGEFNFPQG
AFETAGTYLRLVKINDWTEITQFILEHRAKGS C KYTLPLRIPPSA--- C LSPQAYQQGVTVDSIGMLPRFIPEN
*     .* *  .    .   .* .        *                *                         *.
```

FIG. 9C

```
LKYYVIKDFYRLNGREPPIKFKEALRYDIPYKVNDK--FDDELPSRPHISNTINKTIKE-------IVNLEDYFKNT
HKA-VLLYWYRTHGREPPVRFQEAIRYDRPAIPSGS----EDSKRSNDSRG-ESSGPN-------WIDIENYTPKN
HMTWV-KFWFVYDGGNLPVQFYEAQAFARPVPPDNHPGFDSVESEITQNKTDPKPGQADPKPNQPFKWPSIKHLVPRL
QRT--VAVYSLKIAGWHGPRAPYTSTLLPPELPETPNATQPELAPEDPEDSALLEDPVGTVAPQIPPNWH--------
                *                       *
                                        *
            300
NVIDTTTPTPINNNTPKN-------ITVGIVIIILIILFIIG--FFVYK-RQKIYNNYKKL-----TTNV--------
NVPIIISDDDVPTAPPKGMNNQSVVIPAIVLSCLIIALILGVIYYILRVKRSRSTAYQQLPIHTTHHP---------
DEVDEVI-EPVTKPPKTSKSNSIFVGISVGLGIAGLVLVGVILYVCLRRKKELKVCTERLD--SPTLDL--------
--IPSIQDAATPYHPPATPNNMGLIAGAVGGSLLAALVICGIVYW-MRRRTRKAPKRIRLPHIREDDQPSSHQPLFY
    *                                                         *
```

```
   1    TGAATGTTAA    ATGTTATACT    TTGGATGAAG
  31    CTATAAATAT    GCATTGGAAA    AATAATCCAT
  61    TTAAAGAAAG    GATTCAAATA    CTACAAAACC
  91    TAAGCGATAA    TATGTTAACT    AAGCTTATTC
 121    TTAACGACGC    TTTAAATATA    CACAAATAAA
 151    CATAATTTTT    GTATAACCTA    ACAAATAACT
 181    AAAACATAAA    AATAATAAAA    GGAAATGTAA
 211    TATCGTAATT    ATTTTACTCA    GGAATGGGGT
 241    TAAATATTTA    TATCACGTGT    ATATCTATAC
 271    TGTTATCGTA    TACACTTTAC    AATTACTATT
 301    ACGAATATGC    AAGAGATAAT    AAGATTACGT
 331    ATTTAAGAGA    ATCTTGTCAT    GATAATTGGG
 361    TACGACATAG    TGATAAATGC    TATTTCGCAT
 391    CGTTACATAA    AGTCAGTTGG    AAAGATGGAT
 421    TTGACAGATG    TAACTTAATA    GGTGCAAAAA
 451    TGTTAAATAA    CAGCATTCTA    TCGGAAGATA
 481    GGATACCAGT    TATATTATAC    AAAAATCACT
 511    GGTTGGATAA    AACAGATTCT    GCAATATTCG
 541    TAAAGATGA     AGATTACTGC    GAATTTGTAA
 571    ACTATGACAA    TAAAAAGCCA    TTTATCTCAA
 601    CGACATCGTG    TAATTCTTCC    ATGTTTTATG
 631    TATGTGTTTC    AGATATTATG    AGATTACTAT
 661    AAACTTTTG     TATACTTATA    TTCCGTAAAC
 691    TATATTAATC    ATGAAGAAAA    TGAAAAAGTA
 721    TAGAAGCTGT    TCACGAGCGG    TTGTTGAAAA
 751    CAACAAAATT    ATACATTCAA    GATGGCTTAC
 781    ATATACGTCT    GTGAGGCTAT    CATGGATAAT
 811    GACAATGCAT    CTCTAAATAG    GTTTTTGGAC
 841    AATGGATTCG    ACCCTAACAC    GGAATATGGT
 871    ACTCTACAAT    CTCCTCTTGA    AATGGCTGTA
 901    ATGTTCAAGA    ATACCGAGGC    TATAAAAATC
 931    TTGATGAGGT    ATGGAGCTAA    ACCTGTAGTT
 961    ACTGAATGCA    CAACTTCTTG    TCTGCATGAT
 991    GCGGTGTTGA    GAGACGACTA    CAAAATAGTG
1021    AAAGATCTGT    TGAAGAATAA    CTATGTAAAC
1051    AATGTTCTTT    ACAGCGGAGG    CTTTACTCCT
1081    TTGTGTTTGG    CAGCTTACCT    TAACAAAGTT
1111    AATTTGGTTA    AACTTCTATT    GGCTCATTCG
1141    GCGGATGTAG    ATATTTCAAA    CACGGATCGG
1171    TTAACTCCTC    TACATATAGC    CGTATCAAAT
1201    AAAAATTTAA    CAATGGTTAA    ACTTCTATTG
1231    AACAAGGTG     CTGATACTGA    CTTGCTGGAT
1261    AACATGGAC     GTACTCCTTT    AATGATCGCT
1291    GTACAATCTG    GAAATATTGA    AATATGTAGC
```

FIG. 17B

```
1321    ACACTACTTA    AAAAAATAA     AATGTCCAGA
1351    ACTGGGAAAA    ATTGATCTTG    CCAGCTGTAA
1381    TTCATGGTAG    AAAAGAAGTG    CTCAGGCTAC
1411    TTTTCAACAA    AGGAGCAGAT    GTAAACTACA
1441    TCTTTGAAAG    AAATGGAAAA    TCATATACTG
1471    TTTTGGAATT    GATTAAAGAA    AGTTACTCTG
1501    AGACACAAAA    GAGGTAGCTG    AAGTGGTACT
1531    CTCAAAATGC    AGAACGATGA    CTGCGAAGCA
1561    AGAAGTAGAG    AAATAACACT    TTATGACTTT
1591    CTTAGTTGTA    GAAAGATAG     AGATATAATG
1621    ATGGTCATAA    ATAACTCTGA    TATTGCAAGT
1651    AAATGCAATA    ATAAGTTAGA    TTTATTTAAA
1681    AGGATAGTTA    AAAATAGAAA    AAAAGAGTTA
1711    ATTTGTAGGG    TTAAAATAAT    ACATAAGATC
1741    TTAAAATTTA    TAAATACGCA    TAATAATAAA
1771    AATAGATTAT    ACTTATTACC    TTCAGAGATA
1801    AAATTTAAGA    TATTTACTTA    TTTAACTTAT
1831    AAAGATCTAA    AATGCATAAT    TTCTAAATAA
1861    TGAAAAAAAA    GTACATCATG    AGCAACGCGT
1891    TAGTATATTT    TACAATGGAG    ATTAACGCTC
1921    TATACCGTTC    TATGTTTATT    GATTCAGATG
1951    ATGTTTAGA     AAAGAAAGTT    ATTGAATATG
1981    AAAACTTTAA    TGAAGATGAA    GATGACGACG
2211    ATGATTATTG    TTGTAAATCT    GTTTTAGATG
2041    AAGAAGATGA    CGCGCTAAAG    TATACTATGG
2071    TTACAAAGTA    TAAGTCTATA    CTACTAATGG
2101    CGACTTGTGC    AAGAAGGTAT    AGTATAGTGA
2131    AAATGTTGTT    AGATTATGAT    TATGAAAAAC
2161    CAAATAAATC    AGATCCATAT    CTAAAGGTAT
2191    CTCCTTTGCA    CATAATTTCA    TCTATTCCTA
2221    GTTTAGAATA    CTTTTCATTA    TATTTGTTTA
2251    CAGCTGAAGA    CGAAAAAAAT    ATATCGATAA
2281    TAGAAGATTA    TGTTAACTCT    GCTAATAAGA
2311    TGAAATTGAA    TGAGTCTGTG    ATAATAGCTA
2341    TAATCAGAGA    AGTTCTAAAA    GGAAATAAAA
2371    ATCTAACTGA    TCAGGATATA    AAAACATTGG
2401    CTGATGAAAT    CAACAAGGAG    GAACTGAATA
2431    TAGCTAAACT    ATTGTTAGAT    AGAGGGGCCA
2461    AAGTAAATTA    CAAGGATGTT    TACGGTTCTT
2491    CAGCTCTCCA    TAGAGCTGCT    ATTGGTAGGA
2521    AACAGGATAT    GATAAAGCTG    TTAATCGATC
2551    ATGGAGCTGA    TGTAAACTCT    TTAACTATTG
2581    CTAAAGATAA    TCTTATTAAA    AAAAAATAAT
2611    ATCACGTTTA    GTAATATTAA    AATATATTAA
```

FIG. 17C

```
2641    TAACTCTATT    ACTAATAACT    CCAGTGGATA
2671    TGAACATAAT    ACGAAGTTTA    TACATTCTCA
2701    TCAAAATCTT    ATTGACATCA    AGTTAGATTG
2731    TGAAAATGAG    ATTATGAAAT    TAAGGAATAC
2761    AAAAATAGGA    TGTAAGAACT    TACTAGAATG
2791    TTTTATCAAT    AATGATATGA    ATACAGTATC
2821    TAGGGCTATA    AACAATGAAA    CGATTAAAAA
2851    TTATAAAAAT    CATTTCCCTA    TATATAATAC
2881    GCTCATAGAA    AAATTCATTT    CTGAAAGTAT
2911    ACTAAGACAC    GAATTATTGG    ATGGAGTTAT
2941    AAATTCTTTT    CAAGGATTCA    ATAATAAATT
2971    GCCTTACGAG    ATTCAGTACA    TTATACTGGA
3001    GAATCTTAAT    AACCATGAAC    TAAAAAAAAT
3031    TTTAGATAAT    ATACATTAAA    AAGGTAAATA
3061    GATCATCTGT    TATTATAAGC    AAAGATGCTT
3091    GTTGCCAATA    ATATACAACA    GGTATTTGTT
3121    TTTATTTTA     ACTACATATT    TGATGTTCAT
3151    TCTCTTTATA    TAGTATACAC    AGAAAATTCA
3181    TAATCCACTT    AGAATTTCTA    GTTATCTAG
```

|      |            |            |            |
|------|------------|------------|------------|
| 1    | GATATCTGTG | GTCTATATAT | ACTACACCCT |
| 31   | ACCGATATTA | ACCAACGAGT | TTCTCACAAG |
| 61   | AAAACTTGTT | TAGTAGATAG | AGATTCTTTG |
| 91   | ATTGTGTTTA | AAAGAAGTAC | CAGTAAAAAG |
| 121  | TGTGGCATAT | GCATAGAAGA | AATAAACAAA |
| 151  | AAACATATTT | CCGAACAGTA | TTTTGGAATT |
| 181  | CTCCCAAGTT | GTAAACATAT | TTTTTGCCTA |
| 211  | TCATGTATAA | GACGTTGGGC | AGATACTACC |
| 241  | AGAAATACAG | ATACTGAAAA | TACGTGTCCT |
| 271  | GAATGTAGAA | TAGTTTTTCC | TTTCATAATA |
| 301  | CCCAGTAGGT | ATTGGATAGA | TAATAAATAT |
| 331  | GATAAAAAAA | TATTATATAA | TAGATATAAG |
| 361  | AAAATGATTT | TTACAAAAAT | ACCTATAAGA |
| 391  | ACAATAAAAA | TATAATTACA | TTTACGGAAA |
| 421  | ATAGCTGGTT | TTAGTTTACC | AACTTAGAGT |
| 451  | AATTATCATA | TTGAATCTAT | ATTGTTTTTT |
| 481  | AGTTATATAA | AAACATGATT | AGCCCCCAAT |
| 511  | CGGATGAAAA | TATAAAGAT  | GTTGAGAATT |
| 541  | TCGAATACAA | CAAAAGAGG  | AATCGTACGT |
| 571  | TGTCCATATC | CAAACATATA | AATAAAAATT |
| 601  | CAAAAGTAGT | ATTATACTGG | ATGTTTAGAG |
| 631  | ATCAACGTGT | ACAAGATAAT | TGGGCTTTAA |
| 661  | TTTACGCACA | ACGATTAGCG | TTAAAACTCA |
| 691  | AAATACCTCT | AAGAATATGC | TTTTGTGTCG |
| 721  | TGCCAAAATT | TCACACTACT | ACTTCTAGAC |
| 751  | ACTTTATGTT | TTTAATATCC | GGTCTTAAAG |
| 781  | AAGTCGCGGA | AGAATGTAAA | AGACTATGTA |
| 811  | TAGGGTTTTC | ATTGATATAT | GGCGTACCAA |
| 841  | AAGTAATAAT | TCCGTGTATA | GTAAAAAAT  |
| 871  | ACAGAGTCGG | AGTAATCATA | ACGGATTTCT |
| 901  | TTCCATTACG | TGTTCCCGAA | AGATTAATGA |
| 931  | AACAGACTGT | AATATCTCTT | CCAGATAACA |
| 961  | TACCTTTTAT | ACAAGTAGAC | GCTCATAATA |
| 991  | TAGTACCTTG | TTGGGAAGCT | TCTGATAAAG |
| 1021 | AAGAATACGG | TGCACGAACT | TTAAGAAAAA |
| 1051 | AGATATTTGA | TAAATTATAT | GAATATATGA |
| 1081 | CAGAATTTCC | TGTTGTTCGT | AAACATCCAT |
| 1111 | ACGGTCCATT | TTCTATATCT | ATTGCAAAAC |
| 1141 | CCAAAAATAT | ATCATTAGAC | AAGACGGTAT |
| 1171 | TACCCGTAAA | ATGGGCAACG | CCTGGAACAA |
| 1201 | AAGCTGGAAT | AATTGTTTTA | AAAGAATTTA |
| 1231 | TAAAAACAG  | ATTACCGTCA | TACGACGCGG |
| 1261 | ATCATAACAA | TCCTACGTGT | GACGCTTTGA |
| 1291 | GTAACTTATC | TCCGTGGCTA | CATTTGGTC  |

FIG. 20B

```
1321   ATGTATCCGC   ACAACGTGTT   GCCTTAGAAG
1351   TATTAAATG    TATACGAGAA   AGCAAAAAAA
1381   ACGTTGAAAC   GTTTATAGAT   GAAATAATTG
1411   TAAGAAGAGA   ACTATCGGAT   AATTTTTGTT
1441   ACTATAACAA   ACATTATGAT   AGTATCCAGT
1471   CTACTCATTC   ATGGGTTAGA   AAAACATTAG
1501   AAGATCACAT   TAATGATCCT   AGAAAGTATA
1531   TATATTCCAT   TAAACAACTC   GAAAAGCGG
1561   AAACTCATGA   TCCTCTATGG   AACGCGTCAC
1591   AAATGCAGAT   GGTGAGAGAA   GGAAAAATGC
1621   ATAGTTTTT    ACGAATGTAT   TGGGCTAAGA
1651   AGATACTTGA   ATGGACTAGA   ACACCTGAAG
1681   ACGCTTTGAG   TTATAGTATC   TATTTGAACA
1711   ACAAGTACGA   ACTAGACGGC   ACGGATCCTA
1741   ACGGATACGT   AGGTTGTATG   TGGTCTATTT
1771   GCGGATTACA   CGATAGAGCG   TGGAAAGCAA
1801   GACCGATATT   TGGAAAGATA   AGATATATGA
1831   ATTATGAGAG   TTCTAAGAAG   AAATTTGATG
1861   TTGCTGTATT   TATACAGAAA   TACAATTAAG
1891   ATAAATAATA   TACAGCATTG   TAACCATCGT
1921   CATCCGTTAT   ACGGGAATA    ATATTACCAT
1951   ACAGTATTAT   TAAATTTTCT   TACGAAGAAT
1981   ATAGATCGGT   ATTTATCGTT   AGTTTATTTT
2011   ACATTTATTA   ATTAAACATG   TCTACTATTA
2041   CCTGTTATGG   AAATGACAAA   TTTAGTTATA
2071   TAATTTATGA   TAAAATTAAG   ATAATAATAA
2101   TGAAATCAAA   TAATTATGTA   AATGCTACTA
2141   GATTATGTGA   ATTACGAGGA   AGAAAGTTTA
2161   CGAACTGGAA   AAAATTAAGT   GAATCTAAAA
2191   TATTAGTCGA   TAATGTAAAA   AAAATAAATG
2221   ATAAAACTAA   CCAGTTAAAA   ACGGATATGA
2251   TTATATACGT   TAAGGATATT   GATCATAAAG
2281   GAAGAGATAC   TTGCGGTTAC   TATGTACACC
2311   AAGATCTGGT   ATCTTCTATA   TCAAATTGGA
2341   TATCTCCGTT   ATTCGCCGTT   AAGGTAAATA
2371   AAATTATTAA   CTATTATATA   TGTAATGAAT
2401   ATGATATACG   ACTTAGCGAA   ATGGAATCTG
2431   ATATGACAGA   AGTAATAGAT   GTAGTTGATA
2461   AATTAGTAGG   AGGATACAAT   GATGAAATAG
2491   CAGAAATAAT   ATATTTGTTT   AATAAATTTA
2521   TAGAAAATA    TATTGCTAAC   ATATCGTTAT
2551   CAACTGAATT   ATCTAGTATA   TTAAATAATT
2581   TTATAAATTT   TATAAATTTT   AATAAAAAAT
2611   ACAATAACGA   CATAAAGATA   TTTAATCTTT
```

FIG. 20C

| | | | |
|---|---|---|---|
| 2641 | AATTCTTGAT | CTGAAAAACA | CATCTATAAA |
| 2671 | ACTAGATAAA | AAGTTATTCG | ATAAAGATAA |
| 2701 | TAATGAATCG | AACGATGAAA | AATTGGAAAC |
| 2731 | AGAAGTTGAT | AAGCTAATTT | TTTTCATCTA |
| 2761 | AATAGTATTA | TTTTATTGAA | GTACGAAGTT |
| 2791 | TTACGTTAGA | TAAATAATAA | AGGTCGATTT |
| 2821 | TTACTTTGTT | AAATATCAAA | TATGTCATTA |
| 2851 | TCTGATAAAG | ATACAAAAC | ACACGGTGAT |
| 2881 | TATCAACCAT | CTAACGAACA | GATATTACAA |
| 2911 | AAAATACGTC | GGACTATGGA | AAACGAAGCT |
| 2941 | GATAGCCTCA | ATAGAAGAAG | CATTAAAGAA |
| 2971 | ATTGTTGTAG | ATGTTATGAA | GAATTGGGAT |
| 3001 | CATCCTCAAC | GAAGAAATAG | ATAAAGTTCT |
| 3031 | AAACTGGAAA | AATGATACAT | TAAACGATTT |
| 3061 | AGATCATCTA | AATACAGATG | ATAATATTAA |
| 3091 | GGAAATCATA | CAATGTCTGA | TTAGAGAATT |
| 3121 | TGCGTTTAAA | AAGATCAATT | CTATTATGTA |
| 3151 | TAGTTATGCT | ATGGTAAAAC | TCAATTCAGA |
| 3181 | TAACGAACAT | TGAAAGATAA | AATTAAGGAT |
| 3211 | TATTTTATAG | AAACTATTCT | TAAAGACAAA |
| 3241 | CGTGGTTATA | AACAAAAGCC | ATTACCCGGA |
| 3271 | TTGGAAACTA | AAATACTAGA | TAGTATTATA |
| 3301 | AGATTTTAAA | AACATAAAAT | TAATAGGTTT |
| 3331 | TTATAGATTG | ACTTATTATA | TACAATATGG |
| 3361 | ATAAAGATA | TATATCAACT | AGAAAGTTGA |
| 3391 | ATGACGGATT | CTTAATTTTA | TATTATGATT |
| 3421 | CAATAGAAAT | TATTGTCATG | TCGTGTAATC |
| 2451 | ATTTTATAAA | TATATCAGCG | TTACTAGCTA |
| 3481 | AGAAAAACAA | GGACTTTAAT | GAATGGCTAA |
| 3501 | AGATAGAATC | ATTTAGAGAA | ATAATAGATA |
| 3541 | CTTTAGATAA | AATTAATTAC | GATCTAGGAC |
| 3571 | AACGATATTG | TGAAGAACTT | ACGGCGCATC |
| 3601 | ACATTCCAGT | GTAATTATTG | AGGTCAAAGC |
| 3631 | TAGTAACTTA | ATAGATGACA | GGACAGCTG |

FIG. 21

| FIG. 21A |
|---|
| FIG. 21B |

FIG. 21A

| | | | |
|---|---|---|---|
| 1 | TGTCTGGACT | AACTGATTTC | ATGGAACAAT |
| 31 | TTTCATCAAA | AATATCAGTT | ATACCTAGTT |
| 61 | CTACAAAGAC | AGAACTTTGA | TGTTATGTTT |
| 91 | GTGTTTGTAT | AGAAAATTTT | GGGATACTAA |
| 121 | CTGATATTTC | TGAATATTTC | TGAATATTTC |
| 151 | ATGTTACTTA | CTTACTCCTA | TCTTAGACGA |
| 181 | TAATAAAATT | CGAGGCGTAA | TATGTTTTTC |
| 211 | CAAATATTTG | AAATTCTTAT | ACGTATCGGC |
| 241 | GAAGAAAAGT | AACATACTAT | AAGTGTTATG |
| 271 | CAAGTAAGGT | ATGTTAATGA | TATTGGATTT |
| 301 | AATTTCATTG | ACAATACATA | TGTCCAAACA |
| 331 | TTCCACTCGT | AATTATGTAC | GGAACGACTT |
| 361 | TAGTTAAATA | CTTAGTCACA | AAAAACTTAT |
| 391 | GACTGTCATT | ATCTGAAAAC | GGTGATTCCC |
| 421 | ATAAATCAGA | ATACTTAATA | TTAAATAGAA |
| 461 | TGCTCGCTTC | TGGAGGTTTC | CGGATACTAG |
| 481 | ATAACATATC | TTCTGTATTA | TAGTTTAATT |
| 511 | CACTCATTTT | ATTACATAAT | ACAGTAACAT |
| 541 | CTCCCGAAAC | CAATGATGTT | ATATTAGATT |
| 571 | TACTTACATA | CTTCTTGTAA | CTATCATGAA |
| 601 | TACGTTTGTT | ATGATCTATA | AAGAAGATGG |
| 631 | ATGTATATTC | TGTTCTAGAT | AGCAAGTTCT |
| 661 | TTAAGTTATT | CTTTGTCTGT | ATTACTATCA |
| 691 | TCGTCTTCAT | CATCGTCTAA | AGGTAGCATT |
| 721 | ATATAATAAA | TCTAATAGTT | GATTTCTCGA |
| 751 | TCTATCAGTA | CTCGCTTTCA | ATAACATTTT |
| 781 | TACTATAAGC | ATAATAGAAG | GCGGTGATAT |
| 811 | CACTATATTT | TTATCGGGTA | TTCTTTTAGT |
| 841 | AATTAGTTAG | TTCGTAGAAT | TTCGTAGAGA |
| 871 | TAAAAGCCAA | TTTGTTGTTG | ATACTGCTTA |
| 901 | CGTTACTCAT | GTTTCTTGTT | TCTGTTAATT |
| 931 | AACAGGTATA | CCCTTACAAT | AAGTTTAATT |
| 961 | AACTTTTAGG | TTTTTGTGAA | GAACTTTTAG |
| 991 | CTTCTAGTTC | CCTTATCCAT | AATTGGGTCT |
| 1021 | TAGATCTAGA | TTCTTCCCAT | GTATAAAGGG |
| 1051 | GGACATACCC | AAAATCTTTA | AATGCTTTGT |
| 1081 | CCGTTTCTAT | AGTAAATGTC | GTACATTCCT |
| 1111 | TAATCAAAGT | ATAAGGATTT | AGTAAAGGCG |
| 1141 | TGTAAGAACA | AATAGGTGAT | AGTAATACTC |
| 1171 | TTAAACCTTT | ATTAATATTA | GCGATAAACC |
| 1201 | TTAAACACCA | TAAAGGAAGA | CATGTATTCC |
| 1231 | GTAGATCCAT | CCCTAATTGA | TTAAAGAAAT |
| 1261 | GCATGTTAAA | ATCATGATAA | TGTTCAGTAG |
| 1291 | GAGAGGTATC | GTAACAGTAA | TACACCTTAT |

FIG. 21B

| | | | |
|---|---|---|---|
| 1321 | TGCAGAGAGG | ACTATGTTGA | CCATTTTCTA |
| 1351 | TCATATTTCT | TGCTGCTAAA | ATATGCATCC |
| 1381 | AAGCTACGTT | TCCTGCATAG | ACTCTGCTAT |
| 1411 | GAAATACTTT | ATCATCCGCA | TATTTATACA |
| 1441 | TTTTCCTGCT | TTTATACGAT | CTTCTGTATA |
| 1471 | AAGTTTCTAG | TACTGGACAG | TATTCTCCGA |
| 1501 | AAACACCTAA | TGGGCGTAGC | GACAAGTGCA |
| 1531 | TAATCTAAGT | CCTATATTAG | ACATAGTACC |
| 1561 | GTTAGCTTCT | AGTATATATT | TCTCAGATAA |
| 1591 | CTTGTTTACT | AAGAGGATAA | GCCTCTTTAT |
| 1621 | GGTTAGATTG | ATAATACGTA | TTCTCGTTTC |
| 1651 | CTCTTATCAT | CGCATCTCCG | GAGAAAGTTA |
| 1681 | GGACCTACCG | CAGAATAACT | ACTCGTATAT |
| 1711 | ACTAAGACTC | TTACGCCGTT | ATACAGACAA |
| 1741 | GAATCTACTA | CGTTCTTCGT | TCCGTTGATA |
| 1771 | TTAACGTCCA | TTATAGAGTC | GTTAGTAAAC |
| 1801 | TTACCCGCTA | CATCATTTAT | CGAAGCAATA |
| 1831 | TGAATGACCA | CATCTGCTGA | TCTAAGCGCT |
| 1861 | TCGTCCAAAG | TACTTTTATT | TCTAACATCT |
| 1891 | CCAATCACGG | GAACTATCTT | TATTATATTA |
| 1921 | CATTTTCTA | CAAGATCTAG | TAACCATTGG |
| 1951 | TCGATTCTAA | TATCGTAAAC | ACGAACTTCT |
| 1981 | TTTTAAAGAG | GATTCGAACA | AGATAAGATT |
| 2011 | ATTTATAATG | TGTCTACCTA | AAAATCCACA |
| 2041 | CCCTCCGGTT | ACCACGTATA | CTAGTGTACG |
| 2071 | CATTTGAGT | ATTAACTATA | TAAGACCAAA |
| 2101 | ATTATATTTT | CATTTCTGT | TATATTATAC |
| 2131 | TATATAATAA | AAACAAATAA | ATATACGAAT |
| 2161 | ATTATAAGAA | ATTTAGAACA | CGTTATTAAA |
| 2191 | GTATTGCCTT | TTTTATTAAC | GGCGTGTTCT |
| 2221 | TGTAATTGCC | GTTAGAATA | GTCTTTATTT |
| 2251 | ACTTTAGATA | ACTCTTCTAT | CATAACCGTC |
| 2281 | TCCTTATTCC | AATCTTCTTC | AGAAGTACAT |
| 2311 | GAGTACTTAC | CGAAGTTTAT | CATCATAGAG |
| 2341 | ATTATATATG | AAGAAA | |

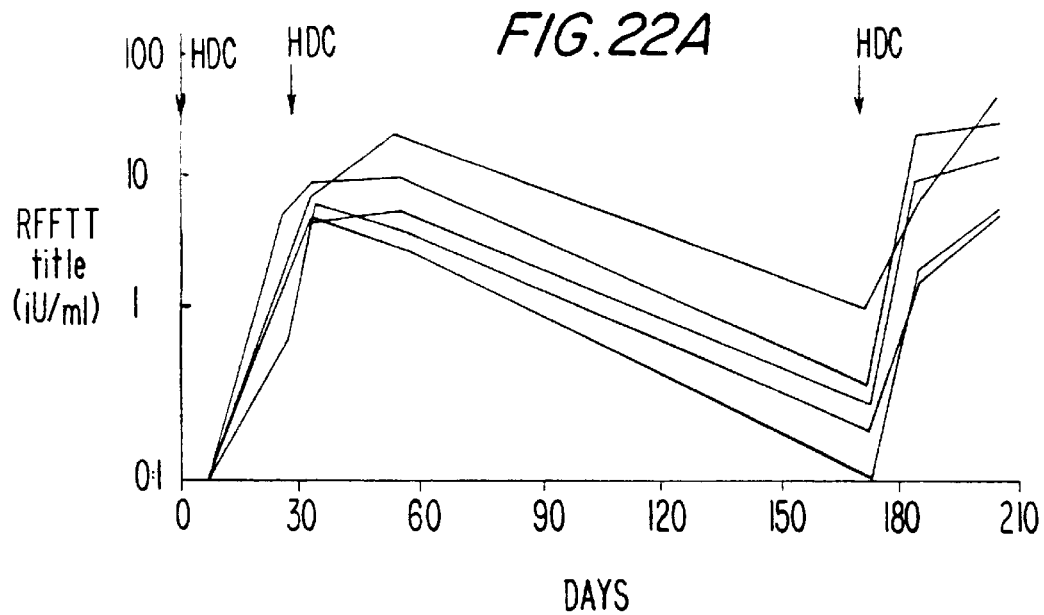
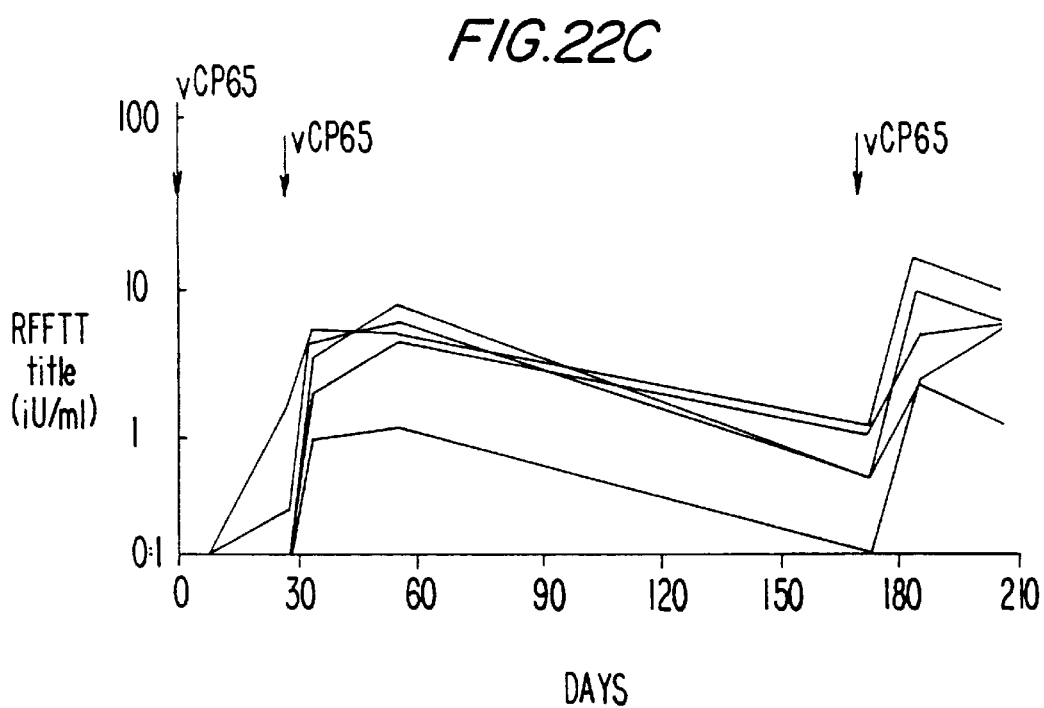

FIG. 23

| FIG. 23A |
| FIG. 23B |
| FIG. 23C |
| FIG. 23D |
| FIG. 23E |
| FIG. 23F |
| FIG. 23G |
| FIG. 23H |
| FIG. 23I |
| FIG. 23J |
| FIG. 23K |
| FIG. 23L |

FIG. 23A pCHV37/vCP320

```
AGTACAATAA    AAAGTATTAA    ATAAAAATAC                    30
TCATGTTATT    TTTCATAATT    TATTTTTATG
              C6 flankin    g arm___>
_____

TTACTTACGA    AAAAATGACT    AATTAGCTAT                    60
AATGAATGCT    TTTTTACTGA    TTAATCGATA
C6 flankin    g arm___>

AAAAACCCGG    GAAAGGATCC    TGATCCTTTT                    90
TTTTTGGGCC    CTTTCCTAGG    ACTAGGAAAA

TCTGGGTAAG    TAATACGTCA    AGGAGAAAAC                   120
AGACCCATTC    ATTATGCAGT    TCCTCTTTTG

GAAACGATCT    GTAGTTAGCG    GCCAAACTCG                   150
CTTTGCTAGA    CATCAATCGC    CGGTTTGAGC

AGGTCGACTG    AGATAAAGTG    AAAATATATA                   180
TCCAGCTGAC    TCTATTTCAC    TTTTATATAT
_____

TCATTATATT    ACAAAGTACA    ATTATTTAGG                   210
AGTAATATAA    TGTTTCATGT    TAATAAATCC
              I3L promot    er_____
_____

TTTAATCATG    TTTTCATTGT    ATCTATATAT                   240
AAATTAGTAC    AAAAGTAACA    TAGATATATA                     8
____>  M      F   S   L     Y   L   Y   I>
              __CHV gB__                >
         ___

TTTTTTTATT    ATTTATACTT    TAATAATATG                   270
AAAAAAATAA    TAAATATGAA    ATTATTATAC                    18
 F   F   I     I   Y   T     L   I   I   C>
              __CHV gB__                >
_____

TGATCCAACA    ACACCGGAAA    GTACTATTAA                   300
ACTAGGTTGT    TGTGGCCTTT    CATGATAATT                    28
 D   P   T     T   P   E     S   T   I   N>
              __CHV gB__                >
_____
```

FIG. 23B

| | | | |
|---|---|---|---|
| TCCATTAAAT<br>AGGTAATTTA<br>P  L  N | CATCACAATT<br>GTAGTGTTAA<br>H  H  N<br>\_\_CHV gB\_\_ | TATCAACACC<br>ATAGTTGTGG<br>L  S  T  P><br>_____> | 330<br><br>38 |
| TAAACCTACT<br>ATTTGGATGA<br>K  P  T | TCGGATGATA<br>AGCCTACTAT<br>S  D  D<br>\_\_CHV gB\_\_ | TTCGTGAAAT<br>AAGCACTTTA<br>I  R  E  I><br>_____> | 360<br><br>48 |
| TTTACGTGAA<br>AAATGCACTT<br>L  R  E | TCCCAAATTG<br>AGGGTTTAAC<br>S  Q  I<br>\_\_CHV gB\_\_ | AATCTGATGA<br>TTAGACTACT<br>E  S  D  D><br>_____> | 390<br><br>58 |
| TACATCAACA<br>ATGTAGTTGT<br>T  S  T | TTTTACATGT<br>AAAATGTACA<br>F  Y  M<br>\_\_CHV gB\_\_ | GCCCACCACC<br>CGGGTGGTGG<br>C  P  P  P><br>_____> | 420<br><br>68 |
| ATCGGGATCA<br>TAGCCCTAGT<br>S  G  S | ACATTGGTGC<br>TGTAACCACG<br>T  L  V<br>\_\_CHV gB\_\_ | GTTTGGAGCC<br>CAAACCTCGG<br>R  L  E  P><br>_____> | 450<br><br>78 |
| ACCTAGAGCA<br>TGGATCTCGT<br>P  R  A | TGTCCTAACT<br>ACAGGATTGA<br>C  P  N<br>\_\_CHV gB\_\_ | ATAAACTTGG<br>TATTTGAACC<br>Y  K  L  G><br>_____> | 480<br><br>88 |
| TAAAAATTTT<br>ATTTTTAAAA<br>K  N  F | ACAGAAGGAA<br>TGTCTTCCTT<br>T  E  G<br>\_\_CHV gB\_\_ | TTGCTGTAAT<br>AACGACATTA<br>I  A  V  I><br>_____> | 510<br><br>98 |
| ATTTAAGGAA<br>TAAATTCCTT<br>F  K  E | AATATTTCTC<br>TTATAAAGAG<br>N  I  S<br>\_\_CHV gB\_\_ | CTTATAAATT<br>GAATATTTAA<br>P  Y  K  F><br>_____> | 540<br><br>108 |

FIG. 23C

| | | | |
|---|---|---|---|
| TAAAGCTAAT<br>ATTTCGATTA<br> K  A  N | ATATACTACA<br>TATATGATGT<br>   I  Y  Y<br>\_\_CHV gB\_\_ | AAAATATTAT<br>TTTTATAATA<br> K  N  I  I><br>             > | 570<br><br>118 |
| TATCACCACT<br>ATAGTGGTGA<br> I  T  T | GTATGGTCTG<br>CATACCAGAC<br>  V  W  S<br>\_\_CHV gB\_\_ | GAAGCACATA<br>CTTCGTGTAT<br> G  S  T  Y><br>            > | 600<br><br>128 |
| TGCAGTAATT<br>ACGTCATTAA<br> A  V  I | ACTAATAGAT<br>TGATTATCTA<br>  T  N  R<br>\_\_CHV gB\_\_ | ATACAGATCG<br>TATGTCTAGC<br> Y  T  D  R><br>           > | 630<br><br>138 |
| TGTACCTATA<br>ACATGGATAT<br> V  P  I | GGTGTTCCTG<br>CCACAAGGAC<br>  G  V  P<br>\_\_CHV gB\_\_ | AAATTACAGA<br>TTTAATGTCT<br> E  I  T  E><br>           > | 660<br><br>148 |
| GTTGATTGAT<br>CAACTAACTA<br> L  I  D | AGAAGAGGTA<br>TCTTCTCCAT<br>  R  R  G<br>\_\_CHV gB\_\_ | TGTGTTTATC<br>ACACAAATAG<br> M  C  L  S><br>           > | 690<br><br>158 |
| AAAAGCTGAT<br>TTTTCGACTA<br> K  A  D | TATATTCGTA<br>ATATAAGCAT<br>  Y  I  R<br>\_\_CHV gB\_\_ | ATAATTATGA<br>TATTAATACT<br> N  N  Y  E><br>           > | 720<br><br>168 |
| ATTTACCGCA<br>TAAATGGCGT<br> F  T  A | TTTGATAAGG<br>AAACTATTCC<br>  F  D  K<br>\_\_CHV gB\_\_ | ATGAAGACCC<br>TACTTCTGGG<br> D  E  D  P><br>           > | 750<br><br>178 |
| CAGAGAAGTT<br>GTCTCTTCAA<br> R  E  V | CATTTAAAGC<br>GTAAATTTCG<br>  H  L  K<br>\_\_CHV gB\_\_ | CTTCAAAGTT<br>GAAGTTTCAA<br> P  S  K  F><br>           > | 780<br><br>188 |

FIG. 23D

```
TAATACACCA    GGATCCCGTG    GATGGCATAC       810
ATTATGTGGT    CCTAGGGCAC    CTACCGTATG
  N  T  P      G  S  R       G  W  H  T>    198
              __CHV gB__                >

AGTTAATGAT    ACTTACACAA    AAATTGGGGG       840
TCAATTACTA    TGAATGTGTT    TTTAACCCCC
  V  N  D      T  Y  T       K  I  G  G>    208
              __CHV gB__                >

TTCTGGATTT    TATCATTCTG    GAACATCTGT       870
AAGACCTAAA    ATAGTAAGAC    CTTGTAGACA
  S  G  F      Y  H  S       G  T  S  V>    218
              __CHV gB__                >

AAATTGTATA    GTTGAAGAAG    TTGATGCCAG       900
TTTAACATAT    CAACTTCTTC    AACTACGGTC
  N  C  I      V  E  E       V  D  A  R>    228
              __CHV gB__                >

ATCTGTTTAT    CCATATGATT    CATTTGCTAT       930
TAGACAAATA    GGTATACTAA    GTAAACGATA
  S  V  Y      P  Y  D       S  F  A  I>    238
              __CHV gB__                >

CTCCACCGGG    GATATAATTC    ATATGTCCCC       960
GAGGTGGCCC    CTATATTAAG    TATACAGGGG
  S  T  G      D  I  I       H  M  S  P>    248
              __CHV gB__                >

TTTTTTTGGA    TTACGAGATG    GTGCTCATAC       990
AAAAAAACCT    AATGCTCTAC    CACGAGTATG
  F  F  G      L  R  D       G  A  H  T>    258
              __CHV gB__                >

TGAATATATT    AGTTATTCAA    CTGATAGATT      1020
ACTTATATAA    TCAATAAGTT    GACTATCTAA
  E  Y  I      S  Y  S       T  D  R  F>    268
              __CHV gB__                >
```

FIG. 23E

| | | | |
|---|---|---|---|
| TCAACAAATA<br>AGTTGTTTAT<br>  Q   Q   I<br>─────────── | GAAGGTTATT<br>CTTCCAATAA<br>  E   G   Y<br>__CHV gB__ | ATCCTATCGA<br>TAGGATAGCT<br> Y  P  I  D><br>          > | 1050<br><br>278 |
| CTTAGATACT<br>GAATCTATGA<br>  L   D   T<br>─────────── | AGACTACAGC<br>TCTGATGTCG<br>  R   L   Q<br>__CHV gB__ | TTGGTGCACC<br>AACCACGTGG<br> L  G  A  P><br>          > | 1080<br><br>288 |
| AGTTTCTAGG<br>TCAAAGATCC<br>  V   S   R<br>─────────── | AATTTTTTAA<br>TTAAAAAATT<br>  N   F   L<br>__CHV gB__ | CAACACAACA<br>GTTGTGTTGT<br> T  T  Q  H><br>          > | 1110<br><br>298 |
| CGTTACTGTT<br>GCAATGACAA<br>  V   T   V<br>─────────── | GCTTGGAATT<br>CGAACCTTAA<br>  A   W   N<br>__CHV gB__ | GGGTTCCAAA<br>CCCAAGGTTT<br> W  V  P  K><br>          > | 1140<br><br>308 |
| AATTCGTGAA<br>TTAAGCACTT<br>  I   R   E<br>─────────── | GTGTGTACTT<br>CACACATGAA<br>  V   C   T<br>__CHV gB__ | TGGCTAAATG<br>ACCGATTTAC<br> L  A  K  W><br>          > | 1170<br><br>318 |
| GCGTGAAATT<br>CGCACTTTAA<br>  R   E   I<br>─────────── | GATGAAATTA<br>CTACTTTAAT<br>  D   E   I<br>__CHV gB__ | TTCGTGATGA<br>AAGCACTACT<br> I  R  D  E><br>          > | 1200<br><br>328 |
| GTATAAGGGA<br>CATATTCCCT<br>  Y   K   G<br>─────────── | TCTTACAGAT<br>AGAATGTCTA<br>  S   Y   R<br>__CHV gB__ | TTACAGCAAA<br>AATGTCGTTT<br> F  T  A  K><br>          > | 1230<br><br>338 |
| ATCAATATCT<br>TAGTTATAGA<br>  S   I   S<br>─────────── | GCAACATTTA<br>CGTTGTAAAT<br>  A   T   F<br>__CHV gB__ | TTTCTGATAC<br>AAAGACTATG<br> I  S  D  T><br>          > | 1260<br><br>348 |

FIG. 23F

| | | | |
|---|---|---|---|
| TACTCAATTT<br>ATGAGTTAAA<br>  T  Q  F | GATATTGATC<br>CTATAACTAG<br>  D  I  D<br>__CHV gB__ | GTGTAAAGTT<br>CACATTTCAA<br> R  V  K  L><br>         > | 1290<br>358 |
| AAGTGATTGT<br>TTCACTAACA<br>  S  D  C | GCCAAACGTG<br>CGGTTTGCAC<br>  A  K  R<br>__CHV gB__ | AAGCCATAGA<br>TTCGGTATCT<br> E  A  I  E><br>         > | 1320<br>368 |
| AGCTATTGAT<br>TCGATAACTA<br>  A  I  D | AAGATCTACA<br>TTCTAGATGT<br>  K  I  Y<br>__CHV gB__ | AAAAAAAATA<br>TTTTTTTTAT<br> K  K  K  Y><br>         > | 1350<br>378 |
| TAATAAAACT<br>ATTATTTTGA<br>  N  K  T | CATATTCAAA<br>GTATAAGTTT<br>  H  I  Q<br>__CHV gB__ | CAGGAGAATT<br>GTCCTCTTAA<br> T  G  E  L><br>         > | 1380<br>388 |
| GGAAACATAC<br>CCTTTGTATG<br>  E  T  Y | TTGGCTAGAG<br>AACCGATCTC<br>  L  A  R<br>__CHV gB__ | GGGGATTTAT<br>CCCCTAAATA<br> G  G  F  I><br>         > | 1410<br>398 |
| TATAGCATTT<br>ATATCGTAAA<br>  I  A  F | AGACCAATGA<br>TCTGGTTACT<br>  R  P  M<br>__CHV gB__ | TTAGTAATGA<br>AATCATTACT<br> I  S  N  E><br>         > | 1440<br>408 |
| GTTAGCAAAA<br>CAATCGTTTT<br>  L  A  K | TTGTATATAA<br>AACATATATT<br>  L  Y  I<br>__CHV gB__ | ATGAGTTAGT<br>TACTCAATCA<br> N  E  L  V><br>         > | 1470<br>418 |
| AAGATCTAAT<br>TTCTAGATTA<br>  R  S  N | CGTACGGTTG<br>GCATGCCAAC<br>  R  T  V<br>__CHV gB__ | ATTTGAAATC<br>TAAACTTTAG<br> D  L  K  S><br>         > | 1500<br>428 |

FIG. 23G

| | | | |
|---|---|---|---|
| TCTTTTAAAT<br>AGAAAATTTA<br>  L  L  N | CCATCTGTAA<br>GGTAGACATT<br>  P  S  V<br>__CHV gB__ | GAGGGGGGGC<br>CTCCCCCCCG<br>  R  G  G  A><br>                 > | 1530<br><br>438 |
| TAGAAAGAGA<br>ATCTTTCTCT<br>  R  K  R | AGATCAGTAG<br>TCTAGTCATC<br>  R  S  V<br>__CHV gB__ | AGGAAAATAA<br>TCCTTTTATT<br>  E  E  N  K><br>                 > | 1560<br><br>448 |
| AAGATCAAAA<br>TTCTAGTTTT<br>  R  S  K | CGTAATATTG<br>GCATTATAAC<br>  R  N  I<br>__CHV gB__ | AAGGTGGTAT<br>TTCCACCATA<br>  E  G  G  I><br>                 > | 1590<br><br>458 |
| TGAAAATGTA<br>ACTTTTACAT<br>  E  N  V | AATAATTCAA<br>TTATTAAGTT<br>  N  N  S<br>__CHV gB__ | CAATAATTAA<br>GTTATTAATT<br>  T  I  I  K><br>                 > | 1620<br><br>468 |
| GACAACTTCA<br>CTGTTGAAGT<br>  T  T  S | TCTGTTCATT<br>AGACAAGTAA<br>  S  V  H<br>__CHV gB__ | TTGCTATGCT<br>AACGATACGA<br>  F  A  M  L><br>                 > | 1650<br><br>478 |
| TCAGTTTGCC<br>AGTCAAACGG<br>  Q  F  A | TATGATCATA<br>ATACTAGTAT<br>  Y  D  H<br>__CHV gB__ | TTCAATCACA<br>AAGTTAGTGT<br>  I  Q  S  H><br>                 > | 1680<br><br>488 |
| TGTTAATGAA<br>ACAATTACTT<br>  V  N  E | ATGCTTAGTA<br>TACGAATCAT<br>  M  L  S<br>__CHV gB__ | GAATTGCAAC<br>CTTAACGTTG<br>  R  I  A  T><br>                 > | 1710<br><br>498 |
| TGCATGGTGT<br>ACGTACCACA<br>  A  W  C | AATCTTCAAA<br>TTAGAAGTTT<br>  N  L  Q<br>__CHV gB__ | ATAAAGAGAG<br>TATTTCTCTC<br>  N  K  E  R><br>                 > | 1740<br><br>508 |
| AACCCTTTGG<br>TTGGGAAACC<br>  T  L  W | AATGAAGTTA<br>TTACTTCAAT<br>  N  E  V<br>__CHV gB__ | TGAAACTTAA<br>ACTTTGAATT<br>  M  K  L  N><br>                 > | 1770<br><br>518 |

FIG. 23H

| | | | | |
|---|---|---|---|---|
| TCCAACTAGT<br>AGGTTGATCA<br>P  T  S | GTGGCTTCGG<br>CACCGAAGCC<br>V  A  S<br>__CHV gB__ | TTGCTATGGA<br>AACGATACCT<br>V  A  M  D><br>_____> | 1800<br>528 |
| TCAAAGAGTT<br>AGTTTCTCAA<br>Q  R  V | TCAGCACGAA<br>AGTCGTGCTT<br>S  A  R<br>__CHV gB__ | TGTTAGGGGA<br>ACAATCCCCT<br>M  L  G  D><br>_____> | 1830<br>538 |
| TGTTCTTGCA<br>ACAAGAACGT<br>V  L  A | GTTACTCAAT<br>CAATGAGTTA<br>V  T  Q<br>__CHV gB__ | GTGTTAATAT<br>CACAATTATA<br>C  V  N  I><br>_____> | 1860<br>548 |
| ATCAGGTTCT<br>TAGTCCAAGA<br>S  G  S | AGTGTTTTTA<br>TCACAAAAAT<br>S  V  F<br>__CHV gB__ | TTCAAAATTC<br>AAGTTTTAAG<br>I  Q  N  S><br>_____> | 1890<br>558 |
| CATGCGTGTT<br>GTACGCACAA<br>M  R  V | TTAGGGTCAA<br>AATCCCAGTT<br>L  G  S<br>__CHV gB__ | CAACTACATG<br>GTTGATGTAC<br>T  T  T  C><br>_____> | 1920<br>568 |
| TTACAGTCGT<br>AATGTCAGCA<br>Y  S  R | CCTCTTATAT<br>GGAGAATATA<br>P  L  I<br>__CHV gB__ | CATTTAAAGC<br>GTAAATTTCG<br>S  F  K  A><br>_____> | 1950<br>578 |
| ACTAGAAAAC<br>TGATCTTTTG<br>L  E  N | TCAACTAACT<br>AGTTGATTGA<br>S  T  N<br>__CHV gB__ | ATATTGAAGG<br>TATAACTTCC<br>Y  I  E  G><br>_____> | 1980<br>588 |
| ACAACTTGGG<br>TGTTGAACCC<br>Q  L  G | GAAAATAATG<br>CTTTTATTAC<br>E  N  N<br>__CHV gB__ | AACTATTAGT<br>TTGATAATCA<br>E  L  L  V><br>_____> | 2010<br>598 |
| AGAACGAAAG<br>TCTTGCTTTC<br>E  R  K | CTAATTGAAC<br>GATTAACTTG<br>L  I  E<br>__CHV gB__ | CATGTACAGC<br>GTACATGTCG<br>P  C  T  A><br>_____> | 2040<br>608 |

FIG. 231

| | | | |
|---|---|---|---|
| TAACCATAAA<br>ATTGGTATTT<br> N   H   K | AGATATTTTA<br>TCTATAAAAT<br> R   Y   F<br>__CHV gB__ | AATTTGGTGC<br>TTAAACCACG<br> K   F   G  A><br>             > | 2070<br><br>618 |
| AGATTATGTA<br>TCTAATACAT<br> D   Y   V | TATTTTGAAA<br>ATAAAACTTT<br> Y   F   E<br>__CHV gB__ | ACTATGCATA<br>TGATACGTAT<br> N   Y   A  Y><br>             > | 2100<br><br>628 |
| TGTTCGAAAG<br>ACAAGCTTTC<br> V   R   K | GTACCTCTTA<br>CATGGAGAAT<br> V   P   L<br>__CHV gB__ | ATGAAATTGA<br>TACTTTAACT<br> N   E   I  E><br>             > | 2130<br><br>638 |
| AATGATCAGT<br>TTACTAGTCA<br> M   I   S | GCATATGTAG<br>CGTATACATC<br> A   Y   V<br>__CHV gB__ | ATCTTAATAT<br>TAGAATTATA<br> D   L   N  I><br>             > | 2160<br><br>648 |
| TACATTACTT<br>ATGTAATGAA<br> T   L   L | GAGGATCGTG<br>CTCCTAGCAC<br> E   D   R<br>__CHV gB__ | AATTTTACC<br>TTAAAAATGG<br> E   F   L  P><br>             > | 2190<br><br>658 |
| ACTAGAGGTA<br>TGATCTCCAT<br> L   E   V | TATACTCGAG<br>ATATGAGCTC<br> Y   T   R<br>__CHV gB__ | CAGAGTTAGA<br>GTCTCAATCT<br> A   E   L  E><br>             > | 2220<br><br>668 |
| AGATACAGGA<br>TCTATGTCCT<br> D   T   G | CTATTGGACT<br>GATAACCTGA<br> L   L   D<br>__CHV gB__ | ATAGTGAGAT<br>TATCACTCTA<br> Y   S   E  I><br>             > | 2250<br><br>678 |
| TCAACGTAGA<br>AGTTGCATCT<br> Q   R   R | AATCAACTAC<br>TTAGTTGATG<br> N   Q   L<br>__CHV gB__ | ATGCACTTAA<br>TACGTGAATT<br> H   A   L  K><br>             > | 2280<br><br>688 |
| GTTTTATGAT<br>CAAAATACTA<br> F   Y   D | ATTGACAGTG<br>TAACTGTCAC<br> I   D   S<br>__CHV gB__ | TTGTAAAAGT<br>AACATTTTCA<br> V   V   K  V><br>             > | 2310<br><br>698 |

FIG. 23J

| | | | |
|---|---|---|---|
| TGATAATAAT<br>ACTATTATTA<br>  D  N  N | GTTGTAATTA<br>CAACATTAAT<br> V  V  I<br>\_\_CHV gB\_\_ | TGAGGGGCAT<br>ACTCCCCGTA<br> M  R  G  I><br>            > | 2340<br><br>708 |
| TGCAAATTTT<br>ACGTTTAAAA<br>  A  N  F | TTCCAAGGAC<br>AAGGTTCCTG<br> F  Q  G<br>\_\_CHV gB\_\_ | TTGGAGATGT<br>AACCTCTACA<br> L  G  D  V><br>           > | 2370<br><br>718 |
| TGGAGCGGGA<br>ACCTCGCCCT<br>  G  A  G | TTTGGAAAAG<br>AAACCTTTTC<br> F  G  K<br>\_\_CHV gB\_\_ | TTGTTTTGGG<br>AACAAAACCC<br> V  V  L  G><br>           > | 2400<br><br>728 |
| TGCTGCAAAT<br>ACGACGTTTA<br>  A  A  N | GCTGTTATTG<br>CGACAATAAC<br> A  V  I<br>\_\_CHV gB\_\_ | CAACTGTTTC<br>GTTGACAAAG<br> A  T  V  S><br>           > | 2430<br><br>738 |
| TGGAGTGTCC<br>ACCTCACAGG<br>  G  V  S | TCGTTTCTTA<br>AGCAAAGAAT<br> S  F  L<br>\_\_CHV gB\_\_ | ATAACCCATT<br>TATTGGGTAA<br> N  N  P  F><br>           > | 2460<br><br>748 |
| TGGGGCGCTA<br>ACCCCGCGAT<br>  G  A  L | GCCGTTGGAT<br>CGGCAACCTA<br> A  V  G<br>\_\_CHV gB\_\_ | TGCTGATTTT<br>ACGACTAAAA<br> L  L  I  L><br>           > | 2490<br><br>758 |
| AGCTGGACTA<br>TCGACCTGAT<br>  A  G  L | TTTGCAGCGT<br>AAACGTCGCA<br> F  A  A<br>\_\_CHV gB\_\_ | TTTTGGCTTA<br>AAAACCGAAT<br> F  L  A  Y><br>           > | 2520<br><br>768 |
| TAGATATGTT<br>ATCTATACAA<br>  R  Y  V | TCTAAACTTA<br>AGATTTGAAT<br> S  K  L<br>\_\_CHV gB\_\_ | AGTCAAATCC<br>TCAGTTTAGG<br> K  S  N  P><br>           > | 2550<br><br>778 |
| AATGAAAGCA<br>TTACTTTCGT<br>  M  K  A | CTATACCCAG<br>GATATGGGTC<br> L  Y  P<br>\_\_CHV gB\_\_ | TAACTACAAA<br>ATTGATGTTT<br> V  T  T  K><br>           > | 2580<br><br>788 |

FIG. 23K

| | | | |
|---|---|---|---|
| AAATTTAAAA<br>TTTAAATTTT<br>  N  L  K | GAAAGTGTTA<br>CTTTCACAAT<br>  E  S  V<br>__CHV gB__ | AGAATGGTAA<br>TCTTACCATT<br> K  N  G  N> | 2610<br><br>798 |
| TTCTGGAAAT<br>AAGACCTTTA<br>  S  G  N | AATAGTGATG<br>TTATCACTAC<br>  N  S  D<br>__CHV gB__ | GAGAAGAAAA<br>CTCTTCTTTT<br>  G  E  E  N> | 2640<br><br>808 |
| TGATGATAAT<br>ACTACTATTA<br>  D  D  N | ATCGATGAAG<br>TAGCTACTTC<br>  I  D  E<br>__CHV gB__ | AAAAGCTTCA<br>TTTTCGAAGT<br>  E  K  L  Q> | 2670<br><br>818 |
| ACAAGCTAAA<br>TGTTCGATTT<br>  Q  A  K | GAAATGATTA<br>CTTTACTAAT<br>  E  M  I<br>__CHV gB__ | AATATATGTC<br>TTATATACAG<br>  K  Y  M  S> | 2700<br><br>828 |
| TCTAGTTTCT<br>AGATCAAAGA<br>  L  V  S | GCTATGGAAC<br>CGATACCTTG<br>  A  M  E<br>__CHV gB__ | AGCAGGAACA<br>TCGTCCTTGT<br>  Q  Q  E  H> | 2730<br><br>838 |
| TAAAGCTATT<br>ATTTCGATAA<br>  K  A  I | AAAAAAAATA<br>TTTTTTTTAT<br>  K  K  N<br>__CHV gB__ | GTGGCCCTGC<br>CACCGGGACG<br>  S  G  P  A> | 2760<br><br>848 |
| CCTTCTAGCA<br>GGAAGATCGT<br>  L  L  A | AGTCACATTA<br>TCAGTGTAAT<br>  S  H  I<br>__CHV gB__ | CAAACCTATC<br>GTTTGGATAG<br>  T  N  L  S> | 2790<br><br>858 |
| TCTTAAACAT<br>AGAATTTGTA<br>  L  K  H | CGTGGTCCAA<br>GCACCAGGTT<br>  R  G  P<br>__CHV gB__ | AATACAAACG<br>TTATGTTTGC<br>  K  Y  K  R> | 2820<br><br>868 |
| TTTGAAAAAT<br>AAACTTTTTA<br>  L  K  N | GTAAATGAAA<br>CATTTACTTT<br>  V  N  E<br>__CHV gB__ | ATGAAAGTAA<br>TACTTTCATT<br>  N  E  S  K> | 2850<br><br>878 |

FIG. 23L

| | | | |
|---|---|---|---|
| AGTTTAACCC | GGGTACCGAG | CTCGAATTCT | 2880 |
| TCAAATTGGG | CCCATGGCTC | GAGCTTAAGA | |
| V> | | | 879 |
| ___> | | | |
| TTTTATTGAT | TAACTAGTCA | AATGAGTATA | 2910 |
| AAAATAACTA | ATTGATCAGT | TTACTCATAT | |
| | ___ | _____> | |
| TATAATTGAA | AAAGTAAAAT | ATAAATCATA | 2940 |
| ATATTAACTT | TTTCATTTTA | TATTTAGTAT | |
| _____ | C6 flankin | g arm____> | |
| TAATAATGAA | A | | 2951 |
| ATTATTACTT | T | | |
| _____ | _> | | |

FIG. 24A

```
GAGCTCGCGG   CCGCCTATCA   AAAGTCTTAA         30
CTCGAGCGCC   GGCGGATAGT   TTTCAGAATT
       C6    flanking     arm      >

TGAGTTAGGT   GTAGATAGTA   TAGATATTAC         60
ACTCAATCCA   CATCTATCAT   ATCTATAATG
       C6    flanking     arm      >

TACAAAGGTA   TTCATATTTC   CTATCAATTC         90
ATGTTTCCAT   AAGTATAAAG   GATAGTTAAG
       C6    flanking     arm      >

TAAAGTAGAT   GATATTAATA   ACTCAAAGAT        120
ATTTCATCTA   CTATAATTAT   TGAGTTTCTA
       C6    flanking     arm      >

GATGATAGTA   GATAATAGAT   ACGCTCATAT        150
CTACTATCAT   CTATTATCTA   TGCGAGTATA
       C6    flanking     arm      >

AATGACTGCA   AATTTGGACG   GTTCACATTT        180
TTACTGACGT   TTAAACCTGC   CAAGTGTAAA
       C6    flanking     arm      >

TAATCATCAC   GCGTTCATAA   GTTTCAACTG        210
ATTAGTAGTG   CGCAAGTATT   CAAAGTTGAC
       C6    flanking     arm      >

CATAGATCAA   AATCTCACTA   AAAAGATAGC        240
GTATCTAGTT   TTAGAGTGAT   TTTTCTATCG
       C6    flanking     arm      >

CGATGTATTT   GAGAGAGATT   GGACATCTAA        270
GCTACATAAA   CTCTCTCTAA   CCTGTAGATT
       C6    flanking     arm      >

CTACGCTAAA   GAAATTACAG   TTATAAATAA        300
GATGCGATTT   CTTTAATGTC   AATATTTATT
       C6    flanking     arm      >

TACATAATGG   ATTTTGTTAT   CATCAGTTAT        330
ATGTATTACC   TAAAACAATA   GTAGTCAATA
       C6    flanking     arm      >
```

FIG. 24B

```
ATTTAACATA  AGTACAATAA  AAAGTATTAA              360
TAAATTGTAT  TCATGTTATT  TTTCATAATT
        C6  flanking    arm       >

ATAAAAATAC  TTACTTACGA  AAAAATGACT              390
TATTTTTATG  AATGAATGCT  TTTTTACTGA
        C6  flanking    arm      >
                                 >

AATTAGCTAT  AAAAACCCGG  GCTGCAGCTC              420
TTAATCGATA  TTTTTGGGCC  CGACGTCGAG
                _Cloning sites    >

GAGGAATTCT  TTTTATTGAT  TAACTAGTCA              450
CTCCTTAAGA  AAAATAACTA  ATTGATCAGT
                _Cloning sites _>
                                 >

AATGAGTATA  TATAATTGAA  AAAGTAAAAT              480
TTACTCATAT  ATATTAACTT  TTTCATTTTA
        C6  flanking    arm       >

ATAAATCATA  TAATAATGAA  ACGAAATATC              510
TATTTAGTAT  ATTATTACTT  TGCTTTATAG
        C6  flanking    arm       >

AGTAATAGAC  AGGAACTGGC  AGATTCTTCT              540
TCATTATCTG  TCCTTGACCG  TCTAAGAAGA
        C6  flanking    arm       >

TCTAATGAAG  TAAGTACTGC  TAAATCTCCA              570
AGATTACTTC  ATTCATGACG  ATTTAGAGGT
        C6  flanking    arm       >

AAATTAGATA  AAAATGATAC  AGCAAATACA              600
TTTAATCTAT  TTTTACTATG  TCGTTTATGT
        C6  flanking    arm       >

GCTTCATTCA  ACGAATTACC  TTTTAATTTT              630
CGAAGTAAGT  TGCTTAATGG  AAAATTAAAA
        C6  flanking    arm       >
```

FIG. 24C

| | | | |
|---|---|---|---|
| TTCAGACACA<br>AAGTCTGTGT<br>‾‾‾‾‾‾‾C6 | CCTTATTACA<br>GGAATAATGT<br>flanking | AACTAACTAA<br>TTGATTGATT<br>arm‾‾‾‾‾‾> | 660 |
| GTCAGATGAT<br>CAGTCTACTA<br>‾‾‾‾‾‾‾C6 | GAGAAAGTAA<br>CTCTTTCATT<br>flanking | ATATAAATTT<br>TATATTTAAA<br>arm‾‾‾‾‾‾> | 690 |
| AACTTATGGG<br>TTGAATACCC<br>‾‾‾‾‾‾‾C6 | TATAATATAA<br>ATATTATATT<br>flanking | TAAAGATTCA<br>ATTTCTAAGT<br>arm‾‾‾‾‾‾> | 720 |
| TGATATTAAT<br>ACTATAATTA<br>‾‾‾‾‾‾‾C6 | AATTTACTTA<br>TTAAATGAAT<br>flanking | ACGATGTTAA<br>TGCTACAATT<br>arm‾‾‾‾‾‾> | 750 |
| TAGACTTATT<br>ATCTGAATAA<br>‾‾‾‾‾‾‾C6 | CCATCAACCC<br>GGTAGTTGGG<br>flanking | CTTCAAACCT<br>GAAGTTTGGA<br>arm‾‾‾‾‾‾> | 780 |
| TTCTGGATAT<br>AAGACCTATA<br>‾‾‾‾‾‾‾C6 | TATAAAATAC<br>ATATTTTATG<br>flanking | CAGTTAATGA<br>GTCAATTACT<br>arm‾‾‾‾‾‾> | 810 |
| TATTAAAATA<br>ATAATTTTAT<br>‾‾‾‾‾‾‾C6 | GATTGTTTAA<br>CTAACAAATT<br>flanking | GAGATGTAAA<br>CTCTACATTT<br>arm‾‾‾‾‾‾> | 840 |
| TAATTATTTG<br>ATTAATAAAC<br>‾‾‾‾‾‾‾C6 | GAGGTAAAGG<br>CTCCATTTCC<br>flanking | ATATAAAATT<br>TATATTTTAA<br>arm‾‾‾‾‾‾> | 870 |
| AGTCTATCTT<br>TCAGATAGAA<br>‾‾‾‾‾‾‾C6 | TCACATGGAA<br>AGTGTACCTT<br>flanking | ATGAATTACC<br>TACTTAATGG<br>arm‾‾‾‾‾‾> | 900 |
| TAATATTAAT<br>ATTATAATTA<br>‾‾‾‾‾‾‾C6 | AATTATGATA<br>TTAATACTAT<br>flanking | GGAATTTTTT<br>CCTTAAAAAA<br>arm‾‾‾‾‾‾> | 930 |
| AGGATTTACA<br>TCCTAAATGT<br>‾‾‾‾‾‾‾C6 | GCTGTTATAT<br>CGACAATATA<br>flanking | GTATCAACAA<br>CATAGTTGTT<br>arm‾‾‾‾‾‾> | 960 |

FIG. 24D

| | | | |
|---|---|---|---|
| TACAGGCAGA ATGTCCGTCT _____C6 | TCTATGGTTA AGATACCAAT flanking | TGGTAAAACA ACCATTTGT arm_____> | 990 |
| CTGTAACGGG GACATTGCCC _____C6 | AAGCAGCATT TTCGTCGTAA flanking | CTATGGTAAC GATACCATTG arm_____> | 1020 |
| TGGCCTATGT ACCGGATACA _____C6 | TTAATAGCCA AATTATCGGT flanking | GATCATTTTA CTAGTAAAAT arm_____> | 1050 |
| CTCTATAAAC GAGATATTTG _____C6 | ATTTTACCAC TAAAATGGTG flanking | AAATAATAGG TTTATTATCC arm_____> | 1080 |
| ATCCTCTAGA TAGGAGATCT _____C6 | TATTTAATAT ATAAATTATA flanking | TATATCTAAC ATATAGATTG arm_____> | 1110 |
| AACAACAAAA TTGTTGTTTT _____C6 | AAATTTAACG TTTAAATTGC flanking | ATGTATGGCC TACATACCGG arm_____> | 1140 |
| AGAAGTATTT TCTTCATAAA _____C6 | TCTACTAATA AGATGATTAT flanking | AAGATAAAGA TTCTATTTCT arm_____> | 1170 |
| TAGTCTATCT ATCAGATAGA _____C6 | TATCTACAAG ATAGATGTTC flanking | ATATGAAAGA TATACTTTCT arm_____> | 1200 |
| AGATAATCAT TCTATTAGTA _____C6 | TTAGTAGTAG AATCATCATC flanking | CTACTAATAT GATGATTATA arm_____> | 1230 |
| GGAAAGAAAT CCTTTCTTTA _____C6 | GTATACAAAA CATATGTTTT flanking | ACGTGGAAGC TGCACCTTCG arm_____> | 1260 |
| TTTTATATTA AAAATATAAT _____C6 | AATAGCATAT TTATCGTATA flanking | TACTAGAAGA ATGATCTTCT arm_____> | 1290 |

FIG. 24E

```
TTTAAAATCT  AGACTTAGTA  TAACAAAACA         1320
AAATTTTAGA  TCTGAATCAT  ATTGTTTTGT
_____C6 flanking    arm_____>

GTTAAATGCC  AATATCGATT  CTATATTTCA         1350
CAATTTACGG  TTATAGCTAA  GATATAAAGT
_____C6 flanking    arm_____>

TCATAACAGT  AGTACATTAA  TCAGTGATAT         1380
AGTATTGTCA  TCATGTAATT  AGTCACTATA
_____C6 flanking    arm_____>

ACTGAAACGA  TCTACAGACT  CAACTATGCA         1410
TGACTTTGCT  AGATGTCTGA  GTTGATACGT
_____C6 flanking    arm_____>

AGGAATAAGC  AATATGCCAA  TTATGTCTAA         1440
TCCTTATTCG  TTATACGGTT  AATACAGATT
_____C6 flanking    arm_____>

TATTTTAACT  TTAGAACTAA  AACGTTCTAC         1470
ATAAAATTGA  AATCTTGATT  TTGCAAGATG
_____C6 flanking    arm_____>

CAATACTAAA  AATAGGATAC  GTGATAGGCT         1500
GTTATGATTT  TTATCCTATG  CACTATCCGA
_____C6 flanking    arm_____>

GTTAAAAGCT  GCAATAAATA  GTAAGGATGT         1530
CAATTTTCGA  CGTTATTTAT  CATTCCTACA
_____C6 flanking    arm_____>

AGAAGAAATA  CTTTGTTCTA  TACCTTCGGA         1560
TCTTCTTTAT  GAAACAAGAT  ATGGAAGCCT
_____C6 flanking    arm_____>

GGAAAGAACT  TTAGAACAAC  TTAAGTTTAA         1590
CCTTTCTTGA  AATCTTGTTG  AATTCAAATT
_____C6 flanking    arm_____>

TCAAACTTGT  ATTTATGAAG  GTACC             1615
AGTTTGAACA  TAAATACTTC  CATGG
_____C6 flanking    arm__>
```

FIG. 26

| FIG. 26A |
| FIG. 26B |
| FIG. 26C |
| FIG. 26D |
| FIG. 26E |
| FIG. 26F |
| FIG. 26G |

FIG. 26A

| | | | |
|---|---|---|---|
| AGTACAATAA | AAAGTATTAA | ATAAAAATAC | 30 |
| TCATGTTATT | TTTCATAATT | TATTTTTATG | |
| ____C6 | flanking | arm____> | |
| TTACTTACGA | AAAAATGACT | AATTAGCTAT | 60 |
| AATGAATGCT | TTTTTACTGA | TTAATCGATA | |
| __C6 flank | ing arm_> | | |
| AAAAACCCGG | GAAAGGATCC | TGATCCTTTT | 90 |
| TTTTTGGGCC | CTTTCCTAGG | ACTAGGAAAA | |
| TCTGGGTAAG | TAATACGTCA | AGGAGAAAAC | 120 |
| AGACCCATTC | ATTATGCAGT | TCCTCTTTTG | |
| GAAACGATCT | GTAGTTAGCG | GCCAAACTCG | 150 |
| CTTTGCTAGA | CATCAATCGC | CGGTTTGAGC | |
| AGGTCGACGG | TATCGATAAG | CTTGATTCTT | 180 |
| TCCAGCTGCC | ATAGCTATTC | GAACTAAGAA | |
| | | ____> | |
| TATTCTATAC | TTAAAAGTG | AAAATAAATA | 210 |
| ATAAGATATG | AATTTTTCAC | TTTTATTTAT | |
| ____H6 | promoter__ | ____> | |
| CAAAGGTTCT | TGAGGGTTGT | GTTAAATTGA | 240 |
| GTTTCCAAGA | ACTCCCAACA | CAATTTAACT | |
| ____H6 | promoter__ | ____> | |
| AAGCGAGAAA | TAATCATAAA | TTATTTCATT | 270 |
| TTCGCTCTTT | ATTAGTATTT | AATAAAGTAA | |
| ____H6 | promoter__ | ____> | |
| ATCGCGATAT | CCGTTAAGTT | TGTATCGTAA | 300 |
| TAGCGCTATA | GGCAATTCAA | ACATAGCATT | |
| ____H6 | promoter__ | ____> | |
| | | ____> | |
| TGAGTTTTAA | AAATTTTTAT | CTAATATATG | 330 |
| ACTCAAAATT | TTTAAAAATA | GATTATATAC | |
| M S F K | N F Y | L I Y> | 10 |
| | __CHV gC__ | | |
| _____ | | ____> | |

FIG. 26B

| | | | |
|---|---|---|---|
| TAATTATAAT<br>ATTAATATTA<br>V  I  I  I | TTTTATAAAC<br>AAAATATTTG<br>F  I  N<br>__CHV gC__ | TCGATAATAA<br>AGCTATTATT<br>S  I  I> | 360<br>20 |
| CTTCGGCATC<br>GAAGCCGTAG<br>T  S  A  S | TACATCCAAA<br>ATGTAGGTTT<br>T  S  K<br>__CHV gC__ | CCTTCAACAC<br>GGAAGTTGTG<br>P  S  T> | 390<br>30 |
| CTACCATAAT<br>GATGGTATTA<br>P  T  I  I | TCCAACTTCA<br>AGGTTGAAGT<br>P  T  S<br>__CHV gC__ | GCAAATGAAT<br>CGTTTACTTA<br>A  N  E> | 420<br>40 |
| CACCTGCTTC<br>GTGGACGAAG<br>S  P  A  S | CATAGATACA<br>GTATCTATGT<br>I  D  T<br>__CHV gC__ | ACTATAACAA<br>TGATATTGTT<br>T  I  T> | 450<br>50 |
| AACCTATATC<br>TTGGATATAG<br>K  P  I  S | TACAGAGGCA<br>ATGTCTCCGT<br>T  E  A<br>__CHV gC__ | AATAATTTAA<br>TTATTAAATT<br>N  N  L> | 480<br>60 |
| AATCAGTAAG<br>TTAGTCATTC<br>K  S  V  S | TACCTCAATT<br>ATGGAGTTAA<br>T  S  I<br>__CHV gC__ | AAACCACCTA<br>TTTGGTGGAT<br>K  P  P> | 510<br>70 |
| AAAACTTAAA<br>TTTTGAATTT<br>K  N  L  K | AAAAAAATTA<br>TTTTTTTAAT<br>K  K  L<br>__CHV gC__ | CTTAAATCTA<br>GAATTTAGAT<br>L  K  S> | 540<br>80 |
| AATGTAGAGA<br>TTACATCTCT<br>K  C  R  D | TAATGTTATT<br>ATTACAATAA<br>N  V  I<br>__CHV gC__ | TATAGGCCAT<br>ATATCCGGTA<br>Y  R  P> | 570<br>90 |
| ATTTTAGTCA<br>TAAAATCAGT<br>Y  F  S  Q | ATTAGAAATT<br>TAATCTTTAA<br>L  E  I<br>__CHV gC__ | AACTGTACTA<br>TTGACATGAT<br>N  C  T> | 600<br>100 |

FIG. 26C

| | | | |
|---|---|---|---|
| TAACTAAAAA ATTGATTTTT I T K K | GCAAAATTTA CGTTTTAAAT Q N L _CHV gC_ | AGTAATCCTT TCATTAGGAA S N P> > | 630 110 |
| TAATTGAGTT ATTAACTCAA L I E L | ATGGTTTAAA TACCAAATTT W F K _CHV gC_ | GAACTTTCTA CTTGAAAGAT E L S > | 660 120 |
| CATATAATAA GTATATTATT T Y N K | AACCAATGAA TTGGTTACTT T N E _CHV gC_ | AATGTTGAAA TTACAACTTT N V E> > | 690 130 |
| GTTTAAAAAC CAAATTTTTG S L K T | AGATATATCA TCTATATAGT D I S _CHV gC_ | AAAAATATTT TTTTTATAAA K N I> > | 720 140 |
| TATTATTTTC ATAATAAAAG L L F S | GACAAAAAAT CTGTTTTTTA T K N _CHV gC_ | AATAGTGATA TTATCACTAT N S D> > | 750 150 |
| ACTTTTATAA TGAAAATATT N F Y N | TGATTTTTTA ACTAAAAAAT D F L _CHV gC_ | TTAGGTATAC AATCCATATG L G I> > | 780 160 |
| AAAATCAACC TTTTAGTTGG Q N Q P | AGTAAATTAT TCATTTAATA V N Y _CHV gC_ | AAACTTTACG TTTGAAATGC K L Y> > | 810 170 |
| GTTCCCAATT CAAGGGTTAA G S Q F | TTATGATAAT AATACTATTA Y D N _CHV gC_ | GGAAACATAT CCTTTGTATA G N I> > | 840 180 |
| TACTAAATAT ATGATTTATA L L N I | AAAGTCGGTT TTTCAGCCAA K S V _CHV gC_ | GACTTTAAAA CTGAAATTTT D F K> > | 870 190 |

FIG. 26D

| | | | |
|---|---|---|---|
| CCTCTGGAAT<br>GGAGACCTTA<br>T  S  G  I | ATATACTTGG<br>TATATGAACC<br>  Y  T  W<br>__CHV gC__ | AAACTATATA<br>TTTGATATAT<br>K  L  Y> | 900<br>200<br>> |
| ATTCAAATAA<br>TAAGTTTATT<br>N  S  N  N | TGAAAGTATT<br>ACTTTCATAA<br>  E  S  I<br>__CHV gC__ | TTTGAAACTT<br>AAACTTTGAA<br>F  E  T> | 930<br>210<br>> |
| TTAAAATTCA<br>AATTTTAAGT<br>F  K  I  Q | AGTATATGCA<br>TCATATACGT<br>  V  Y  A<br>__CHV gC__ | TATCATTCCC<br>ATAGTAAGGG<br>Y  H  S> | 960<br>220<br>> |
| CAAATGTAAA<br>GTTTACATTT<br>P  N  V  N | CTTAAAATCA<br>GAATTTTAGT<br>  L  K  S<br>__CHV gC__ | AACCCAAGTT<br>TTGGGTTCAA<br>N  P  S> | 990<br>230<br>> |
| TATATAATGA<br>ATATATTACT<br>L  Y  N  E | AAACTACAGC<br>TTTGATGTCG<br>  N  Y  S<br>__CHV gC__ | GCTATTTGTA<br>CGATAAACAT<br>A  I  C> | 1020<br>240<br>> |
| CAATAGCAAA<br>GTTATCGTTT<br>T  I  A  N | TTACTTTCCA<br>AATGAAAGGT<br>  Y  F  P<br>__CHV gC__ | TTGGAATCTA<br>AACCTTAGAT<br>L  E  S> | 1050<br>250<br>> |
| CGGAAATATT<br>GCCTTTATAA<br>T  E  I  F | TTGGTTTAAC<br>AACCAAATTG<br>  W  F  N<br>__CHV gC__ | GATGGACAAC<br>CTACCTGTTG<br>D  G  Q> | 1080<br>260<br>> |
| CTATTGATAA<br>GATAACTATT<br>P  I  D  K | AAAATATATA<br>TTTTATATAT<br>  K  Y  I<br>__CHV gC__ | GATGAAACTT<br>CTACTTTGAA<br>D  E  T> | 1110<br>270<br>> |
| ATAGTGTATG<br>TATCACATAC<br>Y  S  V  W | GATTGACGGT<br>CTAACTGCCA<br>  I  D  G<br>__CHV gC__ | CTTATAACAC<br>GAATATTGTG<br>L  I  T> | 1140<br>280<br>> |

FIG. 26E

| | | | |
|---|---|---|---|
| GCACTTCAAT<br>CGTGAAGTTA<br>R T S I | ATTATCCCTT<br>TAATAGGGAA<br>L S L<br>__CHV gC__ | CCCTTTTCCG<br>GGGAAAAGGC<br>P F S><br>_____> | 1170<br><br>290 |
| AAGCCATGGA<br>TTCGGTACCT<br>E A M E | AAGCCCCCCC<br>TTCGGGGGGG<br>S P P<br>__CHV gC__ | AATTTGCGAT<br>TTAAACGCTA<br>N L R><br>_____> | 1200<br><br>300 |
| GTAATGTTGA<br>CATTACAACT<br>C N V E | ATGGTATAAA<br>TACCATATTT<br>W Y K<br>__CHV gC__ | AATTCAAAGG<br>TTAAGTTTCC<br>N S K><br>_____> | 1230<br><br>310 |
| CATCAAAAAA<br>GTAGTTTTTT<br>A S K K | ATTTTCAAAT<br>TAAAAGTTTA<br>F S N<br>__CHV gC__ | ACCGTTATTC<br>TGGCAATAAG<br>T V I><br>_____> | 1260<br><br>320 |
| CAAAAGTTTA<br>GTTTTCAAAT<br>P K V Y | CTATAAACCT<br>GATATTTGGA<br>Y K P<br>__CHV gC__ | TTTATATCTA<br>AAATATAGAT<br>F I S><br>_____> | 1290<br><br>330 |
| TAAAATTTGA<br>ATTTTAAACT<br>I K F D | TAATGGTTTA<br>ATTACCAAAT<br>N G L<br>__CHV gC__ | GCTATTTGTG<br>CGATAAACAC<br>A I C><br>_____> | 1320<br><br>340 |
| ATGCTAAATG<br>TACGATTTAC<br>D A K C | TGTTTCCCGT<br>ACAAAGGGCA<br>V S R<br>__CHV gC__ | GAAAATAATA<br>CTTTTATTAT<br>E N N><br>_____> | 1350<br><br>350 |
| AATTACAATG<br>TTAATGTTAC<br>K L Q W | GTTAGTTAAA<br>CAATCAATTT<br>L V K<br>__CHV gC__ | GATATACCTA<br>CTATATGGAT<br>D I P><br>_____> | 1380<br><br>360 |
| TAAATGGTGA<br>ATTTACCACT<br>I N G D | TGATATTATA<br>ACTATAATAT<br>D I I<br>__CHV gC__ | AGCGGCCCCT<br>TCGCCGGGGA<br>S G P><br>_____> | 1410<br><br>370 |

FIG. 26F

| | | | |
|---|---|---|---|
| GTTTAAACCA<br>CAAATTTGGT<br>C L N H | CCCTGGTTTG<br>GGGACCAAAC<br>P G L<br>__CHV gC__ | GTCAATATTC<br>CAGTTATAAG<br>V N I><br>> | 1440<br>380 |
| AAAATAAAAT<br>TTTTATTTTA<br>Q N K I | AGATATATCG<br>TCTATATAGC<br>D I S<br>__CHV gC__ | GATTATGATG<br>CTAATACTAC<br>D Y D><br>> | 1470<br>390 |
| AACCTGTTAC<br>TTGGACAATG<br>E P V T | CTATAAATGT<br>GATATTTACA<br>Y K C<br>__CHV gC__ | TCAATTATTG<br>AGTTAATAAC<br>S I I><br>> | 1500<br>400 |
| GTTATCCAAT<br>CAATAGGTTA<br>G Y P I | AATTTTCCC<br>TTAAAAGGG<br>I F P<br>__CHV gC__ | AACTTTATG<br>TTGAAAATAC<br>N F Y><br>> | 1530<br>410 |
| ATGAAAAGGT<br>TACTTTTCCA<br>D E K V | GTTTGATGCA<br>CAAACTACGT<br>F D A<br>__CHV gC__ | TCGGATGAAA<br>AGCCTACTTT<br>S D E><br>> | 1560<br>420 |
| ATGTTAGTAA<br>TACAATCATT<br>N V S K | ATCGATGTTA<br>TAGCTACAAT<br>S M L<br>__CHV gC__ | ATAAGTATTA<br>TATTCATAAT<br>I S I><br>> | 1590<br>430 |
| CCACAATAAT<br>GGTGTTATTA<br>T T I I | TGGTGGAGCC<br>ACCACCTCGG<br>G G A<br>__CHV gC__ | ATTTTTGTTA<br>TAAAAACAAT<br>I F V><br>> | 1620<br>440 |
| TAGTATTGAT<br>ATCATAACTA<br>I V L I | TTTTATAACA<br>AAAATATTGT<br>F I T<br>__CHV gC__ | GCTTTATGTT<br>CGAAATACAA<br>A L C><br>> | 1650<br>450 |
| TTTATTGTTC<br>AAATAACAAG<br>F Y C S | AAAAAATAAT<br>TTTTTTATTA<br>K N N<br>__CHV gC__ | AAGATCTAAC<br>TTCTAGATTG<br>K I><br>> | 1680<br>459 |

FIG. 26G

| | | | |
|---|---|---|---|
| TGCAAATTCT | TTTTATTGAT | TAACTAGTCA | 1710 |
| ACGTTTAAGA | AAAATAACTA | ATTGATCAGT | |
| | | ———> | |
| AATGAGTATA | TATAATTGAA | AAAGTAAAAT | 1740 |
| TTACTCATAT | ATATTAACTT | TTTCATTTTA | |
| ———C6 | flanking | arm———> | |
| ATAAATCATA | TAATAATGAA | A | 1761 |
| TATTTAGTAT | ATTATTACTT | T | |
| —C6 flank | ing arm | —> | |

FIG. 28A

| | | | |
|---|---|---|---|
| AGTACAATAA<br>TCATGTTATT<br>____C6 | AAAGTATTAA<br>TTTCATAATT<br>flanking | ATAAAAATAC<br>TATTTTTATG<br>arm____> | 30 |
| TTACTTACGA<br>AATGAATGCT<br>_C6 flank | AAAAATGACT<br>TTTTTACTGA<br>ing arm_> | AATTAGCTAT<br>TTAATCGATA | 60 |
| AAAAACCCGG<br>TTTTTGGGCC | GAAAGGATCC<br>CTTTCCTAGG | TGATCCTTTT<br>ACTAGGAAAA | 90 |
| TCTGGGTAAG<br>AGACCCATTC | TAATACGTCA<br>ATTATGCAGT | AGGAGAAAAC<br>TCCTCTTTTG | 120 |
| GAAACGATCT<br>CTTTGCTAGA | GTAGTTAGCG<br>CATCAATCGC | GCCAAACTCG<br>CGGTTTGAGC | 150 |
| AGGTCGACGG<br>TCCAGCTGCC | TATCGATAAG<br>ATAGCTATTC | CTTGATTCTT<br>GAACTAAGAA<br>_____> | 180 |
| TATTCTATAC<br>ATAAGATATG<br>____H6 | TTAAAAGTG<br>AATTTTTCAC<br>promoter__ | AAAATAAATA<br>TTTTATTTAT<br>_____> | 210 |
| CAAAGGTTCT<br>GTTTCCAAGA<br>____H6 | TGAGGGTTGT<br>ACTCCCAACA<br>promoter__ | GTTAAATTGA<br>CAATTTAACT<br>_____> | 240 |
| AAGCGAGAAA<br>TTCGCTCTTT<br>____H6 | TAATCATAAA<br>ATTAGTATTT<br>promoter__ | TTATTTCATT<br>AATAAAGTAA<br>_____> | 270 |
| ATCGCGATAT<br>TAGCGCTATA<br>____H6 | CCGTTAAGTT<br>GGCAATTCAA<br>promoter__ | TGTATCGTAA<br>ACATAGCATT<br>_____><br>_> | 300 |
| TGATTAAACT<br>ACTAATTTGA<br>M I K L | TCTATTTATC<br>AGATAAATAG<br>L F I<br>_CHV gD__ | TTATTTATT<br>AATAAAATAA<br>L F Y><br>_____> | 330<br>10 |

FIG. 28B

| | | | |
|---|---|---|---|
| TTAACCCAAT<br>AATTGGGTTA<br>F  N  P  I | AACTGGATAT<br>TTGACCTATA<br>  T  G  Y<br>__CHV gD__ | AAATGGGTAG<br>TTTACCCATC<br>  K  W  V><br>          > | 360<br>20 |
| ACCCTCCTCG<br>TGGGAGGAGC<br>D  P  P  R | TAGGTATAAT<br>ATCCATATTA<br>  R  Y  N<br>__CHV gD__ | TACACCGTTT<br>ATGTGGCAAA<br>  Y  T  V><br>          > | 390<br>30 |
| TAAGAATGAT<br>ATTCTTACTA<br>L  R  M  I | TCCAGATATT<br>AGGTCTATAA<br>  P  D  I<br>__CHV gD__ | CCAAATCCAA<br>GGTTTAGGTT<br>  P  N  P><br>          > | 420<br>40 |
| TGGATCCTTC<br>ACCTAGGAAG<br>M  D  P  S | TAAAACGCT<br>ATTTTTGCGA<br>  K  N  A<br>__CHV gD__ | GAAGTTCGGT<br>CTTCAAGCCA<br>  E  V  R><br>          > | 450<br>50 |
| ATGTAACTTC<br>TACATTGAAG<br>Y  V  T  S | TACTGACCCA<br>ATGACTGGGT<br>  T  D  P<br>__CHV gD__ | TGTGATATGG<br>ACACTATACC<br>  C  D  M><br>          > | 480<br>60 |
| TTGCTTTGAT<br>AACGAAACTA<br>V  A  L  I | TTCTAATCCA<br>AAGATTAGGT<br>  S  N  P<br>__CHV gD__ | AATATAGAAT<br>TTATATCTTA<br>  N  I  E><br>          > | 510<br>70 |
| CTACAATTAA<br>GATGTTAATT<br>S  T  I  K | AACGATTCAA<br>TTGCTAAGTT<br>  T  I  Q<br>__CHV gD__ | TTTGTGCAAA<br>AAACACGTTT<br>  F  V  Q><br>          > | 540<br>80 |
| AGAAAAAATT<br>TCTTTTTTAA<br>K  K  K  F | TTACAATGCA<br>AATGTTACGT<br>  Y  N  A<br>__CHV gD__ | TCTCTTAGTT<br>AGAGAATCAA<br>  S  L  S><br>          > | 570<br>90 |
| GGTTTAAAGT<br>CCAAATTTCA<br>W  F  K  V | TGGAGATGAT<br>ACCTCTACTA<br>  G  D  D<br>__CHV gD__ | TGTACATATC<br>ACATGTATAG<br>  C  T  Y><br>          > | 600<br>100 |

FIG. 28C

| | | | |
|---|---|---|---|
| CAATATATTT GTTATATAAA P I Y L | AATTCAATAT TTAAGTTATA I Q Y ⎯CHV gD⎯ | TTTGATTGTG AAACTAACAC F D C> ⎯⎯⎯⎯⎯> | 630<br>110 |
| ATCCTCAAAG TAGGAGTTTC D P Q R | AGAATTGGC TCTTAAACCG E F G ⎯CHV gD⎯ | ATATGTTTAA TATACAAATT I C L> ⎯⎯⎯⎯⎯> | 660<br>120 |
| AAAGATCTCC TTTCTAGAGG K R S P | AGATTTTGG TCTAAAACC D F W ⎯CHV gD⎯ | AAACCATCGT TTTGGTAGCA K P S> ⎯⎯⎯⎯⎯> | 690<br>130 |
| TAGTTGGTTA ATCAACCAAT L V G Y | CACATTTTA GTGTAAAAAT T F L ⎯CHV gD⎯ | ACTGATGATG TGACTACTAC T D D> ⎯⎯⎯⎯⎯> | 720<br>140 |
| AATTGGGATT TTAACCCTAA E L G L | AGTTTAGCT TCAAAATCGA V L A ⎯CHV gD⎯ | GCCCCCGCTC CGGGGGCGAG A P A> ⎯⎯⎯⎯⎯> | 750<br>140 |
| CATTTAATCA GTAAATTAGT P F N Q | AGGTCAATAT TCCAGTTATA G Q Y ⎯CHV gD⎯ | AGACGGGTTA TCTGCCCAAT R R V> ⎯⎯⎯⎯⎯> | 780<br>150 |
| TTCAAATTGA AAGTTTAACT I Q I E | AAATGAAGTT TTTACTTCAA N E V ⎯CHV gD⎯ | TTTTATACTG AAAATATGAC F Y T> ⎯⎯⎯⎯⎯> | 810<br>160 |
| ATTTTATGGT TAAAATACCA D F M V | TCAATTACCA AGTTAATGGT Q L P ⎯CHV gD⎯ | CGAGAAACTT GCTCTTTGAA R E T> ⎯⎯⎯⎯⎯> | 840<br>170 |
| GTTATTTTTC CAATAAAAAG C Y F S | TAAAGAAGAT ATTTCTTCTA K E D ⎯CHV gD⎯ | AAATTTGAAC TTTAAACTTG K F E> ⎯⎯⎯⎯⎯> | 870<br>180 |

FIG. 28D

| | | | |
|---|---|---|---|
| CAACTTTTAT<br>GTTGAAAATA<br>P  T  F  M | GGAATGGTGT<br>CCTTACCACA<br>E  W  C<br>__CHV gD__ | AAGGAATCTA<br>TTCCTTAGAT<br>K  E  S><br>_____> | 900<br>190 |
| GATCTGTAGG<br>CTAGACATCC<br>R  S  V  G | AGCATCAAAA<br>TCGTAGTTTT<br>A  S  K<br>__CHV gD__ | GTTGACGATG<br>CAACTGCTAC<br>V  D  D><br>_____> | 930<br>200 |
| AACTTTTTA<br>TTGAAAAAT<br>E  L  F  Y | TCTAAATAGA<br>AGATTTATCT<br>L  N  R<br>__CHV gD__ | GCTGGTCCCC<br>CGACCAGGGG<br>A  G  P><br>_____> | 960<br>210 |
| AAACCCTGCT<br>TTTGGGACGA<br>Q  T  L  L | TAAATATTAT<br>ATTTATAATA<br>K  Y  Y<br>__CHV gD__ | GTTATTAAAG<br>CAATAATTTC<br>V  I  K><br>_____> | 990<br>220 |
| ATTTTTATAG<br>TAAAAATATC<br>D  F  Y  R | ACTTAACGGT<br>TGAATTGCCA<br>L  N  G<br>__CHV gD__ | AGAGAACCTC<br>TCTCTTGGAG<br>R  E  P><br>_____> | 1020<br>230 |
| CAATAAAATT<br>GTTATTTTAA<br>P  I  K  F | TAAAGAAGCT<br>ATTTCTTCGA<br>K  E  A<br>__CHV gD__ | CTTAGATACG<br>GAATCTATGC<br>L  R  Y><br>_____> | 1050<br>240 |
| ATATACCATA<br>TATATGGTAT<br>D  I  P  Y | TAAAGTGAAT<br>ATTTCACTTA<br>K  V  N<br>__CHV gD__ | GATAAATTTG<br>CTATTTAAAC<br>D  K  F><br>_____> | 1080<br>250 |
| ATGATGAATT<br>TACTACTTAA<br>D  D  E  L | ACCATCGAGG<br>TGGTAGCTCC<br>P  S  R<br>__CHV gD__ | CCACATATTA<br>GGTGTATAAT<br>P  H  I><br>_____> | 1110<br>260 |
| GTAATACTAT<br>CATTATGATA<br>S  N  T  I | TAATAAAACT<br>ATTATTTTGA<br>N  K  T<br>__CHV gD__ | ATTAAAGAAA<br>TAATTTCTTT<br>I  K  E><br>_____> | 1140<br>270 |

FIG. 28E

```
TTGTAAATCT      TGAAGATTAT      TTTAAAAATA          1170
AACATTTAGA      ACTTCTAATA      AAATTTTTAT
  I  V  N  L     E   D   Y       F   K   N>         280
                 __CHV gD__                 >

CAAATGTTAT      AGATACTACT      ACCCCAACAC          1200
GTTTACAATA      TCTATGATGA      TGGGGTTGTG
  T  N  V  I      D   T   T      T   P   T>         290
                 __CHV gD__                 >

CAATAAATAA      TACCCCAAAA      AATATAACCG          1230
GTTATTTATT      ATGGGGTTTT      TTATATTGGC
  P  I  N  N      T   P   K      N   I   T>         300
                 __CHV gD__                 >

TGGGAATTGT      TATAATTATA      TTAATAATAC          1260
ACCCTTAACA      ATATTAATAT      AATTATTATG
  V  G  I  V      I   I   I      L   I   I>         310
                 __CHV gD__                 >

TATTTATAAT      TGGATTTTTT      GTTTATAAAA          1290
ATAAATATTA      ACCTAAAAAA      CAAATATTTT
  L  F  I  I      G   F   F      V   Y   K>         320
                 __CHV gD__                 >

GACAAAAAAT      ATATAATAAT      TATAAAAAAT          1320
CTGTTTTTTA      TATATTATTA      ATATTTTTTA
  R  Q  K  I      Y   N   N      Y   K   K>         330
                 __CHV gD__                 >

TAACAACAAA      TGTTTAGGAA      TTCTTTTTAT          1350
ATTGTTGTTT      ACAAATCCTT      AAGAAAAATA
  L  T  T  N      V>                                335
__CHV gD__           >

TGATTAACTA      GTCAAATGAG      TATATATAAT          1380
ACTAATTGAT      CAGTTTACTC      ATATATATTA
                 __C6 flank     ing arm___>

TGAAAAAGTA      AAATATAAAT      CATATAATAA          1410
ACTTTTTCAT      TTTATATTTA      GTATATTATT
         C6     flanking        arm_____>

TGAAA                                               1415
ACTTT
_____>
```

NUCLEOTIDE AND AMINO ACID SEQUENCES OF CANINE HERPESVIRUS GD AND USES THEREFOR

RELATED APPLICATIONS

This application is a division of application Ser. No. 08/413,118, filed Mar. 29, 1995, now U.S. Pat. No. 5,688,920, which is a continuation in part of application Ser. No. 08/220,151, filed Mar. 30, 1994, now U.S. Pat. No. 5,529,780.

Each of the above-mentioned patents are hereby incorporated herein by reference.

FIELD OF THE INVENTION

This invention relates to canine herpesvirus (CHV), nucleotides or isolated nucleic acids encoding the CHV gB, gC and gD glycoproteins, and the amino acid sequences thereof, vectors, such as a recombinant poxvirus, e.g., vaccinia and avipox virus recombinants, containing the CHV gB, gC and/or gD coding or expressing the same, glycoproteins therefrom, vaccines, immunological or antigenic compositions from the nucleotide (such as from vectors, for instance, recombinant poxvirus, e.g., vaccinia or avipox virus recombinants containing the CHV, gB, gC and/or gD coding and expressing glycoprotein(s) therefrom), or, from the glycoproteins, for instance, from expression of the nucleotides in a vector system, and, to methods employing the nucleotides, glycoproteins, and compositions.

Several publications are cited in the following text, with full citation of each set forth in the section headed References. The publications cited throughout the text are hereby incorporated herein by reference.

BACKGROUND OF THE INVENTION

Canine herpesvirus (CHV) causes a fatal, hemorrhagic disease in neonatal puppies and a self-limiting, usually subclinical, upper respiratory tract infection in adult dogs (Appel, 1987). Little is known about the genomic structure of CHV. The genome has not been mapped and no nucleotide sequence has been published. In particular, genes encoding immunologically pertinent proteins have not been identified.

Herpesvirus glycoproteins mediate essential viral functions such as cellular attachment and penetration, cell to cell spread of the virus and, importantly, determine the pathogenicity profile of infection. Herpesvirus glycoproteins are critical components in the interaction with the host immune system (Spear, 1985a; Spear 1985b). Herpesvirus glycoproteins are antigens recognized by both the humoral and cellular immune systems and, have been shown to evoke protective immune responses in vaccinated hosts (Wachsman et al., 1987; Marchioli et al., 1987; Eberle et al., 1980; Papp-Vid et al., 1979).

During a herpesvirus infection, the majority of the immune response is directed against viral envelope glycoproteins. These antigens have been shown to elicit both humoral and cellular immune responses. Several reports have indicated that in other herpesvirus systems immunization with the herpesvirus gB, gC and/or gD glycoproteins can induce a protective immune response.

The well characterized glycoproteins of herpes simplex virus include gB, gC, gD, gE, gG, gH, gI, gJ, gK, gL and gM (Spear, 1985a; Spear 1985b; Ackermann et al., 1986; Frink et al. 1983; Frame et al., 1986; Longnecker et al., 1987; Richman et al., 1986; Swain et al., 1985; Zezulak, 1984; Roizman and Sears, 1990; Hutchinson et al., 1992a; Hutchinson et al., 1992b; Baines and Roizman, 1993). A number of studies have indicated the importance of herpes simplex virus glycoproteins in eliciting immune responses. Hence, it has been reported that gB and gD can elicit important immune responses (Berman et al., 1983; Cantin et al., 1987; Cremer et al., 1985; Lasky et al., 1984; Martin et al., 1987a; Martin et al., 1987b; Paoletti et al., 1984; Perkus et al., 1985; Rooney et al., 1988; Wachsman et al., 1987; Zarling et al., 1986a; Zarling et al., 1986b). gC can stimulate class I restricted cytotoxic lymphocytes (Glorioso et al., 1985; Rosenthal et al., 1987) whereas gD can stimulate class II cytotoxic T cell responses (Martin et al., 1987a; Martin et al., 1987b; Wachsman et al., 1987; Zarling et al., 1986a; Zarling 1986b). gG was shown to be a target for complement-dependent antibody directed virus neutralization (Sullivan et al., 1987; Sullivan et al., 1988). A number of glycoproteins from other herpesviruses have also been shown to elicit important immune responses.

Both subtypes of equine herpesvirus (EHV) express six abundant glycoproteins (Allen et al., 1986; Allen et al., 1987). The genomic portions of the DNA sequences encoding gp2, gp10, gp13, gp14, gp17/18, and gp21/22a have been determined using lambda gtll expression vectors and monoclonal antibodies (Allen et al., 1987). Glycoproteins gp13 and gp14 were located in the same locations within the L component of the genome to which the gC and gB homologs, respectively, of herpes simplex virus map (Allen et al., 1987). The envelope glycoproteins are the principal immunogens of herpesviruses involved in eliciting both humoral and cellular host immune responses (Ben-Porat et al., 1986; Cantin et al., 1987; Glorioso et al., 1984; Wachsman et al., 1988; Wachsman et al., 1989) and so are of the highest interest for those attempting to design vaccines.

Recently, the nucleotide sequence of the Kentucky T431 strain of the EHV-1 transcriptional unit encoding gp13 has been reported (Allen et al., 1988). The glycoprotein was shown to be homologous to the herpes simplex virus (HSV) gC-1 and gC-2, to the pseudorabies virus (PRV) gIII and the varicella-zoster virus (VZV) gpV (Allen et al., 1988). EHV-1 gp13 is thus the structural homolog of the herpesvirus gC-like glycoproteins.

The nucleotide sequence of EHV-1 gp14 (Whalley et al., 1989; Riggio et al., 1989) has recently been reported. Analysis of the predicted amino acid sequence of gp14 glycoprotein revealed significant homology to the corresponding glycoprotein of HSV, gB.

Monoclonal antibodies directed against some EHV-1 glycoproteins have been shown to be neutralizing (Sinclair et al., 1989). Passive immunization experiments demonstrated that monoclonal antibodies directed against gp13 or gp14 (Shimizu et al., 1989) or against gp13, gp14 or gp17/18 (Stokes et al., 1989) could protect hamsters against a lethal challenge. Other gB and gC glycoprotein analogs are also involved in protection against diseases caused by alphaherpesviruses (Cantin et al., 1987; Cranage et al., 1986; Glorioso et al., 1984).

Pseudorabies virus (PRV), an alphaherpesvirus, is the causative agent of Aujesky's disease. The PRV genome consists of a $90 \times 10^6$ dalton double stranded DNA (Rubenstein et al., 1975) separated by inverted repeat sequences into unique long ($U_L$) or unique short ($U_S$) segments (Stevely, 1977; Ben-Porat et al., 1979). The PRV genome encodes approximately 100 polypeptides whose expression is regulated in a cascade-like fashion similar to other herpesviruses (Ben-Porat et al., 1985; Hampl et al., 1984).

PRV glycoprotein gp50 is the Herpes simplex virus type 1 (HSV-1) gD analog (Wathen et al., 1984). The DNA open reading frame encodes 402 amino acids (Petrovskis et al., 1986). The mature glycosylated form (50–60 kDa) contains O-linked carbohydrate without N-linked glycosylation (Petrovskis et al., 1986). Swine serum is highly reactive with PRV gp50, suggesting its importance as an immunogen. Monoclonal antibodies to gp50 neutralize PRV in vitro with or without complement (Wathen et al., 1984; Wathen 1985; Eloit et al., 1988) and passively protect mice (Marchioli et al., 1988; Wathen et al., 1985; Eloit et al., 1988) and swine (Marchioli et al., 1988). Vaccinia virus recombinants expressing PRV gp50 induced serum neutralizing antibodies and protected both mice and swine against lethal PRV challenge (Kost et al., 1989; Marchioli et al., 1987; Ishii et al., 1988).

PRV gIII is the HSV-1 gC analog (Robbins et al., 1986). Functional replacement of PRV gIII by HSVgC was not observed (Whealy et al., 1989). Although PRV gIII is nonessential for replication in vitro (Wathen et al., 1986; Robbins et al., 1986), the mature glycosylated form (98 kDa) is an abundant constituent of the PRV envelope. Anti-gpIII monoclonal antibodies neutralize the virus in vitro with or without complement (Hampl et al., 1984; Eloit et al., 1988; Wathen et al., 1986) and can passively protect mice and swine (Marchioli et al., 1988). The PRV glycoprotein gIII can protect mice and swine from lethal PRV challenge after immunization with a Cro/gIII fusion protein expressed in E. coli (Robbins, A., R. Watson, L. Enquist, European Patent application 0162738A1) or when expressed in a vaccinia recombinant (Panicali, D., L. Gritz, G. Mazzara, European Patent application 0261940A2).

PRV gpII is the HSV-1 gB homolog (Robbins et al., 1987). Monoclonal antibodies directed against PRV gpII have been shown to neutralize the virus in vitro (Ben-Porat et al., 1986) with or without complement (Wittmann et al., 1989). Moreover, passive immunization studies demonstrated that neutralizing monoclonal antibodies partially protected swine (Marchioli et al., 1988). Immunization with NYVAC (highly attenuated vaccinia virus)-based recombinants expressing pseudorabies virus (PRV) gII (gB) or gp50 (gD) has been shown to protect swine against a virulent PRV challenge (Brockmeier et al., 1993). Furthermore, vaccinia recombinants expressing PRV gII and gp50, or gII, gIII (gC) and gp50 have been shown to elicit a higher level of protection than recombinants expressing gII or gp50 alone, suggesting a potential synergistic effect with these glycoproteins (Riviere et al., 1992).

The herpes simplex virus type 1 (HSV1) genome encodes at least eleven antigenically distinct glycoproteins: gB, gC, gD, gE, gG, gH, gI, gJ, gK, gL and gM (Roizman et al., 1990). Mice immunized with purified HSV1 gB, gC or gD are protected against lethal HSV1 challenge (Chan, 1983). Mice have also been protected against lethal HSV1 or HSV2 challenge by passive immunization with antibodies to total HSV1 (Davis et al., 1979) or HSV2 (Oakes et al., 1978) virus and with antibodies to the individual HSV2 gB, gC, gD or gE glycoproteins (Balachandran et al., 1982).

Vaccinia virus vectors expressing HSV1 gB (McLaughlin-Taylor et al., 1988) and HSV1 gC (Rosenthal et al., 1987) have been shown to induce cytotoxic T-cell responses. In addition, it has been shown that mice immunized with recombinant vaccinia virus expressing either HSV1 gB (Cantin et al., 1987), HSV1 gC (Weir et al., 1989) or HSV1 gD (Paoletti et al., 1984) are protected against a lethal challenge of HSV1. A recombinant vaccinia virus expressing HSV1 gD has also been shown to be protective against HSV2 in a guinea pig model system (Wachsman et al., 1987).

Bovine herpesvirus 1 (BHV1) specifies more than 30 structural polypeptides, 11 of which are glycosylated (Misra et al., 1981). Three of these glycoproteins, gI, gIII and gIV, have been characterized and found to be homologous to the herpes simplex virus (HSV) glycoproteins gB, gC and gD (Lawrence et al., 1986; Zamb, 1987). Immunization with purified bovine herpesvirus type 1 (BHV1) gI (gB), gIII (gC) and/or gIV (gD) has been shown to protect cattle against a BHV1/*Pasteurella haemolytica* challenge (Babiuk et al., 1987).

Feline herpesvirus type-1 (FHV-1) has been shown to contain at least 23 different proteins (Meas et al., 1984; Fargeaud et al., 1984). Of these, at least five are glycosylated (Fargeaud et al., 1984; Compton, 1989) with reported molecular masses ranging from 120 kDa to 60 kDa. The FHV-1 glycoproteins have been shown to be immunogenic (Meas et al., 1984; Compton, 1989). Like several other alphaherpesviruses, FHV-1 appears to have a homolog of glycoprotein B (gB) of HSV-1 (Maeda et al., 1992). The FHV-1 gB glycoprotein is a 134 kDa complex which is dissociated with B-mercaptoethanol into two glycoproteins of 66 kDa and 60 kDa. The FHV-1 DNA genome is approximately 134 Kb in size (Rota et al., 1986).

Epstein Barr Virus (EBV), a human B lymphotropic herpesvirus, is a member of the genus lymphocryptovirus which belongs to the subfamily gammaherpesvirus (Roizman et al., 1990). Since the EBV genome was completely sequenced (Baer et al., 1984) as the genomes of VZV (Davison et al., 1986), HSV1 (McGeoch et al., 1988), MCHV (Chee et al., 1990) and EHV1 (Telford et al., 1992) numerous homologies between these different herpesviruses have been described (Kieff et al., 1990).

Human cytomegalovirus (HCMV) is a member of the betaherpesvirinae subfamily (family Herpesviridae). Three immunologically distinct families of glycoproteins associated with the HCMV envelope have been described (Gretch et al., 1988): gCI (gp55 and gp93–130); gCII (gp47–52); and gCIII (gp85–p145). The gene coding for gCI is homologous to HSVI gB.

In addition, immunization with a fowlpox recombinant expressing Marek's disease virus (MDV) gB has been shown to protect chickens against a virulent MDV challenge (Nazarian et al., 1992).

The results of these studies indicate that an immune response against gB, gC and/or gD glycoproteins can protect target species animals against a herpesvirus challenge and, that the provision of nucleotides for CHV gB, gC and gD glycoproteins is a valuable advance over the current state of the art as it allows for the provision of the glycoproteins and, antigenic, immunological or vaccine compositions from the vector systems or from the glycoproteins. Further, the glycoproteins from expression of the nucleotides can be used to elicit antibodies which can be further used in antibody binding diagnostic assays, kits or tests for ascertaining the presence or absence in a sample such as sera of the glycoprotein(s) and therefore the presence or absence of CHV or of an immune or antigenic response (to either CHV or to the glycoproteins). Thus, many utilities flow from the provision of the nucleotides for CHV gB, gC and gD glycoproteins.

Various vector systems exist for the expression of exogenous DNA, such as the phage, e.g., lambda, and *E. coli* systems (Allen et al., 1987; Robbins, EPA 0162738A1; Panicali, EPA 0261940A2, each of which is expressly incorporated herein by reference).

Vaccinia virus and more recently other poxviruses have been used for the insertion and expression of foreign genes.

The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179, 993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, $TK^-$ recombinant vaccinia generated equivalent anti-vaccinia neutralizing antibodies as compared with the parental $TK^+$ vaccinia virus, indicating that in this test system the loss of TK function does not significantly decrease immunogenicity of the vaccinia virus vector. Following intranasal inoculation of mice with $TK^-$ and $TK^+$ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmitt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA$^-$ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982b) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993 a,b; Taylor et al., 1992; 1991b; 1988b).

Thus, heretofore, the nucleotide and amino acid sequences for the CHV gB, gC and gD glycoproteins, have not been taught or suggested and, providing these sequences would be of great value. Further, vaccine, antigenic or immunological compositions from the nucleotides for the CHV gB, gC and gD glycoproteins (such as from vector systems containing such nucleotides) as well as from the glycoproteins themselves (such as from expression by the vector systems) have not heretofore been taught or suggested and, these nucleotides, vector systems, glycoproteins and compositions would be of great value.

OBJECTS AND SUMMARY OF THE INVENTION

It is therefore an object of the invention to provide nucleotides or isolated nucleic acids coding for CHV gB, gC and gD.

It is a further object of the invention to provide vectors containing nucleotides or isolated nucleic acids coding for CHV gB, gC and/or gD.

It is another object of the invention to provide CHV gB, gC and/or gD glycoproteins, especially from expression of nucleotides or isolated nucleic acids therefor in a vector system.

It is an additional object of the invention to provide antigenic, vaccine or immunological compositions from the CHV gB, gC and/or gD nucleotides or isolated nucleic acids or a vector containing them or, from the glycoproteins themselves, such as by way of expression by the vector.

It is yet another object of this invention to provide modified recombinant viruses, which viruses have enhanced safety, and to provide a method of making such recombinant viruses.

It is an additional object of this invention to provide a recombinant poxvirus antigenic, vaccine or immunological composition having an increased level of safety compared to known recombinant poxvirus antigenic, vaccine or immunological compositions.

It is a further object of this invention to provide a modified vector for expressing a gene product in a host, wherein the vector is modified so that it has attenuated virulence in the host.

It is another object of this invention to provide a method for expressing a gene product, such as CHV gB, gC and/or gD, in a cell cultured in vitro using a modified recombinant virus or modified vector having an increased level of safety.

These and other objects and advantages of the present invention will become more readily apparent after consideration of the following.

The present invention involves the elucidation of the CHV gB, gC and gD nucleotides, glycoproteins therefrom and, antigenic, vaccine or immunological compositions employing the nucleotide sequences and the glycoproteins.

Accordingly, the present invention provides a nucleotide or isolated nucleic acid coding for canine herpesvirus gB glycoprotein.

The present invention provides a nucleotide or isolated nucleic acid coding for canine herpesvirus gC glycoprotein.

The present invention provides a nucleotide or isolated nucleic acid coding for canine herpesvirus gD glycoprotein.

The nucleotides are preferably DNA. The nucleotides or isolated nucleic acids preferably have the DNA sequences as set forth in FIGS. 1, 4 and 7.

The present invention also provides canine herpesvirus glycoprotein gB.

The present invention provides canine herpesvirus glycoprotein gC.

The present invention provides canine herpesvirus glycoprotein gD.

The present invention further provides a vector containing the nucleotide or isolated nucleic acid for canine herpesvirus gB, gC and/or gD. Preferably the vector is a recombinant poxvirus such as a recombinant vaccinia or avipox virus, more preferably the vaccinia or avipox virus is attenuated such as NYVAC, ALVAC or TROVAC.

Thus, in one preferred aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus and canarypox virus. The modified recombinant virus can include, within a non-essential region of the virus genome, a heterologous DNA sequence which encodes a CHV antigenic protein, e.g., CHV gC, gB, and gD or any combination thereof.

In a still further preferred aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for a CHV gB, gC and gD, or any combination thereof. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992).

The present invention still further provides an antigenic, vaccine or immunological composition for inducing an antigenic or immunological response in a host, such as a canine, comprising a suitable vector containing the nucleotide(s) or isolated nucleic acid(s) for canine herpesvirus gB, gC and/or gD and a suitable carrier; or, canine herpesvirus gB, gC and/or gD glycoprotein(s), such as from expression thereof in a vector containing the nucleotide(s) of the invention, and a suitable carrier.

The present invention yet further provides methods employing the inventive nucleotide(s) or isolated nucleic acid(s), glycoprotein(s), composition(s).

Thus, the invention provides a method for preparing canine herpesvirus gB, gC and/or gD comprising inserting the nucleotide(s) or isolated nucleic acid(s) therefor into a suitable vector, cultivating the vector, and, collecting the glycoprotein from the vector. The vector can be a poxvirus, such as vaccinia or avipox virus, a phage such as lambda, or *E. coli* or any other suitable virus or bacterial vector. The cultivating can be infecting cells susceptible to viral infection by the virus vector or, growing colonies of the bacterial vector system, such as by plate or broth methods. And, collecting can be by separating the glycoprotein(s) from the viral-infected cells or from the bacterial cells.

Thus, in a preferred aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., CHV gB, gC and gD, or any combination thereof.

Likewise, the invention provides a method for inoculating or for stimulating an antigenic or immunological response in a host such as a canine against canine herpesvirus comprising administering the inventive antigenic, vaccine or immunological composition to the host, e.g., canine. Additionally, the invention includes an antibody elicited by the expression of the inventive nucleotide(s). The antibody can be generated into a monoclonal antibody by known techniques and, the antibody or the monoclonal antibody can be employed in a binding diagnostic assay, test or kit to determine the presence or absence of CHV gB, gC and/or gD in a sample such as sera and therefore the presence or absence of CHV or, of an antibody or immune response to CHV or to glycoproteins thereof.

These and other embodiments within the present invention are described or are obvious from the following detailed description.

BRIEF DESCRIPTION OF DRAWINGS

The following detailed description, given by way of example, but not intended to limit the invention solely to the specific embodiments described, may best be understood in conjunction with the accompanying drawings, in which:

FIG. 1 shows the nucleotide sequence and predicted amino acid sequence of the CHV gB homologue (SEQ ID NOS:1, 2);

FIG. 2 shows the hydropathicity analysis of the CHV gB homologue;

FIGS. 3A and 3B show the amino acid homology of 8 gB homologues (SEQ ID NOS:3–10);

FIG. 4 shows the nucleotide sequence and predicted amino acid sequence of the CHV gC homologue and ORF2 (SEQ ID NOS:11–13);

FIG. 5 shows the hydropathicity analysis of the CHV gC homologue;

FIG. 6 shows the amino acid homology of 4 gC homologues (SEQ ID NOS:14–17);

FIG. 7 shows the nucleotide sequence and predicted amino acid sequence of the CHV gD homologue; SEQ ID NOS:18–20);

FIG. 8 shows the hydropathicity analysis of the CHV gD homologue;

FIG. 9 shows amino acid homology of 4 gD homologues (SEQ ID NOS:16–20);

FIG. 10 schematically shows a method for the construction of plasmid pSD460 for deletion of thymidine kinase gene and generation of recombinant vaccinia virus vP410;

FIG. 11 schematically shows a method for the construction of plasmid pSD486 for deletion of hemorrhagic region and generation of recombinant vaccinia virus vP553;

FIG. 12 schematically shows a method for the construction of plasmid pMP494Δ for deletion of ATI region and generation of recombinant vaccinia virus vP618;

FIG. 13 schematically shows a method for the construction of plasmid pSD467 for deletion of hemagglutinin gene and generation of recombinant vaccinia virus vP723;

FIG. 14 schematically shows a method for the construction of plasmid pMPCK1Δ for deletion of gene cluster [C7L–K1L] and generation of recombinant vaccinia virus vP804;

FIG. 15 schematically shows a method for the construction of plasmid pSD548 for deletion of large subunit, ribonucleotide reductase and generation of recombinant vaccinia virus vP866 (NYVAC);

FIG. 16 schematically shows a method for the construction of plasmid pRW842 for insertion of rabies glycoprotein G gene into the TK deletion locus and generation of recombinant vaccinia virus vP879;

FIG. 17 shows the DNA sequence (SEQ ID NO:62) of a canarypox PvuII fragment containing the C5 ORF.

FIGS. 18A and 18B schematically show a method for the construction of recombinant canarypox virus vCP65 (ALVAC-RG);

FIG. 19 shows schematically the ORFs deleted to generate NYVAC;

FIG. 20 shows the nucleotide sequence (SEQ ID NO:72) of a fragment of TROVAC DNA containing an F8 ORF;

FIG. 21 shows the DNA sequence (SEQ ID NO:75) of a 2356 base pair fragment of TROVAC DNA containing the F7 ORF;

FIGS. 22A to 22D show graphs of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208);

FIG. 23 shows the nucleotide sequence of the I3L-promoted CHV gB gene contained in pCHV37 and vCP320;

FIG. 24 shows the nucleotide sequence of the ALVAC C6 flanking arms;

FIG. 25 shows the immunoprecipitation analysis of vCP320-infected cells (Lysates from $^{35}S$-labeled mock-infected cells (lane A), ALVAC-infected cells (lane B), vCP320-infected cells (lane C) and CHV-infected cells (lane D) were immunoprecipitated with a CHV gB-specific monoclonal antibody, 1125B2 (obtained from Rhone Merieux, Lyon, France), and resolved on an SDS-polyacrylamide gel. Molecular weight standards are resolved in lane E);

FIG. 26 shows the nucleotide sequence of the H6-promoted CHV gC gene contained in pCHV40 and vCP322;

FIG. 27 shows the immunoprecipitation analysis of vCP322-infected cells (Lysates from $^{35}S$-labeled mock-infected cells (lane A), ALVAC-infected cells (lane B), vCP322-infected cells (lane C) and CHV-infected cells (lane D) were immunoprecipitated with a CHV gC-specific monoclonal antibody, 2011A9 (obtained from Rhone Merieux, Lyon, France), and resolved on an SDS-polyacrylamide gel. Molecular weight standards are resolved in lane E);

FIG. 28 shows the nucleotide sequence of the H6-promoted CHV gD gene contained in pCHV26 and vCP294; and FIG. 29 shows the immunoprecipitation analysis of vCP294-infected cells (Lysates from $^{35}S$-labeled mock-infected cells (lane A), ALVAC-infected cells (lane B), vCP294-infected cells (lane C) and CHV-infected cells (lane D) were immunoprecipitated with a CHV gD-specific monoclonal antibody, 208D11 (obtained from Rhone Merieux, Lyon, France), and resolved on an SDS-polyacrylamide gel. Molecular weight standards are resolved in lane E).

DETAILED DESCRIPTION

Figure 2:
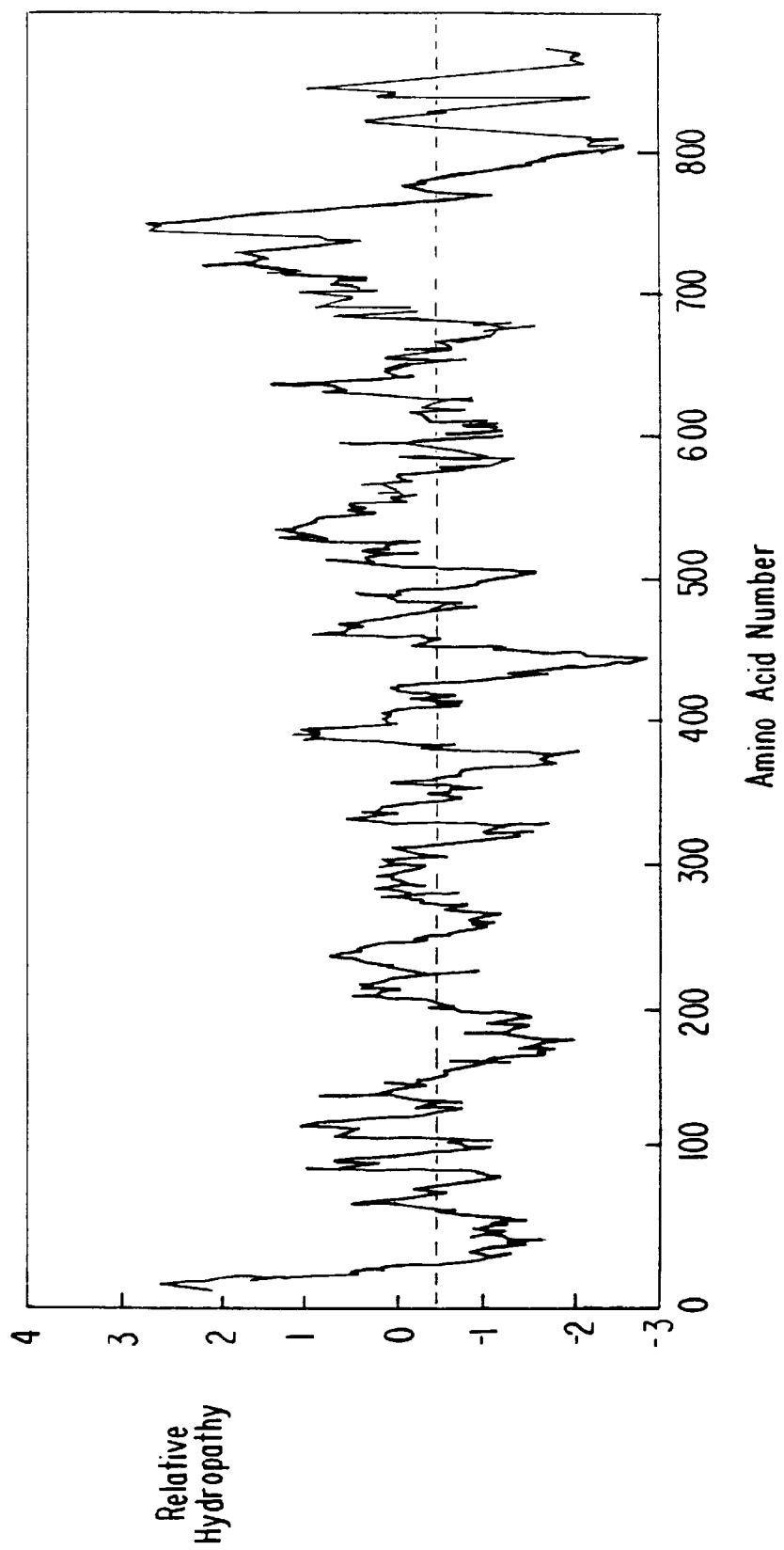

This invention provides nucleotides coding for the CHV gB, gC and gD genes. These genes encode polypeptides of 879, 459 and 345 amino acids, respectively. Comparison of the predicted amino acid sequence of these glycoproteins with the gB, gC and gD amino acid sequences of other herpesviruses indicates that CHV is an alpha-herpesvirus; a conclusion that is consistent with the previous classification of this virus according to biological properties. This analysis also revealed that the homology among gB homologues is greater than the homology among gC or gD homologues, suggesting that the structural and functional constraints on gB may be greater than those on gC or gD.

Alignment of homologous gB, gC and gD polypeptides revealed that the vast majority of cysteine residues are perfectly conserved. These results suggest that these cysteine residues, due to their ability to form disulfide bonds, are important in maintaining the structural and functional integrity of the gB, gC and gD glycoproteins. In fact, in HSV1 gD, it has been shown that cysteine 1 forms a disulfide bond with cysteine 5, cysteine 2 forms a disulfide bond with cysteine 6 and cysteine 3 forms a disulfide bond with cysteine 4 (Long et al., 1992). Furthermore, it has been shown that a mutation of any of these residues has a profound effect on the conformation, processing and function of the resulting glycoprotein (Wilcox et al., 1988; Long et al., 1990). Therefore, the conservation of cysteine residues in the glycoproteins of the invention may also have structural significance.

The high degree of homology among the gC, gD and, in particular, gB homologues also suggests that these glycoproteins have common functions. In fact, it has been shown that the BHV1 gB homologue can rescue a $gB^-$ PRV virus, indicating that these 2 glycoproteins are functionally equivalent (Kopp & Mettenleiter, 1992).

Alignment of the gB, gC and gD amino acid sequences also revealed that potential N-linked glycosylation sites are somewhat conserved. N-linked glycosylation is thought to play a role in a variety of functions, such as maintenance of protein conformation and protection against proteolytic degradation. The biological significance of N-linked carbohydrates on herpesvirus glycoproteins, however, is not completely understood. For example, tunicamycin treatment of HSV1 infected cells has been shown to inhibit the production of infectious virions (Pizer et al., 1980). In addition, endoglycosidase treatment of HSV1 virions has been shown to decrease infectivity (Kuhn et al., 1988). On the other hand, N-linked glycosylation of HSV1 gD does not appear to be absolutely essential, since mutagenesis of the glycosylation sites on this glycoprotein does not affect infectivity (Sodora et al., 1991). Therefore, although the glycosylation sites on the gB, gC and gD glycoproteins are relatively well conserved, proper glycosylation of each of these polypeptides may not be absolutely essential.

The G+C content of herpesviruses varies from 33%–75% (Roizman, 1982). It has been suggested that this extensive variability is due to a nonselective mutational bias based on the presence (or absence) of virally encoded or induced enzymes involved in nucleotide metabolism (Honess, 1984). For example, VZV and herpesvirus saimiri (HVS) both have relatively low G+C contents (46% and 46%, respectively) and both encode an enzyme, thymidylate synthetase, which is involved in TTP synthesis (Davison & Scott, 1986; Honess et al., 1986). HSV1, HCMV and EBV, on the other hand, have relatively high G+C contents (68%, 57% and 60%, respectively) and do not appear to encode a thymidylate synthetase (Honess et al., 1986). CHV has been determined by DNA density analysis to have the lowest G+C content of any herpesvirus, 33% (Plummer et al., 1969; Roizman, 1982); a value which is consistent with the relatively low G+C content of the nucleotides of the invention (29%). Without wishing it to be bound by the theory that CHV does not encode an enzyme involved in nucleotide metabolism, from the present invention the ORF located immediately downstream from the CHV gC gene is not homologous to VZV thymidylate synthetase. Therefore, if CHV contains a thymidylate synthetase gene, it is not found at the same genomic location as VZV.

Newborn pups exposed to CHV usually die without forming CHV-specific neutralizing antibodies. Also, the maternal antibodies or treatment with immune serum from seropositive dogs can protect pups from a fatal CHV infection (Carmichael, 1970). Therefore, serum neutralizing antibodies can protect pups against a fatal CHV infection. Likewise, serum neutralizing antibodies can protect adult dogs from the self-limiting subclinical, upper respiratory tract infection.

Three CHV glycoproteins, gp145/112, gp80 and gp47, are known to elicit CHV neutralizing antibodies (Xuan et al., 1991). The genes encoding these glycoproteins have not been identified. Without wishing to be bound by any one theory, it is possible, however, that these antigens are encoded by the gB, gC and gD genes of this invention. Since several reports have indicated that an immune response against gB, gC and/or gD can provide protection of target species animals against a herpesvirus challenge (Babiuk et al., 1987; Nazarian et al., 1992; Riviere et al., 1992; Brockmeier et al., 1993), the CHV gB, gC and gD genes of this invention provide efficacious CHV glycoproteins, immunological or vaccine compositions and methods of using the same.

In particular, the nucleotides of this invention can be inserted into any suitable vector system for expression. For instance, the nucleotide(s) can be inserted into any suitable bacterial vector system such as the *E. coli* system, employing known methods (see, e.g., Robbins, EPA 0162738A1; Panicali, EPA 0261940A2).

The nucleotide(s) can be inserted into any suitable phage or viral vector system such as lambda, poxvirus, herpesvirus (see Roizman, U.S. Pat. No. 4,769,331, incorporated herein by reference), baculovirus, polio virus (see Kitson et al., J. Virol. 65, 3068–3075, 1991, incorporated herein by reference), and adenovirus (see Grunhaus et al., 1992, "Adenovirus as cloning vectors," Seminars in Virology (Vol. 3) p. 237–52, 1993; Ballay et al., EMBO Journal, vol. 4, p. 3861–65; Graham, Tibtech 8, 85–87, April, 1990; Prevec et al., J. Gen. Virol. 70, 429–434, each of which is incorporated herein by reference) systems employing known methods.

The preferred vector system is a poxvirus vector system, especially an avipox vaccinia virus system wherein recombination is as in U.S. Pat. Nos. 4,769,330, 4,772,848, 4,603,112, 5,100,587 and 5,179,993. However, an attenuated poxvirus system is even more preferred.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L–K1L) vP804; and (6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCS) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH") (U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

After growing the bacteria or infecting cells with the recombinant virus, the glycoprotein(s) are collected by known techniques such as chromatography (see Robbins, EPA 0162738A1; Panicali, EPA 0261940A2).

The collected glycoprotein(s) can then be employed in a vaccine, antigenic or immunological composition which also contains a suitable carrier. Accordingly, the inventive nucleotides are quite useful.

Alternatively, the viral vector system, especially the preferred poxvirus vector system, can be employed in a vaccine, antigenic or immunological composition which also contains a suitable carrier. The CHV recombinant poxvirus in the composition expresses the CHV glycoprotein in vivo after administration or inoculation.

The antigenic, immunological or vaccine composition of the invention (either containing glycoprotein(s) expressed from a vector system containing the inventive nucleotide(s) or containing a suitable vector system such as the CHV recombinant poxvirus) is administered to pups in the same fashion as maternal antibodies or immune serum from seropositive dogs (Carmichael, 1970). Seronegative dogs are administered the composition in the same fashion as other antigenic, vaccine or immunological compositions are administered. One skilled in the veterinary arts can determine dosage from this disclosure without undue experimentation, taking into consideration such factors as the age, weight, breed, sex and general health of the particular dog or pup.

Additionally, the inventive recombinant poxvirus and the expression products therefrom stimulate an immune or antibody response in animals. From those antibodies, by techniques well-known in the art, monoclonal antibodies can be prepared and, those monoclonal antibodies or the antigens expressed from the inventive nucleotides, can be employed in well known antibody binding assays, diagnostic kits or tests to determine the presence or absence of particular CHV gB, gC and/or gD antigen(s) or antibodies thereto and therefrom the presence or absence of the virus or, to determine whether an immune response to the virus or antigen(s) has simply been stimulated.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Additionally, the inventive nucleotides can be used as probes to ascertain the presence of CHV DNA in samples, as well as in the generation of PCR primers for replicating or cloning CHV DNA. Methods for using DNA as probes or for preparing PCR primers are known in the art.

Thus, the inventive nucleotides and expression products of the inventive nucleotides (and therefore the nucleotides) are quite useful.

The following non-limiting Examples are given by way of illustration only and are not to be considered a limitation of this invention.

EXAMPLES

Methods and Materials

Preparation of genomic CHV DNA. CHV (obtained from L. Carmichael, Cornell University) was propagated on Madin-Darby canine kidney (MDCK) cells (ATCC CCL34). Viral DNA was isolated by standard methodology (Tartaglia et al., 1990).

DNA Hybridization.

CHV genomic DNA was digested with restriction enzymes, run on agarose gels and transferred to Gene-Screen membranes (New England Nuclear) under conditions recommended by the manufacturers. Hybridizations were performed at 44° C., 53° C. or 59° C. in 1M NaCl, 1% SDS and 10% dextran sulfate. The hybridization probe included a 1800 bp BamHI-XbaI fragment, containing an internal segment of the feline herpesvirus (FHV) gB gene, a 950 bp BamHI-EcoRI fragment, containing the 3'-end of the FHV gC gene and a 970 bp BamHI-HindIII fragment, containing the 3'-end of the FHV gD gene (Audonnet, unpublished results).

Cloning and DNA Sequencing.

CHV genomic fragments were subcloned into pBluescriptSK (Stratagene). Plasmid DNA was prepared and manipulated using standard techniques. Nucleotide sequencing was performed on double-stranded plasmid templates, using the modified T7 enzyme, Sequenase (U.S. Biochemical Corporation), and standard protocols recommended by the manufacturer. M13 forward and reverse primers were used to obtain initial sequence, and custom primers, prepared with a Biosearch 8700 or an Applied Biosystems 380B oligonucleotide synthesizer, were used for subsequent reactions.

DNA and Amino Acid Sequence Analyses.

DNA and amino acid sequence analyses were performed with PC/GENE (IntelliGenetics, Incorporated), ALIGN Plus (Scientific and Educational Software) and IBI-Pustell (International Biotechnologies, Incorporated) software packages. Homology searches were conducted on the SWISS-PROT (Release 20 or 23) (IntelliGenetics, Incorporated) database, using the FASTA program (Pearson & Lipman, 1988).

DNA Cloning and Synthesis.

Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection.

The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scale from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

Identification and Sequencing of the CHV gB Gene

Hybridization of CHV genomic DNA at relatively low stringency with a radiolabelled probe containing the feline herpesvirus (FHV) gB, gC and gD genes (Audonnet, unpublished results) identified one complimentary sequence. A 6 kb XbaI fragment containing this sequence was cloned and the nucleotide sequence of the hybridizing region was determined. The sequence of the nucleotide coding the CHV gB gene is shown in FIG. 1 together with the predicted amino acid expression (gB glycoprotein) therefrom. The putative transmembrane regions and potential TATA, CAAT and polyadenylation signal sequences are underlined. Nucleotides and predicted amino acid residues are numbered to the right of the sequence.

An open reading frame (ORF) starting at position 201 and ending at position 2840 was identified. The translation product (predicted) of this ORF is 879 amino acids long. Comparison of this amino acid sequence with the SWISS-PROT (Release 20) database revealed significant homology with the gB glycoprotein of numerous herpesviruses. Additional analyses revealed that the CHV gene product (predicted) was more homologous to the gB glycoprotein of alpha-herpesviruses, such as herpes simplex virus type 1 (HSV1), than beta- or gamma-herpesviruses, such as human cytomegalovirus (HCMV) or Epstein-Barr virus (EBV). These analyses and the results thereof are shown in Table 1 below. These results indicate that CHV should be classified as an alpha-herpesvirus; a conclusion that is consistent with the previous classification of this virus according to biological properties (Carmichael et al., 1965; Roizman, 1982).

TABLE 1

HOMOLOGY BETWEEN THE PREDICTED AMINO ACID
SEQUENCES OF 10 HERPESVIRUS gB GLYCOPROTEINS

|      | FHV | EHV1 | PRV | BHV1 | VZV | MDV | HSV1 | HCMV | EBV |
|------|-----|------|-----|------|-----|-----|------|------|-----|
| CHV  | 78  | 61   | 61  | 59   | 55  | 52  | 50   | 29   | 27  |
| FHV  |     | 57   | 59  | 58   | 51  | 48  | 48   | 27   | 27  |
| EHV1 |     |      | 52  | 52   | 47  | 45  | 44   | 27   | 26  |
| PRV  |     |      |     | 63   | 52  | 48  | 50   | 29   | 29  |
| BHV1 |     |      |     |      | 52  | 46  | 48   | 28   | 28  |
| VZV  |     |      |     |      |     | 49  | 48   | 30   | 28  |
| MDV  |     |      |     |      |     |     | 48   | 30   | 29  |
| HSV1 |     |      |     |      |     |     |      | 28   | 29  |
| HCMV |     |      |     |      |     |     |      |      | 32  |

Values in Table 1 were obtained using the ALIGN Plus program and are expressed as percent homology. The entire gB amino acid sequence was used. The alignment parameters were: mismatch penalty=2, open gap penalty=4, extended gap penalty=1. References: FHV (Maeda et al., 1992), EHV1 (Whalley et al., 1989), PRV (Robbins et al., 1987), BHV1 (Whitbeck et al., 1988), VZV (Keller et al., 1986), MDV (Ross et al., 1989), HSV1 (Bzik et al., 1984), HCMV (Kouzarides et al., 1987) and EBV (Pellett et al., 1985).

Example 2

Analysis of the CHV gB Nucleotide Sequence

The 5'- and 3'-noncoding regions of the CHV gB gene contain numerous RNA polymerase II regulatory sequence motifs, such as TATA box, CAAT box and polyadenylation signal sequences (Corden et al., 1980; Proudfoot & Brownlee, 1976) (FIG. 1). Potential TATA box sequences are found at positions 34, 36, 119 and 148, approximately 165 bp, 160 bp, 80 bp and 50 bp upstream from the CHV gB initiation codon. Potential CAAT box sequences (ATTG) are found at positions 89, 97 and 165, approximately 110 bp, 100 bp and 35 bp upstream from the gB initiation codon. Potential polyadenylation signal sequences (AATAAA) are found at positions 2839 and 2961, approximately 0 bp and 120 bp downstream from the CHV gB termination codon.

The nucleotide sequence surrounding the initiation codon has been shown to affect the efficiency of translation initiation (Kozak, 1986). In particular, the sequence, [A/G]NN ATGG, has been found to be most efficient. Therefore, relative to Kozak's rules, the nucleotide sequence surrounding the CHV gB initiation codon (AGTATGT) is favorable at position −3, but not at position +4 (FIG. 1). The fact that the CHV gB gene does not follow Kozak's rules is not unusual. The FHV (Maeda et al., 1992), PRV (Robbins et al., 1987), varicella-zoster virus (VZV) (Keller et al., 1986), MDV (Ross et al., 1989) and HSV1 (Bzik et al., 1984) gB genes also contain a pyrimidine at position +4.

Example 3

Analysis of the Predicted CHV gB Amino Acid Sequence

The deduced amino acid sequence of the CHV gB homologue is presented in FIG. 1. Hydropathicity analysis of this amino acid sequence is shown in FIG. 2. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gB homologue.

Hydropathicity analysis of this amino acid sequence revealed the presence of 2 prominent hydrophobic peaks. The first peak, located at the N-terminus, without wishing to be bound by any one theory, represents a potential signal sequence. N-terminal signal sequences initiate transport across the endoplasmic reticulum membrane and can be critical for the proper post-translational modification and targeting of glycoproteins (Blobel, 1980). Signal sequences vary in length from about 15–30 residues and usually consist of a basic N-terminal region, a central hydrophobic region and a short, relatively polar C-terminal region. In addition, the cleavage site usually conforms to the −3,−1 rule, where the residue at position −1 is small (Ala, Ser, Gly, Cys, Thr or Gln) and the residue at position −3 is not aromatic (Phe, His, Tyr or Trp), charged (Asp, Glu, Lys or Arg) or large and polar (Asn or Gln), and residues −3 through +1 are not Pro (von Heijne, 1986). Although analysis with PSIGNAL, a PC/GENE program designed to detect eukaryotic signal sequences, does not identify the N-terminal end of CHV gB as a potential signal sequence, this region does have elements consistent with typical signal sequences; namely a hydrophobic core (residues 2–17) and a relatively polar C-terminal region (FIG. 1). The fact that PSIGNAL does not detect a signal sequence in the N-terminal region of CHV gB is not unique. This algorithm also does not detect a signal sequence in the N-terminal region of the VZV gB homologue.

The second, very broad, hydrophobic peak(s) (FIG. 2), with predicted membrane-spanning segments between amino acid residues 725 and 741 and 746–750 and 766–772 (using the method of Klein et al. (1985)), without wishing to be bound by any one theory, functions as a membrane anchor region. It has been hypothesized that the transmembrane domain of HSV1 gB, as well as other gB homologues, transverses the membrane 3 times (Pellett et al., .1985). Hydropathicity analysis of CHV gB reveals the presence of at least 2 distinct hydrophobic peaks. Therefore, CHV gB and HSV1 gB have similar transmembrane structures.

Alignment of the CHV gB amino acid sequence with similar sequences from other herpesviruses revealed extensive homology throughout the entire sequence, with the exception of the N-terminus, a region surrounding the putative cleavage site (see below) and a region near the C-terminus. FIGS. 3A and 3B show the amino acid homology of 8 gB homologues. The amino acid sequences of the CHV, FHV, EHV1, PRV, HSV1, VZV, HCMV and EBV gB homologues (for references from which the sequences were obtained, see text below Table 1) were aligned using the PC/GENE CLUSTAL program. Gaps, indicated by dashes, were introduced to maximize homology. Aligned residues which are identical in all 8 sequences are indicated by an asterisk (*). Aligned residues which are identical in the majority of sequences are indicated by a period (.). Conserved cysteine residues are boxed. Potential N-linked glycosylation sites are shaded. Putative proteolytic cleavage sites are underlined.

This alignment also revealed that the vast majority of cysteine residues are perfectly conserved. For example, CHV gB contains 11 cysteine residues, 10 of which are perfectly conserved in all alpha-, beta- and gamma-herpesviruses. In fact, the only cysteine residue in CHV gB that is not conserved is found near the N-terminus and may be located in the putative signal sequence. These results show that the gB glycoproteins have relatively similar tertiary structures.

Alignment of the gB amino acid sequences also revealed that the potential N-linked glycosylation sites are relatively well conserved (FIGS. 3A and 3B). N-linked oligosaccharides can be added to Asn residues that have the sequence Asn-X-Ser or Asn-X-Thr, where X is not Pro (Bause, 1983). CHV gB contains 13 potential N-linked glycosylation sites. Three of these sites, however, are situated in the putative cytoplasmic domain and, therefore, may not be glycosylated. The location of the potential N-linked glycosylation sites is relatively well conserved in the majority of gB glycoproteins (FIGS. 3A and 3B).

The gB glycoprotein of most herpesviruses is cleaved internally during maturation, with the subsequent peptides being held together by disulfide bonds. The VZV gB homologue (gpII), for example, is cleaved between Arg and Ser residues, resulting in 2 glycoproteins of approximately 60 kd (Keller et al., 1986). The gB glycoproteins of FHV (Maeda et al., 1992), equine herpesvirus type 1 (EHV1) (Whalley et al., 19989), PRV (Robbins et al., 1987), BHV1 (Whitbeck et al., 1988), MDV (Ross et al., 1989) and HCMV (Kouzarides et al., 1987) are also cleaved. Furthermore, a sequence, Arg-X-Arg-Arg/Lys—Ser/Ala, similar to the sequence at the VZV cleavage site, Arg-Thr-Arg-Arg—Ser, is present at virtually the same location in each of these gB glycoptoteins. Conversely, this sequence is not found in the HSV1 (Bzik et al., 1984) and EBV (Pellett et al., 1985) gB glycoproteins, which are not cleaved. The significance of this cleavage event is unknown. It does not appear, however, to be essential for replication, in vitro, since strains of BHV1 (Blewett & Misra, 1991) and HCMV (Spaete et al., 1990) that have been mutated at the cleavage site, and therefore encode an uncleaved gB glycoprotein, are still infectious. Without wishing to be bound by the theory that CHV gB is cleaved internally, proteolytically, the sequence, Arg-Lys-Arg-Arg—Ser, is present at the same location in CHV as in VZV, FHV, EHV1, PRV, BHV1, MDV and HCMV.

Example 4

Identification and Sequencing of the CHV gC Gene

CHV genomic fragments were randomly cloned into pBluescriptSK. The nucleotide sequence of the termini of these fragments was determined and the predicted amino acid sequence of potential ORFs were analyzed for homology against the SWISS-PROT (Release 20) amino acid database. Using this methodology, a 12 kb XbaI fragment encoding an ORF with homology to herpesvirus gC glycoproteins was identified. The nucleotide sequence of this ORF is presented in FIG. 4. FIG. 4 shows the nucleotide sequence and predicted amino acid sequence of the CHV gC homologue and ORF2. The putative transmembrane region and potential TATA, CAAT and polyadenylation signal sequences are underlined. Nucleotides and predicted amino acid residues are numbered to the right of the sequence. The putative CHV gC gene starts at position 201 and ends at position 1580. The predicted translation product is 459 amino acids long. Comparison of this amino acid sequence with the sequence of gC glycoproteins from other herpesviruses is shown in Table 2, below, and revealed extensive homology, indicating that this ORF encodes the CHV gC homologue (Table 2).

TABLE 2

HOMOLOGY BETWEEN THE PREDICTED AMINO ACID
SEQUENCES OF 9 HERPESVIRUS gC GLYCOPROTEINS

|      | FHV | EHV1 | EHV4 | PRV | BHV1 | VZV | MDV | HSV1 |
|------|-----|------|------|-----|------|-----|-----|------|
| CHV  | 44  | 32   | 34   | 27  | 27   | 29  | 27  | 25   |
| FHV  |     | 32   | 33   | 29  | 31   | 28  | 25  | 23   |
| EHV1 |     |      | 81   | 31  | 32   | 30  | 27  | 27   |

TABLE 2-continued

HOMOLOGY BETWEEN THE PREDICTED AMINO ACID
SEQUENCES OF 9 HERPESVIRUS gC GLYCOPROTEINS

|      | FHV | EHV1 | EHV4 | PRV | BHV1 | VZV | MDV | HSV1 |
|------|-----|------|------|-----|------|-----|-----|------|
| EHV4 |     |      |      | 32  | 31   | 31  | 25  | 27   |
| PRV  |     |      |      |     | 37   | 27  | 25  | 29   |
| BHV1 |     |      |      |     |      | 29  | 25  | 27   |
| VzV  |     |      |      |     |      |     | 22  | 22   |
| MDV  |     |      |      |     |      |     |     | 23   |

Values in Table 2 were obtained using the ALIGN Plus program and are expressed as percent homology. The entire gC amino acid sequence was used. See Table 1 for alignment parameters. References: FHV (Audonnet, unpublished results), EHV1 (Allen & Coogle, 1988), EHV4 (Nicolson & Onions, 1990), PRV (Robbins et al., 1986), BHV1 (Fitzpatrick et al., 1989), VZV (Davison & Scott, 1986), MDV (Ihara et al., 1989) and HSV1 (McGeoch et al., 1988).

Example 5

Analysis of the CHV gC Nucleotide Sequence

Potential TATA box sequences (TATA) are found at positions 22 and 81, approximately 180 bp and 120 bp upstream from the CHV gC initiation codon (FIG. 4). An additional TATA sequence is found at position 175. Due to its proximity to the gC initiation codon, however, this sequence may not be a potential TATA box sequence. Potential CAAT box sequences (CAAT and ATTG) are found at positions 13, 59 and 119, approximately 190 bp, 140 bp and 80 bp upstream from the gC initiation codon. A potential polyadenylation signal sequence (AATAAA) is found at position 1744, approximately 165 bp downstream from the CHV gC termination codon and 45 bp within ORF2 (see below). Other potential polyadenylation signal-like sequences are also found in the gC 3'-noncoding region.

Like the CHV gB gene, the nucleotide sequence surrounding the CHV gC initiation codon (AAAATGA) is favorable with respect to Kozak's rules at position −3, but not at position +4 (FIG. 4). The FHV (Audonnet, unpublished results), EHV1 (Allen & Coogle, 1988) and VZV (Davison & Scott, 1986) gC genes also contain an unfavorable nucleotide at position +4.

Example 6

Analysis of the CHV gC Amino Acid Sequence Predicted

Figure 5:
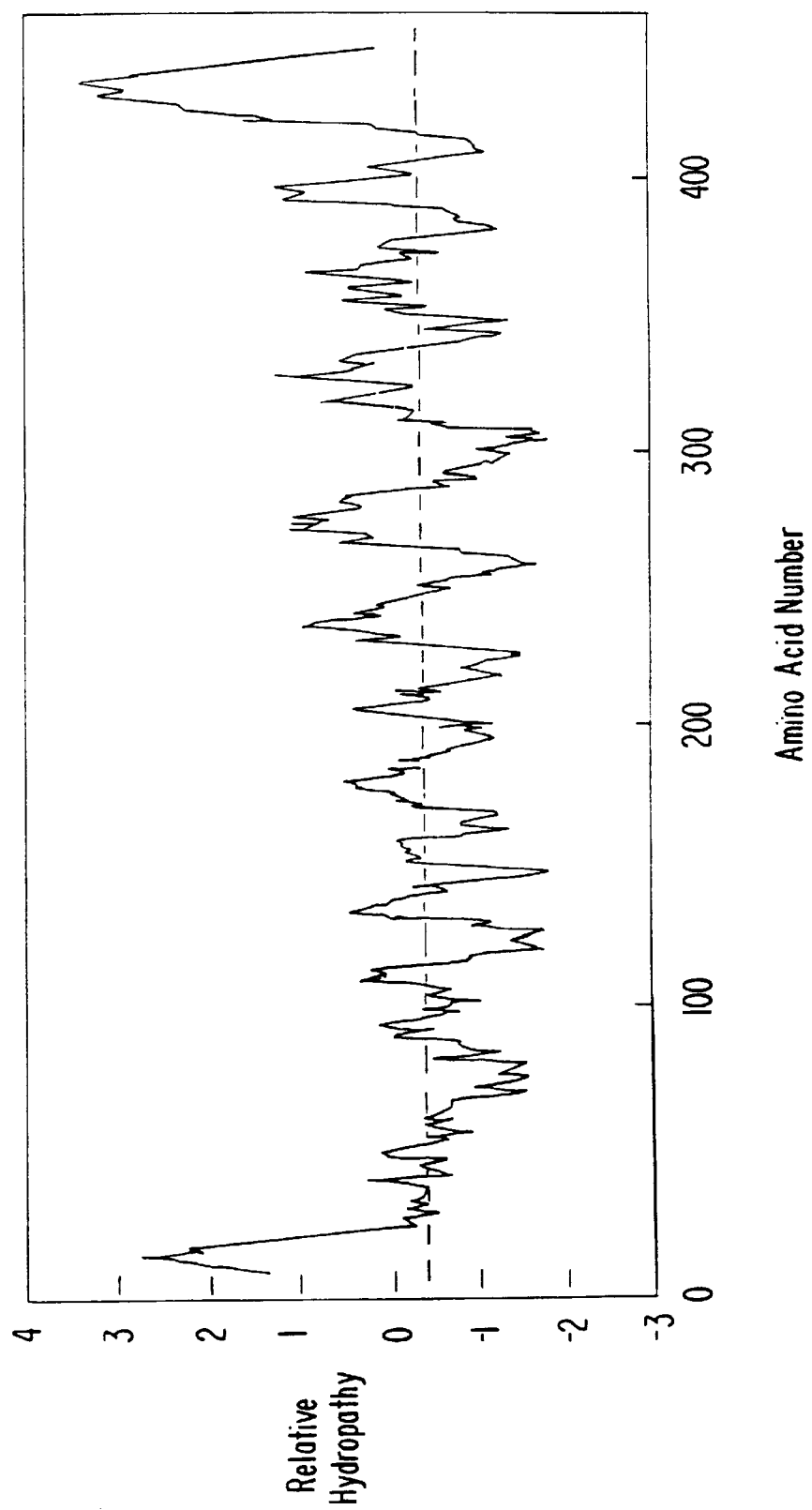

The deduced amino acid sequence of the CHV gC homologue is presented in FIG. 4. FIG. 5 shows the hydropathicity analysis of the CHV gC homologue. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gC homologue.

Hydropathicity analysis of the predicted CHV gC amino acid sequence revealed the presence of 2 prominent hydrophobic peaks (FIG. 5). The first peak, located at the N-terminus, without wishing to be bound by any one theory, represents a potential signal sequence. Although analysis with PSIGNAL does not identify the N-terminal end of this polypeptide as a potential signal sequence, this region does have a basic N-terminal region, a hydrophobic core (residues 6–20) and a relatively polar C-terminal region (FIG. 4). The second hydrophobic peak, with a predicted membrane-spanning segment between residues 424–433 and 449–456 (using the method of Klein et al. (1985)), without wishing to be bound by any one theory, functions as a membrane anchor region. FIG. 6 shows the amino acid homology of 4 gC homologues. The amino acid sequences of the CHV, FHV, EHV1 and HSV1 gC homologues (for references see Table 2) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded.

Alignment of the CHV gC amino acid sequence with homologous sequences from other herpesviruses revealed a moderate level of homology throughout the entire sequence, with the exception of the N-terminus (FIG. 6). This alignment also revealed that the majority of cysteine residues are perfectly conserved. For example, CHV gC contains 10 cysteine residues, 8 of which are perfectly conserved in all alpha-herpesviruses. In fact, the only cysteine residues in CHV gC that are not conserved are located in the putative transmembrane or intracellular domains. These results show that the gC glycoproteins have relatively similar tertiary structures. Alignment with other gC sequences also revealed the relative conservation of potential N-linked glycosylation sites.

Example 7

Identification and Sequencing of ORF2

Nucleotide sequence analysis of the region downstream from the CHV gC gene revealed the presence of a second ORF (FIG. 4). This ORF (ORF2) starts at position 1699 and ends at position 2226. The predicted translation product is 175 amino acids long. Table 3, below, shows the comparison of this amino acid sequence with the SWISS-PROT (Release 23) database revealed significant homology with the ORFs located downstream from other alpha-herpesvirus gC genes, The homology scores for the ORF2 homologues shows that in CHV, FHV, EHV1, equine herpesvirus type 4 (EHV4), MDV, herpesvirus of turkey (HVT) and possibly HSV1, the ORF located downstream from the gC gene represents a highly divergent, but evolutionarily related, gene family. Conversely, the ORF (gene 13) located next to the VZV gC gene does not exhibit significant homology with any of the other comparably positioned ORFs. Furthermore, gene 13 is oriented on the genome in the opposite direction relative to all the other ORF2-like genes (Davison & Scott, 1986). These results are consistent with the proposed functions of the proteins encoded by these 2 groups of genes; VZV gene 13 encodes a thymidylate synthetase (Davison and Scott, 1986), whereas the HSV1 ORF2-like gene (UL45) encodes a putative virion protein (Telford et al., 1992). Therefore, the ORFs located next to the gC gene in CHV, FHV, EHV1, EHV4, MDV, HVT and possibly HSV1 encode proteins that are structurally and functionally unrelated to the protein encoded downstream from the VZV gC homologue.

TABLE 3

HOMOLOGY BETWEEN THE PREDICTED AMINO ACID SEQUENCES OF THE ORFS LOCATED ADJACENT TO THE gC GENE IN 8 HERPESVIRUSES

|  | FHV | EHV1 | EHV4 | MDV | HTV | HSV1 | VZV |
|---|---|---|---|---|---|---|---|
| CHV | 197(22) | 211(22) | 219(21) | 62(4) | 105(13) | 53(4) | 31(0) |
| FHV |  | 177(24) | 167(18) | 69(4) | 66(4) | 40(1) | 52(1) |
| EHV1 |  |  | 470(50) | 95(8) | 104(9) | 79(7) | 58(3) |
| EHV4 |  |  |  | 132(8) | 130(11) | 60(5) | 30(0) |
| MDV |  |  |  |  | 767(75) | 83(6) | 28(0) |
| HTV |  |  |  |  |  | 91(7) | 33(0) |
| HSV1 |  |  |  |  |  |  | 49(2) |

Values in Table 3 were obtained using the FASTA and RDF2 programs (Pearson & Lipman, 1988). A ktup of 1 was used. Values in parentheses represent the number of standard deviations between the FASTA score and the mean of the scores obtained from 100 randomly permutated versions of the potentially related sequence. References: FHV (Audonnet, unpublished results), EHV1 (Telford et al., 1992), EHV4 (Nicolson & Onions, 1990), MDV (Ihara et al., 1989), HVT (Kato et al., 1989), HSV1 (McGeoch et al., 1988) and VZV (Davison & Scott, 1986).

Example 8

Analysis of the CHV ORF2 Nucleotide Sequence

Potential TATA box sequences (TATA) are found at positions 1604, 1606, 1635 and 1662, approximately 95, 93, 65 and 35 bp upstream from the ORF2 initiation codon and approximately 24, 26, 55 and 80 bp downstream from the gC gene termination codon (FIG. 4). A potential CAAT box sequence (CAAT) is found at position 1584, approximately 115 bp upstream from the initiation codon. Potential polyadenylation signal sequences (AATAAA) are found at overlapping positions 2225, 2229, 2234 and 2238, approximately 0–15 bp downstream from the ORF2 termination codon. The nucleotide sequence surrounding the ORF2 initiation codon (AATATGG) is favorable with respect to Kozak's rules at positions −3 and +4.

Example 9

Identification and Sequencing of the CHV gD Gene

Employing the same methodology used to map the CHV gC homologue, a 7 kb PstI fragment encoding an ORF with homology to herpesvirus gD glycoproteins was identified. FIG. 7 shows the nucleotide sequence and predicted amino acid sequence of the CHV gD homologue. The putative signal sequence, transmembrane region and potential polyadenylation signal sequences are underlined. Nucleotides and predicted amino acid residues are numbered to the right of the sequence. The CHV gD gene starts at position 201 and ends at position 1238. The translation product (predicted) is 345 amino acids long. Table 4, below, provides comparison of this amino acid sequence with the sequence of other gD glycoproteins and, revealed extensive homology, indicating that this ORF encodes the CHV gD homologue.

TABLE 4

Homology between the predicted amino acid sequences of 6 herpesvirus gD glycoproteins

|  | FHV | EHV1 | PRV | BHV1 | HSV1 |
|---|---|---|---|---|---|
| CHV | 45 | 35 | 27 | 34 | 21 |
| FHV |  | 31 | 30 | 34 | 24 |
| EHV1 |  |  | 26 | 27 | 21 |
| PRV |  |  |  | 37 | 27 |
| BHV1 |  |  |  |  | 24 |

Values in Table 4 were obtained using the ALIGN Plus program and are expressed as percent homology. The entire gD amino acid sequence was used. See Table 1 for alignment parameters. References: FHV (Audonnet, unpublished results), EHV1 (Flowers et al., 1991), PRV (Petrovskis et al., 1986), BHV1 (Tikoo et al., 1990) and HSV1 (Lasky & Dowbenko, 1984).

Example 10

Analysis of the CHV gD Nucleotide Sequence

No TATA or CAAT/ATTG sequences were identified immediately upstream from the CHV gD gene (FIG. 7). Numerous potential TATA box-like sequences, however, were found. Potential polyadehylation signal sequences (AATAAA) were found at positions 1260 and 1287, approximately 25 bp and 50 bp downstream from the CHV gD termination codon. Like the CHV gB and gC genes, the nucleotide sequence surrounding the CHV gD initiation codon (AAAATGA) is favorable with respect to Kozak's rules at position −3, but not at position +4 (FIG. 7). The FHV (Audonnet, unpublished results), EHV1 (Audonnet et al., 1990; Flowers et al., 1991), PRV (Petrovskis et al., 1986) and BHV1 (Tikoo et al., 1990) gD genes also contain an unfavorable nucleotide at position +4.

Example 11

Analysis of the Predicted CHV gD Amino Acid Sequence

Figure 8:
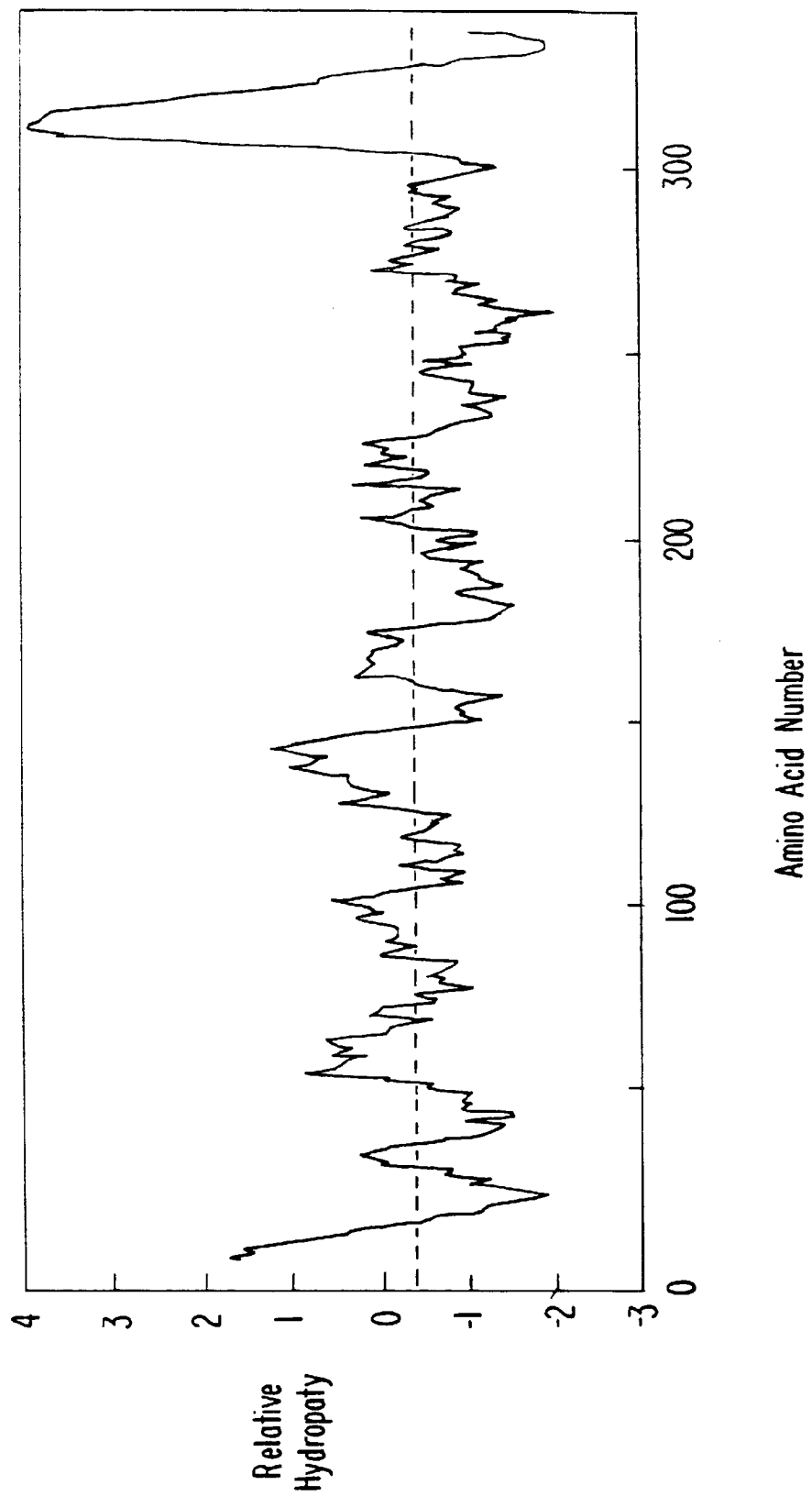

The deduced amino acid sequence of the CHV gD homologue is presented in FIG. 7. FIG. 8 shows the hydropathicity analysis of the CHV gD homologue. The profile was obtained with the PC/GENE SOAP program, using the method of Kyte & Doolittle (1982) and an interval of 11 amino acids. The vertical axis represents relative hydropathicity, where positive values are hydrophobic and negative values are hydrophilic. The horizontal axis represents the amino acid number of the CHV gD homologue.

Hydropathicity analysis of the predicted CHV gD amino acid sequence revealed the presence of 2 prominent hydrophobic peaks (FIG. 8). The first peak, located at the N-terminus, without wishing to be bound by any one theory, represents a potential signal sequence. In fact, PSIGNAL identified a potential cleavage site between positions 16 and 17. The second hydrophobic peak, with a predicted membrane-spanning segment between residues 304–311 and 327–332 (using the method of Klein et al. (1985)), without wishing to be bound by any one theory, functions as a membrane anchor region.

FIG. 9 shows amino acid homology of 4 gD homologues. The amino acid sequences of the CHV, FHV, EHV1 and HSV1 gD homologues (for references see Table 4) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded. Alignment of the CHV gD amino acid sequence with homologous sequences from other herpesviruses revealed a moderate level of homology throughout the entire sequence, with the exception of the N-terminus (FIG. 9). This alignment also revealed that the vast majority of cysteine residues are perfectly conserved. For example, CHV gD contains 6 cysteine residues, all of which are perfectly conserved in all alpha-herpesviruses. These results show that the gD glycoproteins have relatively similar tertiary structures. This alignment also revealed that the potential N-linked glycosylation sites are well conserved. Without wishing to be bound by any theory that the CHV gD glycosylation sites are utilized, it is known that all of the potential HSV1 gD glycosylation sites are used (Sodora et al., 1991).

Example 12

Genomic Organization

The gB, gC and gD genes were not mapped to specific locations on the CHV genome. Nucleotide sequence analyses of the regions flanking these genes, however, indicates that the genomic organization of CHV is similar to other alpha-herpesviruses. For example, the ORF located immediately upstream from the CHV gB gene has homology with gene 30 of VZV (Davison & Scott, 1986) and UL28 of HSV1 (McGeoch et al., 1988), both of which are located immediately upstream from the gB homologue in those viruses. ORF2, located immediately downstream from the CHV gC gene, has homology with the ORFs located immediately downstream from the gC homologue in FHV (Audonnet, unpublished results), EHV1 (Telford et al., 1992), EHV4 (Nicolson & Onions, 1990), HVT (Kato et al., 1988) and perhaps HSV1 (McGeoch et al., 1988. Additionally, the ORF located immediately downstream from the CHV gD gene has homology to the gI gene of EHV1 (Audonnet et al., 1990) and the gp63 gene of PRV (Petrovskis et al., 1986), both of which are located immediately downstream from the gD homologue in those viruses (data not shown).

Example 13

Construction of Plasmid pSD460 for Deletion of Thymidine Kinase Gene (J2R)

Figure 10:
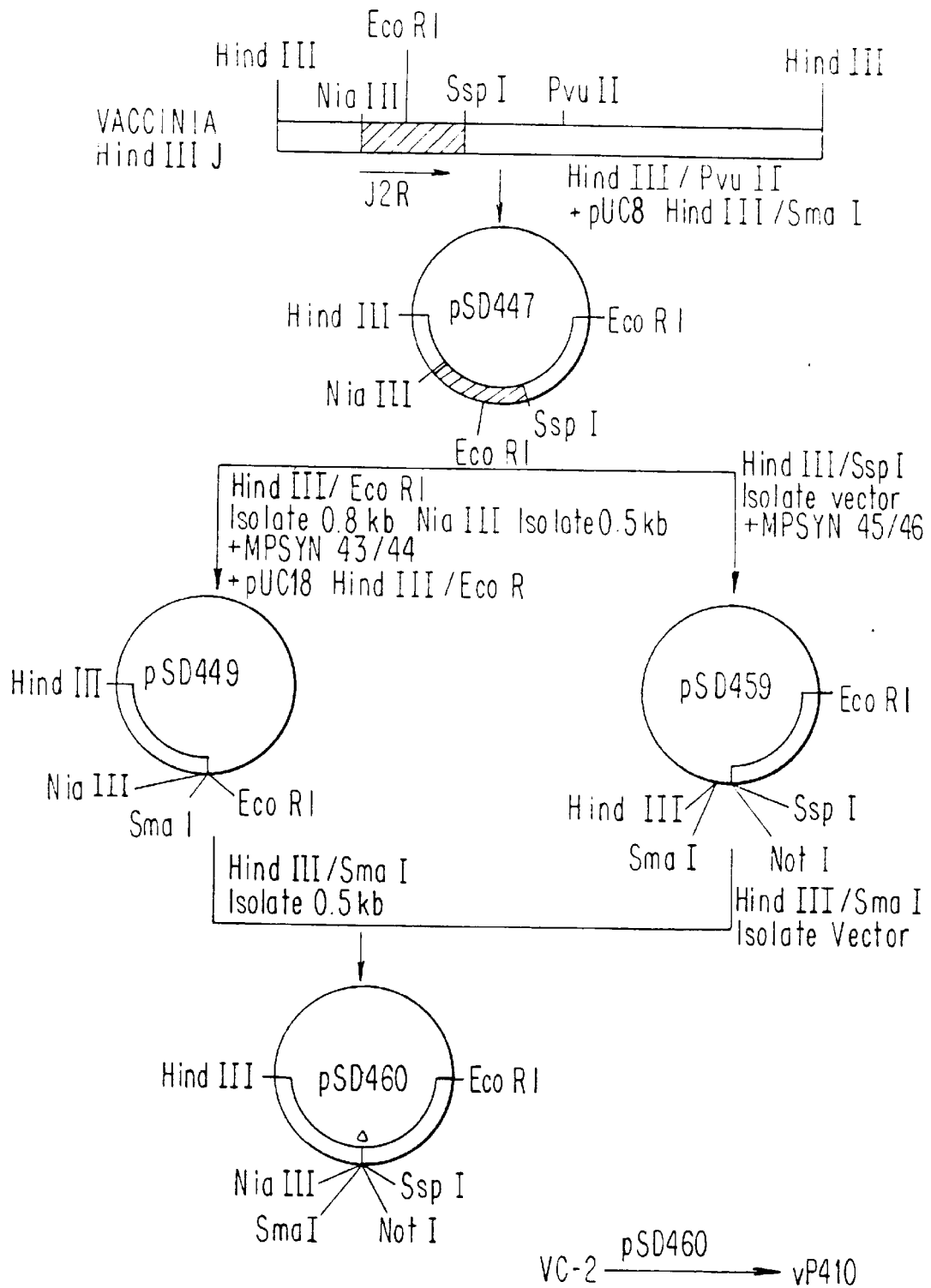

Referring now to FIG. 10, plasmid pSD406 contains vaccinia HindIII J (pos. 83359–88377) cloned into pUC8. pSD406 was cut with HindIII and PvuII, and the 1.7 kb fragment from the left side of HindIII J cloned into PUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 10.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:24/SEQ ID NO:25)

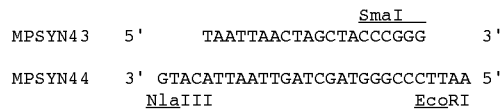

```
                                      SmaI
MPSYN43   5'      TAATTAACTAGCTACCCGGG      3'

MPSYN44   3' GTACATTAATTGATCGATGGGCCCTTAA 5'
            NlaIII                    EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:26/SEQ ID NO:27)

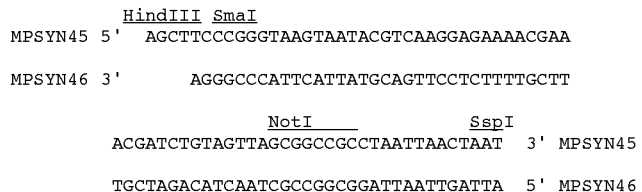

```
            HindIII SmaI
MPSYN45 5'  AGCTTCCCGGGTAAGTAATACGTCAAGGAGAAAACGAA

MPSYN46 3'      AGGGCCCATTCATTATGCAGTTCCTCTTTTGCTT

NotI            SspI
           ACGATCTGTAGTTAGCGGCCGCCTAATTAACTAAT  3' MPSYN45

TGCTAGACATCAATCGCCGGCGGATTAATTGATTA  5' MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}P$ labelled probe was synthesized by primer extension using MPSYN45 (SEQ ID NO:26) as template and the complementary 20 mer oligonucleotide MPSYN47 (SEQ ID NO:28) (5' TTAGTTAATTAGGCGGCCGC 3') as primer. Recombinant virus vP410 was identified by plaque hybridization.

Example 14

Construction of Plasmid pSD486 for Deletion of Hemorrhagic Region (B13R+B14R)

Figure 11:
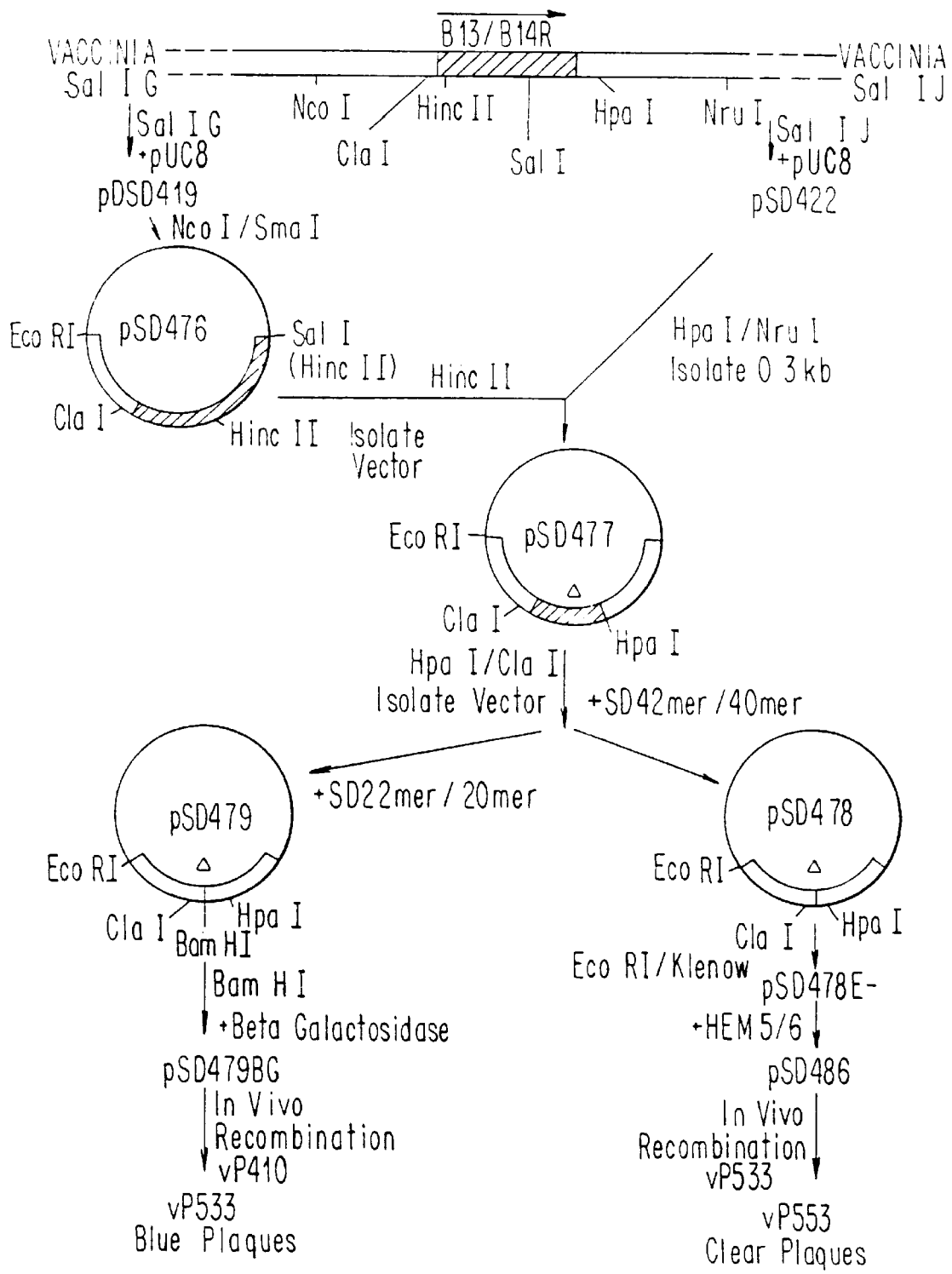

Referring now to FIG. 11, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 11.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:29/SEQ ID NO:30)

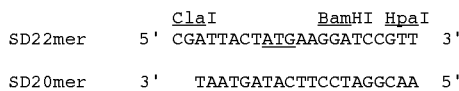

```
                ClaI         BamHI HpaI
SD22mer    5' CGATTACTATGAAGGATCCGTT  3'

SD20mer    3'    TAATGATACTTCCTAGGCAA  5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating otides HEM5/HEM6 (SEQ ID NO:33/SEQ ID NO:34)

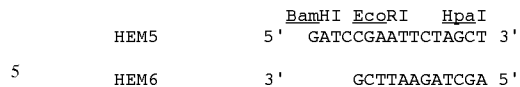

```
              BamHI EcoRI    HpaI
HEM5     5'   GATCCGAATTCTAGCT  3'

HEM6     3'         GCTTAAGATCGA  5'
``` generating plasmid pSD486. pSD486 was used as donor plasmid for recombination with recombinant vaccinia virus vP533, generating vP553, which was isolated as a clear plaque in the presence of X-gal.

Example 15

Construction of Plasmid pMP494Δ for Deletion of ATI Region (A26L)

Figure 12:
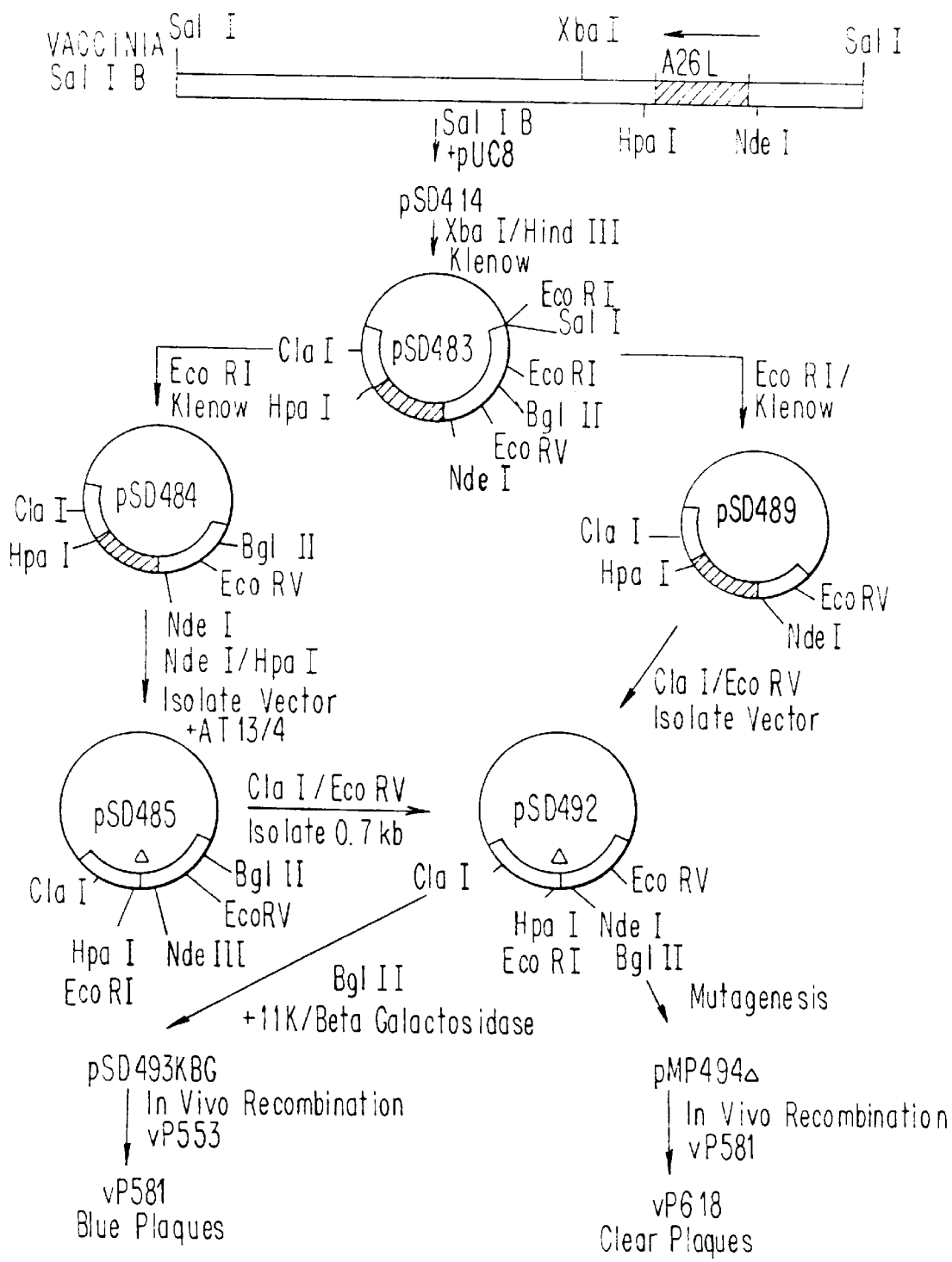

Referring now to FIG. 12, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:35/SEQ ID NO:36)

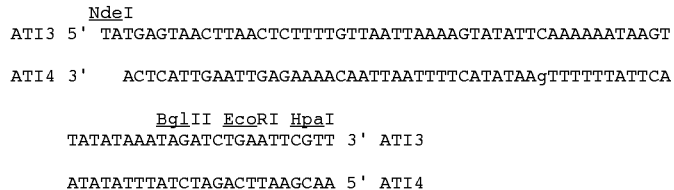

```
            NdeI
ATI3  5' TATGAGTAACTTAACTCTTTTGTTAATTAAAAGTATATTCAAAAAATAAGT

ATI4  3'    ACTCATTGAATTGAGAAAACAATTAATTTTCATATAAgTTTTTTATTCA

BglII  EcoRI  HpaI
         TATATAAATAGATCTGAATTCGTT  3'  ATI3

ATATATTTATCTAGACTTAAGCAA  5'  ATI4
``` pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:31/SEQ ID NO:32)

reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

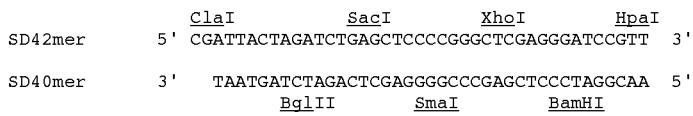

```
               ClaI        SacI        XhoI        HpaI
SD42mer   5' CGATTACTAGATCTGAGCTCCCCGGGCTCGAGGGATCCGTT  3'

SD40mer   3'   TAATGATCTAGACTCGAGGGGCCCGAGCTCCCTAGGCAA  5'
                  BglII       SmaI        BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HpaI and ligated with annealed synthetic oligonucle- A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:37) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 16

Construction of Plasmid pSD467 for Deletion of Hemagglutinin Gene (A56R)

Figure 13:
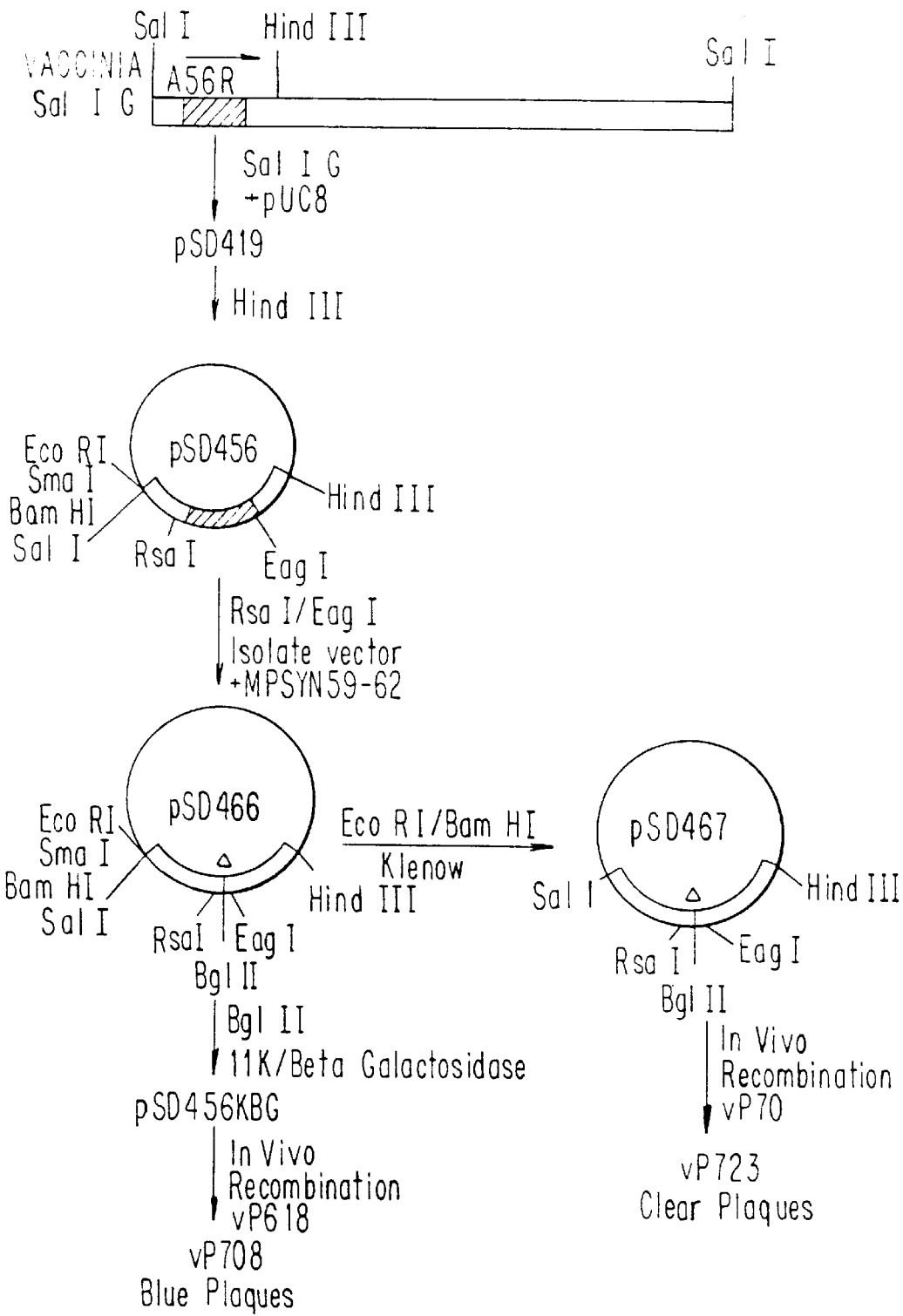

Referring now to FIG. 13, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 13. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:38), MPSYN62 (SEQ ID NO:39), MPSYN60 (SEQ ID NO:40), and MPSYN61 (SEQ ID NO:41)

185–162,053]. The site of the deletion in pSD466 is indicated by a triangle in FIG. 13.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Example 17

Construction of Plasmid pMPCSK1Δ for Deletion of Open Reading Frames [C7L–K1L]

Figure 14:
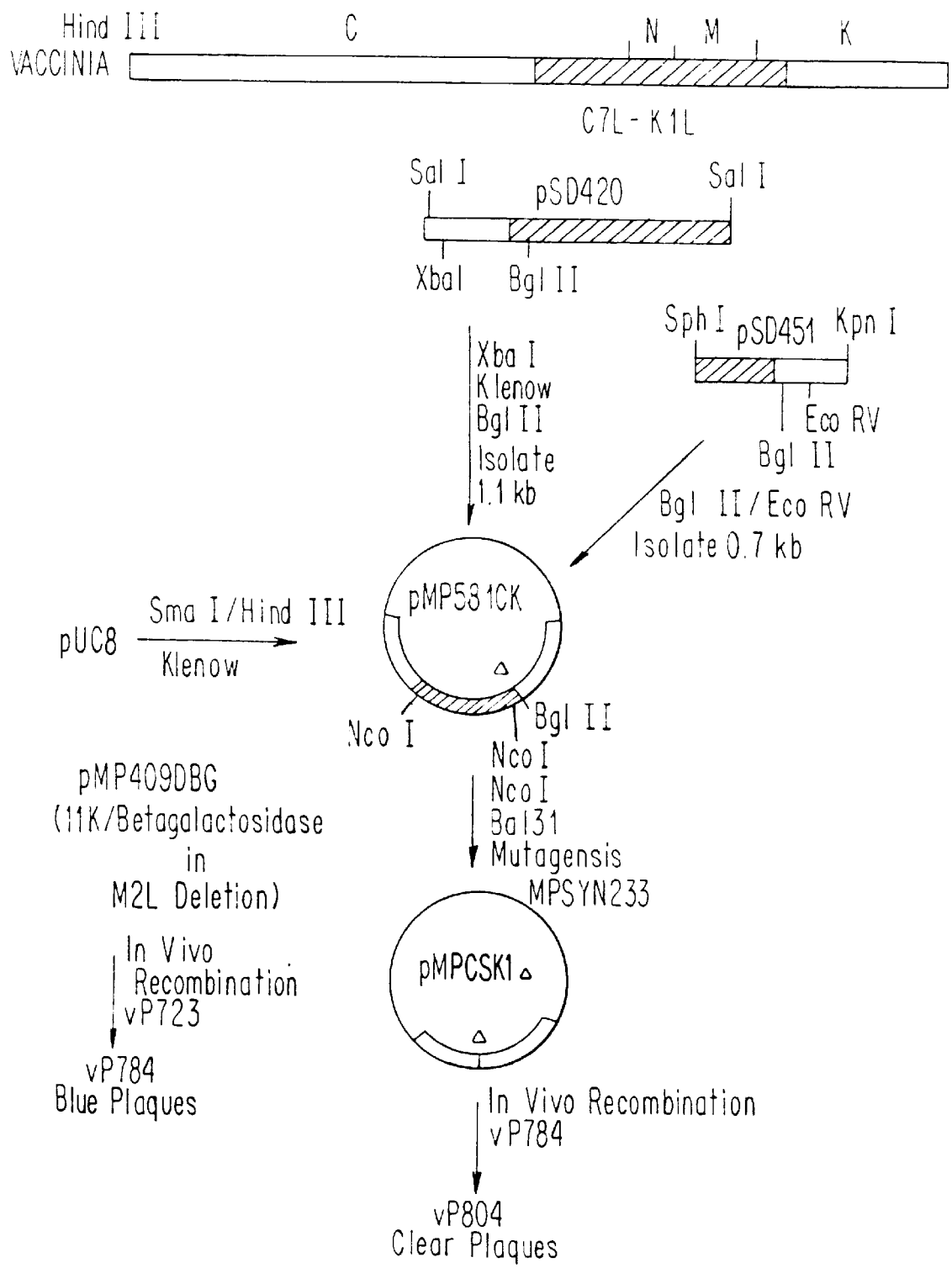

Referring now to FIG. 14, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then

```
              RsaI
MPSYN59    5' ACACGAATGATTTTCTAAAGTATTTGGAAAGTTTTATAGGT-

MPSYN62    3' TGTGCTTACTAAAAGATTTCATAAACCTTTCAAAATATCCA-

MPSYN59       AGTTGATAGAACAAAATACATAATTT 3'

MPSYN62       TCAACTATCT 5'

MPSYN60    5'                    TGTAAAAATAAATCACTTTTTATA-

MPSYN61    3' TGTTTTATGTATTAAAACATTTTTATTTAGTGAAAAATAT-

BglII SmaI  PstI  EagI
MPSYN60       CTAAGATCTCCCGGGCTGCAGC        3'

MPSYN61       GATTCTAGAGGGCCCGACGTCGCCGG 5'
``` reconstructing the DNA sequences upstream from the A56R ORF and replacing the A56R ORF with a polylinker region as indicated above. The resulting plasmid is pSD466. The vaccinia deletion in pSD466 encompasses positions [161, ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
                                                         BglII
MPSYN82 (SEQ ID NO:47)   5' TTTCTGTATATTTGCACCAATTTAGATCTT-
                            ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 14.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:43) 5'-TGTCATTTAACACTATACTCATATTAAT-AAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 15. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 15.

To construct a vector plasmid to accept the left vaccinia flanking arm, pUC8 was cut with BamHI/EcoRI and ligated with annealed synthetic oligonucleotides 518A1/518A2 (SEQ ID NO:44/SEQ ID NO:45)

```
              BamHI    RsaI
518A1  5' GATCCTGAGTACTTTGTAATATAATGATATATATTTTCACTTTATCTCAT

518A2  3'     GACTCATGAAACATTATATTACTATATATAAAAGTGAAATAGAGTA

BglII      EcoRI
         TTGAGAATAAAAAGATCTTAGG        3'    518A1

AACTCTTATTTTTCTAGAATCCTTAA    5'    518A2
``` forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:46/SEQ ID NO:47)

```
             BamHI BglII SmaI
518B1  5'  GATCCAGATCTCCCGGGAAAAAAATTATTTAACTTTTCATTAATAG-

518B2  3'      GTCTAGAGGGCCCTTTTTTTAATAAATTGAAAAGTAATTATC-

RsaI    EcoRI
         GGATTTGACGTATGTAGCGTACTAGG      3'    518B1

CCTAAACTGCATACTACGCATGATCCTTAA  5'    518B2
```

Example 18

Construction of Plasmid pSD548 for Deletion of Large Subunit, Ribonucleotide Reductase (I4L)

Figure 15:
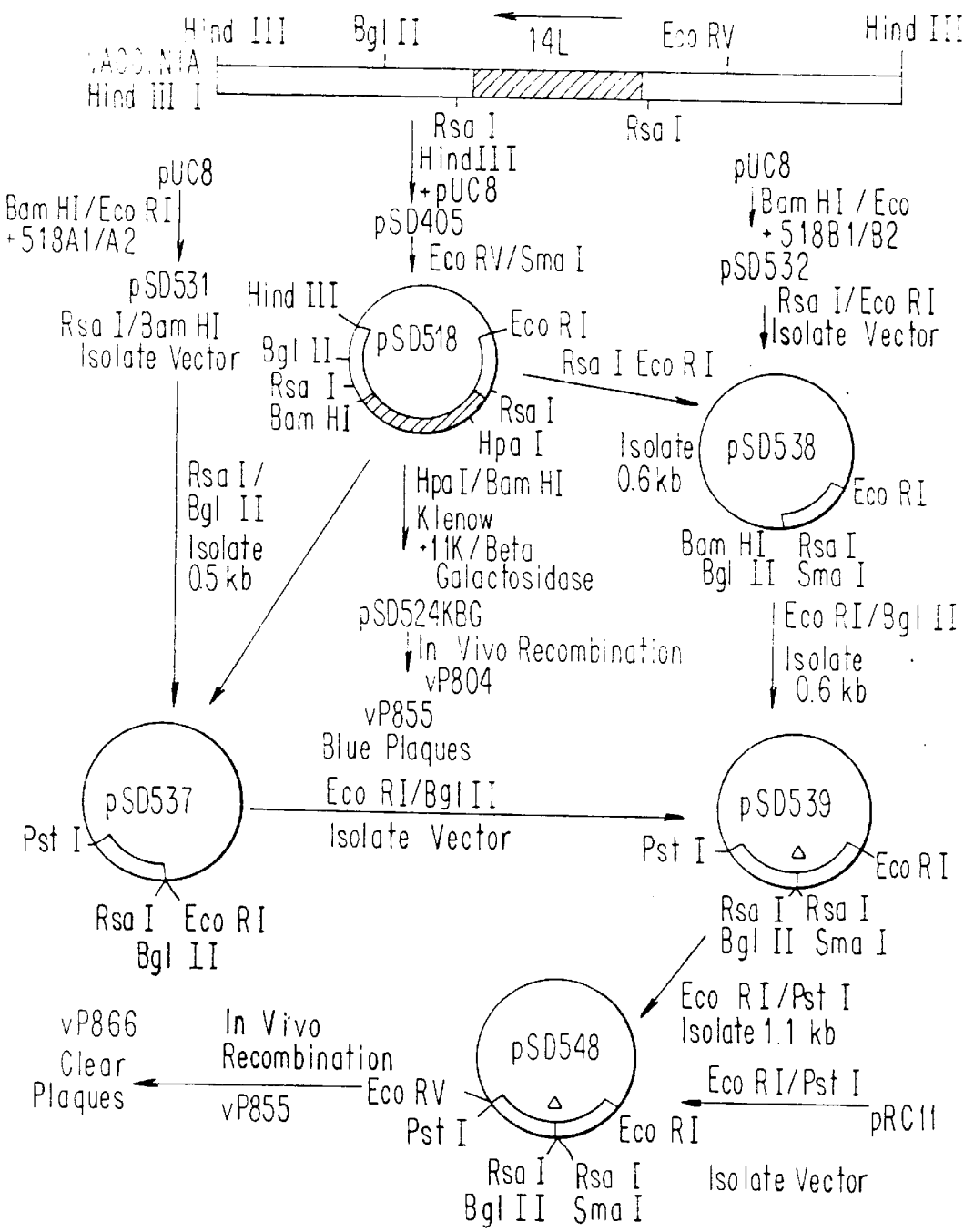

Referring now to FIG. 15, plasmid pSD405 contains vaccinia HindIII I (pos. 63,875–70,367) cloned in pUC8.

forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 15. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 19

Insertion of a Rabies Glycoprotein G Gene into NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 10) except for the presence of a polylinker region.

Figure 16:
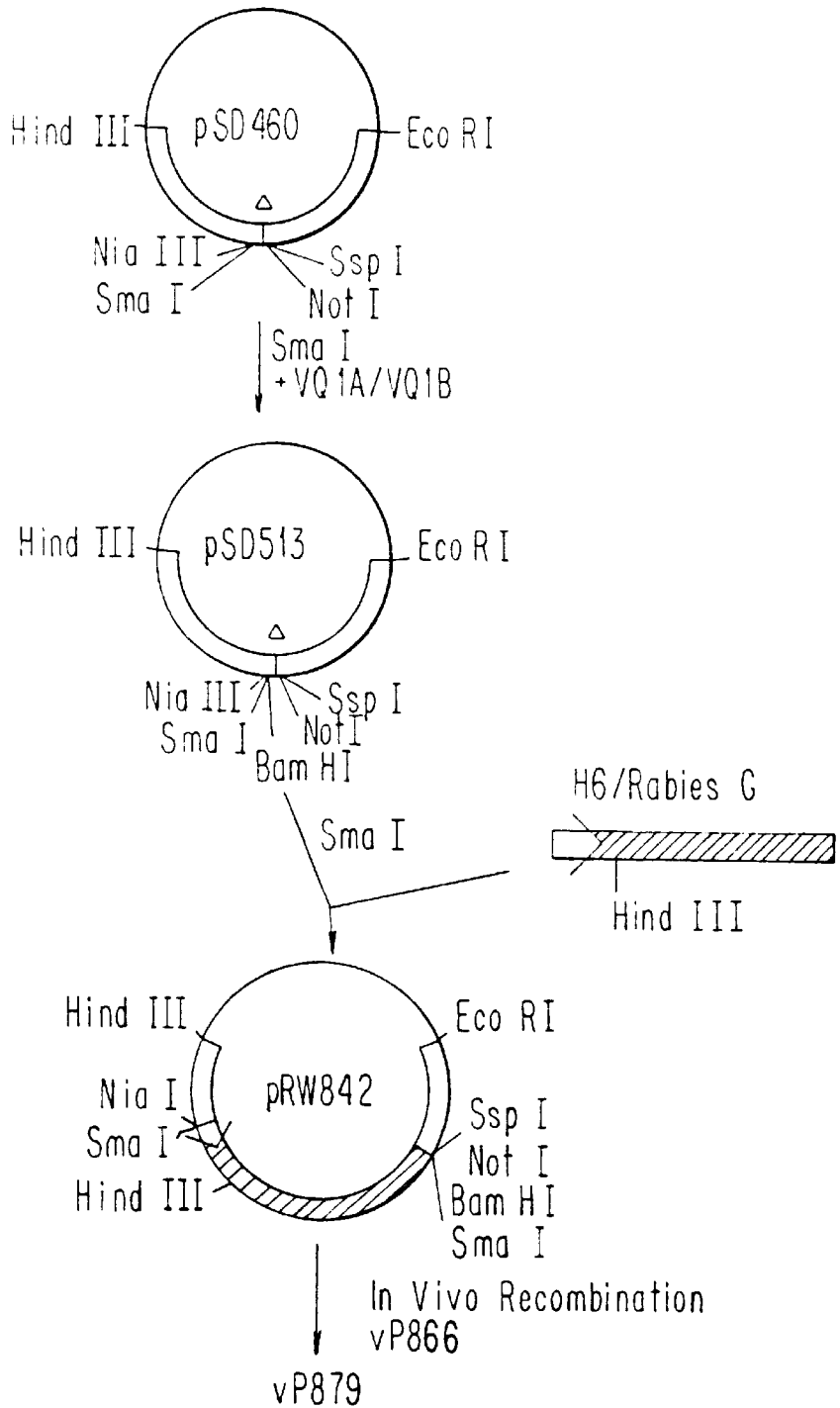

Referring now to FIG. 16, the polylinker region was inserted by cutting pSD460 with SmaI and ligating the plasmid vector with annealed synthetic oligonucleotides VQ1A/VQ1B (SEQ ID NO:48/SEQ ID NO:49)

The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by producing into the cell the modified recombinant virus having foreign DNA which codes for and expresses gene products in the cell.

Example 20

Construction of TROVAC-NDV Expressing the Fusion and Hemagglutinin-neuraminidase Glycoproteins of Newcastle Disease Virus This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses.

The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a Cassette for NDV-F.

A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into

```
         SmaI  BglII XhoI  PstI  NarI  BamHI
VQ1A 5'  GGGAGATCTCTCGAGCTGCAGGGCGCCGGATCCTTTTTCT 3'

VQ1B 3'  CCCTCTAGAGAGCTCGACGTCCCGCGGCCTAGGAAAAAGA 5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors.

pCE13 by digesting pCE13 with SalI, filling in the sticky ends with Klenow fragment of E. coli DNA polymerase and digesting with HindIII. A HindIII - EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:50) and CE76 (SEQ ID NO:51) to generate pCE47.
CE75: CGATATCCGTTAAGTTTGTATCG-
TAATGGGCTCCAGATCTTCTACCAG-
GATCCCGGTAC

CE76: CGGGATCCTGGTAGAAGATCTGGAGC-CCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:52) and CE43 (SEQ ID NO:53) were then inserted to form pCE29.

CE42: AATTCGAGCTCCCCGGG
CE43: CCCGGGGAGCTCG

The 3' end of the NDV-F sequence was then inserted into plasmid pCE20 already containing the 5' end of NDV-F by cloning a PstI - SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII - PstI fragment of pCE47 was inserted into the HindIII and PstI sites of pCE32 to form pCE49. The H6 promoted NDV-F sequences were then transferred to the de-ORFed F8 locus (described below) by cloning a HindIII - NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:54) and CE167 (SEQ ID NO:55) to generate pCE58.

CE166: CTTTTTATAAAAAGTTAACTACGTAG
CE167: GATCCTACGTAGTTAACTTTT-TATAAAAAGAGCT

A perfect 3' end for NDV-F was obtained by using the polymerase chain reaction (PCR) with pCE54 as template and oligonucleotides CE182 (SEQ ID NO:56) and CE183 (SEQ ID NO:57) as primers.

CE182: CTTAACTCAGCTGACTATCC
CE183: TACGTAGTTAACTTTTTATAAAAAT-CATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII - HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN.

Construction of plasmid pRW802 was previously described in Edbauer et al., 1990. This plasmid contains the NDV-HN sequences linked to the 3' end of the vaccinia virus H6 promoter in a pUC9 vector. A HindIII - EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:58) and CE163 (SEQ ID NO:59) into the EcoRI site of pRW830 to form pCE59, the final cassette for NDV-HN.

CE162: AATTCAGGATCGTTCCTTTACTAGTTGAGATTCTCAAGGATGATGGGATTTAATTTTTATAAGCTTG

CE163: AATTCAAGCTTATAAAAATTAAATCCCATCATCCTTGAGAATCTCAACTAGTAAAGGAACGATCCTG

Construction of FPV Insertion Vector.

Plasmid pRW731-15 contains a 10 kb PvuII - PvuII fragment cloned from genomic DNA. The nucleotide sequence was determined on both strands for a 3660 bp PvuII - EcoRV fragment. The limits of an open reading frame designated here as F8 were determined. Plasmid pRW761 is a sub-clone of pRW731-15 containing a 2430 bp EcoRV - EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI - SspI band was isolated from the gel and ligated with the annealed double-stranded oligonucleotides JCA017 (SEQ ID NO:60) and JCA018 (SEQ ID NO:61).

JCA017:5' CTAGACACTTTATGTTTTTTAATATCCGGTCTTAAAAGCTTCCCGGGGATCCTTATACGGGGAATAAT

JCA018:5' ATTATTCCCCGTATAAGGATCCCCCGGGAAGCTTTTAAGACCGGATATTAAAAAACATAAAGTGT

The plasmid resulting from this ligation was designated pJCA002.

Construction of Double Insertion Vector for NDV F and Hn.

The H6 promoted NDV-HN sequence was inserted into the H6 promoted NDV-F cassette by cloning a HindIII fragment from pCE59 that had been filled in with Klenow fragment of E. coli DNA polymerase into the HpaI site of pCE71 to form pCE80. Plasmid pCE80 was completely digested with NdeI and partially digested with BglII to generate an NdeI - BglII 4760 bp fragment containing the NDV F and HN genes both driven by the H6 promoter and linked to F8 flanking arms. Plasmid pJCA021 was obtained by inserting a 4900 bp PvuII - HindII fragment from pRW731-15 into the SmaI and HindII sites of pBSSK+. Plasmid pJCA021 was then digested with NdeI and BglII and ligated to the 4760 bp NdeI - BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV.

Plasmid pJCA024 was transfected into TROVAC infected primary CEF cells by using the calcium phosphate precipitation method previously described (Panicali et al., 1982;

Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence.

Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation.

Immunoprecipitation reactions were performed as described (Taylor et al., 1990) using a polyclonal anti-NDV serum obtained from SPAFAS Inc., Storrs, Conn.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg - Arg - Gln - Arg - Arg (SEQ ID NO:42) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycosylated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 21

Construction of ALVAC Recombinants Expressing Rabies Virus Glycoprotein G

This example describes the development of ALVAC, a canarypox virus vector and, of a canarypox-rabies recombinant designated as ALVAC-RG (vCP65) and its safety and efficacy.

Cells and Viruses.

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector.

An 880 bp canarypox PvuII fragment was cloned between the PvuII sites of pUC9 to form pRW764.5. The sequence of this fragment is shown in FIG. 17 (SEQ ID NO:62) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:63) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:64):
    ACTCTCAAAAGCTTCCCGGGAATTCTAGCTAGCTAGTTTTTATAAA
RW146 (SEQ ID NO:65):
    GATCTTTATAAAAACTAGCTAGCTAGAATTCCCGGGAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene.

Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:66)–(SEQ ID NO:70)) are:

A (SEQ ID NO:66)   CTGAAATTATTTCATTATCGCGATATCCGTTAA
                   GTTTGTATCGTAATGGTTCCTCAGGCTCTCCTGTTTGT

B (SEQ ID NO:67)   CATTACGATACAAACTTAACGGATATCGCGATAA TGAAATAATTTCAG

C (SEQ ID NO:68)   ACCCCTTCTGGTTTTTCCGTTGTGTTTTGGGAAA
                   TTCCCTATTTACACGATCCCAGACAAGCTTAGATCTCAG

D (SEQ ID NO:69)   CTGAGATCTAAGCTTGTCTGGGATCGTGTAAATA GGGAATTTCCCAAAACA

E (SEQ ID NO:70)   CAACGGAAAAACCAGAAGGGGTACAAACAGGACA GCCTGAGGAAC

The diagram of annealed oligonucleotides A through E is as follows:

```
            A                       C
  _____|_____
                  |                    |
  _____|_____|_____
       B                  E                 D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:71): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG.

Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 18A and 18B). The correct insertion of the rabies G gene into the ALVAC genome without subsequent mutation was confirmed by sequence analysis.

Immunofluorescence.

During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation.

Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment.

In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell lines:

(1) Primary chick embryo fibroblast (CEF) cells produced from 11 day old white leghorn embryos;
(2) Vero cells—a continuous line of African Green monkey kidney cells (ATCC # CCL81); and
(3) MRC-5 cells—a diploid cell line derived from human fetal lung tissue (ATCC # CCL171).

The initial inoculation was performed at an m.o.i. of 0.1 pfu per cell using three 60 mm dishes of each cell line containing $2 \times 10^6$ cells per dish. One dish was inoculated in the presence of 40 µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell line was inoculated undiluted onto three dishes of the same cell line (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 5 and 6.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 5 and 6 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell line was inoculated onto a permissive CEF monolayer and harvested at cytopathic effect (CPE) or at 7 days if no CPE was evident. The results of this experiment are shown in Table 7. Even after amplification through a permissive cell line, virus was only detected in MRC-5 and Vero cells for two additional passages. These results indicated that under the conditions used, there was no adaptation of either virus to growth in Vero or MRC-5 cells.

Inoculation of Macaques.

Four HIV seropositive macaques were initially inoculated with ALVAC-RG as described in Table 8. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees.

Two adult male chimpanzees (50 to 65 kg weight range) were inoculated intramuscularly or subcutaneously with $1\times10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice.

Groups of mice were inoculated with 50 to 100 $\mu$l of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats.

Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys.

Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 $\mu$l instilled on the surface of the right eye without scarification; (2) 100 $\mu$l as several droplets in the mouth; (3) 100 $\mu$l in each of two intradermal injection sites in the shaven skin of the external face of the right arm; and (4) 100 $\mu$l in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG.

In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;

(b) MRC-5, human embryonic lung, ATCC # CCL 171;

(c) WISH human amnion, ATCC # CCL 25;

(d) Detroit-532, human foreskin, Downs's syndrome, ATCC # CCL 54; and (e) Primary CEF cells.

Chicken embryo fibroblast cells produced from 11 day old white leghorn embryos were included as a positive control. All inoculations were performed on preformed monolayers of $2 \times 10^6$ cells as discussed below.

A. Methods for DNA Analysis.

Three dishes of each cell line were inoculated at 5 pfu/cell of the virus under test, allowing one extra dish of each cell line un-inoculated. One dish was incubated in the presence of 40 µg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2 \times 10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 µg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of Virus Yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of Expression of Rabies G Gene.

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield.

The results of titration for yield at 72 hours after inoculation at 0.1 pfu per cell are shown in Table 9. The results indicate that while a productive infection can be attained in the avian cells, no increase in virus yield can be detected by this method in the four non-avian cell systems.

Analysis of Viral DNA Accumulation.

In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression.

To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 μl of dilutions inoculated into the footpad of four to six week old mice. Mice were challenged 14 days later by the intracranial route with 300 μl of the CVS strain of rabies virus containing from 15 to 43 mouse $LD_{50}$ as determined by lethality titration in a control group of mice. Potency, expressed as the $PD_{50}$ (Protective dose 50%), was calculated at 14 days post-challenge. The results of the experiment are shown in Table 10. The results indicated that ALVAC-RG was consistently able to protect mice against rabies virus challenge with a $PD_{50}$ value ranging from 3.33 to 4.56 with a mean value of 3.73 (STD 0.48). As an extension of this study, male mice were inoculated intracranially with 50 μl of virus containing 6.0 $\log_{10}$ $TCID_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ $TCID_{50}$ subcutaneously and five animals received 7.7 $\log_{10}$ $TCID_{50}$ by the same route. Animals were bled for analysis for anti-rabies antibody. Animals receiving no inoculation or 6.7 $\log_{10}$ $TCID_{50}$ of ALVAC-RG were challenged at 29 days post-vaccination with 3.7 $\log_{10}$ mouse $LD_{50}$ (dogs, in the temporal muscle) or 4.3 $\log_{10}$ mouse $LD_{50}$ (cats, in the neck) of the NYGS rabies virus challenge strain. The results of the experiment are shown in Table 11.

No adverse reactions to inoculation were seen in either cats or dogs with either dose of inoculum virus. Four of 5 dogs immunized with 6.7 $\log_{10}$ $TCID_{50}$ had antibody titers on day 14 post-vaccination and all dogs had titers at 29 days. All dogs were protected from a challenge which killed three out of four controls. In cats, three of five cats receiving 6.7 $\log_{10}$ $TCID_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ $TCID_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ $TCID_{50}$ of ALVAC-RG. Sera were analyzed for the presence of anti-rabies antibody. The results are shown in Table 12.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An amnanestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 13, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 14.

No adverse reactivity to inoculation was noted by either intramuscular or subcutaneous routes. Both chimpanzees responded to primary inoculation by 14 days and a strongly rising response was detected following re-vaccination.

TABLE 5

Sequential Passage of ALVAC in Avian and non-Avian Cells.

|  |  | CEF | Vero | MRC-5 |
|---|---|---|---|---|
| Pass 1 |  |  |  |  |
| Sample | to[a] | 2.4 | 3.0 | 2.6 |
|  | t7[b] | 7.0 | 1.4 | 0.4 |
|  | t7A[c] | 1.2 | 1.2 | 0.4 |
| Pass 2 |  |  |  |  |
| Sample | to | 5.0 | 0.4 | N.D.[d] |
|  | t7 | 7.3 | 0.4 | N.D. |
|  | t7A | 3.9 | N.D. | N.D. |
| Pass 3 |  |  |  |  |
| Sample | to | 5.4 | 0.4 | N.D. |
|  | t7 | 7.4 | N.D. | N.D. |
|  | t7A | 3.8 | N.D. | N.D. |
| Pass 4 |  |  |  |  |
| Sample | to | 5.2 | N.D. | N.D. |
|  | t7 | 7.1 | N.D. | N.D. |
|  | t7A | 3.9 | N.D. | N.D. |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post infection.
[d]Not detectable

TABLE 6

Sequential Passage of ALVAC-RG in Avian and non-Avian Cells

|  |  | CEF | Vero | MRC-5 |
|---|---|---|---|---|
| Pass 1 | | | | |
| Sample | t0[a] | 3.0 | 2.9 | 2.9 |
|  | t7[b] | 7.1 | 1.0 | 1.4 |
|  | t7A[c] | 1.8 | 1.4 | 1.2 |
| Pass 2 | | | | |
| Sample | t0 | 5.1 | 0.4 | 0.4 |
|  | t7 | 7.1 | N.D.[d] | N.D. |
|  | t7A | 3.8 | N.D. | N.D. |
| Pass 3 | | | | |
| Sample | t0 | 5.1 | 0.4 | N.D. |
|  | t7 | 7.2 | N.D. | N.D. |
|  | t7A | 3.6 | N.D. | N.D. |
| Pass 4 | | | | |
| Sample | t0 | 5.1 | N.D. | N.D. |
|  | t7 | 7.0 | N.D. | N.D. |
|  | t7A | 4.0 | N.D. | N.D |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 $\mu$g/ml of Cytosine arabinoside and harvested at 7 days post-infection.
[d]Not detectable.

TABLE 7

Amplification of residual virus by passage in CEF cells

|  |  | CEF | Vero | MRC-5 |
|---|---|---|---|---|
| a) ALVAC | | | | |
| Pass | 2[a] | 7.0[b] | 6.0 | 5.2 |
|  | 3 | 7.5 | 4.1 | 4.9 |
|  | 4 | 7.5 | N.D.[c] | N.D. |
|  | 5 | 7.1 | N.D. | N.D. |
| b) ALVAC-RG | | | | |
| Pass | 2a | 7.2 | 5.5 | 5.5 |
|  | 3 | 7.2 | 5.0 | 5.1 |
|  | 4 | 7.2 | N.D. | N.D. |
|  | 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 8

Schedule of inoculation of rhesus macaques with ALVAC-RG (vCP65)

| Animal | | Inoculation |
|---|---|---|
| 176L | Primary: | 1 × 10⁸ pfu of vCP65 orally in TANG |
|  | Secondary: | 1 × 10⁷ pfu of vCP65 plus 1 × 10⁷ pfu of VCP82[a] by SC route |
| 185L | Primary: | 1 × 10⁸ pfu of vCP65 orally in Tang |
|  | Secondary: | 1 × 10⁷ pfu of vCP65 plus 1 × 10⁷ pfu of vCP82 by SC route |
| 177L | Primary: | 5 × 10⁷ pfu SC of vCP65 by SC route |
|  | Secondary: | 1 × 10⁷ pfu of vCP65 plus 1 × 10⁷ pfu of vCP82 by SC route |
| 186L | Primary: | 5 × 10⁷ pfu of vCP65 by SC route |
|  | Secondary: | 1 × 10⁷ pfu of vCP65 plus 1 × 10⁷ pfu of vCP82 by SC route |
| 178L | Primary: | 1 × 10⁷ pfu of vCP65 by SC route |
| 182L | Primary: | 1 × 10⁷ pfu of vCP65 by IM route |
| 179L | Primary: | 1 × 10⁶ pfu of vCP65 by SC route |
| 183L | Primary: | 1 × 10⁶ pfu of vCP65 by IM route |

TABLE 8-continued

Schedule of inoculation of rhesus macaques with ALVAC-RG (vCP65)

| Animal | | Inoculation |
|---|---|---|
| 180L | Primary: | 1 × 10⁶ pfu of vCP65 by SC route |
| 184L | Primary: | 1 × 10⁵ pfu of vCP65 by IM route |
| 187L | Primary | 1 × 10⁷ pfu of vCP65 orally |

[a]vCP82 is a canarypox virus recombinant expressing the measles virus fusion and hemagglutinin genes.

TABLE 9

Analysis of yield in avian and non-avian cells inoculated with ALVAC-RG

|  | Sample Time | | |
|---|---|---|---|
| Cell Type | t0 | t72 | t72A[b] |
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 $\mu$g/ml of Cytosine arabinoside

TABLE 10

Potency of ALVAC-RG as tested in mice

| Test | Challenge Dose[a] | PD$_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse LD$_{50}$
[b]Expressed as $\log_{10}$ TCID$_{50}$

TABLE 11

Efficacy of ALVAC-RG in dogs and cats

|  | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 |  |
| N.T. | | | | |

[a]Antibody at day 29 post inoculation expressed as the geometric mean titer in International Units.
[b]Expressed as a ratio of survivors over animals challenged

TABLE 12

Anti-rabies serological response of Squirrel monkeys inoculated with canarypox recombinants

| Monkey # | Previous Exposure | Rabies serum-neutralizing antibody[a] | | | | | | |
|---|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ TCID$_{50}$ of ALVAC
[d]Animals received 5.0 $\log_{10}$ TCID$_{50}$ of vCP37
[e]Animals received 5.0 $\log_{10}$ TCID$_{50}$ of ALVAC-RG
[f]Animals received 7.0 $\log_{10}$ TCID$_{50}$ of ALVAC-RG
[g]Not tested.

TABLE 13

Inoculation of rhesus macaques with ALVAC-RG[a]

| | Route of Primary Inoculation | | | | | | | | | |
|---|---|---|---|---|---|---|---|---|---|---|
| Days post-Inoculation | or/Tang 176L[b]185L | SC 177L | SC 186L | SC 178L | IM 182L | SC 179L | IM 183L | SC 180L | IM 184L | OR 187L[b] |
| −84 | — | — | | — | | | | | | |
| −9 | — | — | — | — | — | — | | | | |
| 3 | — | — | — | — | | | | | | |
| 6 | — | — | ± | ± | | | | | | |
| 11 | — | — | 16[d] | 128 | | | | | | |
| 19 | — | — | 32 | 128 | — | | — | | | |
| 35 | — | — | 32 | 512 | | | | | | |
| 59 | — | — | 64 | 256 | | | | | | |
| 75 | — | — | 64 | 128 | — | | — | | | |
| 99[c] | — | — | 64 | 256 | — | — | — | — | — | — |
| 2 | — | — | 32 | 256 | — | — | — | — | — | — |
| 6 | — | — | 512 | 512 | — | — | — | — | — | — |
| 15 | 16 | 16 | 512 | 512 | 64 | 32 | 64 | 128 | 32 | — |
| 29 | 16 | 32 | 256 | 256 | 64 | 64 | 32 | 128 | 32 | — |
| 55 | | 32 | | | | 32 | | 32 | 16 | — |
| 57 | 16 | | 128 | 128 | 16 | | 16 | | | — |

[a]See Table 9 for schedule of inoculations.
[b]Animals 176L and 185L received 8.0 $\log_{10}$ pfu by the oral route in 5 ml Tang. Animal 187L received 7.0 $\log_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 14

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |

TABLE 14-continued

Inoculation of chimpanzees with ALVAC-RG

| Weeks post-Inoculation | Animal 431 I.M. | Animal 457 S.C. |
|---|---|---|
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation Example 22

Immunization of Humans Using Canarypox Expressing Rabies Glycoprotein (ALVAC-RG; vCP65)

Figure 18A:
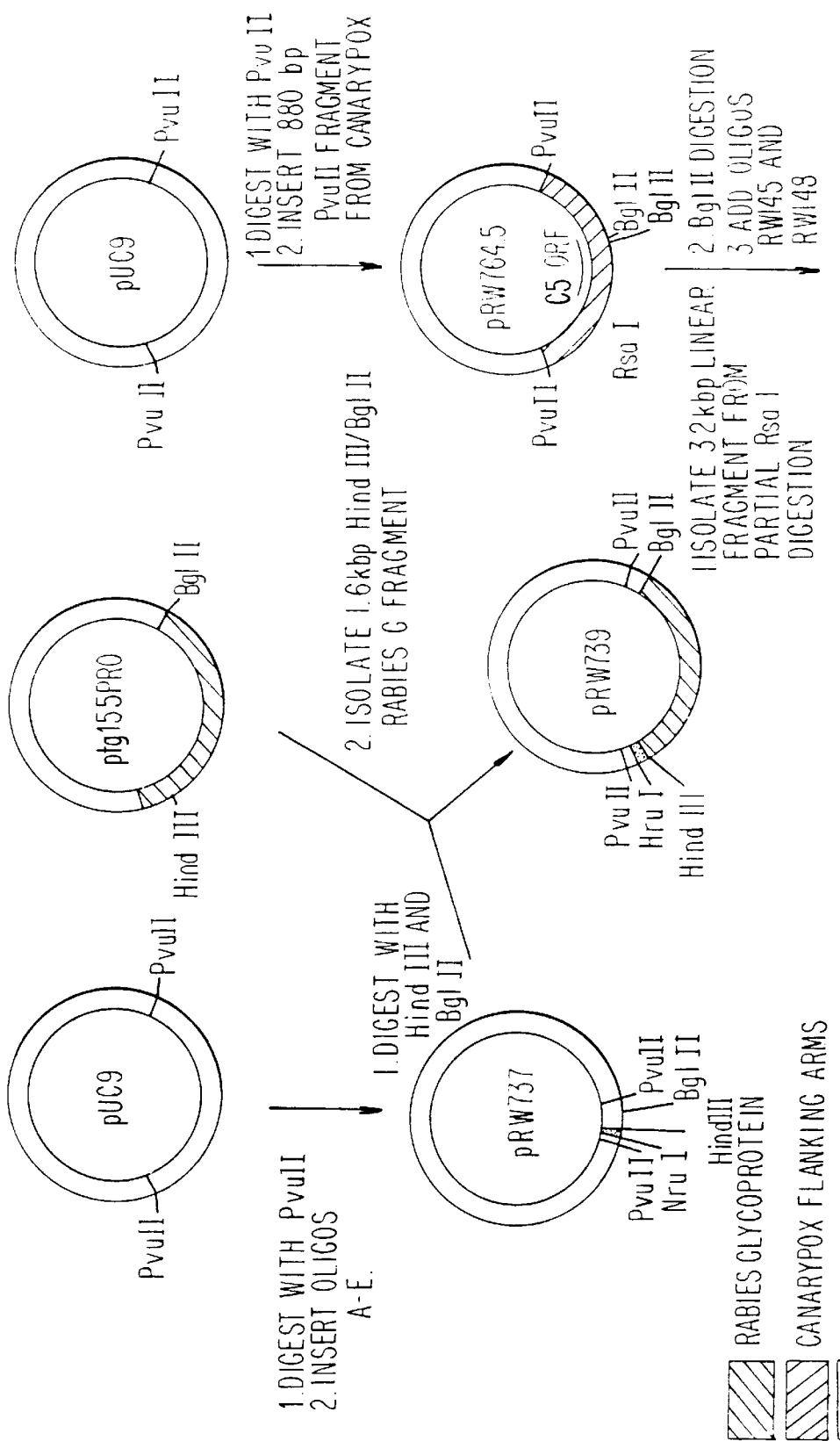
Figure 18B:
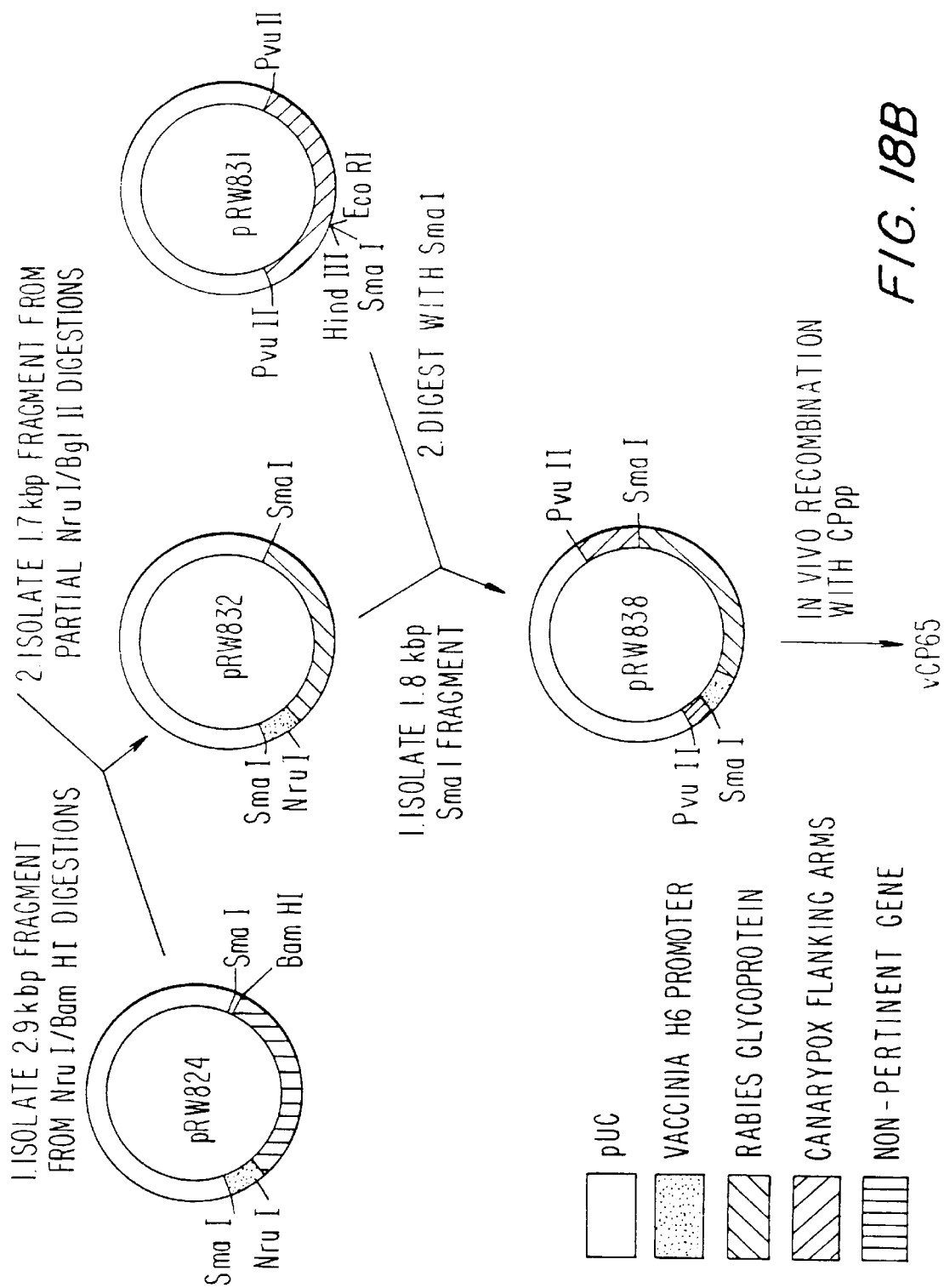

ALVAC-RG (vCP65) was generated as described in Example 21 and FIGS. 18A and 18B. For scaling-up and vaccine manufacturing ALVAC-RG (vCP65) was grown in primary CEF derived from specified pathogen free eggs. Cells were infected at a multiplicity of 0.01 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No undesirable trait was found.

Preclinical Data.

Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers.

Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study Design.

Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose (TCID$_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC - HDC; 2. HDC, HDC - ALVAC-RG (vCP65); 3. ALVAC-RG (vCP65), ALVAC-RG (vCP65) - HDC; 4. ALVAC-RG (vCP65), ALVAC-RG (vCP65), ALVAC-RG (vCP65).

Monitoring of Side Effects.

All subjects were monitored for 1 h after injection and re-examined every day for the next five days. They were asked to record local and systemic reactions for the next three weeks and were questioned by telephone two times a week.

Laboratory Investigators.

Blood specimens were obtained before enrollment and two, four and six days after each injection. Analysis included complete blood cell count, liver enzymes and creatine kinase assays.

Antibody Assays.

Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith & Yaeger, In Laboratory Techniques on Rabies). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis.

Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ TCID$_{50}$), nine subjects received $10^{5.5}$ TCID$_{50}$ and ten received the HDC vaccine.

Safety (Table 14).

During the primary series of immunization, fever greater than 37.7° C. was noted within 24 hours after injection in one HDC recipient (37.8° C.) and in one vCP65 $10^{5.5}$ TCID$_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ TCID$_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 16).

Twenty eight days after the first injection all the HDC recipients had protective titers ($\geq 0.5$ IU/ml). By contrast none in groups A and B ($10^{3.5}$ and $10^{4.5}$ TCID$_{50}$) and only 2/9 in group C ($10^{5.5}$ TCID$_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox Virus (Table 17).

The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection.

The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations.

FIGS. 22A–22D shows graphs of rabies neutralizing antibody titers (Rapid Fluorescent Focus Inhibition Test or RFFIT, IU/ml): Booster effect of HDC and vCP65 ($10^{5.5}$ TCID$_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 22A–22D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65) - ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., Lancet 1991, 337:567–72; Etinger et al., Vaccine 9:470–72, 1991).

Thus, this Example clearly demonstrates that a non-replicating poxvirus can serve as an immunizing vector in animals or humans, with all of the advantages that replicating agents confer on the immune response, but without the safety problem created by a fully permissive virus.

TABLE 15

Reactions in the 5 days following vaccination

| | vCP65 dosage (TCID50) | | | | | | HDC control | |
|---|---|---|---|---|---|---|---|---|
| | $10^{3.5}$ | | $10^{4.5}$ | | $10^{5.5}$ | | | |
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 16

Rabies neutralizing antibodies (REFIT; IU/ml) Individual titers and geometric mean titers GMT)

| | | Days | | | | |
|---|---|---|---|---|---|---|
| No. | TCID50/dose | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |

TABLE 16-continued

Rabies neutralizing antibodies (REFIT; IU/ml) Individual titers and geometric mean titers GMT)

| No. | TCID50/dose | Days | | | | |
|---|---|---|---|---|---|---|
| | | 0 | 7 | 28 | 35 | 56 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| | G.M.T. | <0.1 | <0.1 | 2.96 | 9.0 | 11.5* |

*p = 0.007 student t test

TABLE 17

Canarypox antibodies: ELISA Geometric Mean Titer*

| vCP65 dosage | Days | | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 23

Comparison of the $LD_{50}$ of ALVAC and NYVAC with Various Vaccinia Virus Strains Mice.

Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses.

ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated in CEF cells.

Inoculations.

Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench.

Comparison of the $LD_{50}$ of ALVAC and NYVAC with Various Vaccinia Virus Strains for Normal, Young Outbred Mice by the ic Route.

In young, normal mice, the virulence of NYVAC and ALVAC were several orders of magnitude lower than the other vaccinia virus strains tested (Table 18). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses ($3.85 \times 10^8$ PFUs, ALVAC and $3 \times 10^8$ PFUS, NYVAC) by an undetermined mechanism by this route of inoculation.

Comparison of the $LD_{50}$ of ALVAC and NYVAC with Various Vaccinia Virus Strains for Newborn Outbred Mice by the ic Route.

The relative virulence of 5 poxvirus strains for normal, newborn mice was tested by titration in an intracranial (ic) challenge model system (Table 19). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3 \times 10^7$ PFUs, 100% mortality resulted. Mortality rates of 33.3% were observed at $6.3 \times 10^6$ PFUs. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, 6×10$^8$ and 6×10$^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 LD$_{50}$, survived to day 4.

TABLE 18

Calculated 50% Lethal Dose for mice by various vaccinia virus strains and for canarypox virus (ALVAC) by the ic route.

| POXVIRUS STRAIN | CALCULATED LD$_{50}$ (PFUs) |
|---|---|
| WR(L) | 2.5 |
| VC-2 | 1.26 × 10$^4$ |
| WYETH | 5.00 × 10$^4$ |
| NYVAC | 1.58 × 10$^8$ |
| ALVAC | 1.58 × 10$^8$ |

TABLE 19

Calculated 50% Lethal Dose for newborn mice by various vaccinia virus strains and for canarypox virus (ALVAC) by the ic route.

| POXVIRUS STRAIN | CALCULATED LD$_{50}$ (PFUs) |
|---|---|
| WR(L) | 0.4 |
| VC-2 | 0.1 |
| WYETH | 1.6 |
| NYVAC | 1.58 × 10$^6$ |
| ALVAC | 1.00 × 10$^7$ |

Example 24

Evaluation of NYVAC (vP866) and NYVAC-RG (vP879)

Immunoprecipitations.

Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 $\mu$Ci/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trimarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals.

New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits.

Each of two rabbits was inoculated intradermally at multiple sites with 0.1 ml of PBS containing 10$^4$, 10$^5$, 10$^6$, 10$^7$, or 10$^8$ pfu of each test virus or with PBS alone. The rabbits were observed daily from day 4 until lesion resolution. Indurations and ulcerations were measured and recorded.

Virus Recovery from Inoculation Sites.

A single rabbit was inoculated intradermally at multiple sites of 0/1 ml of PBS containing 10$^6$, 10$^7$, or 10$^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice.

Groups of ten mice, or five in the nude mice experiment, were inoculated ip with one of several dilutions of virus in 0.5 ml of sterile PBS. Reference is also made to Example 23.

Cyclophosphamide (CY) Treatment.

Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per $\mu$l for untreated mice (n=4) and 4,220 cells per $\mu$l for CY-treated control mice (n=5).

Calculation of LD$_{50}$.

The lethal dose required to produce 50% mortality (LD$_{50}$) was determined by the proportional method of Reed and Muench (Reed and Muench 1938).

Potency Testing of NYVAC-RG in Mice.

Four to six week old mice were inoculated in the footpad with 50 to 100 $\mu$l of a range of dilutions (2.0–8.0 log$_{10}$ tissue culture infective dose 50% (TCID$_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 LD$_{50}$ of the rabies virus CVS strain (0.03 ml). On day 28, surviving mice were counted and protective does 50% (PD$_{50}$) calculated.

Derivation of NYVAC (vP866).

Figure 19:
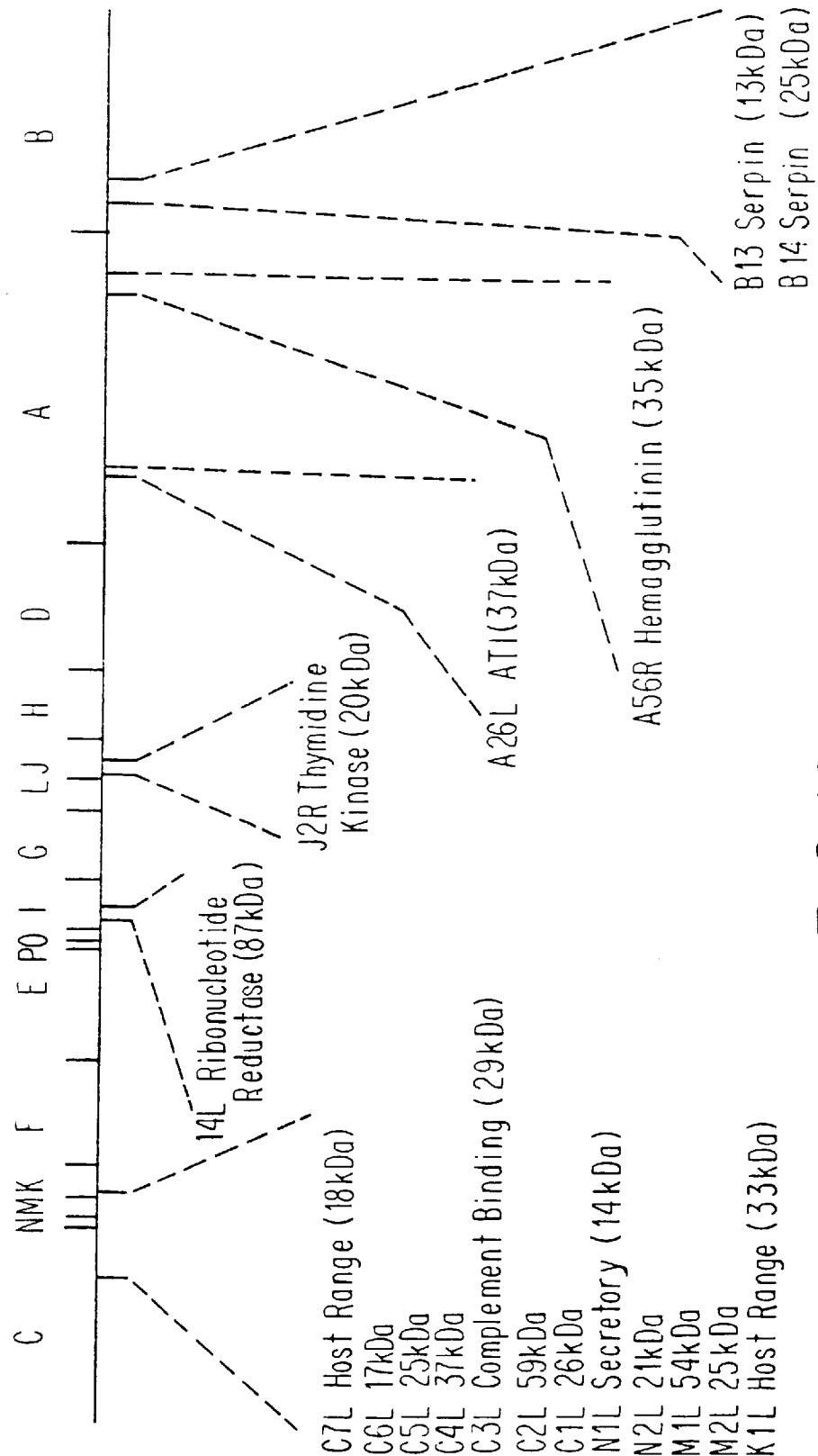
Figure 22B:
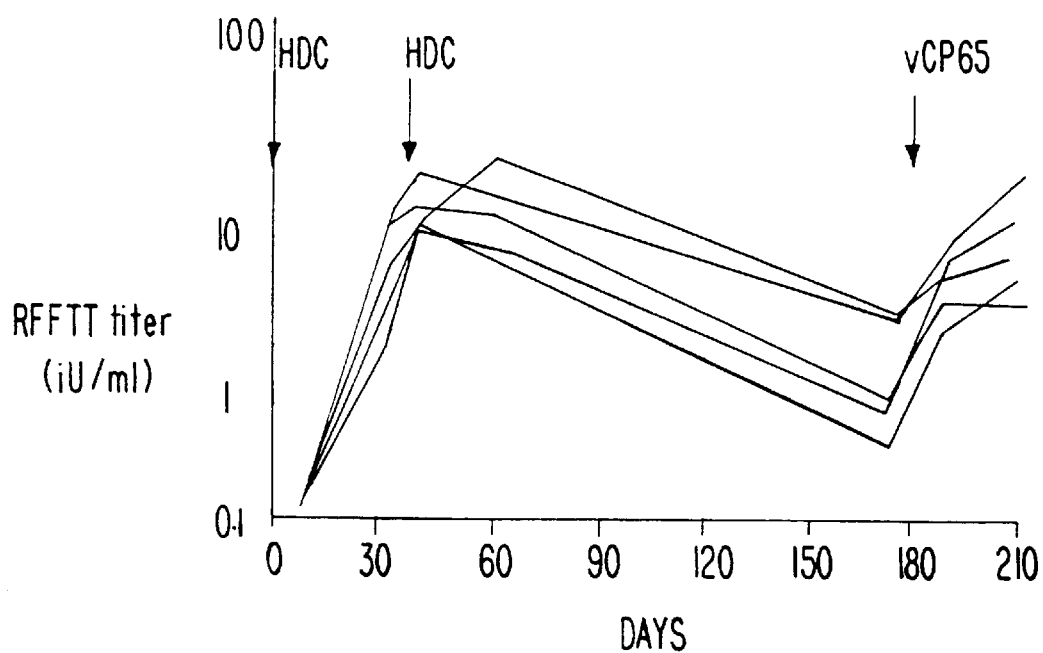
Figure 22D:
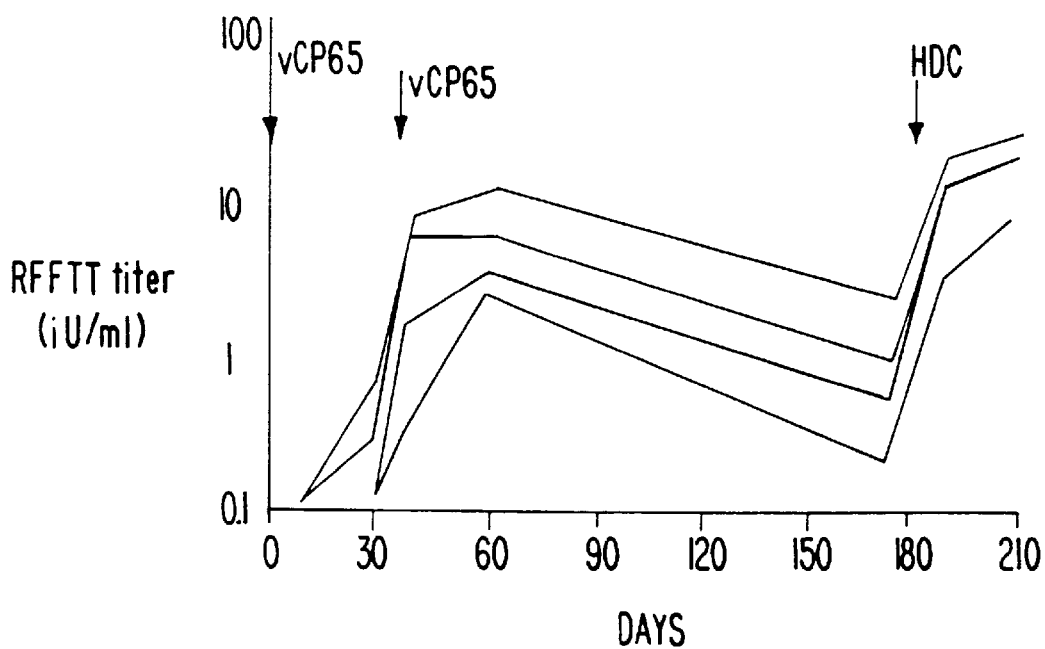

The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 19 schematically depicts the ORFs deleted to generate NYVAC. At the top of FIG. 19 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 13 through 18). Below such deletion locus is listed the ORFs which were deleted from that locus, along with the functions or homologies and molecular weight of their gene products.

Replication Studies of NYVAC and ALVAC on Human Tissue Cell Lines.

In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 20. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contract, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70-151) cells. Replication on these cell lines was significantly reduced when compared to virus yields obtained from NYVAC-infected CEF cells or with parental VC-2 (Table 20). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 20. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells.

In order to determine whether efficient expression of a foreign gene could be obtained in the absence of significant levels of productive viral replication, the same cell lines were inoculated with the NYVAC recombinant expressing the rabies virus glycoprotein (vP879, Example 19) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin.

The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRY-VAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 21). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation.

To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 22). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 22. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice.

Intraperitoneal inoculation of high doses of NYVAC ($5 \times 10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5 \times 10^7$ or $5 \times 10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 23.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5 \times 10^7$ and $5 \times 10^8$ pfu) showed lesions on toes and tails, developed orchitis, and died. Mice injected with $5 \times 10^6$ pfu or less of WYETH showed no signs of disease or lesions.

As shown in Table 23, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG.

In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 24 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations.

NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 23). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 18–24). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 23, Tables 18, 19, 23). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 21 and 22). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 21 and 22). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of genes in NYVAC prevents lesion occurrence.

Together, the results in this Example and in foregoing Examples, including Example 23, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 20) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 24). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1990). Furthermore, the use of NYVAC as a general laboratory expression vector system may greatly reduce the biological hazards associated with using vaccinia virus.

By the following criteria, the results of this Example and the Examples herein, including Example 23, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 20

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 μg/ml of cytosine arabinoside.
[d]Not determined.
*ATCC #CCL25 Human amnionic cells.

TABLE 21

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one sight.
[b]mean maximum size of lesions (mm$^2$)
[c]mean time after inoculation for complete healing of lesion.
[d]no lesions discernable.

TABLE 22

Persistence of poxviruses at the site of intradermal inoculation

| Virus | Inoculum Dose | Total Virus Recovered |
|---|---|---|
| WR | 8.0[a] | 6.14 |
|  | 7.0 | 6.26 |
|  | 6.0 | 6.21 |
| WYETH | 8.0 | 3.66 |
|  | 7.0 | 4.10 |
|  | 6.0 | 3.59 |
| VC-2 | 8.0 | 4.47 |
|  | 7.0 | 4.74 |
|  | 6.0 | 3.97 |
| NYVAC | 8.0 | 0 |
|  | 7.0 | 0 |
|  | 6.0 | 0 |

[a]expressed as $\log_{10}$ pfu.

TABLE 23

Virulence studies in immunocompromised mice

| Poxvirus Strain | $LD_{50}$[a] | |
|---|---|---|
|  | Nude mice | Cyclophosphamide treated mice |
| WR | 422 | 42 |
| VC-2 | >10$^9$ | <1.65 × 10$^5$ |
| WYETW | 1.58 × 10$^7$ | 1.83 × 10$^6$ |
| NYVAC | >5.50 × 10$^8$ | 7.23 × 10$^8$ |
| ALVAC | >10$^9$ | ≧5.00 × 10$^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of 5 × 10$^8$ pfu.

TABLE 24

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $\log_{10}$ tissue culture infection dose 50% (TCID$_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% (LD$_{50}$) per mouse. At day 28, surviving mice were counted and a protective do se 50% (PD$_{50}$) was calculated.

Example 25

Construction of Trovac Recombinants Expressing the Hemagglutinin Glycoproteins of Avian Influenza Viruses This Example describes the development of fowlpox virus recombinants expressing the hemagglutinin genes of three serotypes of avian influenza virus.

Cells and Viruses.

Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus.

Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 20 (SEQ ID NO:72). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:60) and JCA018 (SEQ ID NO:61).

JCA017 (SEQ ID NO:60): 5' CTAGACACTTTATGTTTTTAATATCCGGTCTT

AAAAGCTTCCCGGGGATCCTTATACGGGGAATAAT 3'

JCA018 (SEQ ID NO:61): 5' ATTATTCCCCGTATAAGGATCCCCCGGGAA

GCTTTTAAGACCGGATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:73) and RW179 (SEQ ID NO:74) were cut with EcoRV and BamHI and inserted between the EcoRV and BamHI sites of JCA004 to form pRW846.

This fragment was inserted into pBS-SK (Stratagene, La Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with

```
RW178   (SEQ ID NO:73):5' TCATTATCGCGATATCCGTGTTAACTAGCTA
                          GCTAATTTTTATTTCCCGGGATCCTTATCA 3'
RW179   (SEQ ID NO:74):5' GTATAAGGATCCCGGGAATAAAAATTAGCT
                          AGCTAGTTAACACGGATATCGCGATAATGA 3'
```

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus.

The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 21 (SEQ ID NO:75) was determined for a 2356 bp region encompassing the unique HincII site. Analysis of this sequence revealed that the unique HincII site (FIG. 21, underlined) was situated within an ORF encoding a polypeptide of 90 amino acids. The ORF begins with an ATG at position 1531 and terminates at position 898 (positions marked by arrows in FIG. 21).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:76) (5'-GACAATCTAAGTCCTATATTAGAC-3') and F73PB (SEQ ID NO:77) (5'-GGATTTTTAGGTAGACAC-3'). A 270 bp arm (designated as EH) corresponding to the region downstream from the ORF was amplified using oligonucleotides F75PE (SEQ ID NO:78) (5'-TCATCGTCTTCATCATCG-3') and F73PH1 (SEQ ID NO:79) (5'-GTCTTAAACTTATTGTAAGGGTATACCTG-3').

Fragment EH was digested with EcoRV to generate a 126 bp fragment. The EcoRV site is at the 3'-end and the 5'-end was formed, by PCR, to contain the 3' end of a HincII site. BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the E. coli DNA polymerase in the presence of 2 mM dNTPs. This linearized plasmid was ligated with annealed oligonucleotides F7MCSB (SEQ ID NO:80) (5'-AACGATTAGTTAGTTACTAAAAGCTTGCTGCAG-CCCGGGTTTTTTATTAGTTTAGTTAGTC-3') and F7MCSA (SEQ ID NO:81) (5'-GACTAACTAACTAATAAAAAACCCGGGCTGCAGC-AAGCTTTTTGTAACTAACTAATCGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus.

A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:82) and RW153 (SEQ ID NO:83). These oligonucleotides represent the 3' portion of the H6 promoter from the EcoRV site and align the ATG of the promoter with the ATG of the H4 cDNA.

```
RW152 (SEQ ID NO:82): 5' GCACGGAACAAAGCTTATCGCGATATCCGTTA
                      AGTTTGTATCGTAATGCTATCAATCACGATTCTGTTCCTGTTCCTGCTCATAGC
                      AGAGGGCTCATCTCAGAAT 3'
RW153 (SEQ ID NO:83): 5' ATTCTGAGATGAGCCCTCTGCTATGAGCAGGA
                      ACAGAATCGTGATTGATAGCATTACGATACAAACTTAACGGATATCGC
                      GATAAGCTTTGTTCCGTGC 3'
```

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

Construction of Insertion Plasmid for H5 Hemagglutinin at the F8 Locus.

A cDNA clone of avian influenza H5 derived from A/Turkey/Ireland/1378/83 was received in plasmid pTH29 from Dr. R. Webster. Synthetic oligonucleotides RW10 (SEQ ID NO:84) through RW13 (SEQ ID NO:87) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

nates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and

```
RW10 (SEQ ID NO:84):  5' GAAAAATTTAAAGTCGACCTGTTTTGTTGAGT

TGTTTGCGTGGTAACCAATGCAAATCTGGTC

ACT 3'

RW11 (SEQ ID NO:85):  5' TCTAGCAAGACTGACTATTGCAAAAAGAAGCA

CTATTTCCTCCATTACGATACAAACTTAACG

GAT 3'

R12 (SEQ ID NO:86):   5' ATCCGTTAAGTTTGTATCGTAATGGAGGAAA

TAGTGCTTCTTTTTGCAATAGTCAGTCTTGCTAGAAGTGACCAGATTT

GCATTGGT 3'

R13 (SEQ ID NO:87):   5' TACCACGCAAACAACTCAACAAAACAGGTCG

ACTTTAAATTTTTCTGCA 3'
```

The oligonucleotides were annealed at 95° C. for three minutes followed by slow cooling at room temperature. This results in the following double strand structure with the indicated ends.

```
EcoRV                                    PstI
  ├──────RW12──────┤        ├──RW13──┤
  ├──RW11──┤                ├──RW10──────┤
```

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV elimi- HincII sites of pRW846 (previously described). The resulting plasmid pRW849 contains the H6 promoted avian influenza virus H5 gene in the de-ORFed F8 locus.

Construction of Insertion Vector for H7 Hemagglutinin at the F7 Locus.

Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:88) and RW166 (SEQ ID NO:89) were annealed, cut with HincII and StyI and inserted between the EcoRV and STyI sites of pRW827 to generate pRW845.

```
RW165 (SEQ ID NO:88): 5' GTACAGGTCGACAAGCTTCCCGGGTATCGCG

ATATCCGTTAAGTTTGTATCGTAATGAATACTCAAATTCTAATACTCA

CTCTTGTGGCAGCCATTCACACAAATGCAGACAAAATCTGCCTTGGAC

ATCAT 3'

RW166 (SEQ ID NO:89): 5' ATGATGTCCAAGGCAGATTTTGTCTGCATTTG
```

```
-continued
TGTGAATGGCTGCCACAAGAGTGAGTATTAGAATTTGAGTATTCATTA

CGATACAAACTTAACGGATATCGCGATACCCGGGAAGCTTGTCGACCT

GTAC 3'
```

Oligonucleotides RW165 (SEQ ID NO:88) and RW166 (SEQ ID NO:89) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:90) and RW228 (SEQ ID NO:91). The resulting plasmid was pRW854.

```
RW227   (SEQ ID NO:90):    5' ATAACATGCGGTGCACCATTTGTATAT

AAGTTAACGAATTCCAAGTCAAGC 3'

RW228   (SEQ ID NO:91):    5' GCTTGACTTGGAATTCGTTAACTTATA

TACAAATGGTGCACCGCATGTTAT 3'
```

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the SmaI site of pF7DO described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the E. coli DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants.

Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence.

In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products HA$_1$ and HA$_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the HA$_2$ cleavage product. The HA$_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein HA$_0$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 26

CHV gB, gC and gD Nucleotides in Vector System, Expression Therefrom and Use of Vector System and Expression Product Expression of the CHV gB glycoprotein is accomplished by putting the CHV gB homolog gene under the control of the vaccinia virus I3L promoter. Expression of the CHV gc glycoprotein is accomplished by putting the CHV gC homolog gene under the control of the vaccinia virus H6 promoter. Expression of the CHV gD glycoprotein is accomplished by putting the CHV gD homolog gene under the control of the entomopox virus 42K gene promoter. The gB and gC coding is in the ATI locus and, the gD coding is in the HA locus.

Generation of Donor Plasmid.

The CHV gB coding sequence is PCR-derived. The CHV gB fragment is fused to a PCR-derived fragment containing the I3L promoter element in a plasmid containing the cassette I3L-CHV gB in the ATI deorfed locus. The CHV gC coding is PCR-derived and is fused in the HA deorfed locus in a plasmid.

A donor plasmid is used to insert the I3L-CHV gB—H6-CHV gC double construction in the NYVAC ATI deorfed locus.

In vitro recombination is performed on Vero cells using the donor plasmid and vP866 (NYVAC) as the rescuing virus. Standard protocols were used to identify and purify the recombinant virus (Piccini et al., 1987). The NYVAC-based recombinant containing the CHV gB and gC genes in the ATI deorfed locus is designated NYVAC-CHVgBgC.

Generation of Donor Plasmid.

The CHV gD coding sequence is fused to the 42K promoter and a resulting plasmid therefrom generated for insertion with the NYVAC HA deorfed locus.

In vitro recombination is performed on Vero cells using the CHV gD-42K donor plasmid and recombinant vaccinia virus NYVAC-CHVgBgC (NYVAC background) as the rescuing virus. This is performed with standard procedures (Piccini et al., 1987). The NYVAC-based recombinant containing the CHV gB and gC genes in the ATI deorfed locus and the CHV gD gene in the HA deorfed locus is designated NYVAC-CHVgBgCgD.

Generation of ALVAC donor plasmid.

A plasmid donor plasmid to insert the I3L-CHV gB—H6-CHV gC—42K-CHV gD triple construction in the ALVAC C3 deorfed locus is constructed from the above plasmids.

In vitro recombination is performed on primary chick embryo fibroblasts using the donor plasmid and CPpp (ALVAC) as the rescuing virus. Standard procedures are followed to identify and purify the generated recombinant (Piccini et al., 1987). The ALVAC-based recombinant contains the CHV gB, gC and gD genes in the C3 deorfed locus and is designated ALVAC-CHVgBgCgD.

Analysis confirms expression of the glycoproteins by the recombinants and, the glycoproteins are substantially within the predicted sequences.

Example 27

Generation of vCP320; an Alvac Recombinant Expressing CHV gB EXPRESSING CHV gB vCP320, an ALVAC recombinant expressing CHV gB, was generated by the following procedure. A 6 kb XbaI fragment, containing the CHV gB gene, was isolated from genomic CHV DNA and cloned into the XbaI site of pBSK+. The plasmid generated by this manipulation is called pCHV2.

The CHV gB gene was then cloned between canarypox flanking arms. This was accomplished by cloning the 3,700 bp SacI-EcoRV fragment of pCHV2, containing the CHV gB gene, into the 5,800 bp SacI-NaeI fragment of pBHVC16. (pBHVC16 contains a copy of the BHV1 gC gene cloned between C5 flanking arms.) The plasmid generated by this manipulation is called pCHV14.

Extraneous 3'-noncoding sequence was then eliminated. This was accomplished by cloning a 210 bp SmaI-ClaI-digested PCR fragment, containing the 3'-end of the gB gene, into the 5,500 bp partial SmaI-ClaI fragment of pCHV14. (This PCR fragment was generated from the plasmid, pCHV2, with the primers, CHVP39 (SEQ ID NO: 92; 5'-TAAGAATGGTAATTCT-3') and CHVP40 (SEQ ID NO: 93; 5'-TTCCCGGGTTAAACTTTACTTTCATTTTC-3').) The plasmid generated by this manipulation is called pCHV15.

The I3L promoter was then cloned upstream from the gB initiation codon. In addition, 3 T$_5$NT early transcription termination signal sequences located in the 5'-end of the gB gene were modified. This was accomplished by cloning a 140 bp ScaI-SalI-digested PCR fragment, containing the I3L promoter and the T$_5$NT-modified 5'-end of the gB gene, into the 6,300 bp ScaI-SalI fragment of pCHV15. (This PCR fragment was generated from the plasmid, pCHV2, with the primers, CHVP42 (SEQ ID NO: 94; 5'-TTGTCGACTGAGATAAAGTGAAAATATATCATTATATTACAAAGTACAATTATTTAGG

TTTAATCATGTTTTCATTGTATCTATAT-3')

and

CHVP78 (SEQ ID NO: 95; 5'-TTAGTACTTTCCGGTGTTGTTGGATCACATATTATTAAAGTATAAATAATAAAGAA-3').)

The plasmid generated by this manipulation is called pCHV27.

An error in the sequence flanking the ScaI-SalI fragment of pCHV27 was then corrected. This was accomplished by cloning the 180 bp ScaI-SalI fragment of pCHV27, containing the I3L promoter and the $T_5NT$-modified 5'-end of the gB gene, into the 6,300 bp ScaI-SalI fragment of pCHV15. The plasmid generated by this manipulation is called pCHV28.

An early transcription termination signal sequence near the 3'-end of the CHV gB gene was then modified. This was accomplished by cloning a 330 bp SpeI-Asp718-digested PCR fragment, containing the $T_5NT$-modified region of the CHV gB gene, into the 5,450 bp SpeI-Asp718 fragment of pCHV28. (This PCR fragment was generated from a 150 bp PCR fragment, a 280 bp PCR fragment and the primers, CHVP89 (SEQ ID NO: 96; 5'-TGGAATGAAGTTATGAAACT-3') and CHVP92 (SEQ ID NO: 97; 5'-TGCACTGATCATTTCAATTTC-3'). The 150 bp PCR fragment was generated from the plasmid, pCHV2, with the primers, CHVP89 (SEQ ID NO: 96; 5'-TGGAATGAAGTTATGAAACT-3') and CHVP90 (SEQ IS NO: 98; 5'-TGGAATTTTGAATGAAAACACTAGAACC-3'). The 280 bp PCR fragment was generated from the plasmid, pCHV2, with the primers, CHVP91 (SEQ ID NO: 99; 5'-TTCTAGTGTTTTCATTCAAAATTCCAT-3') and CHVP92 (SEQ ID NO: 97; 5'-TGCACTGATCATTTCAATTTC-3').) The plasmid generated by this manipulation is called pCHV31.

An early transcription termination signal sequence in the middle of the CHV gB gene was then modified. This was accomplished by cloning a 480 bp BamHI-BsaBI-digested PCR fragment, containing the $T_5NT$-modified region of the gB gene, into the 5,000 bp BamHI-BsaBI fragment of pCHV31. (This PCR fragment was generated from a 380 bp PCR fragment, a 210 bp PCR fragment and the primers, CHVP87 (SEQ ID NO: 100; 5'-CCTTCAAAGTTTAATACACC-3') and CHVP94 (SEQ ID NO: 101; 5'-TATGGCTTCACGTTTGGCAC-3'). The 380 bp PCR fragment was generated from the plasmid, pCHV2, with the primers, CHVP93 (SEQ ID NO: 102; 5'-CACCGGGGATATAATTCATATGTCCCCTTTCTTT-GGATTACGAGATGGT-3') and CHVP94 (SEQ ID NO: 101; 5'-TATGGCTTCACGTTTGGCAC-3'). The 210 bp PCR fragment was generated from the plasmid, pCHV2, with the primers, CHVP87 (SEQ ID NO: 100; 5'-CCTTCAAAGTTTAATACACC-3') and CHVP88 (SEQ ID NO: 103; 5'-CCAT-CTCGTAATCCAAAGAAAGGGGACATATGAAT-3').) The plasmid generated by this manipulation is called pCHV32.

A portion of the gB gene removed in the previous manipulation was then cloned back into pCHV32. This was accomplished by cloning the 2,000 bp partial BsaBI-PstI fragment of pCHV31, containing the 3'-end of the gB gene removed in the previous manipulation, into the 5,450 bp BsaBI-PstI fragment of pCHV32. The plasmid generated by this manipulation is called pCHV36.

The I3L-promoted gB gene was then cloned between C6 flanking arms. This was accomplished by cloning the 2,750 bp SalI-SmaI fragment of pCHV36, containing the I3L-promoted gB gene, into the 4,350 bp SalI-SmaI fragment of pHIV34. (pHIV34 contains a copy of the H6-promoted HIV2 gp120 (+TM) gene cloned between C6 flanking arms.) The plasmid generated by this manipulation is called pCHV37. The DNA sequence of the I3L-promoted gB gene in pCHV37 (SEQ ID NOS:104, 105, 106) is shown in FIG. 23. The DNA sequence of the ALVAC C6 flanking arms (SEQ ID NOS: 107, 108) is shown in FIG. 24.

pCHV37 was used in in vitro recombination experiments with ALVAC as the rescuing virus to yield vCP320.

Figure 25:
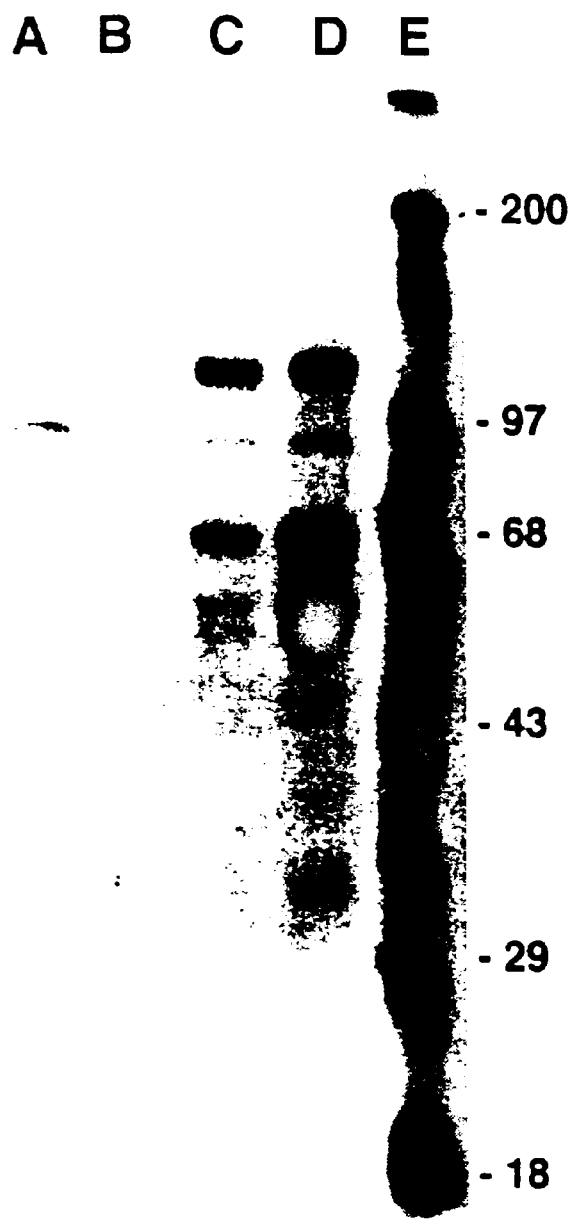
Figure 27:
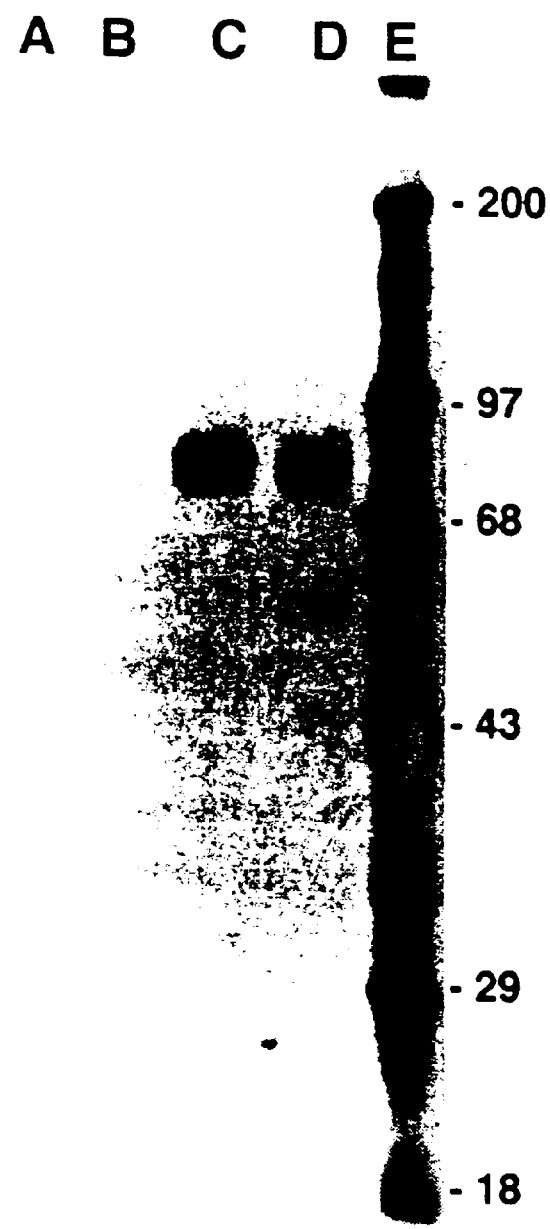
Figure 29:
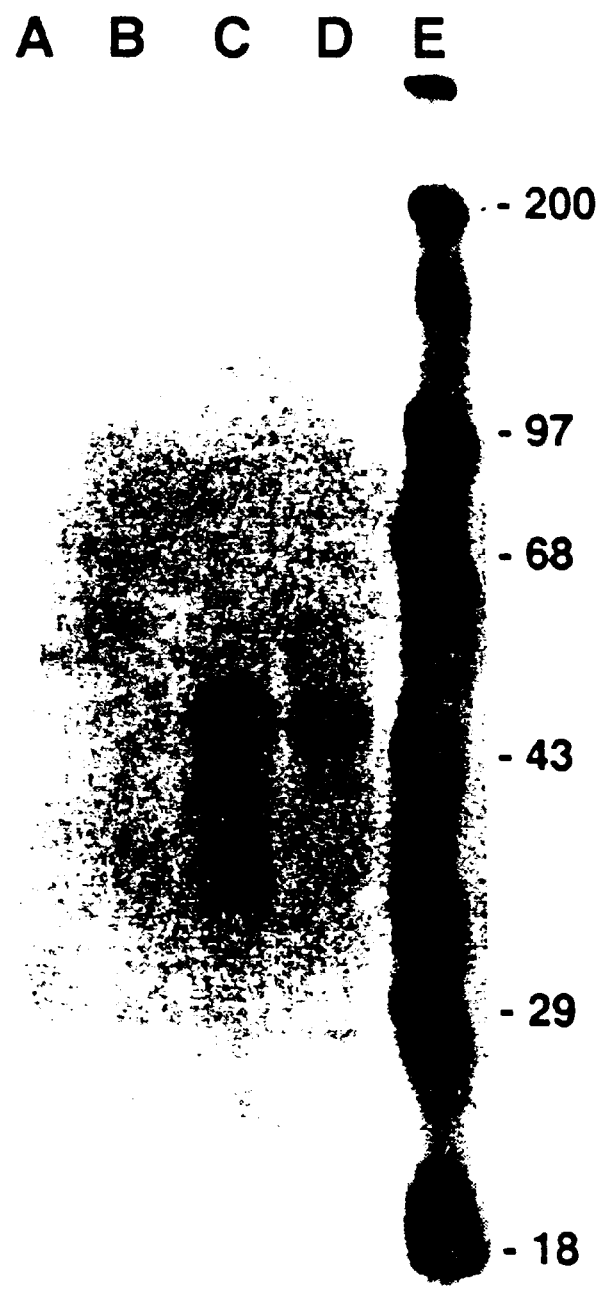

Immunoprecipitation analysis was performed to determine whether vCP320 expresses CHV gB. MDCK cell monolayers were either mock infected or infected with the parental virus (ALVAC) (m.o.i.=15 PFU/cell), vCP320 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 μCi/ml). The lysates were harvested at 18 hrs post-infection in 1 ml 3×buffer A (450 mM NaCl, 3% NP-40, 30 mM Tris (pH=7.4), 3 mM EDTA, 0.03% Na-Azide and 0.6 mg/ml PMSF) and analyzed for CHV gB expression using a 1:100 dilution of a gB-specific monoclonal antibody, 1125B2 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of the appropriate size were precipitated from CHV-infected cells (lane D) and vCP320-infected cells (lane C), but were not precipitated from mock-infected cells (lane A) or ALVAC-infected cells (lane B) (FIG. 25). These results indicate that vCP320 expresses CHV gB.

Example 28

Generation of vCP322; an Alvac Recombinant Expressing CHV gC EXPRESSING CHV gC vCP322, an ALVAC recombinant expressing CHV gC, was generated by the following procedure. A 2.2 kb EcoRI fragment, containing the CHV gC gene, was isolated from genomic CHV DNA and cloned into the EcoRI site of pVQH6CP3LSA. (pVQH6CP3LSA contains a copy of the H6 promoter cloned between C3 flanking arms.) This manipulation positions the gC gene downstream from the H6 promoter and between C3 flanking arms. The plasmid generated by this manipulation is called pCHV17.

Extraneous 3'-noncoding sequence was then eliminated and 3 $T_5NT$ early transcription termination signal sequences located near the 3'-end of the gC gene were modified. This was accomplished by cloning the oligonucleotides, CHVL66 (SEQ ID NO: 109; 5'-CGATGTTAATAAGTATTACCACAATAATTGGTGGAGCCATTTTCGTTATAGTATTGATTT

TCATAACAGCTTTATGTTTCTATTGTTCAAAAAATAATAAGATCTAACTGCA-3')

and

CHVL67 (SEQ ID NO: 110; 5'-GTTAGATCTTATTATTTTTTGAACAATAGAAACATAAAGCTGTTATGAAAATCAATACTA

TAACGAAAATGGCTCCACCAATTATTGTGGTAATACTTATTAACAT-3'), into the 8,400 bp partial ClaI-PstI fragment of pCHV17. The plasmid generated by this manipulation is called pCHV20.

The initiation codon of the gC gene was then aligned with the initiation codon of the H6 promoter. In addition, 2 early transcription termination signal sequences were modified. This was accomplished by cloning a 740 bp NruI-BsrGI-digested PCR fragment, containing the 3'-end of the H6 promoter and the 5'-end of the $T_5NT$-modified gC gene, into the 7,900 bp NruI-BsrGI fragment of pCHV20. (This PCR fragment was generated from a 500 bp PCR fragment, a 300 bp PCR fragment and the oligonucleotides, CHVP96 (SEQ ID NO: 111; 5'-CGTAGATTCCAATGGAAAGT-3') and CHVP97 (SEQ ID NO: 112; 5'-TTTTCGCGATATCCGTTAAGT-3'). The 500 bp PCR fragment was generated from the plasmid, pCHV13, with the oligonucleotides, CHVP68 (SEQ ID NO: 113; 5'-TTTTCGCGATATCCGTTAAGTTTGTATCGTAATG-AGTTTTAAAAATTTCTATCTAATATA TGTAATTATAATTTTCATAAACTCGATAATAAC-3') and CHVP69 (SEQ ID NO: 114; 5'-TTTGTATACCTAATAAGAAATCATTATAAAGT-3'). The 300 bp PCR fragment was generated from the plasmid, pCHV13, with the oligonucleotides, CHVP95 (SEQ ID NO: 115; 5'-CTTTTATAATGATTTCTTATTAGGTATACAAAATC-3') and CHVP96 (SEQ ID NO: 111; 5'-CGTAGATTCCAATGGAAAGT-3'). pCHV13 was obtained by cloning the 2.2 kb EcoRI CHV genomic fragment, containing the gC gene, into the EcoRI site of pBSK+.) The plasmid generated by this manipulation is called pCHV38.

Figures 26, 26A, 26B, 26C, 26D, 26E, 26F, 26G:
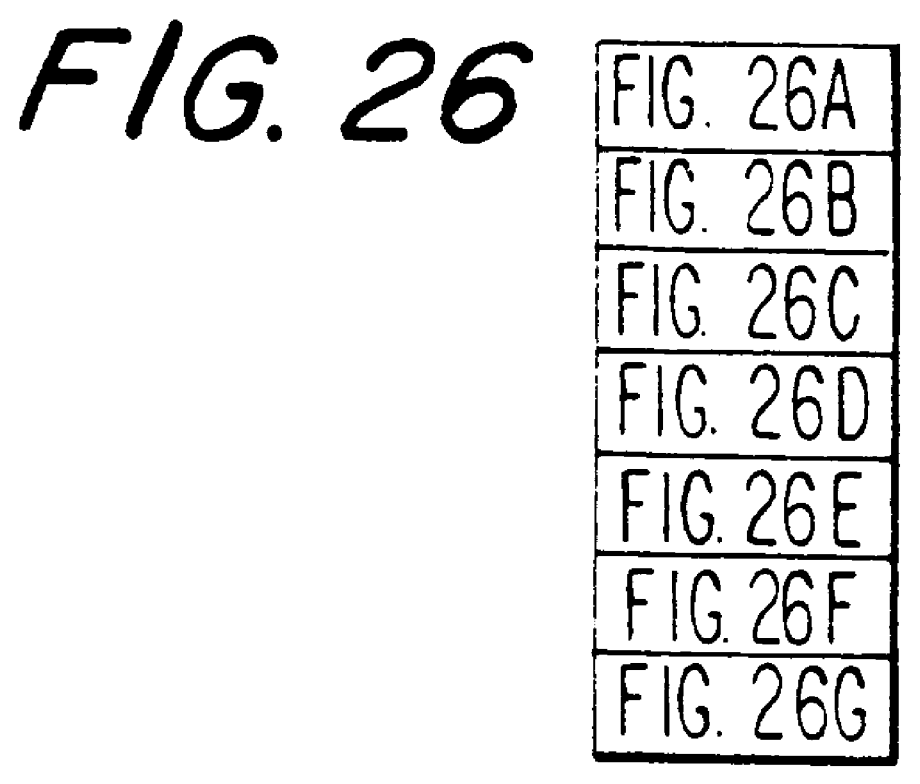

The H6-promoted gC gene was then cloned between C6 flanking arms. This was accomplished by cloning the 1,400 bp NruI-PstI fragment of pCHV38, containing the H6-promoted gC gene, and the oligonucleotide, CHVL98 (SEQ ID NO:116; 5'-AATTTGCA-3'), into the 4,500 bp NruI-EcoRI fragment of pHIV34. (pHIV34 contains a copy of the H6-promoted HIV2 gp120 (+TM) gene cloned between C6 flanking arms.) The plasmid generated by this manipulation is called pCHV40. The DNA sequence of the H6-promoted gC gene in pCHV40 (SEQ ID NOS: 117, 118, 119) is shown in FIG. 26. The DNA sequence of the ALVAC C6 flanking arms (SEQ ID NOS: 107, 108) is shown in FIG. 24.

pCHV40 was used in in vitro recombination experiments with ALVAC as the rescuing virus to yield vCP322.

Immunoprecipitation analysis was performed to determine whether vCP322 expresses CHV gC. MDCK cell monolayers were either mock infected or infected with the parental virus (ALVAC) (m.o.i.=15 PFU/cell), vCP322 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 $\mu$Ci/ml). The lysates were harvested at 18 hrs post-infection in 1 ml 3×buffer A (450 mM NaCl, 3% NP-40, 30 mM Tris (pH=7.4), 3 mM EDTA, 0.03% Na-Azide and 0.6 mg/ml PMSF) and analyzed for CHV gC expression using a 1:100 dilution of a gC-specific monoclonal antibody, 2011A9 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of the appropriate size were precipitated from CHV-infected cells (lane D) and vCP322-infected cells (lane C), but were not precipitated from mock-infected cells (lane A) or ALVAC-infected cells (lane B) (FIG. 27). These results indicate that vCP322 expresses CHV gC.

Example 29

Generation of VCP294; An Alvac Recombinant Expressing CHV gD vCP294, an ALVAC recombinant expressing CHV gD, was generated by the following procedure. A 7 kb PstI fragment, containing the CHV gD gene, was isolated from genomic CHV DNA and cloned into the PstI site of pBSK+. The plasmid generated by this manipulation is called pCHV11.

The CHV gD gene was then cloned between canarypox flanking arms. This was accomplished by cloning the 1,475 bp PstI-SnaBI fragment of pCHV11, containing the CHV gD gene, into the 5,600 bp PstI-SmaI fragment of pHIV34. (pHIV34 contains a copy of the H6-promoted HIV2 gp120 (+TM) gene cloned between C6 flanking arms.) This places the CHV gD gene between C6 flanking arms and downstream from the H6 promoter. The plasmid generated by this manipulation is called pCHV18.

The initiation codon of the H6 promoter was then aligned with the initiation codon of the CHV gD gene. This was accomplished by cloning the oligonucleotides, CHVL81 (SEQ ID NO: 120; 5'-CGATATCCGTTAAGTTTGTATCGTAATGATTAAACTTCTATTTATCTTATTTTATTTTAA CCCAATAA-3')

and

CHVL82 (SEQ ID NO: 121; 5'-TTGGGTTAAAATAAAATAAGATAAATAGAAGTTTAATCATTACGATACAAACTTAACGGA TATCG-3'),

- into the 5,600 bp NruI-PflMI fragment of pCHV18. The plasmid generated by this manipulation is called pCHV21.

Three early transcription termination signal sequences at the 3'-end of the CHVgD gene were then modified. This was accomplished by cloning the 1,400 bp BglII-Asp718 fragment of pCHV22, containing the "$T_5$NT-modified" 3'-end of the CHV gD gene and C3 flanking arm, into the 3,700 bp BglII-Asp718 fragment of pCHV21. (pCHV22 was generated by cloning a 430 bp BglII-EcoRI-digested PCR fragment, containing the "$T_5$NT-modified" 3'-end of the CHV gD gene, into the 3,900 bp BglII-EcoRI fragment of pHIV43 (pHIV43 contains a copy of the H6-promoted HIV1 gp120-murine IL-2 fusion gene cloned between C3 flanking arms). (This PCR fragment was generated from the plasmid, pCHV18, with the oligonucleotides, CHVP79 (SEQ ID NO: 122; 5'-TTGAATTCCTAAACATTTGTTGTTAATTTTTTATAATTAATTATATATTTTTTGTC
TTTTATAAACAAAGAAT-3')

and

CHVP80 (SEQ ID NO:123; 5'-TTAGATCTGTAGGAGCATCAAAAGTTGACGATGAACTTTTGTATCTAAATAGAGC
TGGTCCCCAAACCCTGCTTAAATATTATGTTATTAAAGATTTCTAT-3').))

The plasmid generated by this manipulation is called pCHV24.

The "$T_5$NT-modified" central region of the CHV gD gene was then cloned into pCHV24. This was accomplished by cloning a 240 bp BglII-digested PCR fragment, containing the "$T_5$NT-modified" central region of the CHV gD gene, into the BglII site of pCHV24. (This PCR fragment was generated from the plasmid, pCHV18, with the oligonucleotides, CHVP83 (SEQ ID NO: 124; 5'-TTAGATCTAGATTCCTTACACCATTCCATAAAAGTTGGTTCAAATTTATCTTCTTTAGAG
AAATAACAAGTTTCTCGTGGTAATTGAACCATAAAATCAGTATAGAAAAC-3')

and

CHVP84 (SEQ ID NO: 125; 5'-TATTTTGATTGTGATCC-3').)

The plasmid generated by this manipulation is called pCHV25.

The C3 flanking arm was then replaced with the C6 flanking arm. This was accomplished by cloning the 1,160 bp EcoRI-Asp718 fragment of pCHV21, containing the C6 flanking arm, into the 4,100 bp EcoRI-Asp718 fragment of pCHV25. The plasmid generated by this manipulation is called pCHV26. The DNA sequence of the H6-promoted gD gene in pCHV26 (SEQ ID NOS: 107, 108) is shown in FIG. 28. The DNA sequence of the ALVAC C6 flanking arms (SEQ ID NOS: 107, 105) is shown in FIG. 24.

pCHV26 was used in in vitro recombination experiments with ALVAC as the rescuing virus to yield vCP294.

Immunoprecipitation analysis was performed to determine whether vCP294 expresses CHV gD. MDCK cell monolayers were either mock infected or infected with the parental virus (ALVAC) (m.o.i.=15 PFU/cell), vCP294 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 $\mu$Ci/ml). The lysates were harvested at 18 hrs post-infection in 1 ml 3×buffer A (450 mM NaCl, 3% NP-40, 30 mM Tris (pH=7.4), 3 mM EDTA, 0.03% Na-Azide and 0.6 mg/ml PMSF) and analyzed for CHV gD expression using a 1:100 dilution of a gD-specific monoclonal antibody, 208D11 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of similar size were precipitated from CHV-infected cells (lane D) and vCP294-infected cells (lane C), but were not precipitated from mock-infected cells (lane A) or ALVAC-infected cells (lane B) (FIG. 29). These results indicate that vCP294 expresses CHV gD.

Having thus described in detail preferred embodiments of the present invention, it is to be understood that the invention defined by the appended claims is not to be limited by particular details set forth in the above description as many apparent variations thereof are possible without departing from the spirit or scope thereof.

The recombinants can be used to stimulate an antibody or immune response in pups and adult dogs against CHV and, so too can the expression products which can be isolated from cells infected by the recombinants. Further, the recombinants or the expression products therefrom can be used to generate antibodies in an animal administered the recombinants or the expression products therefrom and, the antibodies can be further used as described herein.

REFERENCES

1. Ackermann, M., R. Longnecker, B. Roizman, and L. Pereira, Virology 150, 207–220 (1986).

2. Allen, G. P. and M. R. Yeargan, J. Virol. 61, 2454–2461 (1987).

3. Allen, G. P. and J. T. Bryans, In: Progress in Veterinary Microbiology and Immunology, Vol. 2, ed. R. Pandey (Basel), pp. 78–144 (1986).

4. Allen, G. P., and L. D. Coogle, J. Virol. 62, 2850–2858 (1988).

5. Altenburger, W., C- P. Suter and J. Altenburger, Archives Virol. 105, 15–27 (1989).

6. Appel, M., In Virus Infections of Vertebrates, vol. 1, pp. 5–15. Edited by M. Appel. Amsterdam-Oxford-New York-Tokyo: Elsevier Science Publishers (1987).

7. Audonnet, J. -C., Winslow, J., Allen, G. & Paoletti, E., Journal of General Virology 71, 2969–2978 (1990).

8. Avery, R. J., and J. Niven., Infect. and Immun. 26, 795–801 (1979).

9. Babiuk, L. A., J. L'Italien, S. van Drunen Littel-van den Hurk, T. Zamb, M. J. P. Lawman, G. Hughes, and G. A. Gifford, J. Virol. 159, 57–66 (1987).

10. Baer, R., A. T. Bankier, M. D. Biggin, P. L. Deininger, P. J. Farrell, T. J. Gibson, G. Hatfull, G. S. Hudson, S. C. Satchwell, C. Seguin, P. S. Tuffnell, and B. G. Barrell, Nature 310, 207–211 (1984).

11. Baines, J., and B. Roizman, J. Virol. 67, 1441–1452 (1993).

12. Balachandran, N., S. Bacchetti, and W. E. Rawls, Infect. Immun. 37, 1132–1137 (1982).

13. Bause, E., Biochemical Journal 209, 331–336 (1983).

14. Behbehani, A. M., Microbiological Reviews 47, 455–509 (1983).

15. Ben-Porat, T., J. DeMarchi, J. Pendrys, R. A. Veach, and A. S. Kaplan, J. Virol. 57, 191–196 (1986).

16. Ben-Porat, T. and A. S. Kaplan, In: The Herpesviruses, vol. 3, ed. B. Roizman (Plenum Publishing Corp., New York) pp. 105–173 (1985).

17. Ben-Porat, T., F. J. Rixon, and M. L. Blankenship, Virology 95, 285–294 (1979).

18. Bergoin, M., and Dales, S., In Comparative Virology, eds. K. Maramorosch and E. Kurstak, (Academic Press, NY) pp. 169–205 (1971).

19. Berman, P. W., D. Dowbenko, L. A. Lasky, and C. C. Simonsen, Science 222, 524–527 (1983).

20. Bertholet, C., Drillien, R., and Wittek, R., Proc. Natl. Acad. Sci. USA 82, 2096–2100 (1985).

21. Blewett, E. & Misra, V., Journal of General Virology 72, 2083–2090 (1991).

22. Blobel, G., Proceedings of the National Academy of Sciences, U.S.A. 77, 1496–1500 (1980).

23. Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).

24. Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).

25. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).

26. Brockmeier, S., Lager, K., Tartaglia, J., Riviere, M., Paoletti, E. & Mengeling, W., Veterinary Microbiology 38, 41–58 (1993).

27. Buller, R. M. L., G. L. Smith, Cremer, K., Notkins, A. L., and Moss, B., Nature 317, 813–815 (1985).

28. Buller, R. M. L., Chakrabarti, S., Cooper, J. A., Twardzik, D. R., and Moss, B., J.Virol. 62, 866–874 (1988).

29. Bzik, D. J., B. A. Fox, N. A. DeLuca, and S. Person, Virology 133, 301–307 (1984).

30. Cadoz, M., A. Strady, B. Meignier, J. Taylor, J. Tartaglia, E. Paoletti and S. Plotkin, The Lancet, 339, 1429 (1992).

31. Cantin, E. M., R. Eberle, J. L. Baldick, B. Moss, D. E. Willey, A. L. Notkins, and H. Openshaw, Proc. Natl. Acad. Sci. USA 84, 5908–5912 (1987).

32. Carmichael, L., Strandberg, J. & Barnes, F., Proceedings of the Society for Experimental Biology and Medicine, 120, 644–650 (1965).

33. Carmichael, L., Journal of the American Veterinary Medical Association 156, 1714–1721 (1970).

34. Chambers, P., N. S. Millar, and P. T. Emmerson, J. Gen. Virol. 67, 2685–2694 (1986).

35. Chan, W., Immunol. 49, 343–352 (1983).

36. Child, S. J., Palumbo, G. J., Buller, R. M. L., and Hruby, D. E. Virology 174, 625–629 (1990).

37. Clewell, D. B., J. Bacteriol. 110, 667–676 (1972).

38. Clewell, D. B. and D. R. Helinski, Proc. Natl. Acad. Sci. USA 62, 1159–1166 (1969).

39. Colinas, R. J., R. C. Condit and E. Paoletti, Virus Research 18, 49–70 (1990).

40. Compton, T., In: Cell Biology of Virus Entry, Replication, and Pathogenesis, eds. Compans, R. W., A. Helenius, and M. B. A. Oldstone (Alan R. Liss, Inc.) pp. 45–56 (1989).

41. Cooney E. L., Corrier A. C., Greenberg P. D., et al., Lancet 337, 567–572 (1991).

42. Corden, J., Wasylyk, B., Buchwalder, A., Sassone-Corsi, P., Kedinger, C. & Chambon, P., Science 209, 1406–1414 (1980).

43. Cranage, M. P., T. Kouzarides, A. T. Bankier, S. Satchwell, K. Weston, P. Tomlinson, B. Barrell, H. Hart, S. E. Bell, A. C. Minson, and G. L. Smith, EMBO J. 5, 3057–3063 (1986).

44. Cremer, K. J., M. Mackett, C. Wohlenberg, A. L. Notkins, and B. Moss, Science 228, 737–740 (1985).

45. Davis, W. B., J. A. Taylor, and J. E. Oakes, J. Infect. Dis. 140, 534–540 (1979).

46. Davison, A. J., and J. E. Scott, J. gen. Virol. 67, 1759–1816 (1986).

47. Drillien, R., F. Koehren and A. Kirn, Virology 111, 488–499 (1981).

48. Eberle, R., and R. J. Courtney, J. Virol. 35, 902–917 (1980).

49. Edbauer, C., R. Weinberg, J. Taylor, A. Rey-Senelonge, J. F. Bouquet, P. Desmettre, and E. Paoletti, Virology 179, 901–904 (1990).

50. Engelke, D. R., Hoener, P. A., and Collins, F. S., Proc. Natl. Acad. Sci. USA 85, 544–548 (1988).

51. Espion, D., S. de Henau, C. Letellier, C. -D. Wemers, R. Brasseur, J. F. Young, M. Gross, M. Rosenberg, G. Meulemans and A. Burny, Arch. Virol. 95, 79–95 (1987).

52. Etinger H. M., Altenburger W., Vaccine 9, 470–472 (1991).

53. Fargeaud, D., C. Benoit Jeannin, F. Kato, and G. Chappuis, Arch. Virol. 80, 69–82 (1984).

54. Fenner, F., Virology 5, 502–529 (1958).

55. Fitzpatrick, D. R., Babiuk, L. A. & Zamb, T. J., Virology 173, 46–57 (1989).

56. Flexner, C., Hugen, A., and Moss, B., Nature 330, 259–262 (1987).

57. Flowers, C., Eastman, E. & O'Callaghan, D., Virology 180, 175–184 (1991).

58. Frame, M. C., H. S. Marsden, and D. J. McGeoch, J. gen. Virol. 67, 745–751 (1986).

59. Fries et al., 32nd Interscience Conference on Antimicrobial Agents and Chemotherapy, Anaheim, Calif. (October 1992).

60. Frink, R. J., M. R. Eisenberg, G. Cohen, and E. K. Wagner, J. Virol. 45, 634–647 (1983).

61. Funahashi, S., T. Sato and H. Shida, J. Gen. Virol. 69, 35–47 (1988).

62. Garten, W., Kohama, T., and H- D. Klenk. J. Gen. Virol. 51, 207–211 (1980).

63. Ghendon, Y. Z., and Chernos, V. I., Acta Virol. 8, 359–368 (1964).

64. Gillard, S., Spehner, D., Drillien, R., and Kirn, A., Proc. Natl. Acad. Sci. USA 83, 5573–5577 (1986).

65. Glorioso, J., C. H. Schroder, G. Kumel, M. Szczesiul, and M. Levine, J. Virol. 50, 805–812 (1984).

66. Glorioso, J., U. Kees, G. Kumel, H. Kirchner, and P. Krammer, J. Immunol. 135, 575–582 (1985).

67. Goebel, S. J., Johnson, G. P., Perkus, M. E., Davis, S. W., Winslow, J. P., Paoletti, E., Virology 179, 247–266 (1990a).

68. Goebel, S. J., G. P. Johnson, M. E. Perkus, S. W. Davis, J. P. Winslow and E. Paoletti, Virology 179, 517–563 (1990b).

69. Goldstein, D. J. and S. K. Weller, Virology 166, 41–51 (1988).

70. Gretch, D. R., B. Kari, L. Rasmussen, R. C. Gehrz, and M. F. Stinski, J. Virol. 62, 875–881 (1988).

71. Guo, P., Goebel, S., Davis, S., Perkus, M. E., Languet, B., Desmettre, P., Allen, G., and Paoletti, E., J. Virol. 63, 4189–4198 (1989).

72. Guo et al., J. Virol. 64, 2399–2406 (1990).

73. Hampl, H., T. Ben-Porat, L. Ehrlicher, K -O. Habermehl, and A. S. Kaplan, J. Virol. 52, 583–590 (1984).

74. Homma, M., and M. Ohuchi, J. Virol. 12, 1457–1465 (1973).

75. Honess, R. W., Journal of General Virology 65, 2077–2107 (1984).

76. Honess, R. W., Bodemer, W., Cameron, K. R., Niller, H.- H. & Fleckenstein, B., Proceedings of the National Academy of Sciences, U.S.A. 83, 3604–3608 (1986).

77. Hruby, D. E., R. A. Maki, D. B. Miller and L. A. Ball, Proc. Natl. Acad. Sci. USA 80, 3411–3415 (1983).

78. Hutchinson, L., Browne, H., Wargents, V., Doris-Poynter, N., Primorac, S., Goldsmith, K., Minson, A., and D. C. Johnson. J. Virol. 66, 2240–2250 (1992).

79. Hutchinson, L., Goldsmith, K., Snoddy, A., Ghash, H., Graham, F. and D. Johnson. J. Virol. 66, 5603–5609 (1992b).

80. Hruby, D. E. and L. A. Ball, J. Virol. 43, 403–409 (1982).

81. Ichihashi, Y. and Dales, S., Virology 46, 533–543 (1971).

82. Ihara, T., Kato, A., Ueda, S., Ishihama, A. & Hirai, K., Virus Genes 3, 127–140 (1989).

83. Ishii, H., Y. Kobayashi, M. Kuroki and Y. Kodama, J. gen. Virol. 69, 1411–1414 (1988).

84. Jacobson, J. G., D. A. Leib, D. J. Goldstein, C. L. Bogard, P. A. Schaffer, S. K. Weller and D. M. Coen, Virology 173, 276–283 (1989).

85. Jamieson, A. T., G. A. Gentry and J. H. Subak-Sharpe, J. Gen. Virol. 24, 465–480 (1974).

86. Kato, A., Sato, I., Ihara, T., Ueda, S., Ishihama, A. & Hirai, K., Gene 84, 399–405 (1989).

87. Kato, S., M. Takahashi, S. Kameyama and J. Kamahora, Biken's 2, 353–363 (1959).

88. Keller, P. M., A. J. Davison, R. S. Lowe, C. D. Bennett, and R. W. Ellis, Virology 152, 181–191 (1986).

89. Kieff, E., and D. Liebowitz, In: Virology, Second Edition, eds. Fields, B. N. et al. (Raven Press, Ltd., New York) pp. 1889–1920 (1990).

90. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).

91. Klein, P., Kanehisa, M. & DeLisi, C., Biochimica Biophysica Acta 815, 468–476 (1985).

92. Konishi et al., Virology 190, 454–458 (1992).

93. Kopp, A. & Mettenleiter, T., Journal of Virology 66, 2754–2762 (1992).

94. Kost, T. A., E. V. Jones, K. M. Smith, A. P Reed, A. L. Brown, and T. J. Miller, Virology 171, 365–376 (1989).

95. Kotwal, G. J., A. W. Hugin and B. Moss, Virology 171, 579–587 (1989a).

96. Kotwal, G. J. and B. Moss, J. Virol. 63, 600–606 (1989b).

97. Kotwal, G. J., S. N. Isaacs, R. McKenzie, M. M. Frank and B. Moss, Science 250, 827–830 (1990).

98. Kotwal, G. J. and Moss, B., Nature (Lond.) 335, 176–178 (1988).

99. Kouzarides, T., Bankier, A. T., Satchwell, S. C., Weston, K., Tomlinson, P. & Barrell, B. G., Virology 157, 397–413 (1987).

100. Kozak, M., Cell 44, 283–292 (1986).

101. Kuhn, J., Eing, B., Brossmer, R., Munk, K. & Braun, R., Journal of General Virology 69, 2847–2858 (1988).

102. Lai, A. C. -K. and B. G. -T. Pogo, Virus Res. 12, 239–250 (1989).

103. Lasky, L. A., D. Dowbenko, C. C. Simonsen, and P. W. Berman, Bio-Technology 2, 527–532 (1984).

104. Lawrence, W. C., R. C. D'Urso, C. A. Kundel, J. C. Whitbeck and L. J. Bello, J. Virol. 60, 405–414 (1986).

105. Le, L., R. Brasseur, C. Wemers, G. Meulemans, and A. Burny, Virus Genes 1, 333–350 (1988).

106. Long, D., Cohen, G., Muggeridge, M. & Eisenberg, R., Journal of Virology 64, 5542–5552 (1990).

107. Long, D., Wilcox, W., Abrams, W., Cohen, G. & Eisenberg, R., Journal of Virology 66, 6668–6685 (1992).

108. Longnecker, R., S. Chatterjee, R. Whitley, and B. Roizman, Proc. Natl. Acad. Sci. USA 84, 4303–4307 (1987).

109. Maeda, K., Horimoto, T., Norimine, J., Kawaguchi, Y., Tomonaga, K., Niikura, M., Kai, C., Takahashi, E. & Mikami, T., Archives of Virology 127, 387–397.

110. Mandecki, W., Proc. Natl. Acad. Sci. USA 83, 7177–7182 (1986).

111. Maniatis, T., E. F. Fritsch, and J. Sambrook, Molecular Cloning: A Laboratory Manual, (Cold Spring Harbor Laboratory, New York) (1982).

112. Marchioli, C. C., R. J. Yancey, Jr., R. C. Wardley, D. R. Thomsen and L. E. Post, Am. J. Vet. Res. 48, 1577–1583 (1987).

113. Marchioli, C., R. J. Yancey, Jr., J. G. Timmins, L. E. Post, B. R. Young, and D. A. Povendo, Am. J. Vet. Res. 49, 860–864 (1988).

114. Marchioli, C. C., R. J. Yancey, Jr., E. A. Petrovskis, J. G. Timmins, and L. E. Post, J. Virol. 61, 3977–3982 (1987).

115. Matthews, R. E. F., Intervirology 17, 42–44 (1982).

116. McGeoch, D. J., M. A. Dalrymple, A. J. Davison, A. Dolan, M. C. Frame, D. McNab, L. J. Perry, J. E. Scott, and P. Taylor, J. gen. Virol. 69, 1531–1574 (1988).

117. McGinnes, L. W., and T. G. Morrison, Virus Research 5, 343–356 (1986).

118. McLaughlin-Taylor, E., D. E. Willey, E. M. Cantin, R. Eberle, B. Moss, and H. Openshaw, J. gen. Virol. 69, 1731–1734 (1988).

119. Meas, R. K., S. L. Fritsch, L. L. Herr, and P. A. Rota, J. Virol. 51, 259–262 (1984).

120. Merz, D. C., A. Scheid, and P. Choppin, J. Exper. Med. 151, 275–288 (1980).

121. Misra, V., R. M. Blumenthal and L. A. Babiuk, J. Virol. 40, 367–378 (1981).

122. Morgan, A. J., M. Mackett, S. Finerty, J. R. Arrand, F. T. Scullion and M. A. Epstein, J. Med. Virol. 25, 189–195 (1988).

123. Moss, B., E. Winters and J. A. Cooper, J. Virol. 40, 387–395 (1981).

124. Nagai, Y., H. D. Klenk, and R. Rott, Virology 72, 494–508 (1976).

125. Nagai, Y., T. Yoshida, M. Hamaguchi, H. Naruse, M. Iinuma, K. Maeno, and T. Matsumoto, Microbiol. Immunol. 24, 173–177 (1980).

126. Nazerian, K., Lee, L., Yanagida, N. & Ogawa, R., Journal of Virology 66, 1409–1413 (1992).

127. Nicolson, L. & Onions, D. E., Virology 179, 378–387 (1990).

128. Norrby, E., and Y. Gollmar, Infect. and Immun. 11, 231–239 (1975).

129. Oakes, J. E., and H. Rosemond-Hornbeak, Infect. Immun. 21, 489–495 (1978).

130. Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).

131. Paez, E., S. Dallo and M. Esteban, Proc. Natl. Acad. Sci. USA 82, 3365–3369 (1985).

132. Palumbo, G. J., Pickup, D. J., Fredrickson, T. N., Mcintyre, L. J., and Buller, R. M. L., Virology 172, 262–273 (1989).

133. Panicali, D., S. W. Davis, S. R. Mercer, and E. Paoletti, J. Virol. 37, 1000–1010 (1981).

134. Panicali, D. and E. Paoletti, Proc. Natl. Acad. Sci. USA 79, 4927–4931 (1982).

135. Panicali, D., Davis, S. W., Mercer, S. R., and Paoletti, E., J. Virol. 37, 1000–1010 (1981).

136. Paoletti, E., B. R. Lipinskas, C. Samsonoff, S. Mercer, and D. Panicali, Proc. Natl. Acad. Sci. USA 81, 193–197 (1984).

137. Papp-Vid, G., and J. B. Derbyshire, Can. J. Comp. Med. 43, 231–233 (1979).

138. Patel, D. D. and Pickup, D. J., EMBO 6, 3787–3794 (1987).

139. Patel, D. D., Ray, C. A., Drucker, R. P., and Pickup, D. J., Proc. Natl. Acad. Sci. USA 85, 9431–9435 (1988).

140. Pearson, W. R. & Lipman, D. J., Proceedings of the National Academy of Sciences 85, 2444–2448 (1988).

141. Pellett, P. E., M. D. Biggin, B. L. Barrell, and B. Roizman, J. Virol. 56, 807–813 (1985).

142. Perkus M. E., Piccini A., Lipinskas B. R., et al., Science 229, 981–984 (1985).

143. Perkus, M. E., K. Limbach, and E. Paoletti, J. Virol. 63, 3829–3836 (1989).

144. Perkus, M. E., A. Piccini, B. R. Lipinskas, and E. Paoletti, Science 229, 981–984 (1985).

145. Perkus, M. E., Goebel, S. J., Davis, S. W., Johnson, G. P., Limbach, K., Norton, E. K., and Paoletti, E., Virology 179, 276–286 (1990).

146. Perkus, M. E., D. Panicali, S. Mercer and E. Paoletti, Virology 152, 285–297 (1986).

147. Perkus, M. E., Limbach, K., and Paoletti, E., J. Virol. 63, 3829–3836 (1989).

148. Perkus, M. E., S. J. Goebel, S. W. Davis, G. P. Johnson, E. K. Norton and E. Paoletti, Virology 180, 406–410 (1991).

149. Petrovskis, E. A., J. G. Timmins, M. A. Armentrout, C. C. Marchioli, R. J. Yancey, Jr., and L. E. Post, J. Virol. 59, 216–223 (1986).

150. Petrovskis, E. A., J. G. Timmins, and L. E. Post, J. Virol. 60, 185–193 (1986).

151. Piccini, A., M. E. Perkus, and E. Paoletti, Methods in Enzymology 153, 545–563 (1987).

152. Piccini, A., M. E. Perkus, and E. Paoletti, In: Methods in Enzymology, Vol. 153, eds. Wu, R., and L. Grossman (Academic Press) pp. 545–563 (1987).

153. Pickup, D. J., B. S. Ink, W. Hu, C. A. Ray and W. K. Joklik, Proc. Natl. Acad. Sci. USA 83, 7698–7702 (1986).

154. Pickup, D. J., B. S. Ink, B. L. Parsons, W. Hu and W. K. Joklik, Proc. Natl. Acad. Sci. USA 81, 6817–6821 (1984).

155. Pizer, L., Cohen, G. & Eisenberg, R., Journal of Virology 34, 142–153 (1980).

156. Plummer, G., Goodheart, C., Henson, D. & Bowling, C., Virology 39, 134–137 (1969).

157. Proudfoot, N. J. & Brownlee, G. G., Nature 163, 211–214 (1976).

158. Reed, L. J. and Muench, H., Am. J. Hyg. 27, 493–497 (1938).

159. Richman, D. D., A. Buckmaster, S. Bell, C. Hodgman and A. C. Minson, J. Virol. 57, 647–655 (1986).

160. Riggio, M. P., A. A. Cullinane, and D. E. Onions, J. Virol. 63, 1123–1133 (1989).

161. Riviere, M., Tartaglia, J., Perkus, M. E., Norton, E. K., Bongermino, C. M., Lacoste, F., Duret, C., Desmettre, P. & Paoletti, E., Journal of Virology 66, 3424–3434 (1992).

162. Robbins, A. K., R. J. Watson, M. E. Whealy, W. W. Hays, and L. W. Enquist, J. Virol. 58, 339–347 (1986).

163. Robbins, A. K., D. J. Dorney, M. W. Wathen, M. E. Whealey, C. Gold, R. J. Watson, L. E. Holland, S. D. Weed, M. Levine, J. C. Glorioso, and L. W. Enquist, J. Virol. 61, 2691–2701 (1987).

164. Roizman, B. and A. E. Sears, In: Virology, eds. Fields, B. N. and D. M. Knipe (Raven Press, Ltd., New York) pp. 1795–1841 (1990).

165. Roizman, B., In The Herpesviruses, vol. 1, pp. 1–23, Ed. B. Roizman, New York & London: Plenum Press (1982).

166. Rooney, J. F., C. Wohlenberg, K. J. Cremer, B. Moss, and A. L. Notkins, J. Virol. 62, 1530–1534 (1988).

167. Rosenthal, K. L., J. R. Smiley, S. South, and D. C. Johnson, J. Virol. 61, 2438–2447 (1987).

168. Ross, L., Sanderson, M., Scott, S., Binns, M., Doel, T. & Milne, B., Journal of General Virology 70, 1789–1804 (1989).

169. Rota, P. A., R. K. Maes, and W. T. Ruyechan, Virology 154, 168–179 (1986).

170. Rubenstein, A. S. and A. S. Kaplan, Virology 66, 385–392 (1975).

171. Sanger, F., S. Nicklen, and A. Coulson, Proc. Natl. Acad. Sci. USA 74, 5463–5467 (1977).

172. Schmidt, J. F. C. and H. G. Stunnenberg, J. Virol. 62, 1889–1897 (1988).

173. Seligmann, E. B., In Laboratory Techniques in Rabies, eds. M. M. Kaplan and H. Koprowski, (World Health Organization, Geneva) pp. 279–285 (1973).

174. Shapira, S. K., Chou, J., Richaud, F. V. and Casadaban, M. J., Gene 25, 71–82 (1983).

175. Shida, H., Virology 150, 451–462 (1986).

176. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).

177. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).

178. Shimizu, M., K. Satou, and N. Nishioka, Arch. Virol. 104, 169–174 (1989).

179. Sinclair, R., R. F. Cook, and J. A. Mumford, J. gen. Virol. 70, 455–459 (1989).

180. Slabaugh, M., N. Roseman, R. Davis and C. Mathews, J. Virol. 62, 519–527 (1988).

181. Smith, J. S., P. A. Yager and G. M. Baer, In Laboratory Techniques in Rabies, eds. M. M. Kaplan and H. Koprowski (WHO Geneva) pp. 354–357 (1973).

182. Sodora, D., Cohen, G., Muggeridge, M. & Eisenberg, R., Journal of Virology 65, 4424–4431 (1991).

183. Spaete, R., Saxena, A., Scott, P., Long, G., Probert, W., Britt, W., Gibson W., Rasmussen, L. & Pachl, C., Journal of Virology 64, 2922–2931 (1990).

184. Spear, P. G., In: The Basis for Serodiagnosis and Vaccines, Immunochemistry of Viruses, Vol. 2, eds. M. H. V. Van Regenmortel and A. R. Neurath (New York), pp. 425–443 (1985a).

185. Spear, P. G., In: The Herpesvirus, Vol. 3, ed. B. Roizman (New York), pp. 315–356 (1985b).

186. Stanberry, L. R., S. Kit and M. G. Myers, J. Virol. 55, 322–328 (1985).

187. Stevely, W. S., J. Virol. 22, 232–234 (1977).

188. Stokes, A., G. P. Allen, L. A. Pullen, and P. K. Murray, J. gen. Virol. 70, 1173–1183 (1989).

189. Sullivan, V. and G. L. Smith, J. gen. Virol. 68, 2587–2598 (1987).

190. Sullivan, V. and G. L. Smith, J. gen. Virol. 69, 859–867 (1988).

191. Swain, M. A., R. W. Peet, and D. A. Galloway, J. Virol, 53, 561–569 (1985).

192. Tabor, S., and C. C. Richardson, Proc. Natl. Acad. Sci. USA 84, 4767–4771 (1987).

193. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990).

194. Tartaglia, J., J. Taylor, W. I. Cox, J. -C. Audonnet, M. E. Perkus, A. Radaelli, C. de Giuli Morghen, B. Meignier, M. Riviere, K. Weinhold & E. Paoletti, In AIDS Research Reviews, W. Koff, F. Wong-Staal & R. C. Kenedy, Eds., Vol. 3, Marcel Dekker, NY (In press) (1993a).

195. Tartaglia, J., Perkus, M. E., Taylor, J., Norton, E. K., Audonnet, J. -C., Cox, W. I., Davis, S. W., Van Der Hoeven, J., Meignier, B., Riviere, M., Languet, B., Paoletti, E., Virology 188, 217–232 (1992).

196. Tartaglia, J., Jarrett, O., Desmettre, P., Paoletti, E. (1993b) J. Virol., in press.

197. Taylor, J., C. Trimarchi, R. Weinberg, B. Languet, F. Guillemin, P. Desmettre and E. Paoletti, Vaccine 9, 190–193 (1991b).

198. Taylor, J., C. Trimarchi, R. Weinberg, B. Languet, F. Guillemin, P. Desmettre & E. Paoletti, Vaccine 9, 190 (1991).

199. Taylor, J., Weinberg, R., Kawaoka, Y., Webster, R. G., and Paoletti, E., Vaccine 6, 504–508 (1988a).

200. Taylor, J., R. Weinberg, B. Lanquet, P. Desmettre, and E. Paoletti, Vaccine 6, 497–503 (1988b).

201. Taylor, J., R. Weinberg, J. Tartaglia, C. Richardson, G. Alkhatib, D. Briedis, M. Appel, E. Norton & E. Paoletti, Virology 187, 321–328 (1992).

202. Taylor, G., E. J. Stott, G. Wertz and A. Ball, J. Gen. Virol. 72, 125–130 (1991a).

203. Taylor, J., Edbauer, C., Rey-Senelonge, A., Bouquet, J. -F., Norton, E., Goebel, S., Desmettre, P., Paoletti, E., J. Virol. 64, 1441–1450 (1990).

204. Telford, E. A., Watson, M. S., McBride, K. & Davison, A. J. (1992). The DNA sequence of equine herpesvirus-1. Virology 189, 304–316.

205. Tikoo, S. K., Fitzpatrick, D. R., Babiuk, L. A. & Zamb, T. J., Journal of Virology 64, 5132–5142 (1990).

206. Toyoda, T., T. Sakaguchi, K. Imai, N. M. Inocencio, B. Gotoh, M. Hamaguchi, and Y. Nagai, Virology 158, 242–247 (1987).

207. Wachsman, M., L. Aurelian, J. C. R. Hunter, M. E. Perkus, and E. Paoletti, Bioscience Reports 8, 323–334 (1988).

208. Wachsman, M., J. H. Luo, L. Aurelian, M. E. Perkus, and E. Paoletti, J. gen. Virol. 70, 2513–2520 (1989).

209. Wachsman, M., L. Aurelian, C. C. Smith, B. R. Lipinskas, M. E. Perkus, and E. Paoletti, J. Infect. Dis. 155, 1188–1197 (1987).

210. Wathen, M. W. and L. M. K. Wathen, J. Virol. 58, 173–178 (1986).

211. Wathen, M. W. and L. M. K. Wathen, J. Virol. 51, 57–62 (1984).

212. Wathen, L. M. K., K. B. Platt, M. W. Wathen, R. A. Van Deusen, C. A. Whetstone, and E. C. Pirtle, Virus Res. 4, 19–29 (1985).

213. Weir, J. P., M. Bennett, E. M. Allen, K. L. Elkins, S. Martin, and B. T. Rouse, J. gen. Virol. 70, 2587–2594 (1989).

214. Weir, J. P. and B. Moss, J. Virol. 46, 530–537 (1983).

215. Whalley, J. M., G. R. Robertson, N. A. Scott, G. C. Hudson, C. W. Bell, and L. M. Woodworth, J. gen. Virol. 70, 383–394 (1989).

216. Whealy, M. E., A. K. Robbins and L. W. Enquist, J. Virol. 63, 4055–4059 (1989).

217. Whitbeck, J. C., L. Z. Bello, and W. C. Lawrence, J. Virol. 62, 3319–3327 (1988).

218. Wilcox, W. C., Long, D., Sodora, D. L., Eisenberg, R. J. & Cohen, G. H., Journal of Virology 62, 1941–1947 (1988).

219. Wittmann, G. and H. -J. Rziha, In: Herpesvirus Diseases of Cattle, Horses and Pigs, ed. G. Wittmann (Kluwer Academic Publishers) pp. 230–325 (1989).

220. Xuan, X., Horimoto, T., Limcumpao, J. A., Takumi, A., Tohya, Y., Takahashi, E. & Mikami, T., Archives of Virology 116, 185–195 (1991).

221. Zamb, T., Abstract No. 330, 68th Annual Meeting of Conference of Research Workers in Animal Disease, Nov. 16, and 17, 1987, Chicago, Ill., USA (1987).

222. Zarling, J. M., P. A. Moran, R. L. Burke, C. Pachl, P. W. Berman, and L. A. Lasky, J. Immunol. 136, 4669–4673 (1986a).

223. Zarling, J. M., P. A. Moran, L. A. Lasky, and B. Moss, J. Virol. 59, 506–509 (1986b).

224. Zezulak, K. M., and P. G. Spear, J. Virol. 49, 741–747 (1984).

225. Zhou, J., L. Crawford, L. McLean, X. Sun, M. Stanley, N. Almond and G. L. Smith, J. Gen. Virol. 71, 2185–2190 (1990).

What is claimed is:

1. An isolated nucleic acid coding for canine herpesvirus gD glycoprotein and having the sequence as set forth in SEQ ID NO:18.

2. The isolated nucleic acid of claim 1 which is DNA.

3. A vector containing the isolated nucleic acid of claim 2.

4. The vector of claim 3 wherein the vector is a poxvirus.

5. The vector of claim 4 wherein the poxvirus is an avipox virus or a vaccinia virus.

6. The vector of claim 5 wherein the poxvirus is a vaccinia virus.

7. The vector of claim 6 wherein the deleted genetic functions include a C7L-K1L open reading frame, or, host range functions.

8. The vector of claim 7 wherein at least one additional open reading frame is deleted; and, the additional open reading frame is selected from the group consisting of: J2R, B13R+B14R, A26L, A56R, and I4L.

9. The vector of claim 7 wherein at least one additional region is deleted; and, the additional region is selected from the group consisting of: a thymidine kinase gene, a hemorrhagic region, an A type inclusion body region, a hemagglutinin gene, and a large subunit, ribonucleotide reductase.

10. The vector of claim 8 wherein J2R, B13R+B14R, A26L, A56R, C7L-K1L and I4L are deleted from the virus.

11. The vector of claim 9 wherein a thymidine kinase gene, a hemorrhagic region, an A type inclusion body region, a hemagglutinin gene, a host range region, and a large subunit, ribonucleotide reductase are deleted from the virus.

12. The vector of claim 10 which is a NYVAC recombinant virus.

13. The vector of claim 5 wherein said virus is a canarypox virus.

14. The vector of claim 13 wherein the canarypox virus is a Rentschler vaccine strain which was attenuated through more than 200 serial passages on chick embryo fibroblasts, a master seed therefrom was subjected to four successive plaque purifications under agar, from which a plaque clone was amplified through five additional passages.

15. A composition for inducing an antigenic or immunological response comprising a vector as claimed in any one of claims 4, 7, 12, 13 or 14 in admixture with a suitable carrier.

16. A method for expressing a gene product in a cell cultured in vitro comprising introducing into the cell a vector as claimed in any one of claims 4, 7, 12 or 14.

* * * * *

SEQUENCE LISTING (1) GENERAL INFORMATION:

(iii) NUMBER OF SEQUENCES: 128

(2) INFORMATION FOR SEQ ID NO:1:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
TTTTCTGGAT TTCAGCTATG TCCTTCGGGA GTTTATATAA CTTATGAAGA AAACTGTCCT      60

TTGGTAGCAG TTTTACAAAG CGGTGTAAAT TGCGAAATTG GACCAACTAC AACTGTAATA     120

TACGACAGTG ATATTTTTTC TCTTCTTTAT ACCGTTCTTC AAAAATTGGC TCCTGGTGTT     180

AATATAGAAA TTTGATAAGT ATGTTTTCAT TGTATCTATA TATTTTTTTT ATTATTTATA     240

CTTTAATAAT ATGTGATCCA ACAACACCGG AAAGTACTAT TAATCCATTA AATCATCACA     300

ATTTATCAAC ACCTAAACCT ACTTCGGATG ATATTCGTGA AATTTTACGT GAATCCCAAA     360

TTGAATCTGA TGATACATCA ACATTTTACA TGTGCCCACC ACCATCGGGA TCAACATTGG     420

TGCGTTTGGA GCCACCTAGA GCATGTCCTA ACTATAAACT TGGTAAAAAT TTTACAGAAG     480

GAATTGCTGT AATATTTAAG GAAAATATTT CTCCTTATAA ATTTAAAGCT AATATATACT     540

ACAAAAATAT TATTATCACC ACTGTATGGT CTGGAAGCAC ATATGCAGTA ATTACTAATA     600

GATATACAGA TCGTGTACCT ATAGGTGTTC CTGAAATTAC AGAGTTGATT GATAGAAGAG     660

GTATGTGTTT ATCAAAAGCT GATTATATTC GTAATAATTA TGAATTTACC GCATTTGATA     720

AGGATGAAGA CCCCAGAGAA GTTCATTTAA AGCCTTCAAA GTTTAATACA CCAGGATCCC     780

GTGGATGGCA TACAGTTAAT GATACTTACA CAAAAATTGG GGGTTCTGGA TTTTATCATT     840

CTGGAACATC TGTAAATTGT ATAGTTGAAG AAGTTGATGC CAGATCTGTT TATCCATATG     900

ATTCATTTGC TATCTCCACC GGGGATATAA TTCATATGTC CCCTTTTTTT GGATTACGAG     960

ATGGTGCTCA TACTGAATAT ATTAGTTATT CAACTGATAG ATTTCAACAA ATAGAAGGTT    1020

ATTATCCTAT CGACTTAGAT ACTAGACTAC AGCTTGGTGC ACCAGTTTCT AGGAATTTTT    1080

TAACAACACA ACACGTTACT GTTGCTTGGA ATTGGGTTCC AAAAATTCGT GAAGTGTGTA    1140

CTTTGGCTAA ATGGCGTGAA ATTGATGAAA TTATTCGTGA TGAGTATAAG GGATCTTACA    1200

GATTTACAGC AAAATCAATA TCTGCAACAT TTATTTCTGA TACTACTCAA TTTGATATTG    1260

ATCGTGTAAA GTTAAGTGAT TGTGCCAAAC GTGAAGCCAT AGAAGCTATT GATAAGATCT    1320

ACAAAAAAAA ATATAATAAA ACTCATATTC AAACAGGAGA ATTGGAAACA TACTTGGCTA    1380

GAGGGGGATT TATTATAGCA TTTAGACCAA TGATTAGTAA TGAGTTAGCA AAATTGTATA    1440
```

```
TAAATGAGTT AGTAAGATCT AATCGTACGG TTGATTTGAA ATCTCTTTTA AATCCATCTG      1500

TAAGAGGGGG GGCTAGAAAG AGAAGATCAG TAGAGGAAAA TAAAAGATCA AAACGTAATA      1560

TTGAAGGTGG TATTGAAAAT GTAAATAATT CAACAATAAT TAAGACAACT TCATCTGTTC      1620

ATTTTGCTAT GCTTCAGTTT GCCTATGATC ATATTCAATC ACATGTTAAT GAAATGCTTA      1680

GTAGAATTGC AACTGCATGG TGTAATCTTC AAAATAAAGA GAGAACCCTT TGGAATGAAG      1740

TTATGAAACT TAATCCAACT AGTGTGGCTT CGGTTGCTAT GGATCAAAGA GTTTCAGCAC      1800

GAATGTTAGG GGATGTTCTT GCAGTTACTC AATGTGTTAA TATATCAGGT TCTAGTGTTT      1860

TTATTCAAAA TTCCATGCGT GTTTTAGGGT CAACAACTAC ATGTTACAGT CGTCCTCTTA      1920

TATCATTTAA AGCACTAGAA AACTCAACTA ACTATATTGA AGGACAACTT GGGGAAAATA      1980

ATGAACTATT AGTAGAACGA AAGCTAATTG AACCATGTAC AGCTAACCAT AAAAGATATT      2040

TTAAATTTGG TGCAGATTAT GTATATTTTG AAAACTATGC ATATGTTCGA AAGGTACCTC      2100

TTAATGAAAT TGAAATGATC AGTGCATATG TAGATCTTAA TATTACATTA CTTGAGGATC      2160

GTGAATTTTT ACCACTAGAG GTATATACTC GAGCAGAGTT AGAAGATACA GGACTATTGG      2220

ACTATAGTGA GATTCAACGT AGAAATCAAC TACATGCACT TAAGTTTTAT GATATTGACA      2280

GTGTTGTAAA AGTTGATAAT AATGTTGTAA TTATGAGGGG CATTGCAAAT TTTTTCCAAG      2340

GACTTGGAGA TGTTGGAGCG GGATTTGGAA AAGTTGTTTT GGGTGCTGCA AATGCTGTTA      2400

TTGCAACTGT TTCTGGAGTG TCCTCGTTTC TTAATAACCC ATTTGGGGCG CTAGCCGTTG      2460

GATTGCTGAT TTTAGCTGGA CTATTTGCAG CGTTTTTGGC TTATAGATAT GTTTCTAAAC      2520

TTAAGTCAAA TCCAATGAAA GCACTATACC CAGTAACTAC AAAAAATTTA AAAGAAAGTG      2580

TTAAGAATGG TAATTCTGGA AATAATAGTG ATGGAGAAGA AAATGATGAT AATATCGATG      2640

AAGAAAAGCT TCAACAAGCT AAAGAAATGA TTAAATATAT GTCTCTAGTT TCTGCTATGG      2700

AACAGCAGGA ACATAAAGCT ATTAAAAAAA ATAGTGGCCC TGCCCTTCTA GCAAGTCACA      2760

TTACAAACCT ATCTCTTAAA CATCGTGGTC CAAAATACAA ACGTTTGAAA AATGTAAATG      2820

AAAATGAAAG TAAAGTTTAA TAAAAAATTT AAATATTACG TAAAATTTTC TGACTCTGCC      2880

CACTTTTTTT ATAATATAAA TTTTAGAAAA TTTTACTCAT TTTATTATCT TTTATAAACC      2940

TCCAACTATT TATAAAGGAT AATAAATGGA CATTTCTGCG GTGCCTGTAT ATCCTACTAA      3000
```

(2) INFORMATION FOR SEQ ID NO:2:

(i) SEQUENCE CHARACTERISTICS:
        (A) LENGTH: 879 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:2:

```
Met Phe Ser Leu Tyr Leu Tyr Ile Phe Phe Ile Ile Tyr Thr Leu Ile
 1               5                  10                  15

Ile Cys Asp Pro Thr Thr Pro Glu Ser Thr Ile Asn Pro Leu Asn His
                20                  25                  30

His Asn Leu Ser Thr Pro Lys Pro Thr Ser Asp Asp Ile Arg Glu Ile
            35                  40                  45

Leu Arg Glu Ser Gln Ile Glu Ser Asp Asp Thr Ser Thr Phe Tyr Met
        50                  55                  60
```

-continued

```
Cys Pro Pro Pro Ser Gly Ser Thr Leu Val Arg Leu Glu Pro Pro Arg
 65              70                  75                  80

Ala Cys Pro Asn Tyr Lys Leu Gly Lys Asn Phe Thr Glu Gly Ile Ala
                 85                  90                  95

Val Ile Phe Lys Glu Asn Ile Ser Pro Tyr Lys Phe Lys Ala Asn Ile
            100                 105                 110

Tyr Tyr Lys Asn Ile Ile Ile Thr Thr Val Trp Ser Gly Ser Thr Tyr
            115                 120                 125

Ala Val Ile Thr Asn Arg Tyr Thr Asp Arg Val Pro Ile Gly Val Pro
130                 135                 140

Glu Ile Thr Glu Leu Ile Asp Arg Arg Gly Met Cys Leu Ser Lys Ala
145                 150                 155                 160

Asp Tyr Ile Arg Asn Asn Tyr Glu Phe Thr Ala Phe Asp Lys Asp Glu
                165                 170                 175

Asp Pro Arg Glu Val His Leu Lys Pro Ser Lys Phe Asn Thr Pro Gly
            180                 185                 190

Ser Arg Gly Trp His Thr Val Asn Asp Thr Tyr Thr Lys Ile Gly Gly
            195                 200                 205

Ser Gly Phe Tyr His Ser Gly Thr Ser Val Asn Cys Ile Val Glu Glu
            210                 215                 220

Val Asp Ala Arg Ser Val Tyr Pro Tyr Asp Ser Phe Ala Ile Ser Thr
225                 230                 235                 240

Gly Asp Ile Ile His Met Ser Pro Phe Phe Gly Leu Arg Asp Gly Ala
            245                 250                 255

His Thr Glu Tyr Ile Ser Tyr Ser Thr Asp Arg Phe Gln Gln Ile Glu
            260                 265                 270

Gly Tyr Tyr Pro Ile Asp Leu Asp Thr Arg Leu Gln Leu Gly Ala Pro
            275                 280                 285

Val Ser Arg Asn Phe Leu Thr Thr Gln His Val Thr Val Ala Trp Asn
290                 295                 300

Trp Val Pro Lys Ile Arg Glu Val Cys Thr Leu Ala Lys Trp Arg Glu
305                 310                 315                 320

Ile Asp Glu Ile Ile Arg Asp Glu Tyr Lys Gly Ser Tyr Arg Phe Thr
                325                 330                 335

Ala Lys Ser Ile Ser Ala Thr Phe Ile Ser Asp Thr Thr Gln Phe Asp
            340                 345                 350

Ile Asp Arg Val Lys Leu Ser Asp Cys Ala Lys Arg Glu Ala Ile Glu
            355                 360                 365

Ala Ile Asp Lys Ile Tyr Lys Lys Tyr Asn Lys Thr His Ile Gln
370                 375                 380

Thr Gly Glu Leu Glu Thr Tyr Leu Ala Arg Gly Gly Phe Ile Ile Ala
385                 390                 395                 400

Phe Arg Pro Met Ile Ser Asn Glu Leu Ala Lys Leu Tyr Ile Asn Glu
                405                 410                 415

Leu Val Arg Ser Asn Arg Thr Val Asp Leu Lys Ser Leu Leu Asn Pro
            420                 425                 430

Ser Val Arg Gly Gly Ala Arg Lys Arg Ser Val Glu Glu Asn Lys
            435                 440                 445

Arg Ser Lys Arg Asn Ile Glu Gly Gly Ile Glu Asn Val Asn Asn Ser
450                 455                 460

Thr Ile Ile Lys Thr Thr Ser Ser Val His Phe Ala Met Leu Gln Phe
465                 470                 475                 480

Ala Tyr Asp His Ile Gln Ser His Val Asn Glu Met Leu Ser Arg Ile
                485                 490                 495
```

```
Ala Thr Ala Trp Cys Asn Leu Gln Asn Lys Glu Arg Thr Leu Trp Asn
            500                 505                 510
Glu Val Met Lys Leu Asn Pro Thr Ser Val Ala Ser Val Ala Met Asp
        515                 520                 525
Gln Arg Val Ser Ala Arg Met Leu Gly Asp Val Leu Ala Val Thr Gln
    530                 535                 540
Cys Val Asn Ile Ser Gly Ser Ser Val Phe Ile Gln Asn Ser Met Arg
545                 550                 555                 560
Val Leu Gly Ser Thr Thr Thr Cys Tyr Ser Arg Pro Leu Ile Ser Phe
            565                 570                 575
Lys Ala Leu Glu Asn Ser Thr Asn Tyr Ile Glu Gly Gln Leu Gly Glu
        580                 585                 590
Asn Asn Glu Leu Leu Val Glu Arg Lys Leu Ile Glu Pro Cys Thr Ala
    595                 600                 605
Asn His Lys Arg Tyr Phe Lys Phe Gly Ala Asp Tyr Val Tyr Phe Glu
610                 615                 620
Asn Tyr Ala Tyr Val Arg Lys Val Pro Leu Asn Glu Ile Glu Met Ile
625                 630                 635                 640
Ser Ala Tyr Val Asp Leu Asn Ile Thr Leu Leu Glu Asp Arg Glu Phe
            645                 650                 655
Leu Pro Leu Glu Val Tyr Thr Arg Ala Glu Leu Glu Asp Thr Gly Leu
        660                 665                 670
Leu Asp Tyr Ser Glu Ile Gln Arg Arg Asn Gln Leu His Ala Leu Lys
    675                 680                 685
Phe Tyr Asp Ile Asp Ser Val Val Lys Val Asp Asn Asn Val Val Ile
690                 695                 700
Met Arg Gly Ile Ala Asn Phe Phe Gln Gly Leu Gly Asp Val Gly Ala
705                 710                 715                 720
Gly Phe Gly Lys Val Leu Gly Ala Ala Asn Ala Val Ile Ala Thr
            725                 730                 735
Val Ser Gly Val Ser Ser Phe Leu Asn Asn Pro Phe Gly Ala Leu Ala
            740                 745                 750
Val Gly Leu Leu Ile Leu Ala Gly Leu Phe Ala Ala Phe Leu Ala Tyr
        755                 760                 765
Arg Tyr Val Ser Lys Leu Lys Ser Asn Pro Met Lys Ala Leu Tyr Pro
770                 775                 780
Val Thr Thr Lys Asn Leu Lys Glu Ser Val Lys Asn Gly Asn Ser Gly
785                 790                 795                 800
Asn Asn Ser Asp Gly Glu Glu Asn Asp Asp Asn Ile Asp Glu Glu Lys
            805                 810                 815
Leu Gln Gln Ala Lys Glu Met Ile Lys Tyr Met Ser Leu Val Ser Ala
        820                 825                 830
Met Glu Gln Gln Glu His Lys Ala Ile Lys Lys Asn Ser Gly Pro Ala
    835                 840                 845
Leu Leu Ala Ser His Ile Thr Asn Leu Ser Leu Lys His Arg Gly Pro
850                 855                 860
Lys Tyr Lys Arg Leu Lys Asn Val Asn Glu Asn Glu Ser Lys Val
865                 870                 875

(2) INFORMATION FOR SEQ ID NO:3:

(i) SEQUENCE CHARACTERISTICS:
        (A) LENGTH: 879 amino acids
        (B) TYPE: amino acid
        (C) STRANDEDNESS: single
```

(D) TOPOLOGY: linear (ii) MOLECULE TYPE: peptide (v) FRAGMENT TYPE: N-terminal (xi) SEQUENCE DESCRIPTION: SEQ ID NO:3:

```
Met Phe Ser Leu Tyr Leu Tyr Ile Phe Phe Ile Ile Tyr Thr Leu Ile
1               5                   10                  15

Ile Cys Asp Pro Thr Pro Glu Ser Thr Ile Asn Pro Leu Asn His
                20                  25                  30

His Asn Leu Ser Thr Pro Lys Pro Thr Ser Asp Asp Ile Arg Glu Ile
            35                  40                  45

Leu Arg Glu Ser Gln Ile Glu Ser Asp Asp Thr Ser Thr Phe Tyr Met
50                      55                  60

Cys Pro Pro Pro Ser Gly Ser Thr Leu Val Arg Leu Glu Pro Pro Arg
65                  70                  75                  80

Ala Cys Pro Asn Tyr Lys Leu Gly Lys Asn Phe Thr Glu Gly Ile Ala
                85                  90                  95

Val Ile Phe Lys Glu Asn Ile Ser Pro Tyr Lys Phe Lys Ala Asn Ile
                100                 105                 110

Tyr Tyr Lys Asn Ile Ile Thr Thr Val Trp Ser Gly Ser Thr Tyr
            115                 120                 125

Ala Val Ile Thr Asn Arg Tyr Thr Asp Arg Val Pro Ile Gly Val Pro
130                 135                 140

Glu Ile Thr Glu Leu Ile Asp Arg Arg Gly Met Cys Leu Ser Lys Ala
145                 150                 155                 160

Asp Tyr Ile Arg Asn Asn Tyr Glu Phe Thr Ala Phe Asp Lys Asp Glu
                165                 170                 175

Asp Pro Arg Glu Val His Leu Lys Pro Ser Lys Phe Asn Thr Pro Gly
                180                 185                 190

Ser Arg Gly Trp His Thr Val Asn Asp Thr Tyr Thr Lys Ile Gly Gly
            195                 200                 205

Ser Gly Phe Tyr His Ser Gly Thr Ser Val Asn Cys Ile Val Glu Glu
            210                 215                 220

Val Asp Ala Arg Ser Val Tyr Pro Tyr Asp Ser Phe Ala Ile Ser Thr
225                 230                 235                 240

Gly Asp Ile Ile His Met Ser Pro Phe Phe Gly Leu Arg Asp Gly Ala
                245                 250                 255

His Thr Glu Tyr Ile Ser Tyr Ser Thr Asp Arg Phe Gln Gln Ile Glu
                260                 265                 270

Gly Tyr Tyr Pro Ile Asp Leu Asp Thr Arg Leu Gln Leu Gly Ala Pro
            275                 280                 285

Val Ser Arg Asn Phe Leu Thr Thr Gln His Val Thr Val Ala Trp Asn
290                 295                 300

Trp Val Pro Lys Ile Arg Glu Val Cys Thr Leu Ala Lys Trp Arg Glu
305                 310                 315                 320

Ile Asp Glu Ile Ile Arg Asp Glu Tyr Lys Gly Ser Tyr Arg Phe Thr
                325                 330                 335

Ala Lys Ser Ile Ser Ala Thr Phe Ile Ser Asp Thr Gln Phe Asp
                340                 345                 350

Ile Asp Arg Val Lys Leu Ser Asp Cys Ala Lys Arg Glu Ala Ile Glu
                355                 360                 365

Ala Ile Asp Lys Ile Tyr Lys Lys Tyr Asn Lys Thr His Ile Gln
370                 375                 380
```

```
Thr Gly Glu Leu Glu Thr Tyr Leu Ala Arg Gly Gly Phe Ile Ile Ala
385             390                 395                 400

Phe Arg Pro Met Ile Ser Asn Glu Leu Ala Lys Leu Tyr Ile Asn Glu
                405                 410                 415

Leu Val Arg Ser Asn Arg Thr Val Asp Leu Lys Ser Leu Leu Asn Pro
            420                 425                 430

Ser Val Arg Gly Gly Ala Arg Lys Arg Arg Ser Val Glu Glu Asn Lys
            435                 440                 445

Arg Ser Lys Arg Asn Ile Glu Gly Ile Glu Asn Val Asn Asn Ser
450                 455                 460

Thr Ile Ile Lys Thr Thr Ser Ser Val His Phe Ala Met Leu Gln Phe
465                 470                 475                 480

Ala Tyr Asp His Ile Gln Ser His Val Asn Glu Met Leu Ser Arg Ile
                485                 490                 495

Ala Thr Ala Trp Cys Asn Leu Gln Asn Lys Glu Arg Thr Leu Trp Asn
                500                 505                 510

Glu Val Met Lys Leu Asn Pro Thr Ser Val Ala Ser Val Ala Met Asp
                515                 520                 525

Gln Arg Val Ser Ala Arg Met Leu Gly Asp Val Leu Ala Val Thr Gln
            530                 535                 540

Cys Val Asn Ile Ser Gly Ser Ser Val Phe Ile Gln Asn Ser Met Arg
545                 550                 555                 560

Val Leu Gly Ser Thr Thr Thr Cys Tyr Ser Arg Pro Leu Ile Ser Phe
                565                 570                 575

Lys Ala Leu Glu Asn Ser Thr Asn Tyr Ile Glu Gly Gln Leu Gly Glu
                580                 585                 590

Asn Asn Glu Leu Leu Val Glu Arg Lys Leu Ile Glu Pro Cys Thr Ala
            595                 600                 605

Asn His Lys Arg Tyr Phe Lys Phe Gly Ala Asp Tyr Val Tyr Phe Glu
            610                 615                 620

Asn Tyr Ala Tyr Val Arg Lys Val Pro Leu Asn Glu Ile Glu Met Ile
625                 630                 635                 640

Ser Ala Tyr Val Asp Leu Asn Ile Thr Leu Leu Glu Asp Arg Glu Phe
                645                 650                 655

Leu Pro Leu Glu Val Tyr Thr Arg Ala Glu Leu Glu Asp Thr Gly Leu
                660                 665                 670

Leu Asp Tyr Ser Glu Ile Gln Arg Arg Asn Gln Leu His Ala Leu Lys
            675                 680                 685

Phe Tyr Asp Ile Asp Ser Val Val Lys Val Asp Asn Asn Val Val Ile
            690                 695                 700

Met Arg Gly Ile Ala Asn Phe Phe Gln Gly Leu Gly Asp Val Gly Ala
705                 710                 715                 720

Gly Phe Gly Lys Val Val Leu Gly Ala Ala Asn Ala Val Ile Ala Thr
                725                 730                 735

Val Ser Gly Val Ser Ser Phe Leu Asn Asn Pro Phe Gly Ala Leu Ala
            740                 745                 750

Val Gly Leu Leu Ile Leu Ala Gly Leu Phe Ala Ala Phe Leu Ala Tyr
            755                 760                 765

Arg Tyr Val Ser Lys Leu Lys Ser Asn Pro Met Lys Ala Leu Tyr Pro
            770                 775                 780

Val Thr Thr Lys Asn Leu Lys Glu Ser Val Lys Asn Gly Asn Ser Gly
785                 790                 795                 800

Asn Asn Ser Asp Gly Glu Glu Asn Asp Asn Ile Asp Glu Glu Lys
                805                 810                 815
```

```
Leu Gln Gln Ala Lys Glu Met Ile Lys Tyr Met Ser Leu Val Ser Ala
            820                 825                 830

Met Glu Gln Gln Glu His Lys Ala Ile Lys Lys Asn Ser Gly Pro Ala
            835                 840                 845

Leu Leu Ala Ser His Ile Thr Asn Leu Ser Leu Lys His Arg Gly Pro
            850                 855                 860

Lys Tyr Lys Arg Leu Lys Asn Val Asn Glu Asn Glu Ser Lys Val
865                 870                 875

(2) INFORMATION FOR SEQ ID NO:4:

(i) SEQUENCE CHARACTERISTICS:
        (A) LENGTH: 1041 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:4:

Met Ser Thr Arg Gly Asp Leu Gly Lys Arg Arg Gly Ser Arg Trp
1               5                   10                  15

Gln Gly His Ser Gly Tyr Phe Arg Gln Arg Cys Phe Phe Pro Ser Leu
            20                  25                  30

Leu Gly Ile Ala Ala Thr Gly Ser Arg His Gly Asn Gly Ser Ser Gly
            35                  40                  45

Leu Thr Arg Leu Ala Arg Tyr Val Ser Phe Ile Trp Ile Val Leu Phe
            50                  55                  60

Leu Val Gly Pro Arg Pro Val Glu Gly Gln Ser Gly Ser Thr Ser Glu
65                  70                  75                  80

Gln Pro Arg Arg Thr Val Ala Thr Pro Glu Val Gly Thr Pro Pro
            85                  90                  95

Lys Pro Thr Thr Asp Pro Thr Asp Met Ser Asp Met Arg Glu Ala Leu
            100                 105                 110

Arg Ala Ser Gln Ile Glu Ala Asn Gly Pro Ser Thr Phe Tyr Met Cys
            115                 120                 125

Pro Pro Pro Ser Gly Ser Thr Val Val Arg Leu Glu Pro Pro Arg Ala
            130                 135                 140

Cys Pro Asp Tyr Lys Leu Gly Lys Asn Phe Thr Glu Gly Ile Ala Val
145                 150                 155                 160

Ile Phe Lys Glu Asn Ile Ala Pro Tyr Lys Phe Lys Ala Asn Ile Tyr
            165                 170                 175

Tyr Lys Asn Ile Ile Met Thr Thr Val Trp Ser Gly Ser Ser Tyr Ala
            180                 185                 190

Val Thr Thr Asn Arg Tyr Thr Asp Arg Val Pro Val Lys Val Gln Glu
            195                 200                 205

Ile Thr Asp Leu Ile Asp Arg Arg Gly Met Cys Leu Ser Lys Ala Asp
            210                 215                 220

Tyr Val Arg Asn Asn Tyr Gln Phe Thr Ala Phe Asp Arg Asp Glu Asp
225                 230                 235                 240

Pro Arg Glu Leu Pro Leu Lys Pro Ser Lys Phe Asn Thr Pro Gln Ser
            245                 250                 255

Arg Gly Trp His Thr Tyr Lys Phe Lys Ala Thr Val Tyr Tyr Lys Asp
            260                 265                 270

Val Ile Val Ser Thr Ala Trp Ala Gly Ser Ser Tyr Thr Gln Ile Thr
```

-continued

```
                275                 280                 285
Asn Arg Tyr Ala Asp Arg Val Pro Ile Pro Val Ser Glu Ile Thr Asp
    290                 295                 300
Thr Ile Asp Lys Phe Gly Lys Cys Ser Ser Lys Ala Thr Tyr Val Arg
305                 310                 315                 320
Asn Asn His Lys Val Glu Ala Phe Asn Glu Asp Lys Asn Pro Gln Asp
                325                 330                 335
Met Pro Leu Ile Ala Ser Lys Tyr Asn Ser Val Gly Ser Lys Ala Trp
                340                 345                 350
His Thr Thr Asn Glu Thr Tyr Thr Lys Ile Gly Ala Ala Gly Phe His
                355                 360                 365
His Ser Gly Thr Ser Val Asn Cys Ile Val Glu Val Asp Ala Arg
370                 375                 380
Ser Val Tyr Pro Tyr Asp Ser Phe Ala Ile Ser Thr Gly Asp Val Ile
385                 390                 395                 400
His Met Ser Pro Phe Phe Gly Leu Arg Asp Gly Ala His Val Glu His
                405                 410                 415
Thr Ser Tyr Ser Ser Asp Arg Phe Gln Gln Ile Glu Gly Tyr Tyr Pro
                420                 425                 430
Ile Asp Leu Asp Thr Arg Leu Gln Leu Gly Ala Pro Val Ser Arg Asn
                435                 440                 445
Phe Leu Glu Thr Pro His Val Thr Val Ala Trp Asn Trp Thr Pro Lys
450                 455                 460
Cys Gly Arg Val Cys Thr Leu Ala Lys Trp Arg Glu Ile Asp Glu Met
465                 470                 475                 480
Leu Arg Asp Glu Tyr Gln Gly Ser Tyr Arg Phe Thr Val Lys Thr Ile
                485                 490                 495
Ser Ala Thr Phe Ile Ser Asn Thr Ser Gln Phe Glu Ile Asn Arg Ile
                500                 505                 510
Arg Leu Gly Asp Cys Ala Thr Lys Glu Ala Ala Glu Ala Ile Asp Arg
                515                 520                 525
Ile Tyr Lys Ser Lys Tyr Ser Leu Thr His Ile Gln Thr Gly Thr Leu
530                 535                 540
Glu Thr Tyr Leu Ala Arg Gly Gly Phe Leu Ile Ala Phe Arg Pro Met
545                 550                 555                 560
Ile Ser Asn Glu Leu Ala Lys Leu Tyr Ile Asn Glu Leu Ala Arg Ser
                565                 570                 575
Asn Arg Thr Val Asp Leu Ser Ala Leu Leu Asn Pro Ser Gly Glu Thr
                580                 585                 590
Val Gln Arg Thr Arg Gly Ser Val Pro Ser Asn Gln His His Arg Ser
                595                 600                 605
Arg Arg Ser Thr Ile Glu Gly Gly Ile Glu Thr Val Asn Asn Ala Ser
610                 615                 620
Leu Leu Lys Thr Thr Ser Ser Val Glu Phe Ala Met Ile Gln Phe Ala
625                 630                 635                 640
Tyr Asp Tyr Ile Gln Ala His Val Asn Glu Met Leu Ser Arg Ile Ala
                645                 650                 655
Thr Ala Trp Cys Thr Leu Gln Asn Arg Glu His Val Leu Trp Thr Glu
                660                 665                 670
Thr Leu Lys Leu Asn Pro Gly Gly Val Val Ser Met Ala Leu Glu Arg
                675                 680                 685
Arg Val Ser Ala Arg Leu Leu Gly Asp Ala Val Ala Val Thr Gln Cys
                690                 695                 700
```

-continued

```
Val Asn Ile Ser Ser Gly His Val Tyr Ile Gln Asn Ser Met Arg Val
705                 710                 715                 720

Thr Gly Ser Ser Thr Thr Cys Tyr Ser Arg Pro Leu Val Ser Phe Arg
            725                 730                 735

Ala Leu Asn Asp Ser Glu Tyr Ile Gly Gln Leu Gly Glu Asn Asn
            740                 745                 750

Asp Leu Leu Val Glu Arg Lys Leu Ile Glu Pro Cys Thr Val Asn Asn
            755                 760                 765

Lys Arg Tyr Phe Lys Phe Gly Ala Asp Tyr Val Tyr Phe Glu Asp Tyr
770                 775                 780

Ala Tyr Val Arg Lys Val Pro Leu Ser Glu Ile Glu Leu Ile Ser Ala
785                 790                 795                 800

Tyr Val Asp Leu Asn Leu Thr Leu Leu Glu Asp Arg Glu Phe Leu Pro
                805                 810                 815

Leu Glu Val Tyr Thr Arg Ala Glu Leu Glu Asp Thr Gly Leu Leu Asp
                820                 825                 830

Tyr Ser Glu Ile Gln Arg Arg Asn Gln Leu His Ala Leu Lys Phe Tyr
            835                 840                 845

Asp Ile Asp Ser Ile Val Arg Val Asp Asn Asn Leu Val Ile Met Arg
850                 855                 860

Gly Met Ala Asn Phe Phe Gln Gly Leu Gly Asp Val Gly Ala Gly Phe
865                 870                 875                 880

Gly Lys Val Val Leu Gly Ala Ala Ser Ala Val Ile Ser Thr Val Ser
                885                 890                 895

Gly Val Ser Ser Phe Leu Asn Asn Pro Phe Gly Ala Leu Ala Val Gly
            900                 905                 910

Leu Leu Ile Leu Ala Gly Ile Val Ala Ala Phe Leu Ala Tyr Arg Tyr
            915                 920                 925

Ile Ser Arg Leu Arg Ala Asn Pro Met Lys Ala Leu Tyr Pro Val Thr
            930                 935                 940

Thr Arg Asn Leu Lys Gln Thr Ala Lys Ser Pro Ala Ser Thr Ala Gly
945                 950                 955                 960

Gly Asp Ser Asp Pro Gly Val Asp Asp Phe Asp Glu Glu Lys Leu Met
                965                 970                 975

Gln Ala Arg Glu Met Ile Lys Tyr Met Ser Leu Val Ser Ala Met Glu
            980                 985                 990

Gln Gln Glu His Lys Ala Met Lys Lys Asn Lys Gly Pro Ala Ile Leu
            995                 1000                1005

Thr Ser His Leu Thr Asn Met Ala Leu Arg Arg Gly Pro Lys Tyr
            1010                1015                1020

Gln Arg Leu Asn Asn Leu Asp Ser Gly Asp Asp Thr Glu Thr Asn Leu
1025                1030                1035                1040

Val
```

(2) INFORMATION FOR SEQ ID NO:5:

(i) SEQUENCE CHARACTERISTICS:
        (A) LENGTH: 980 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:5:

```
Met Ser Ser Gly Cys Arg Ser Val Gly Ser Thr Trp Gly Asn Trp
1               5                   10                  15

Arg Gly Asp Gly Gly Asp Leu Arg Gln Arg Arg Val Leu Ser Pro Val
                20                  25                  30

Cys Ser Ala Pro Ala Ala Gly Ser Trp Ile Gly Ser Gln Leu Gly Asn
        35                  40                  45

Val Gly Asn Leu Leu Ala Thr Pro His Pro Leu Gly Lys Pro Ala Ser
    50                  55                  60

Ser Arg Val Gly Thr Ile Val Leu Ala Cys Leu Leu Leu Phe Gly Ser
65                  70                  75                  80

Cys Val Val Arg Ala Val Pro Thr Thr Pro Ser Pro Thr Ser Thr
                85                  90                  95

Pro Thr Ser Met Ser Thr His Ser His Gly Thr Val Asp Pro Thr Leu
            100                 105                 110

Leu Pro Thr Glu Thr Pro Asp Pro Leu Arg Leu Ala Val Arg Glu Ser
            115                 120                 125

Gly Ile Leu Ala Glu Asp Gly Asp Phe Tyr Thr Cys Pro Pro Pro Thr
130                 135                 140

Gly Ser Thr Val Val Arg Ile Glu Pro Pro Arg Thr Cys Pro Lys Phe
145                 150                 155                 160

Asp Leu Gly Arg Asn Phe Thr Glu Gly Ile Ala Val Ile Phe Lys Glu
                165                 170                 175

Asn Ile Ala Pro Tyr Lys Phe Arg Ala Asn Val Tyr Tyr Lys Asp Ile
                180                 185                 190

Val Val Thr Arg Val Trp Lys Gly Tyr Ser His Thr Ser Leu Ser Asp
            195                 200                 205

Arg Tyr Asn Asp Arg Val Pro Val Ser Val Glu Ile Phe Gly Leu
210                 215                 220

Ile Asp Ser Lys Gly Lys Cys Ser Ser Lys Ala Glu Tyr Leu Arg Asp
225                 230                 235                 240

Asn Ile Met His His Ala Tyr His Asp Asp Glu Asp Val Glu Leu
            245                 250                 255

Asp Leu Cys Arg Pro Ser Leu Gln Leu Arg Gly Ala Arg Ala Trp Gln
            260                 265                 270

Thr Thr Asn Asp Thr Thr Ser Tyr Val Gly Trp Met Pro Trp Arg His
            275                 280                 285

Tyr Thr Ser Thr Ser Val Asn Cys Ile Val Glu Glu Val Glu Ala Arg
290                 295                 300

Ser Val Tyr Pro Tyr Asp Ser Phe Ala Leu Ser Thr Gly Asp Ile Val
305                 310                 315                 320

Tyr Ala Ser Pro Phe Tyr Gly Leu Arg Ala Ala Arg Ile Glu His
                325                 330                 335

Asn Ser Tyr Ala Gln Glu Arg Phe Arg Gln Val Glu Gly Tyr Arg Pro
            340                 345                 350

Arg Asp Leu Asp Ser Lys Leu Gln Ala Glu Glu Pro Val Thr Lys Asn
            355                 360                 365

Phe Ile Thr Thr Pro His Val Thr Val Ser Trp Asn Trp Thr Glu Lys
            370                 375                 380

Lys Val Glu Ala Cys Thr Leu Thr Lys Trp Lys Glu Val Asp Glu Leu
385                 390                 395                 400

Val Arg Asp Glu Phe Arg Gly Ser Tyr Arg Phe Thr Ile Arg Ser Ile
                405                 410                 415

Ser Ser Thr Phe Ile Ser Asn Thr Thr Gln Phe Lys Leu Glu Ser Ala
            420                 425                 430
```

-continued

```
Pro Leu Thr Glu Cys Val Ser Lys Glu Ala Lys Glu Ala Ile Asp Ser
        435                 440                 445

Ile Tyr Lys Lys Gln Tyr Glu Ser Thr His Val Phe Ser Gly Asp Val
    450                 455                 460

Glu Tyr Tyr Leu Ala Arg Gly Gly Phe Leu Ile Ala Phe Arg Pro Met
465                 470                 475                 480

Leu Ser Asn Glu Leu Ala Arg Leu Tyr Leu Asn Glu Leu Val Arg Ser
                485                 490                 495

Asn Arg Thr Tyr Asp Leu Lys Asn Leu Leu Asn Pro Asn Ala Asn Asn
            500                 505                 510

Asn Asn Asn Thr Thr Arg Arg Arg Ser Leu Leu Ser Val Pro Glu
            515                 520                 525

Pro Gln Pro Thr Gln Asp Gly Val His Arg Glu Gln Ile Leu His Arg
        530                 535                 540

Leu His Lys Arg Ala Val Glu Ala Thr Ala Gly Thr Asp Ser Ser Asn
545                 550                 555                 560

Val Thr Ala Lys Gln Leu Glu Leu Ile Lys Thr Thr Ser Ser Ile Glu
                565                 570                 575

Phe Ala Met Leu Gln Phe Ala Tyr Asp His Ile Gln Ser His Val Asn
            580                 585                 590

Glu Met Leu Ser Arg Ile Ala Thr Ala Trp Cys Thr Leu Gln Asn Lys
        595                 600                 605

Glu Arg Thr Leu Trp Asn Glu Met Val Lys Ile Asn Pro Ser Ala Ile
    610                 615                 620

Val Ser Ala Thr Leu Asp Glu Arg Val Ala Ala Arg Val Leu Gly Asp
625                 630                 635                 640

Val Ile Ala Ile Thr His Cys Ala Lys Ile Glu Gly Asn Val Tyr Leu
                645                 650                 655

Gln Asn Ser Met Arg Ser Met Asp Ser Asn Thr Cys Tyr Ser Arg Pro
            660                 665                 670

Pro Val Thr Phe Thr Ile Thr Lys Asn Ala Asn Asn Arg Gly Ser Ile
        675                 680                 685

Glu Gly Gln Leu Gly Glu Glu Asn Glu Ile Phe Thr Glu Arg Lys Leu
    690                 695                 700

Ile Glu Pro Cys Ala Leu Asn Gln Lys Arg Tyr Phe Lys Phe Gly Lys
705                 710                 715                 720

Glu Tyr Val Tyr Tyr Glu Asn Tyr Thr Phe Val Arg Lys Val Pro Pro
                725                 730                 735

Thr Glu Ile Glu Val Ile Ser Thr Tyr Val Glu Leu Asn Leu Thr Leu
            740                 745                 750

Leu Glu Asp Arg Glu Phe Leu Pro Leu Glu Val Tyr Thr Arg Ala Glu
        755                 760                 765

Leu Glu Asp Thr Gly Leu Leu Asp Tyr Ser Glu Ile Gln Arg Arg Asn
    770                 775                 780

Gln Leu His Ala Leu Arg Phe Tyr Asp Ile Asp Ser Val Val Asn Val
785                 790                 795                 800

Asp Asn Thr Ala Val Ile Met Gln Gly Ile Ala Ser Phe Phe Lys Gly
                805                 810                 815

Leu Gly Lys Val Gly Glu Ala Val Gly Thr Leu Val Leu Gly Ala Ala
            820                 825                 830

Gly Ala Val Val Ser Thr Val Ser Gly Ile Ala Ser Phe Leu Asn Asn
        835                 840                 845

Pro Phe Gly Gly Leu Ala Ile Gly Leu Leu Val Ile Ala Gly Leu Val
```

6,017,542

113

114

-continued

```
         850                 855                 860
Ala Ala Phe Phe Ala Tyr Arg Tyr Val Met Gln Ile Arg Ser Asn Pro
865                 870                 875                 880

Met Lys Ala Leu Tyr Pro Ile Thr Thr Lys Ala Leu Lys Asn Lys Ala
                885                 890                 895

Lys Thr Ser Tyr Gly Gln Asn Glu Glu Asp Asp Gly Ser Asp Phe Asp
                900                 905                 910

Glu Ala Lys Leu Glu Glu Ala Arg Glu Met Ile Lys Tyr Met Ser Met
                915                 920                 925

Val Ser Ala Leu Glu Lys Gln Glu Lys Lys Ala Ile Lys Lys Asn Ser
                930                 935                 940

Gly Val Gly Leu Ile Ala Ser Asn Val Ser Lys Leu Ala Leu Arg Arg
945                 950                 955                 960

Arg Gly Pro Lys Tyr Thr Arg Leu Gln Gln Asn Asp Thr Met Glu Asn
                965                 970                 975

Glu Lys Met Val
                980
```

(2) INFORMATION FOR SEQ ID NO:6:

(i) SEQUENCE CHARACTERISTICS:
        (A) LENGTH: 913 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:6:

```
Met Pro Ala Gly Gly Gly Leu Trp Arg Gly Pro Arg Gly His Arg Pro
1                   5                  10                  15

Gly His His Gly Gly Ala Gly Leu Gly Arg Leu Trp Pro Ala Pro His
                20                  25                  30

His Ala Ala Ala Ala Arg Gly Ala Val Ala Leu Ala Leu Leu Leu Leu
                35                  40                  45

Ala Leu Ala Ala Ala Pro Pro Cys Gly Ala Ala Ala Val Thr Arg Ala
50                  55                  60

Ala Ser Ala Ser Pro Thr Pro Gly Thr Gly Ala Thr Pro Asn Asp Val
65                  70                  75                  80

Ser Ala Glu Ala Ser Leu Glu Glu Ile Glu Ala Phe Ser Pro Gly Pro
                85                  90                  95

Ser Glu Ala Pro Asp Gly Glu Tyr Gly Asp Leu Asp Ala Arg Thr Ala
                100                 105                 110

Val Arg Ala Ala Ala Thr Glu Arg Asp Arg Phe Tyr Val Cys Pro Pro
                115                 120                 125

Pro Ser Gly Ser Thr Val Val Arg Leu Glu Pro Glu Gln Ala Cys Pro
130                 135                 140

Glu Tyr Ser Gln Gly Arg Asn Phe Thr Glu Gly Ile Ala Val Leu Phe
145                 150                 155                 160

Lys Glu Asn Ile Ala Pro His Lys Phe Lys Ala His Ile Tyr Tyr Lys
                165                 170                 175

Asn Val Ile Val Thr Thr Val Trp Ser Gly Ser Thr Tyr Ala Ala Ile
                180                 185                 190

Thr Asn Arg Phe Thr Asp Arg Val Pro Val Pro Val Gln Glu Ile Thr
                195                 200                 205
```

-continued

```
Asp Val Ile Asp Arg Arg Gly Lys Cys Val Ser Lys Ala Glu Tyr Val
210                 215                 220
Arg Asn Asn His Lys Val Thr Ala Phe Asp Arg Asp Glu Asn Pro Val
225                 230                 235                 240
Glu Val Asp Leu Arg Pro Ser Arg Leu Asn Ala Leu Gly Thr Arg Gly
                245                 250                 255
Trp His Thr Thr Asn Asp Thr Tyr Thr Lys Ile Gly Ala Ala Gly Phe
            260                 265                 270
Tyr His Thr Gly Thr Ser Val Asn Cys Ile Val Glu Glu Val Glu Ala
            275                 280                 285
Arg Ser Val Tyr Pro Tyr Asp Ser Phe Ala Leu Ser Thr Gly Asp Ile
290                 295                 300
Val Tyr Met Ser Pro Phe Tyr Gly Leu Arg Glu Gly Ala His Gly Glu
305                 310                 315                 320
His Ile Gly Tyr Ala Pro Gly Arg Phe Gln Gln Val Glu His Tyr Tyr
                325                 330                 335
Pro Ile Asp Leu Asp Ser Arg Leu Arg Ala Ser Glu Ser Val Thr Arg
            340                 345                 350
Asn Phe Leu Arg Thr Pro His Phe Thr Val Ala Trp Asp Trp Ala Pro
            355                 360                 365
Lys Thr Arg Arg Val Cys Ser Leu Ala Lys Trp Arg Glu Ala Glu Glu
370                 375                 380
Met Thr Arg Asp Glu Thr Arg Asp Gly Ser Phe Arg Phe Thr Ser Arg
385                 390                 395                 400
Ala Leu Gly Ala Ser Phe Val Ser Asp Val Thr Gln Leu Asp Leu Gln
                405                 410                 415
Arg Val His Leu Gly Asp Cys Val Leu Arg Glu Ala Ser Glu Ala Ile
            420                 425                 430
Asp Ala Ile Tyr Arg Arg Tyr Asn Ser Thr His Val Leu Ala Gly
            435                 440                 445
Asp Arg Pro Glu Val Tyr Leu Ala Arg Gly Gly Phe Val Val Ala Phe
450                 455                 460
Arg Pro Leu Ile Ser Asn Glu Leu Ala Gln Leu Tyr Ala Arg Glu Leu
465                 470                 475                 480
Glu Arg Leu Gly Leu Ala Gly Val Val Gly Pro Ala Ala Pro Ala Ala
                485                 490                 495
Ala Arg Arg Ala Arg Arg Ser Pro Gly Pro Ala Gly Thr Pro Glu Pro
            500                 505                 510
Pro Ala Val Asn Gly Thr Gly His Leu Arg Ile Thr Thr Gly Ser Ala
            515                 520                 525
Glu Phe Ala Arg Leu Gln Phe Thr Tyr Asp His Ile Gln Ala His Val
530                 535                 540
Asn Asp Met Leu Gly Arg Ile Ala Ala Ala Trp Cys Glu Leu Gln Asn
545                 550                 555                 560
Lys Asp Arg Thr Leu Trp Ser Glu Met Ser Arg Leu Asn Pro Ser Ala
                565                 570                 575
Val Ala Thr Ala Ala Leu Gly Gln Arg Val Ser Ala Arg Met Leu Gly
            580                 585                 590
Asp Val Met Ala Ile Ser Arg Cys Val Glu Val Arg Gly Gly Val Tyr
            595                 600                 605
Val Gln Asn Ser Met Arg Val Pro Gly Glu Arg Gly Thr Cys Tyr Ser
610                 615                 620
Arg Pro Leu Val Thr Phe Glu His Asn Gly Thr Gly Val Ile Glu Gly
625                 630                 635                 640
```

```
Gln Leu Gly Asp Asp Asn Glu Leu Leu Ile Ser Arg Asp Leu Ile Glu
            645                 650                 655

Pro Cys Thr Gly Asn His Arg Arg Tyr Phe Lys Leu Gly Ser Gly Tyr
            660                 665                 670

Val Tyr Tyr Glu Asp Tyr Asn Tyr Val Arg Met Val Glu Val Pro Glu
            675                 680                 685

Thr Ile Ser Thr Arg Val Thr Leu Asn Leu Thr Leu Glu Asp Arg
690                 695                 700

Glu Phe Leu Pro Leu Glu Val Tyr Thr Arg Glu Glu Leu Ala Asp Thr
705                 710                 715                 720

Gly Leu Leu Asp Tyr Ser Glu Ile Gln Arg Arg Asn Gln Leu His Ala
            725                 730                 735

Leu Lys Phe Tyr Asp Ile Asp Arg Val Val Lys Val Asp His Asn Val
            740                 745                 750

Val Leu Leu Arg Gly Ile Ala Asn Phe Phe Gln Gly Leu Gly Asp Val
            755                 760                 765

Gly Ala Ala Val Gly Lys Val Val Leu Gly Ala Thr Gly Ala Val Ile
            770                 775                 780

Ser Ala Val Gly Gly Met Val Ser Phe Leu Ser Asn Pro Phe Gly Ala
785                 790                 795                 800

Leu Ala Ile Gly Leu Leu Val Leu Ala Gly Leu Val Ala Ala Phe Leu
            805                 810                 815

Ala Tyr Arg His Ile Ser Arg Leu Arg Arg Asn Pro Met Lys Ala Leu
            820                 825                 830

Tyr Pro Val Thr Thr Lys Thr Leu Lys Glu Asp Gly Val Asp Glu Gly
            835                 840                 845

Asp Val Asp Glu Ala Lys Leu Asp Gln Ala Arg Asp Met Ile Arg Tyr
850                 855                 860

Met Ser Ile Val Ser Ala Leu Glu Gln Gln Glu His Lys Ala Arg Lys
865                 870                 875                 880

Lys Asn Ser Gly Pro Ala Leu Leu Ala Ser Arg Val Gly Ala Met Ala
            885                 890                 895

Thr Arg Arg Arg His Tyr Gln Arg Leu Glu Ser Glu Asp Pro Asp Ala
            900                 905                 910

Leu
```

(2) INFORMATION FOR SEQ ID NO:7:

(i) SEQUENCE CHARACTERISTICS:
        (A) LENGTH: 868 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:7:

```
Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30

His Leu Gly Asp Gly Asp Glu Ile Arg Glu Ala Ile His Lys Ser Gln
            35                  40                  45

Asp Ala Glu Thr Lys Pro Thr Phe Tyr Val Cys Pro Pro Thr Gly
50                  55                  60
```

-continued

Ser Thr Ile Val Arg Leu Glu Pro Thr Arg Thr Cys Pro Asp Tyr His
65                      70                      75                      80

Leu Gly Lys Asn Phe Thr Glu Gly Ile Ala Val Tyr Lys Glu Asn
                85                      90                      95

Ile Ala Ala Tyr Lys Phe Lys Ala Thr Val Tyr Tyr Lys Asp Val Ile
                100                     105                     110

Val Ser Thr Ala Trp Ala Gly Ser Ser Tyr Thr Gln Ile Thr Asn Arg
                115                     120                     125

Tyr Ala Asp Arg Val Pro Ile Pro Val Ser Glu Ile Thr Asp Thr Ile
        130                     135                     140

Asp Lys Phe Gly Lys Cys Ser Ser Lys Ala Thr Tyr Val Arg Asn Asn
145                     150                     155                     160

His Lys Val Glu Ala Phe Asn Glu Asp Lys Asn Pro Gln Asp Met Pro
                165                     170                     175

Leu Ile Ala Ser Lys Tyr Asn Ser Val Gly Ser Lys Ala Trp His Thr
                180                     185                     190

Thr Asn Asp Thr Tyr Met Val Ala Gly Thr Pro Gly Thr Tyr Arg Thr
        195                     200                     205

Gly Thr Ser Val Asn Cys Ile Ile Glu Glu Val Glu Ala Arg Ser Ile
210                     215                     220

Phe Pro Tyr Asp Ser Phe Gly Leu Ser Thr Gly Asp Ile Ile Tyr Met
225                     230                     235                     240

Ser Pro Phe Phe Gly Leu Arg Asp Gly Ala Tyr Arg Glu His Ser Asn
                245                     250                     255

Tyr Ala Met Asp Arg Phe His Gln Phe Glu Gly Tyr Arg Gln Arg Asp
                260                     265                     270

Leu Asp Thr Arg Ala Leu Leu Glu Pro Ala Ala Arg Asn Phe Leu Val
        275                     280                     285

Thr Pro His Leu Thr Val Gly Trp Asn Trp Lys Pro Lys Arg Thr Glu
        290                     295                     300

Val Cys Ser Leu Val Lys Trp Arg Glu Val Glu Asp Val Val Arg Asp
305                     310                     315                     320

Glu Tyr Ala His Asn Phe Arg Phe Thr Met Lys Thr Leu Ser Thr Thr
                325                     330                     335

Phe Ile Ser Glu Thr Asn Glu Phe Asn Leu Asn Gln Ile His Leu Ser
                340                     345                     350

Gln Cys Val Lys Glu Glu Ala Arg Ala Ile Ile Asn Arg Ile Tyr Thr
        355                     360                     365

Thr Arg Tyr Asn Ser Ser His Val Arg Thr Gly Asp Ile Gln Thr Tyr
370                     375                     380

Leu Ala Arg Gly Gly Phe Val Val Phe Gln Pro Leu Leu Ser Asn
385                     390                     395                     400

Ser Leu Ala Arg Leu Tyr Leu Gln Glu Leu Val Arg Glu Asn Thr Asn
                405                     410                     415

His Ser Pro Gln Lys His Pro Thr Arg Asn Thr Arg Ser Arg Arg Ser
        420                     425                     430

Val Pro Val Glu Leu Arg Ala Asn Arg Thr Ile Thr Thr Ser Ser
                435                     440                     445

Val Glu Phe Ala Met Leu Gln Phe Thr Tyr Asp His Ile Gln Glu His
        450                     455                     460

Val Asn Glu Met Leu Ala Arg Ile Ser Ser Ser Trp Cys Gln Leu Gln
465                     470                     475                     480

Asn Arg Glu Arg Ala Leu Trp Ser Gly Leu Phe Pro Ile Asn Pro Ser

```
                          485                 490                 495
Ala Leu Ala Ser Thr Ile Leu Asp Gln Arg Val Lys Ala Arg Ile Leu
            500                 505                 510

Gly Asp Val Ile Ser Val Ser Asn Cys Pro Glu Leu Gly Ser Asp Thr
            515                 520                 525

Arg Ile Ile Leu Gln Asn Ser Met Arg Val Ser Gly Ser Thr Thr Arg
            530                 535                 540

Cys Tyr Ser Arg Pro Leu Ile Ser Ile Val Ser Leu Asn Gly Ser Gly
545                 550                 555                 560

Thr Val Glu Gly Gln Leu Gly Thr Asp Asn Glu Leu Ile Met Ser Arg
            565                 570                 575

Asp Leu Leu Glu Pro Cys Val Ala Asn His Lys Arg Tyr Phe Leu Phe
            580                 585                 590

Gly His His Tyr Val Tyr Tyr Glu Asp Tyr Arg Tyr Val Arg Glu Ile
            595                 600                 605

Ala Val His Asp Val Gly Met Ile Ser Thr Tyr Val Asp Leu Asn Leu
            610                 615                 620

Thr Leu Leu Lys Asp Arg Glu Phe Met Pro Leu Gln Val Tyr Thr Arg
625                 630                 635                 640

Asp Glu Leu Arg Asp Thr Gly Leu Leu Asp Tyr Ser Glu Ile Gln Arg
            645                 650                 655

Arg Asn Gln Met His Ser Leu Arg Phe Tyr Asp Ile Asp Lys Val Val
            660                 665                 670

Gln Tyr Asp Ser Gly Thr Ala Ile Met Gln Gly Met Ala Gln Phe Phe
            675                 680                 685

Gln Gly Leu Gly Thr Ala Gly Gln Ala Val Gly His Val Val Leu Gly
            690                 695                 700

Ala Thr Gly Ala Leu Leu Ser Thr Val His Gly Phe Thr Thr Phe Leu
705                 710                 715                 720

Ser Asn Pro Phe Gly Ala Leu Ala Val Gly Leu Leu Val Leu Ala Gly
            725                 730                 735

Leu Val Ala Ala Phe Phe Ala Tyr Arg Tyr Val Leu Lys Leu Lys Thr
            740                 745                 750

Ser Pro Met Lys Ala Leu Tyr Pro Leu Thr Thr Lys Gly Leu Lys Gln
            755                 760                 765

Leu Pro Glu Gly Met Asp Pro Phe Ala Glu Lys Pro Asn Ala Thr Asp
770                 775                 780

Thr Pro Ile Glu Glu Ile Gly Asp Ser Gln Asn Thr Glu Pro Ser Val
785                 790                 795                 800

Asn Ser Gly Phe Asp Pro Asp Lys Phe Arg Glu Ala Gln Glu Met Ile
            805                 810                 815

Lys Tyr Met Thr Leu Val Ser Ala Ala Glu Arg Gln Glu Ser Lys Ala
            820                 825                 830

Arg Lys Lys Asn Lys Thr Ser Ala Leu Leu Thr Ser Arg Leu Thr Gly
            835                 840                 845

Leu Ala Leu Arg Asn Arg Arg Gly Tyr Ser Arg Val Arg Thr Glu Asn
            850                 855                 860

Val Thr Gly Val
865
```

(2) INFORMATION FOR SEQ ID NO:8:

(i) SEQUENCE CHARACTERISTICS:
        (A) LENGTH: 903 amino acids
        (B) TYPE: amino acid (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:8:

Met His Gln Gly Ala Pro Ser Trp Gly Arg Arg Trp Phe Val Val Trp
1               5                   10                  15

Ala Leu Leu Gly Leu Thr Leu Gly Val Leu Ala Ser Ala Ala Pro
            20                  25                  30

Ser Ser Pro Gly Thr Pro Gly Val Ala Arg Asp Pro Gly Gly Glu Arg
        35                  40                  45

Gly Pro Cys His Ser Gly Ala Ala Leu Gly Ala Ala Pro Thr Gly
    50                  55                  60

Asp Pro Lys Pro Lys Lys Asn Lys Lys Pro Lys Asn Pro Thr Pro Pro
65              70                  75                  80

Arg Pro Ala Gly Asp Asn Ala Thr Val Ala Gly His Ala Thr Leu
                85                  90                  95

Arg Glu His Leu Arg Asp Ile Lys Ala Glu Asn Thr Asp Ala Asn Phe
                100                 105                 110

Tyr Val Cys Pro Pro Pro Thr Gly Ala Thr Val Val Gln Phe Glu Gln
            115                 120                 125

Pro Arg Arg Cys Pro Thr Arg Pro Glu Gly Gln Asn Tyr Thr Glu Gly
    130                 135                 140

Ile Ala Val Val Phe Lys Glu Asn Ile Ala Pro Tyr Lys Phe Lys Ala
145                 150                 155                 160

Thr Met Tyr Tyr Lys Asp Val Thr Val Ser Gln Val Trp Phe Gly His
                165                 170                 175

Arg Tyr Ser Gln Phe Met Gly Ile Phe Glu Asp Arg Ala Pro Val Pro
            180                 185                 190

Phe Glu Glu Val Ile Asp Lys Ile Asn Ala Lys Gly Val Cys Arg Ser
        195                 200                 205

Thr Ala Lys Tyr Val Arg Asn Asn Leu Glu Thr Thr Ala Phe His Arg
210                 215                 220

Asp Asp His Glu Thr Asp Met Glu Leu Lys Pro Ala Asn Ala Ala Thr
225                 230                 235                 240

Arg Thr Ser Arg Gly Trp His Thr Thr Asp Leu Lys Tyr Asn Pro Ser
                245                 250                 255

Arg Val Glu Ala Phe His Arg Tyr Gly Thr Thr Val Asn Cys Ile Val
            260                 265                 270

Glu Glu Val Asp Ala Arg Ser Val Tyr Pro Tyr Asp Glu Phe Val Leu
        275                 280                 285

Ala Thr Gly Asp Phe Val Tyr Met Ser Pro Phe Tyr Gly Tyr Arg Glu
290                 295                 300

Gly Ser His Thr Glu His Thr Thr Tyr Ala Ala Asp Arg Phe Lys Gln
305                 310                 315                 320

Val Asp Gly Phe Tyr Ala Arg Asp Leu Thr Thr Lys Ala Arg Ala Thr
                325                 330                 335

Ala Pro Thr Thr Arg Asn Leu Leu Thr Thr Pro Lys Phe Thr Val Ala
            340                 345                 350

Trp Asp Trp Val Pro Lys Arg Pro Ser Val Cys Thr Met Thr Lys Trp
        355                 360                 365

Gln Glu Val Asp Glu Met Leu Arg Ser Glu Tyr Gly Gly Ser Phe Arg
370                 375                 380

-continued

```
Phe Ser Ser Asp Ala Ile Ser Thr Thr Phe Thr Thr Asn Leu Thr Glu
385                 390                 395                 400

Tyr Pro Leu Ser Arg Val Asp Leu Gly Asp Cys Ile Gly Lys Asp Ala
                405                 410                 415

Arg Asp Ala Met Asp Arg Ile Phe Ala Arg Arg Tyr Asn Ala Thr His
                420                 425                 430

Ile Lys Val Gly Gln Pro Gln Tyr Tyr Leu Ala Asn Gly Gly Phe Leu
                435                 440                 445

Ile Ala Tyr Gln Pro Leu Leu Ser Asn Thr Leu Ala Glu Leu Tyr Val
450                 455                 460

Arg Glu His Leu Arg Glu Gln Ser Arg Lys Pro Pro Asn Pro Thr Pro
465                 470                 475                 480

Pro Pro Pro Gly Ala Ser Ala Asn Ala Ser Val Glu Arg Ile Lys Thr
                485                 490                 495

Thr Ser Ser Ile Glu Phe Ala Arg Leu Gln Phe Thr Tyr Asn His Ile
                500                 505                 510

Gln Arg His Val Asn Asp Met Leu Gly Arg Val Ala Ile Ala Trp Cys
                515                 520                 525

Glu Leu Gln Asn His Glu Leu Thr Leu Trp Asn Glu Ala Arg Lys Leu
530                 535                 540

Asn Pro Asn Ala Ile Ala Ser Val Thr Val Gly Arg Arg Val Ser Ala
545                 550                 555                 560

Arg Met Leu Gly Asp Val Met Ala Val Ser Thr Cys Val Pro Val Ala
                565                 570                 575

Ala Asp Asn Val Ile Val Gln Asn Ser Met Arg Ile Ser Ser Arg Pro
                580                 585                 590

Gly Ala Cys Tyr Ser Arg Pro Leu Val Ser Phe Arg Tyr Glu Asp Gln
                595                 600                 605

Gly Pro Leu Val Glu Gly Gln Leu Gly Glu Asn Asn Glu Leu Arg Leu
                610                 615                 620

Thr Arg Asp Ala Ile Glu Pro Cys Thr Val Gly His Arg Arg Tyr Phe
625                 630                 635                 640

Thr Phe Gly Gly Gly Tyr Val Tyr Phe Glu Glu Tyr Ala Tyr Ser His
                645                 650                 655

Gln Leu Ser Arg Ala Asp Ile Thr Thr Val Ser Thr Phe Ile Asp Leu
                660                 665                 670

Asn Ile Thr Met Leu Glu Asp His Glu Phe Val Pro Leu Glu Val Tyr
                675                 680                 685

Thr Arg His Glu Ile Lys Asp Ser Gly Leu Leu Asp Tyr Thr Glu Val
                690                 695                 700

Gln Arg Arg Asn Gln Leu His Asp Leu Arg Phe Ala Asp Ile Asp Thr
705                 710                 715                 720

Val Ile His Ala Asp Ala Asn Ala Met Phe Ala Gly Leu Gly Ala
                725                 730                 735

Phe Phe Glu Gly Met Gly Asp Leu Gly Arg Ala Val Gly Lys Val Val
                740                 745                 750

Met Gly Leu Val Gly Gly Val Val Ser Ala Val Ser Gly Val Ser Ser
                755                 760                 765

Phe Met Ser Asn Pro Phe Gly Ala Leu Ala Val Gly Leu Leu Val Leu
                770                 775                 780

Ala Gly Leu Ala Ala Ala Phe Phe Ala Phe Arg Tyr Val Met Arg Leu
785                 790                 795                 800

Gln Ser Asn Pro Met Lys Ala Leu Tyr Pro Leu Thr Thr Lys Glu Leu
```

```
                        805                 810                 815
Lys Asn Pro Thr Asn Pro Asp Ala Ser Gly Glu Gly Glu Glu Gly Gly
                820                 825                 830

Asp Phe Asp Glu Ala Lys Leu Ala Glu Ala Arg Glu Met Ile Arg Tyr
            835                 840                 845

Met Ala Leu Val Ser Ala Met Glu Arg Thr Glu His Lys Ala Lys Lys
        850                 855                 860

Lys Gly Thr Ser Arg Leu Leu Ser Ala Lys Val Thr Asp Met Val Met
865                 870                 875                 880

Arg Lys Arg Arg Asn Thr Asn Tyr Thr Gln Val Pro Asn Lys Asp Gly
                885                 890                 895

Asp Ala Asp Glu Asp Leu
            900
```

(2) INFORMATION FOR SEQ ID NO:9:

(i) SEQUENCE CHARACTERISTICS:
        (A) LENGTH: 906 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:9:

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240
```

-continued

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
                260                 265                 270

Val Val Tyr Ile Ser Pro Phe Tyr Asn Gly Thr Asn Arg Asn Ala Ser
                275                 280                 285

Tyr Phe Gly Glu Asn Ala Asp Lys Phe Phe Ile Phe Pro Asn Tyr Thr
            290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
            435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
                515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

```
Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
            755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
            805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Asn Val
            900                 905

(2) INFORMATION FOR SEQ ID NO:10:

(i) SEQUENCE CHARACTERISTICS:
        (A) LENGTH: 857 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:10:

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
            20                  25                  30

Thr Thr Val Gln Pro Thr Ala Thr Arg Gln Gln Thr Ser Phe Pro Phe
                35                  40                  45

Arg Val Cys Glu Leu Ser Ser His Gly Asp Leu Phe Arg Phe Ser Ser
    50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
```

-continued

```
                100                 105                 110
Tyr Ala Asp Ser Val Thr Asn Arg His Glu Glu Lys Phe Ser Val Asp
            115                 120                 125
Ser Tyr Glu Thr Asp Gln Met Asp Thr Ile Tyr Gln Cys Tyr Asn Ala
130                 135                 140
Val Lys Met Thr Lys Asp Gly Leu Thr Arg Val Tyr Val Asp Arg Asp
145                 150                 155                 160
Gly Val Asn Ile Thr Val Asn Leu Lys Pro Thr Gly Gly Leu Ala Asn
                165                 170                 175
Gly Val Arg Arg Tyr Ala Ser Gln Thr Glu Leu Tyr Asp Ala Pro Gly
                180                 185                 190
Trp Leu Ile Trp Thr Tyr Arg Thr Arg Thr Val Asn Cys Leu Ile
                195                 200                 205
Thr Asp Met Met Ala Lys Ser Asn Ser Pro Phe Asp Phe Val Thr
210                 215                 220
Thr Thr Gly Gln Thr Val Glu Met Ser Pro Phe Tyr Asp Gly Lys Asn
225                 230                 235                 240
Lys Glu Thr Phe His Glu Arg Ala Asp Ser Phe His Val Arg Thr Asn
                245                 250                 255
Tyr Lys Ile Val Asp Tyr Asp Asn Arg Gly Thr Asn Pro Gln Gly Glu
                260                 265                 270
Arg Arg Ala Phe Leu Asp Lys Gly Thr Tyr Thr Leu Ser Trp Lys Leu
                275                 280                 285
Glu Asn Arg Thr Ala Tyr Cys Pro Leu Gln His Trp Gln Thr Phe Asp
                290                 295                 300
Ser Thr Ile Ala Thr Glu Thr Gly Lys Ser Ile His Phe Val Thr Asp
305                 310                 315                 320
Glu Gly Thr Ser Ser Phe Val Thr Asn Thr Thr Val Gly Ile Glu Leu
                325                 330                 335
Pro Asp Ala Phe Lys Cys Ile Glu Glu Gln Val Asn Lys Thr Met His
                340                 345                 350
Glu Lys Tyr Glu Ala Val Gln Asp Arg Tyr Thr Lys Gly Gln Glu Ala
                355                 360                 365
Ile Thr Tyr Phe Ile Thr Ser Gly Gly Leu Leu Leu Ala Trp Leu Pro
                370                 375                 380
Leu Thr Pro Arg Ser Leu Ala Thr Val Lys Asn Leu Thr Glu Leu Thr
385                 390                 395                 400
Thr Pro Thr Ser Ser Pro Pro Ser Ser Pro Pro Ala Pro Ser
                405                 410                 415
Ala Ala Arg Gly Ser Thr Pro Ala Ala Val Leu Arg Arg Arg Arg
                420                 425                 430
Asp Ala Gly Asn Ala Thr Thr Pro Val Pro Pro Thr Ala Pro Gly Lys
                435                 440                 445
Ser Leu Gly Thr Leu Asn Asn Pro Ala Thr Val Gln Ile Gln Phe Ala
                450                 455                 460
Tyr Asp Ser Leu Arg Arg Gln Ile Asn Arg Met Leu Gly Asp Leu Ala
465                 470                 475                 480
Arg Ala Trp Cys Leu Glu Gln Lys Arg Gln Asn Met Val Leu Arg Glu
                485                 490                 495
Leu Thr Lys Ile Asn Pro Thr Thr Val Met Ser Ser Ile Tyr Gly Lys
                500                 505                 510
Ala Val Ala Ala Lys Arg Leu Gly Asp Val Ile Ser Val Ser Gln Cys
                515                 520                 525
```

```
Val Pro Val Asn Gln Ala Thr Val Thr Leu Arg Lys Ser Met Arg Val
    530                 535                 540
Pro Gly Ser Glu Thr Met Cys Tyr Ser Arg Pro Leu Val Ser Phe Ser
545                 550                 555                 560
Phe Ile Asn Asp Thr Lys Thr Tyr Glu Gly Gln Leu Gly Thr Asp Asn
                565                 570                 575
Glu Ile Phe Leu Thr Lys Lys Met Thr Glu Val Cys Gln Ala Thr Ser
            580                 585                 590
Gln Tyr Tyr Phe Gln Ser Gly Asn Glu Ile His Val Tyr Asn Asp Tyr
        595                 600                 605
His His Phe Lys Thr Ile Glu Leu Asp Gly Ile Ala Thr Leu Gln Thr
    610                 615                 620
Phe Ile Ser Leu Asn Thr Ser Leu Ile Glu Asn Ile Asp Phe Ala Ser
625                 630                 635                 640
Leu Glu Leu Tyr Ser Arg Asp Glu Gln Arg Ala Ser Asn Val Phe Asp
                645                 650                 655
Leu Glu Gly Ile Phe Arg Glu Tyr Asn Phe Gln Ala Gln Asn Ile Ala
            660                 665                 670
Gly Leu Arg Lys Asp Leu Asp Asn Ala Val Ser Asn Gly Arg Asn Gln
        675                 680                 685
Phe Val Asp Gly Leu Gly Glu Leu Met Asp Ser Leu Gly Ser Val Gly
    690                 695                 700
Gln Ser Ile Thr Asn Leu Val Ser Thr Val Gly Gly Leu Phe Ser Ser
705                 710                 715                 720
Leu Val Ser Gly Phe Ile Ser Phe Phe Lys Asn Pro Phe Gly Gly Met
                725                 730                 735
Leu Ile Leu Val Leu Val Ala Gly Val Val Ile Leu Val Ile Ser Leu
            740                 745                 750
Thr Arg Arg Thr Arg Gln Met Ser Gln Gln Pro Val Gln Met Leu Tyr
        755                 760                 765
Pro Gly Ile Asp Glu Leu Ala Gln Gln His Ala Ser Gly Glu Gly Pro
    770                 775                 780
Gly Ile Asn Pro Ile Ser Lys Thr Glu Leu Gln Ala Ile Met Leu Ala
785                 790                 795                 800
Leu His Glu Gln Asn Gln Glu Gln Lys Arg Ala Ala Gln Arg Ala Ala
                805                 810                 815
Gly Pro Ser Val Ala Ser Arg Ala Leu Gln Ala Ala Arg Asp Arg Phe
            820                 825                 830
Pro Gly Leu Arg Arg Arg Arg Tyr His Asp Pro Glu Thr Ala Ala Ala
        835                 840                 845
Leu Leu Gly Glu Ala Glu Thr Glu Phe
    850                 855

(2) INFORMATION FOR SEQ ID NO:11:

(i) SEQUENCE CHARACTERISTICS:
        (A) LENGTH: 2280 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CGAGCCCTAA TTATTGGTTT GTATATGACT GTTGGAATTT GTTACATTTT TATTAAAACA        60

ATAAATTAAA TTTTTTAAAC TATATTACGG TTGTGTGTGT TTTAAGTTTT AAATAAAGCA       120
```

-continued

```
ATATTTCGAA TTCACATTTA TCAAAAACAT TAAAACCCAA CACAAAAAAA TTTCTATAAT      180

CATTAAGGTA ATAAGTCAAA ATGAGTTTTA AAAATTTTTA TCTAATATAT GTAATTATAA      240

TTTTTATAAA CTCGATAATA ACTTCGGCAT CTACATCCAA ACCTTCAACA CCTACCATAA      300

TTCCAACTTC AGCAAATGAA TCACCTGCTT CCATAGATAC AACTATAACA AAACCTATAT      360

CTACAGAGGC AAATAATTTA AAATCAGTAA GTACCTCAAT TAAACCACCT AAAAACTTAA      420

AAAAAAAATT ACTTAAATCT AAATGTAGAG ATAATGTTAT TTATAGGCCA TATTTTAGTC      480

AATTAGAAAT TAACTGTACT ATAACTAAAA AGCAAAATTT AAGTAATCCT TTAATTGAGT      540

TATGGTTTAA AGAACTTTCT ACATATAATA AAACCAATGA AAATGTTGAA AGTTTAAAAA      600

CAGATATATC AAAAAATATT TTATTATTTT CGACAAAAAA TAATAGTGAT AACTTTTATA      660

ATGATTTTTT ATTAGGTATA CAAAATCAAC CAGTAAATTA TAAACTTTAC GGTTCCCAAT      720

TTTATGATAA TGGAAACATA TTACTAAATA TAAAGTCGGT TGACTTTAAA ACCTCTGGAA      780

TATATACTTG GAAACTATAT AATTCAAATA ATGAAAGTAT TTTTGAAACT TTTAAAATTC      840

AAGTATATGC ATATCATTCC CCAAATGTAA ACTTAAAATC AAACCCAAGT TTATATAATG      900

AAAACTACAG CGCTATTTGT ACAATAGCAA ATTACTTTCC ATTGGAATCT ACGGAAATAT      960

TTTGGTTTAA CGATGGACAA CCTATTGATA AAAAATATAT AGATGAAACT TATAGTGTAT     1020

GGATTGACGG TCTTATAACA CGCACTTCAA TATTATCCCT TCCCTTTTCC GAAGCCATGG     1080

AAAGCCCCCC CAATTTGCGA TGTAATGTTG AATGGTATAA AAATTCAAAG GCATCAAAAA     1140

AATTTTCAAA TACCGTTATT CCAAAAGTTT ACTATAAACC TTTTATATCT ATAAAATTTG     1200

ATAATGGTTT AGCTATTTGT GATGCTAAAT GTGTTTCCCG TGAAAATAAT AAATTACAAT     1260

GGTTAGTTAA AGATATACCT ATAAATGGTG ATGATATTAT AAGCGGCCCC TGTTTAAACC     1320

ACCCTGGTTT GGTCAATATT CAAAATAAAA TAGATATATC GGATTATGAT GAACCTGTTA     1380

CCTATAAATG TTCAATTATT GGTTATCCAA TAATTTTTCC CAACTTTTAT GATGAAAAGG     1440

TGTTTGATGC ATCGGATGAA AATGTTAGTA AATCGATGTT AATAAGTATT ACCACAATAA     1500

TTGGTGGAGC CATTTTTGTT ATAGTATTGA TTTTTATAAC AGCTTTATGT TTTTATTGTT     1560

CAAAAAATAA TAAGATCTAA TATCAATATT TACGTAAATG GATTATATAA TGTTATATTC     1620

GTGTTATTAT GATTTATAAG TTCATCAAAT TTAAAAATTT GTATAGTATT AAGATTTTTA     1680

ATAGGGGTAT CGTTTAATAT GGCTCAGTTA GTTTTAACTG ATATTCCCCT CGAAGATGTG     1740

GAAAATAAAA ATACTTCATC CGACGAAGAA ACAACTAACT TAAACCAGAA AAAATCAACA     1800

TGTCAATGTT TATGTGTTAC CCTTGGATTT TTTGCAGCTG GAATTTATT AACCATAGCT      1860

GCAATAATTT TTACTTTTAT TTTTACAGTA CCATTAGAAA TGCTTGGATC TATTAATTGT     1920

CCTCCATCTA CATTTGGTAT TGATAATGTT TGTATCGAAC CAATAAAAAA ATCTATTAAT     1980

TCTTATTCAG AATTATCTAA AATATGTTAT GATAGATTGT CAAATCCGAT AAATCAGAGT     2040

ACTATTAACT CCTTATTAAC TGTTTTAAAT ATGTTTGCAG ATAAAAACTA TGAAAATGTT     2100

TATAATTGTA ATACAATGAG TGAAAAAACA TGTAATTCAT CAATAGCTAT TTGTCAAACT     2160

AATCATCCAC TAAGTTCATT GGGAAATTTT GTTATTAAAA TTAGAAAAAT TTTTGGGTTT     2220

AAATAATAAA TAAAATAAAT AAACATTACT TTTTGTTTTT GTCTTTATTA AACAGTTGTA     2280
```

(2) INFORMATION FOR SEQ ID NO:12:

(i) SEQUENCE CHARACTERISTICS:
        (A) LENGTH: 459 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:12:

```
Met Ser Phe Lys Asn Phe Tyr Leu Ile Tyr Val Ile Ile Phe Ile
1               5                   10                  15

Asn Ser Ile Ile Thr Ser Ala Ser Thr Ser Lys Pro Ser Thr Pro Thr
            20                  25                  30

Ile Ile Pro Thr Ser Ala Asn Glu Ser Pro Ala Ser Ile Asp Thr Thr
            35                  40                  45

Ile Thr Lys Pro Ile Ser Thr Glu Ala Asn Asn Leu Lys Ser Val Ser
            50                  55                  60

Thr Ser Ile Lys Pro Pro Lys Asn Leu Lys Lys Leu Leu Lys Ser
65                  70                  75                  80

Lys Cys Arg Asp Asn Val Ile Tyr Arg Pro Tyr Phe Ser Gln Leu Glu
                85                  90                  95

Ile Asn Cys Thr Ile Thr Lys Lys Gln Asn Leu Ser Asn Pro Leu Ile
            100                 105                 110

Glu Leu Trp Phe Lys Glu Leu Ser Thr Tyr Asn Lys Thr Asn Glu Asn
            115                 120                 125

Val Glu Ser Leu Lys Thr Asp Ile Ser Lys Asn Ile Leu Leu Phe Ser
            130                 135                 140

Thr Lys Asn Asn Ser Asp Asn Phe Tyr Asn Asp Phe Leu Leu Gly Ile
145                 150                 155                 160

Gln Asn Gln Pro Val Asn Tyr Lys Leu Tyr Gly Ser Gln Phe Tyr Asp
                165                 170                 175

Asn Gly Asn Ile Leu Leu Asn Ile Lys Ser Val Asp Phe Lys Thr Ser
            180                 185                 190

Gly Ile Tyr Thr Trp Lys Leu Tyr Asn Ser Asn Asn Glu Ser Ile Phe
            195                 200                 205

Glu Thr Phe Lys Ile Gln Val Tyr Ala Tyr His Ser Pro Asn Val Asn
            210                 215                 220

Leu Lys Ser Asn Pro Ser Leu Tyr Asn Glu Asn Tyr Ser Ala Ile Cys
225                 230                 235                 240

Thr Ile Ala Asn Tyr Phe Pro Leu Glu Ser Thr Glu Ile Phe Trp Phe
                245                 250                 255

Asn Asp Gly Gln Pro Ile Asp Lys Lys Tyr Ile Asp Thr Tyr Ser
            260                 265                 270

Val Trp Ile Asp Gly Leu Ile Thr Arg Thr Ser Ile Leu Ser Leu Pro
            275                 280                 285

Phe Ser Glu Ala Met Glu Ser Pro Asn Leu Arg Cys Asn Val Glu
290                 295                 300

Trp Tyr Lys Asn Ser Lys Ala Ser Lys Lys Phe Ser Asn Thr Val Ile
305                 310                 315                 320

Pro Lys Val Tyr Tyr Lys Pro Phe Ile Ser Ile Lys Phe Asp Asn Gly
                325                 330                 335

Leu Ala Ile Cys Asp Ala Lys Cys Val Ser Arg Glu Asn Asn Lys Leu
            340                 345                 350

Gln Trp Leu Val Lys Asp Ile Pro Ile Asn Gly Asp Asp Ile Ile Ser
            355                 360                 365

Gly Pro Cys Leu Asn His Pro Gly Leu Val Asn Ile Gln Asn Lys Ile
370                 375                 380

Asp Ile Ser Asp Tyr Asp Glu Pro Val Thr Tyr Lys Cys Ser Ile Ile
```

```
                  385                 390                 395                 400
Gly Tyr Pro Ile Ile Phe Pro Asn Phe Tyr Asp Glu Lys Val Phe Asp
                    405                 410                 415

Ala Ser Asp Glu Asn Val Ser Lys Ser Met Leu Ile Ser Ile Thr Thr
                420                 425                 430

Ile Ile Gly Gly Ala Ile Phe Val Ile Val Leu Ile Phe Ile Thr Ala
                435                 440                 445

Leu Cys Phe Tyr Cys Ser Lys Asn Asn Lys Ile
450                 455
```

(2) INFORMATION FOR SEQ ID NO:13:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:13:

```
Met Ala Gln Leu Val Leu Thr Asp Ile Pro Leu Glu Asp Val Glu Asn
1               5                   10                  15

Lys Asn Thr Ser Ser Asp Glu Glu Thr Thr Asn Leu Asn Gln Lys Lys
                20                  25                  30

Ser Thr Cys Gln Cys Leu Cys Val Thr Leu Gly Phe Phe Ala Ala Gly
            35                  40                  45

Ile Leu Leu Thr Ile Ala Ala Ile Ile Phe Thr Phe Ile Phe Thr Val
50                  55                  60

Pro Leu Glu Met Leu Gly Ser Ile Asn Cys Pro Pro Ser Thr Phe Gly
65              70                  75                  80

Ile Asp Asn Val Cys Ile Glu Pro Ile Lys Lys Ser Ile Asn Ser Tyr
                85                  90                  95

Ser Glu Leu Ser Lys Ile Cys Tyr Asp Arg Leu Ser Asn Pro Ile Asn
                100                 105                 110

Gln Ser Thr Ile Asn Ser Leu Leu Thr Val Leu Asn Met Phe Ala Asp
            115                 120                 125

Lys Asn Tyr Glu Asn Val Tyr Asn Cys Asn Thr Met Ser Glu Lys Thr
130                 135                 140

Cys Asn Ser Ser Ile Ala Ile Cys Gln Thr Asn His Pro Leu Ser Ser
145                 150                 155                 160

Leu Gly Asn Phe Val Ile Lys Ile Arg Lys Ile Phe Gly Phe Lys
                165                 170                 175
```

(2) INFORMATION FOR SEQ ID NO:14:

(i) SEQUENCE CHARACTERISTICS:
        (A) LENGTH: 459 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:14:

```
Met Ser Phe Lys Asn Phe Tyr Leu Ile Tyr Val Ile Ile Ile Phe Ile
1               5                   10                  15
```

-continued

```
Asn Ser Ile Ile Thr Ser Ala Ser Thr Ser Lys Pro Ser Thr Pro Thr
                 20                  25                  30

Ile Ile Pro Thr Ser Ala Asn Glu Ser Pro Ala Ser Ile Asp Thr Thr
             35                  40                  45

Ile Thr Lys Pro Ile Ser Thr Glu Ala Asn Asn Leu Lys Ser Val Ser
 50                  55                          60

Thr Ser Ile Lys Pro Pro Lys Asn Leu Lys Lys Lys Leu Leu Lys Ser
 65                  70                  75                  80

Lys Cys Arg Asp Asn Val Ile Tyr Arg Pro Tyr Phe Ser Gln Leu Glu
                 85                  90                  95

Ile Asn Cys Thr Ile Thr Lys Lys Gln Asn Leu Ser Asn Pro Leu Ile
                100                 105                 110

Glu Leu Trp Phe Lys Glu Leu Ser Thr Tyr Asn Lys Thr Asn Glu Asn
            115                 120                 125

Val Glu Ser Leu Lys Thr Asp Ile Ser Lys Asn Ile Leu Leu Phe Ser
130                 135                 140

Thr Lys Asn Asn Ser Asp Asn Phe Tyr Asn Asp Phe Leu Leu Gly Ile
145                 150                 155                 160

Gln Asn Gln Pro Val Asn Tyr Lys Leu Tyr Gly Ser Gln Phe Tyr Asp
                165                 170                 175

Asn Gly Asn Ile Leu Leu Asn Ile Lys Ser Val Asp Phe Lys Thr Ser
                180                 185                 190

Gly Ile Tyr Thr Trp Lys Leu Tyr Asn Ser Asn Asn Glu Ser Ile Phe
            195                 200                 205

Glu Thr Phe Lys Ile Gln Val Tyr Ala Tyr His Ser Pro Asn Val Asn
210                 215                 220

Leu Lys Ser Asn Pro Ser Leu Tyr Asn Glu Asn Tyr Ser Ala Ile Cys
225                 230                 235                 240

Thr Ile Ala Asn Tyr Phe Pro Leu Glu Ser Thr Glu Ile Phe Trp Phe
                245                 250                 255

Asn Asp Gly Gln Pro Ile Asp Lys Lys Tyr Ile Asp Glu Thr Tyr Ser
                260                 265                 270

Val Trp Ile Asp Gly Leu Ile Thr Arg Thr Ser Ile Leu Ser Leu Pro
            275                 280                 285

Phe Ser Glu Ala Met Glu Ser Pro Pro Asn Leu Arg Cys Asn Val Glu
290                 295                 300

Trp Tyr Lys Asn Ser Lys Ala Ser Lys Lys Phe Ser Asn Thr Val Ile
305                 310                 315                 320

Pro Lys Val Tyr Tyr Lys Pro Phe Ile Ser Ile Lys Phe Asp Asn Gly
                325                 330                 335

Leu Ala Ile Cys Asp Ala Lys Cys Val Ser Arg Glu Asn Asn Lys Leu
                340                 345                 350

Gln Trp Leu Val Lys Asp Ile Pro Ile Asn Gly Asp Asp Ile Ile Ser
            355                 360                 365

Gly Pro Cys Leu Asn His Pro Gly Leu Val Asn Ile Gln Asn Lys Ile
370                 375                 380

Asp Ile Ser Asp Tyr Asp Glu Pro Val Thr Tyr Lys Cys Ser Ile Ile
385                 390                 395                 400

Gly Tyr Pro Ile Ile Phe Pro Asn Phe Tyr Asp Glu Lys Val Phe Asp
                405                 410                 415

Ala Ser Asp Glu Asn Val Ser Lys Ser Met Leu Ile Ser Ile Thr Thr
                420                 425                 430

Ile Ile Gly Gly Ala Ile Phe Val Ile Val Leu Ile Phe Ile Thr Ala
            435                 440                 445
```

```
Leu Cys Phe Tyr Cys Ser Lys Asn Asn Lys Ile
    450                 455
```

(2) INFORMATION FOR SEQ ID NO:15:

(i) SEQUENCE CHARACTERISTICS:
        (A) LENGTH: 533 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:15:

```
Met Arg Arg Tyr Arg Met Gly Arg Gly Ile Tyr Leu Leu Tyr Ile Cys
1               5                   10                  15

Leu Leu Tyr Thr Tyr Leu Gln Phe Gly Thr Ser Ser Thr Thr Ala Val
            20                  25                  30

Ser Ile Glu Asn Ser Asp Asn Ser Thr Ala Glu Met Leu Ser Ser Thr
                35                  40                  45

Ser Met Ser Ala Thr Thr Pro Ile Ser Gln Pro Thr Ser Pro Phe Thr
    50                  55                  60

Thr Pro Thr Arg Arg Ser Thr Asn Ile Ala Thr Ser Ser Ser Thr Thr
65                  70                  75                  80

Gln Ala Ser Gln Pro Thr Ser Thr Leu Thr Thr Leu Thr Arg Ser Ser
                85                  90                  95

Thr Thr Ile Ala Thr Ser Pro Ser Thr Thr Gln Ala Ala Thr Phe Ile
                100                 105                 110

Gly Ser Ser Thr Asp Ser Asn Thr Thr Leu Leu Lys Thr Thr Lys Lys
            115                 120                 125

Pro Lys Arg Lys Lys Asn Lys Asn Asn Gly Ala Arg Phe Lys Leu Asp
130                 135                 140

Cys Gly Tyr Lys Gly Val Ile Tyr Arg Pro Tyr Phe Ser Pro Leu Gln
145                 150                 155                 160

Leu Asn Cys Thr Leu Pro Thr Glu Pro His Ile Thr Asn Pro Ile Asp
                165                 170                 175

Phe Glu Ile Trp Phe Lys Pro Arg Thr Arg Phe Gly Asp Phe Leu Gly
            180                 185                 190

Asp Lys Glu Asp Phe Val Gly Asn His Thr Arg Thr Ser Ile Leu Leu
        195                 200                 205

Phe Ser Ser Arg Asn Gly Ser Val Asn Ser Met Asp Leu Gly Asp Ala
210                 215                 220

Thr Leu Gly Ile Leu Gln Ser Arg Ile Pro Asp Tyr Thr Leu Tyr Asn
225                 230                 235                 240

Ile Pro Ile Gln His Thr Glu Ala Met Ser Leu Gly Ile Lys Ser Val
                245                 250                 255

Glu Ser Ala Thr Ser Gly Val Tyr Thr Trp Arg Val Tyr Gly Gly Asp
                260                 265                 270

Gly Leu Asn Lys Thr Val Leu Gly Gln Val Asn Val Ser Val Val Ala
            275                 280                 285

Tyr His Pro Pro Ser Val Asn Leu Thr Pro Arg Ala Ser Leu Phe Asn
    290                 295                 300

Lys Thr Phe Glu Ala Val Cys Ala Val Ala Asn Tyr Phe Pro Arg Ser
305                 310                 315                 320

Thr Lys Leu Thr Trp Tyr Leu Asp Gly Lys Pro Ile Glu Arg Gln Tyr
```

-continued

```
                325                 330                 335
Ile Ser Asp Thr Ala Ser Val Trp Ile Asp Gly Leu Ile Thr Arg Ser
            340                 345                 350

Ser Val Leu Ala Ile Pro Thr Thr Glu Thr Asp Ser Glu Lys Pro Asp
            355                 360                 365

Ile Arg Cys Asp Leu Glu Trp His Glu Ser Pro Val Ser Tyr Lys Arg
            370                 375                 380

Phe Thr Lys Ser Val Ala Pro Asp Val Tyr Tyr Pro Thr Val Ser
385                 390                 395                 400

Val Thr Phe Ala Asp Thr Arg Ala Ile Cys Asp Val Lys Cys Val Pro
                405                 410                 415

Arg Asp Gly Ile Ser Leu Met Trp Lys Ile Gly Asn Tyr His Leu Pro
                420                 425                 430

Lys Ala Met Ser Ala Asp Ile Leu Ile Thr Gly Pro Cys Ile Glu Arg
                435                 440                 445

Pro Gly Leu Val Asn Ile Gln Ser Met Cys Asp Ile Ser Glu Thr Asp
                450                 455                 460

Gly Pro Val Ser Tyr Thr Cys Gln Thr Ile Gly Tyr Pro Pro Ile Leu
465                 470                 475                 480

Pro Gly Phe Tyr Asp Thr Gln Val Tyr Asp Ala Ser Pro Glu Ile Val
                485                 490                 495

Ser Glu Ser Met Leu Val Ser Val Val Ala Val Ile Leu Gly Ala Val
                500                 505                 510

Leu Ile Thr Val Phe Ile Phe Ile Thr Ala Leu Cys Leu Tyr Tyr Ser
                515                 520                 525

His Pro Arg Arg Leu
                530
```

(2) INFORMATION FOR SEQ ID NO:16:

(i) SEQUENCE CHARACTERISTICS:
        (A) LENGTH: 468 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:16:

```
Met Trp Leu Pro Asn Leu Val Arg Phe Val Ala Val Ala Tyr Leu Ile
1               5                   10                  15

Cys Ala Gly Ala Ile Leu Thr Tyr Ala Ser Gly Ala Ser Ala Ser Ser
                20                  25                  30

Ser Gln Ser Thr Pro Ala Thr Pro Thr His Thr Thr Pro Asn Leu Thr
            35                  40                  45

Thr Ala His Gly Ala Gly Ser Asp Asn Thr Thr Asn Ala Asn Gly Thr
        50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
                100                 105                 110

Arg Thr Pro Phe Ser Gly Thr Pro Pro Gly Asp Glu Asn Tyr Ile
            115                 120                 125
```

-continued

```
Asn His Asn Ala Thr Lys Asp Gln Thr Leu Leu Phe Ser Thr Ala
    130                 135                 140
Glu Arg Lys Lys Ser Arg Arg Gly Asp Leu Ser Val His Pro Ser Leu
145                 150                 155                 160
Lys Gly Glu Asn Tyr Arg Ala Thr Cys Val Val Ala Ser Tyr Phe Pro
                165                 170                 175
His Ser Ser Val Lys Leu Arg Trp Tyr Lys Asn Ala Arg Glu Val Asp
            180                 185                 190
Phe Thr Lys Tyr Val Thr Asn Ala Ser Ser Val Trp Val Asp Gly Leu
        195                 200                 205
Ile Thr Arg Ile Ser Thr Val Ser Ile Pro Val Asp Pro Glu Glu Glu
    210                 215                 220
Tyr Thr Gly Gln Leu Gly Val Ile Pro Asp Arg Leu Pro Lys Arg Gln
225                 230                 235                 240
Leu Phe Asn Leu Pro Leu His Thr Glu Gly Gly Thr Lys Phe Pro Leu
                245                 250                 255
Thr Ile Lys Ser Val Asp Trp Arg Thr Ala Gly Ile Tyr Val Trp Ser
            260                 265                 270
Leu Tyr Ala Lys Asn Gly Thr Leu Val Asn Ser Thr Ser Val Thr Val
        275                 280                 285
Ser Thr Tyr Asn Ala Pro Leu Leu Pro Ser Leu Arg Cys Ser Ile Asp
    290                 295                 300
Trp Tyr Arg Asp Glu Val Ser Phe Ala Arg Ile Ala Lys Ala Gly Thr
305                 310                 315                 320
Pro Ser Val Phe Val Ala Pro Thr Val Ser Val Ser Val Glu Asp Gly
                325                 330                 335
Asp Ala Val Cys Thr Ala Lys Cys Val Pro Ser Thr Gly Val Phe Val
            340                 345                 350
Ser Trp Ser Val Asn Asp His Leu Pro Gly Val Pro Ser Gln Asp Met
        355                 360                 365
Thr Thr Gly Val Cys Pro Ser His Ser Gly Leu Val Asn Met Gln Ser
    370                 375                 380
Arg Arg Pro Leu Ser Glu Glu Asn Gly Glu Arg Glu Tyr Ser Cys Ile
385                 390                 395                 400
Ile Glu Gly Tyr Pro Asp Gly Leu Pro Met Phe Ser Asp Thr Val Val
                405                 410                 415
Tyr Asp Ala Ser Pro Ile Val Glu Asp Arg Pro Val Leu Thr Ser Ile
            420                 425                 430
Ile Ala Val Thr Cys Gly Ala Ala Ala Leu Ala Leu Val Val Leu Ile
        435                 440                 445
Thr Ala Val Cys Phe Tyr Cys Ser Lys Pro Ser Gln Ala Pro Tyr Lys
    450                 455                 460
Lys Ser Asp Phe
465
```

(2) INFORMATION FOR SEQ ID NO:17:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:17:

```
Met Ala Pro Gly Arg Val Gly Leu Ala Val Val Leu Trp Ser Leu Leu
 1               5                  10                  15

Trp Leu Gly Ala Gly Val Ser Gly Ser Glu Thr Ala Ser Thr Gly
             20                  25                  30

Pro Thr Ile Thr Ala Gly Ala Val Thr Asn Ala Ser Glu Ala Pro Thr
             35                  40                  45

Ser Gly Ser Pro Gly Ser Ala Ala Ser Pro Glu Val Thr Pro Thr Ser
 50                  55                  60

Thr Pro Asn Pro Asn Asn Val Thr Gln Asn Lys Thr Thr Pro Thr Glu
 65                  70                  75                  80

Pro Ala Ser Pro Pro Thr Thr Pro Lys Pro Thr Ser Thr Pro Lys Ser
                 85                  90                  95

Pro Pro Thr Ser Thr Pro Asp Pro Lys Pro Lys Asn Asn Thr Thr Pro
                100                 105                 110

Ala Lys Ser Gly Arg Pro Thr Lys Pro Pro Gly Pro Val Trp Cys Asp
            115                 120                 125

Arg Arg Asp Pro Leu Ala Arg Tyr Gly Ser Arg Val Gln Ile Arg Cys
130                 135                 140

Arg Phe Arg Asn Ser Thr Arg Met Glu Phe Arg Leu Gln Ile Trp Arg
145                 150                 155                 160

Tyr Ser Met Gly Pro Ser Pro Ile Ala Pro Ala Pro Asp Leu Glu
                165                 170                 175

Glu Val Leu Thr Asn Ile Thr Ala Pro Pro Gly Gly Leu Leu Val Tyr
            180                 185                 190

Asp Ser Ala Pro Asn Leu Thr Asp Pro His Val Leu Trp Ala Glu Gly
            195                 200                 205

Ala Gly Pro Gly Ala Asp Pro Pro Leu Tyr Ser Val Thr Gly Pro Leu
210                 215                 220

Pro Thr Gln Arg Leu Ile Ile Gly Glu Val Thr Pro Ala Thr Gln Gly
225                 230                 235                 240

Met Tyr Tyr Leu Ala Trp Gly Arg Met Asp Ser Pro His Glu Tyr Gly
                245                 250                 255

Thr Trp Val Arg Val Arg Met Phe Arg Pro Pro Ser Leu Thr Leu Gln
                260                 265                 270

Pro His Ala Val Met Glu Gly Gln Pro Phe Lys Ala Thr Cys Thr Ala
            275                 280                 285

Ala Ala Tyr Tyr Pro Arg Asn Pro Val Glu Phe Val Trp Phe Glu Asp
            290                 295                 300

Asp His Gln Val Phe Asn Pro Gly Gln Ile Asp Thr Gln Thr His Glu
305                 310                 315                 320

His Pro Asp Gly Phe Thr Thr Val Ser Thr Val Thr Ser Glu Ala Val
                325                 330                 335

Gly Gly Gln Val Pro Pro Arg Thr Phe Thr Cys Gln Met Thr Trp His
            340                 345                 350

Arg Asp Ser Val Thr Phe Ser Arg Arg Asn Ala Thr Gly Leu Ala Leu
            355                 360                 365

Val Leu Pro Arg Pro Thr Ile Thr Met Glu Phe Gly Val Arg Ile Val
370                 375                 380

Val Cys Thr Ala Gly Cys Val Pro Glu Gly Val Thr Phe Ala Trp Phe
385                 390                 395                 400

Leu Gly Asp Asp Pro Ser Pro Ala Ala Lys Ser Ala Val Thr Ala Gln
            405                 410                 415

Glu Ser Cys Asp His Pro Gly Leu Ala Thr Val Arg Ser Thr Leu Pro
```

```
                    420                   425                   430
Ile Ser Tyr Asp Tyr Ser Glu Tyr Ile Cys Arg Leu Thr Gly Tyr Pro
        435                   440                   445
Ala Gly Ile Pro Val Leu Glu His His Gly Ser His Gln Pro Pro Pro
450                   455                   460
Arg Asp Pro Thr Glu Arg Gln Val Ile Glu Ala Ile Glu Trp Val Gly
465                   470                   475                   480
Ile Gly Ile Gly Val Leu Ala Ala Gly Val Leu Val Val Thr Ala Ile
                485                   490                   495
Val Tyr Val Val Arg Thr Ser Gln Ser Arg Gln Arg His Arg Arg
                500                   505                   510
```

(2) INFORMATION FOR SEQ ID NO:18:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GATATTTAAT AAAACTATTA TGAAACTTCT TATAACTTAT TTGTTTTTAT TAAATGGGTT      60
GGGTTGGTTT TAAAATTACA TACGTGTATT AAGAATTAAC ATCATAAAGG ACACACCCAT     120
GAAAAACATT TAAATTCTAT TAATTTGAAC GGATTAAACA TTTTCTCATT TTAAGAGTTG     180
CTACGACTTT TGATAGTAAA ATGATTAAAC TTCTATTTAT CTTATTTTAT TTTAACCCAA     240
TAACTGGATA TAAATGGGTA GACCCTCCTC GTAGGTATAA TTACACCGTT TTAAGAATGA     300
TTCCAGATAT TCCAAATCCA ATGGATCCTT CTAAAAACGC TGAAGTTCGG TATGTAACTT     360
CTACTGACCC ATGTGATATG GTTGCTTTGA TTTCTAATCC AAATATAGAA TCTACAATTA     420
AAACGATTCA ATTTGTGCAA AAGAAAAAAT TTTACAATGC ATCTCTTAGT TGGTTTAAAG     480
TTGGAGATGA TTGTACATAT CCAATATATT TAATTCAATA TTTTGATTGT GATCCTCAAA     540
GAGAATTTGG CATATGTTTA AAAAGATCTC CAGATTTTTG GAAACCATCG TTAGTTGGTT     600
ACACATTTTT AACTGATGAT GAATTGGGAT TAGTTTTAGC TGCCCCCGCT CCATTTAATC     660
AAGGTCAATA TAGACGGGTT ATTCAAATTG AAAATGAAGT TTTTTATACT GATTTATGG      720
TTCAATTACC ACGAGAAACT TGTTATTTTT CTAAAGAAGA TAAATTTGAA CCAACTTTTA     780
TGGAATGGTG TAAGGAATCT AGATCTGTAG GAGCATCAAA AGTTGACGAT GAACTTTTTT     840
ATCTAAATAG AGCTGGTCCC CAAACCCTGC TTAAATATTA TGTTATTAAA GATTTTTATA     900
GACTTAACGG TAGAGAACCT CCAATAAAAT TTAAAGAAGC TCTTAGATAC GATATACCAT     960
ATAAAGTGAA TGATAAATTT GATGATGAAT TACCATCGAG GCCACATATT AGTAATACTA    1020
TTAATAAAAC TATTAAAGAA ATTGTAAATC TTGAAGATTA TTTTAAAAAT ACAAATGTTA    1080
TAGATACTAC TACCCCAACA CCAATAAATA ATACCCCAAA AAATATAACC GTGGGAATTG    1140
TTATAATTAT ATTAATAATA CTATTTATAA TTGGATTTTT TGTTTATAAA AGACAAAAAA    1200
TATATAATAA TTATAAAAAA TTAACAACAA ATGTTTAGCC TTTATAAATT AATTTACAGA    1260
ATAAACAACT GGGCGGTCTT TTGTTTAATA AAAATTCATG TACCTACAAC TTTTATTCAC    1320
```

(2) INFORMATION FOR SEQ ID NO:19:

(i) SEQUENCE CHARACTERISTICS:
        (A) LENGTH: 345 amino acids
        (B) TYPE: amino acid (C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:19:

```
Met Ile Lys Leu Leu Phe Ile Leu Phe Tyr Phe Asn Pro Ile Thr Gly
 1               5                  10                  15

Tyr Lys Trp Val Asp Pro Pro Arg Arg Tyr Asn Tyr Thr Val Leu Arg
            20                  25                  30

Met Ile Pro Asp Ile Pro Asn Pro Met Asp Pro Ser Lys Asn Ala Glu
        35                  40                  45

Val Arg Tyr Val Thr Ser Thr Asp Pro Cys Asp Met Val Ala Leu Ile
50                  55                  60

Ser Asn Pro Asn Ile Glu Ser Thr Ile Lys Thr Ile Gln Phe Val Gln
65                  70                  75                  80

Lys Lys Lys Phe Tyr Asn Ala Ser Leu Ser Trp Phe Lys Val Gly Asp
                85                  90                  95

Asp Cys Thr Tyr Pro Ile Tyr Leu Ile Gln Tyr Phe Asp Cys Asp Pro
            100                 105                 110

Gln Arg Glu Phe Gly Ile Cys Leu Lys Arg Ser Pro Asp Phe Trp Lys
        115                 120                 125

Pro Ser Leu Val Gly Tyr Thr Phe Leu Thr Asp Asp Glu Leu Gly Leu
130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                165                 170                 175

Pro Arg Glu Thr Cys Tyr Phe Ser Lys Glu Asp Lys Phe Glu Pro Thr
            180                 185                 190

Phe Met Glu Trp Cys Lys Glu Ser Arg Ser Val Gly Ala Ser Lys Val
        195                 200                 205

Asp Asp Glu Leu Phe Tyr Leu Asn Arg Ala Gly Pro Gln Thr Leu Leu
210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                245                 250                 255

Asn Asp Lys Phe Asp Asp Glu Leu Pro Ser Arg Pro His Ile Ser Asn
            260                 265                 270

Thr Ile Asn Lys Thr Ile Lys Glu Ile Val Asn Leu Glu Asp Tyr Phe
        275                 280                 285

Lys Asn Thr Asn Val Ile Asp Thr Thr Thr Pro Thr Pro Ile Asn Asn
290                 295                 300

Thr Pro Lys Asn Ile Thr Val Gly Ile Val Ile Ile Leu Ile Ile
305                 310                 315                 320

Leu Phe Ile Ile Gly Phe Phe Val Tyr Lys Arg Gln Lys Ile Tyr Asn
                325                 330                 335

Asn Tyr Lys Lys Leu Thr Thr Asn Val
            340                 345
```

(2) INFORMATION FOR SEQ ID NO:20:

(i) SEQUENCE CHARACTERISTICS:
(A) LENGTH: 345 amino acids (B) TYPE: amino acid
          (C) STRANDEDNESS: single
          (D) TOPOLOGY: linear (ii) MOLECULE TYPE: peptide (v) FRAGMENT TYPE: N-terminal (xi) SEQUENCE DESCRIPTION: SEQ ID NO:20:

```
Met Ile Lys Leu Leu Phe Ile Leu Phe Tyr Phe Asn Pro Ile Thr Gly
1               5                   10                  15

Tyr Lys Trp Val Asp Pro Pro Arg Arg Tyr Asn Tyr Thr Val Leu Arg
                20                  25                  30

Met Ile Pro Asp Ile Pro Asn Pro Met Asp Pro Ser Lys Asn Ala Glu
            35                  40                  45

Val Arg Tyr Val Thr Ser Thr Asp Pro Cys Asp Met Val Ala Leu Ile
        50                  55                  60

Ser Asn Pro Asn Ile Glu Ser Thr Ile Lys Thr Ile Gln Phe Val Gln
65                  70                  75                  80

Lys Lys Lys Phe Tyr Asn Ala Ser Leu Ser Trp Phe Lys Val Gly Asp
                85                  90                  95

Asp Cys Thr Tyr Pro Ile Tyr Leu Ile Gln Tyr Phe Asp Cys Asp Pro
                100                 105                 110

Gln Arg Glu Phe Gly Ile Cys Leu Lys Arg Ser Pro Asp Phe Trp Lys
            115                 120                 125

Pro Ser Leu Val Gly Tyr Thr Phe Leu Thr Asp Asp Glu Leu Gly Leu
130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                165                 170                 175

Pro Arg Glu Thr Cys Tyr Phe Ser Lys Glu Asp Lys Phe Glu Pro Thr
            180                 185                 190

Phe Met Glu Trp Cys Lys Glu Ser Arg Ser Val Gly Ala Ser Lys Val
        195                 200                 205

Asp Asp Glu Leu Phe Tyr Leu Asn Arg Ala Gly Pro Gln Thr Leu Leu
210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                245                 250                 255

Asn Asp Lys Phe Asp Asp Glu Leu Pro Ser Arg Pro His Ile Ser Asn
            260                 265                 270

Thr Ile Asn Lys Thr Ile Lys Glu Ile Val Asn Leu Glu Asp Tyr Phe
        275                 280                 285

Lys Asn Thr Asn Val Ile Asp Thr Thr Thr Pro Thr Pro Ile Asn Asn
290                 295                 300

Thr Pro Lys Asn Ile Thr Val Gly Ile Val Ile Ile Leu Ile Ile
305                 310                 315                 320

Leu Phe Ile Ile Gly Phe Phe Val Tyr Lys Arg Gln Lys Ile Tyr Asn
                325                 330                 335

Asn Tyr Lys Lys Leu Thr Thr Asn Val
                340                 345
```

(2) INFORMATION FOR SEQ ID NO:21:

(i) SEQUENCE CHARACTERISTICS:

(A) LENGTH: 374 amino acids
(B) TYPE: amino acid
(C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:21:

```
Met Met Thr Arg Leu His Phe Trp Trp Cys Gly Ile Phe Ala Val Leu
1               5                   10                  15

Lys Tyr Leu Val Cys Thr Ser Ser Leu Thr Thr Thr Pro Lys Thr Thr
            20                  25                  30

Thr Val Tyr Val Lys Gly Phe Asn Ile Pro Pro Leu Arg Tyr Asn Tyr
        35                  40                  45

Thr Gln Ala Arg Ile Val Pro Lys Ile Pro Gln Ala Met Asp Pro Lys
    50                  55                  60

Ile Thr Ala Glu Val Arg Tyr Val Thr Ser Met Asp Ser Cys Gly Met
65                  70                  75                  80

Val Ala Leu Ile Ser Glu Pro Asp Ile Asp Ala Thr Ile Arg Thr Ile
                85                  90                  95

Gln Leu Ser Gln Lys Lys Thr Tyr Asn Ala Thr Ile Ser Trp Phe Lys
            100                 105                 110

Val Thr Gln Gly Cys Glu Tyr Pro Met Phe Leu Met Asp Met Arg Leu
        115                 120                 125

Cys Asp Pro Lys Arg Glu Phe Gly Ile Cys Ala Leu Arg Ser Pro Ser
    130                 135                 140

Tyr Trp Leu Glu Pro Leu Thr Lys Tyr Met Phe Leu Thr Asp Asp Glu
145                 150                 155                 160

Leu Gly Leu Ile Met Met Ala Pro Ala Gln Phe Asn Gln Gly Gln Tyr
                165                 170                 175

Arg Arg Val Ile Thr Ile Asp Gly Ser Met Phe Tyr Thr Asp Phe Met
            180                 185                 190

Val Gln Leu Ser Pro Thr Pro Cys Trp Phe Ala Lys Pro Asp Arg Tyr
        195                 200                 205

Glu Glu Ile Leu His Glu Trp Cys Arg Asn Val Lys Thr Ile Gly Leu
    210                 215                 220

Asp Gly Ala Arg Asp Tyr His Tyr Tyr Trp Val Pro Tyr Asn Pro Gln
225                 230                 235                 240

Pro His His Lys Ala Val Leu Leu Tyr Trp Tyr Arg Thr His Gly Arg
                245                 250                 255

Glu Pro Pro Val Arg Phe Gln Glu Ala Ile Arg Tyr Asp Arg Pro Ala
            260                 265                 270

Ile Pro Ser Gly Ser Glu Asp Ser Lys Arg Ser Asn Asp Ser Arg Gly
        275                 280                 285

Glu Ser Ser Gly Pro Asn Trp Ile Asp Ile Glu Asn Tyr Thr Pro Lys
    290                 295                 300

Asn Asn Val Pro Ile Ile Ile Ser Asp Asp Val Pro Thr Ala Pro
305                 310                 315                 320

Pro Lys Gly Met Asn Asn Gln Ser Val Val Ile Pro Ala Ile Val Leu
                325                 330                 335

Ser Cys Leu Ile Ile Ala Leu Ile Leu Gly Val Ile Tyr Tyr Ile Leu
            340                 345                 350

Arg Val Lys Arg Ser Arg Ser Thr Ala Tyr Gln Gln Leu Pro Ile Ile
        355                 360                 365
```

```
His Thr Thr His His Pro
    370

(2) INFORMATION FOR SEQ ID NO:22:

(i) SEQUENCE CHARACTERISTICS:
        (A) LENGTH: 442 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:22:

Met Pro Ala Val Leu Leu Val Leu Tyr Val Asn Pro Pro Ser Val
1               5                  10                  15

Cys Ile Leu Thr Gln Lys Leu Ser Leu Gly Leu Tyr Asn Gln Trp Trp
                20                  25                  30

Arg Val Cys Arg Ser Val Pro Pro Trp Tyr Val Phe Asn Lys
                35                  40                  45

Arg Ser Met Ser Thr Phe Lys Leu Met Met Asp Gly Arg Leu Val Phe
            50                  55                  60

Ala Met Ala Ile Ala Ile Leu Ser Val Val Leu Ser Cys Gly Thr Cys
65                      70                  75                  80

Glu Lys Ala Lys Arg Ala Val Arg Gly Arg Gln Asp Arg Pro Lys Glu
                    85                  90                  95

Phe Pro Pro Pro Arg Tyr Asn Tyr Thr Ile Leu Thr Arg Tyr Asn Ala
                100                 105                 110

Thr Ala Leu Ala Ser Pro Phe Ile Asn Asp Gln Val Lys Asn Val Asp
                115                 120                 125

Leu Arg Ile Val Thr Ala Thr Arg Pro Cys Glu Met Ile Ala Leu Ile
    130                 135                 140

Ala Lys Thr Asn Ile Asp Ser Ile Leu Lys Glu Leu Ala Ala Gln
145                 150                 155                 160

Lys Thr Tyr Ser Ala Arg Leu Thr Trp Phe Lys Ile Met Pro Thr Cys
                    165                 170                 175

Ala Thr Pro Ile His Asp Val Ser Tyr Met Lys Cys Asn Pro Lys Leu
                180                 185                 190

Ser Phe Ala Met Cys Asp Glu Arg Ser Asp Ile Leu Trp Gln Ala Ser
                195                 200                 205

Leu Ile Thr Met Ala Ala Glu Thr Asp Asp Glu Leu Gly Leu Val Leu
    210                 215                 220

Ala Ala Pro Ala His Ser Ala Ser Gly Leu Tyr Arg Arg Val Ile Glu
225                 230                 235                 240

Ile Asp Gly Arg Arg Ile Tyr Thr Asp Phe Ser Val Thr Ile Pro Ser
                245                 250                 255

Glu Arg Cys Pro Ile Ala Phe Glu Leu Asn Phe Gly Asn Pro Asp Arg
                260                 265                 270

Cys Lys Thr Pro Glu Gln Tyr Ser Arg Gly Glu Val Phe Thr Arg Arg
            275                 280                 285

Phe Leu Gly Glu Phe Asn Phe Pro Gln Gly Glu His Met Thr Trp Val
        290                 295                 300

Lys Phe Trp Phe Val Tyr Asp Gly Gly Asn Leu Pro Val Gln Phe Tyr
305                 310                 315                 320

Glu Ala Gln Ala Phe Ala Arg Pro Val Pro Pro Asp Asn His Pro Gly
                    325                 330                 335
```

```
Phe Asp Ser Val Glu Ser Glu Ile Thr Gln Asn Lys Thr Asp Pro Lys
                340                 345                 350

Pro Gly Gln Ala Asp Pro Lys Pro Asn Gln Pro Phe Lys Trp Pro Ser
            355                 360                 365

Ile Lys His Leu Val Pro Arg Leu Asp Glu Val Asp Glu Val Ile Glu
        370                 375                 380

Pro Val Thr Lys Pro Pro Lys Thr Ser Lys Ser Asn Ser Thr Phe Val
385                 390                 395                 400

Gly Ile Ser Val Gly Leu Gly Ile Ala Gly Leu Val Leu Val Gly Val
                405                 410                 415

Ile Leu Tyr Val Cys Leu Arg Arg Lys Lys Glu Leu Lys Val Cys Thr
                420                 425                 430

Glu Arg Leu Asp Ser Pro Thr Leu Asp Leu
            435                 440
```

(2) INFORMATION FOR SEQ ID NO:23:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:23:

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Leu Asp Gln Leu Thr Asp Pro Pro Gly Val Arg Arg Val Tyr His
50                  55                  60

Ile Gln Ala Gly Leu Pro Asn Pro Phe Gln Pro Pro Ser Leu Pro Ile
65                  70                  75                  80

Thr Val Tyr Arg Arg Val Glu Arg Ala Cys Arg Ser Val Leu Leu Asn
                85                  90                  95

Ala Pro Ser Glu Ala Pro Gln Ile Val Arg Gly Ala Ser Glu Asp Val
            100                 105                 110

Arg Lys Gln Pro Tyr Asn Leu Thr Ile Ala Trp Phe Arg Met Gly Gly
        115                 120                 125

Asn Cys Ala Ile Pro Ile Thr Val Met Glu Tyr Thr Glu Cys Ser Tyr
130                 135                 140

Asn Lys Ser Leu Gly Ala Cys Pro Ile Arg Thr Gln Pro Arg Trp Asn
145                 150                 155                 160

Tyr Tyr Asp Ser Phe Ser Ala Val Ser Glu Asp Asn Leu Gly Phe Leu
                165                 170                 175

Met His Ala Pro Ala Phe Glu Thr Ala Gly Thr Tyr Leu Arg Leu Val
            180                 185                 190

Lys Ile Asn Asp Trp Thr Glu Ile Thr Gln Phe Ile Leu Glu His Arg
        195                 200                 205

Ala Lys Gly Ser Cys Lys Tyr Thr Leu Pro Leu Arg Ile Pro Pro Ser
    210                 215                 220

Ala Cys Leu Ser Pro Gln Ala Tyr Gln Gln Gly Val Thr Val Asp Ser
```

```
               225                 230                 235                 240
Ile Gly Met Leu Pro Arg Phe Ile Pro Glu Asn Gln Arg Thr Val Ala
                245                 250                 255
Val Tyr Ser Leu Lys Ile Ala Gly Trp His Gly Pro Arg Ala Pro Tyr
                260                 265                 270
Thr Ser Thr Leu Leu Pro Pro Glu Leu Pro Glu Thr Pro Asn Ala Thr
                275                 280                 285
Gln Pro Glu Leu Ala Pro Glu Asp Pro Glu Asp Ser Ala Leu Leu Glu
                290                 295                 300
Asp Pro Val Gly Thr Val Ala Pro Gln Ile Pro Pro Asn Trp His Ile
305                 310                 315                 320
Pro Ser Ile Gln Asp Ala Ala Thr Pro Tyr His Pro Pro Ala Thr Pro
                325                 330                 335
Asn Asn Met Gly Leu Ile Ala Gly Ala Val Gly Gly Ser Leu Leu Ala
                340                 345                 350
Ala Leu Val Ile Cys Gly Ile Val Tyr Trp Met Arg Arg Arg Thr Arg
                355                 360                 365
Lys Ala Pro Lys Arg Ile Arg Leu Pro His Ile Arg Glu Asp Asp Gln
370                 375                 380
Pro Ser Ser His Gln Pro Leu Phe Tyr
385                 390
```

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TAATTAACTA GCTACCCGGG                                              20

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GTACATTAAT TGATCGATGG GCCCTTAA                                  28

(2) INFORMATION FOR SEQ ID NO:26:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

AGCTTCCCGG GTAAGTAATA CGTCAAGGAG AAAACGAAAC GATCTGTAGT TAGCGGCCGC    60

CTAATTAACT AAT                                                                  73

(2) INFORMATION FOR SEQ ID NO:27:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
AGGGCCCATT CATTATGCAG TTCCTCTTTT GCTTTGCTAG ACATCAATCG CCGGCGGATT      60

AATTGATTA                                                              69
```

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
TTAGTTAATT AGGCGGCCGC                                                  20
```

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
CGATTACTAT GAAGGATCCG TT                                               22
```

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
TAATGATACT TCCTAGGCAA                                                  20
```

(2) INFORMATION FOR SEQ ID NO:31:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
CGATTACTAG ATCTGAGCTC CCCGGGCTCG AGGGATCCGT T                          41
```

(2) INFORMATION FOR SEQ ID NO:32:

(i) SEQUENCE CHARACTERISTICS:

```
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

TAATGATCTA GACTCGAGGG GCCCGAGCTC CCTAGGCAA                          39

(2) INFORMATION FOR SEQ ID NO:33:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

GATCCGAATT CTAGCT                                                   16

(2) INFORMATION FOR SEQ ID NO:34:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:34:

GCTTAAGATC GA                                                       12

(2) INFORMATION FOR SEQ ID NO:35:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:35:

TATGAGTAAC TTAACTCTTT TGTTAATTAA AAGTATATTC AAAAAATAAG TTATATAAAT   60

AGATCTGAAT TCGTT                                                   75

(2) INFORMATION FOR SEQ ID NO:36:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:36:

ACTCATTGAA TTGAGAAAAC AATTAATTTT CATATAAGTT TTTTATTCAA TATATTTATC   60

TAGACTTAAG CAA                                                     73

(2) INFORMATION FOR SEQ ID NO:37:

(i) SEQUENCE CHARACTERISTICS:
            (A) LENGTH: 49 base pairs
```

(B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:37:

AAAATGGGCG TGGATTGTTA ACTTTATATA ACTTATTTTT TGAATATAC                49

(2) INFORMATION FOR SEQ ID NO:38:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:38:

ACACGAATGA TTTTCTAAAG TATTTGGAAA GTTTTATAGG TAGTTGATAG AACAAAATAC    60

ATAATTT                                                              67

(2) INFORMATION FOR SEQ ID NO:39:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:39:

TGTGCTTACT AAAAGATTTC ATAAACCTTT CAAAATATCC ATCAACTATC T             51

(2) INFORMATION FOR SEQ ID NO:40:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:40:

TGTAAAAATA AATCACTTTT TATACTAAGA TCTCCCGGGC TGCAGC                   46

(2) INFORMATION FOR SEQ ID NO:41:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:41:

TGTTTTATGT ATTAAAACAT TTTTATTTAG TGAAAAATAT GATTCTAGAG GGCCCGACGT    60

CGCCGG                                                               66

(2) INFORMATION FOR SEQ ID NO:42:

(i) SEQUENCE CHARACTERISTICS:
            (A) LENGTH: 50 base pairs
            (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:42:

TTTCTGTATA TTTGCACCAA TTTAGATCTT ACTCAAAATA TGTAACAATA          50

(2) INFORMATION FOR SEQ ID NO:43:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:43:

TGTCATTTAA CACTATACTC ATATTAATAA AAATAATATT TATT               44

(2) INFORMATION FOR SEQ ID NO:44:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:44:

GATCCTGAGT ACTTTGTAAT ATAATGATAT ATATTTTCAC TTTATCTCAT TTGAGAATAA    60

AAAGATCTTA GG                                                        72

(2) INFORMATION FOR SEQ ID NO:45:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:45:

GACTCATGAA ACATTATATT ACTATATATA AAAGTGAAAT AGAGTAAACT CTTATTTTTC    60

TAGAATCCTT AA                                                        72

(2) INFORMATION FOR SEQ ID NO:46:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:46:

GATCCAGATC TCCCGGGAAA AAAATTATTT AACTTTTCAT TAATAGGGAT TTGACGTATG    60

TAGCGTACTA GG                                                        72

(2) INFORMATION FOR SEQ ID NO:47:

(i) SEQUENCE CHARACTERISTICS:
            (A) LENGTH: 72 base pairs
```

(B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:47:

GTCTAGAGGG CCCTTTTTTT AATAAATTGA AAAGTAATTA TCCCTAAACT GCATACTACG      60

CATGATCCTT AA                                                         72

(2) INFORMATION FOR SEQ ID NO:48:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:48:

GGGAGATCTC TCGAGCTGCA GGGCGCCGGA TCCTTTTTCT                            40

(2) INFORMATION FOR SEQ ID NO:49:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:49:

CCCTCTAGAG AGCTCGACGT CCCGCGGCCT AGGAAAAAGA                            40

(2) INFORMATION FOR SEQ ID NO:50:

(i) SEQUENCE CHARACTERISTICS:
          (A) LENGTH: 59 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:50:

CGATATCCGT TAAGTTTGTA TCGTAATGGG CTCCAGATCT TCTACCAGGA TCCCGGTAC       59

(2) INFORMATION FOR SEQ ID NO:51:

(i) SEQUENCE CHARACTERISTICS:
          (A) LENGTH: 55 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:51:

CGGGATCCTG GTAGAAGATC TGGAGCCCAT TACGATACAA ACTTAACGGA TATCG           55

(2) INFORMATION FOR SEQ ID NO:52:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:52:

AATTCGAGCT CCCCGGG                                                              17

(2) INFORMATION FOR SEQ ID NO:53:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

CCCGGGGAGC TCG                                                                  13

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

CTTTTTATAA AAAGTTAACT ACGTAG                                                    26

(2) INFORMATION FOR SEQ ID NO:55:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

GATCCTACGT AGTTAACTTT TTATAAAAAG AGCT                                           34

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CTTAACTCAG CTGACTATCC                                                           20

(2) INFORMATION FOR SEQ ID NO:57:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

```
TACGTAGTTA ACTTTTTATA AAAATCATAT TTTTGTAGTG GCTC                       44

(2) INFORMATION FOR SEQ ID NO:58:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

AATTCAGGAT CGTTCCTTTA CTAGTTGAGA TTCTCAAGGA TGATGGGATT TAATTTTTAT       60

AAGCTTG                                                                67

(2) INFORMATION FOR SEQ ID NO:59:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

AATTCAAGCT TATAAAAATT AAATCCCATC ATCCTTGAGA ATCTCAACTA GTAAAGGAAC       60

GATCCTG                                                                67

(2) INFORMATION FOR SEQ ID NO:60:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CTAGACACTT TATGTTTTTT AATATCCGGT CTTAAAAGCT TCCCGGGGAT CCTTATACGG       60

GGAATAAT                                                               68

(2) INFORMATION FOR SEQ ID NO:61:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

ATTATTCCCC GTATAAGGAT CCCCCGGGAA GCTTTTAAGA CCGGATATTA AAAACATAA        60

AGTGT                                                                  65

(2) INFORMATION FOR SEQ ID NO:62:

(i) SEQUENCE CHARACTERISTICS:
        (A) LENGTH: 3209 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:62:

```
TGAATGTTAA ATGTTATACT TTGGATGAAG CTATAAATAT GCATTGGAAA AATAATCCAT      60

TTAAAGAAAG GATTCAAATA CTACAAAACC TAAGCGATAA TATGTTAACT AAGCTTATTC     120

TTAACGACGC TTTAAATATA CACAAATAAA CATAATTTTT GTATAACCTA ACAAATAACT     180

AAAACATAAA AATAATAAAA GGAAATGTAA TATCGTAATT ATTTTACTCA GGAATGGGGT     240

TAAATATTTA TATCACGTGT ATATCTATAC TGTTATCGTA TACTCTTTAC AATTACTATT     300

ACGAATATGC AAGAGATAAT AAGATTACGT ATTTAAGAGA ATCTTGTCAT GATAATTGGG     360

TACGACATAG TGATAAATGC TATTTCGCAT CGTTACATAA AGTCAGTTGG AAAGATGGAT     420

TTGACAGATG TAACTTAATA GGTGCAAAAA TGTTAAATAA CAGCATTCTA TCGGAAGATA     480

GGATACCAGT TATATTATAC AAAAATCACT GGTTGGATAA AACAGATTCT GCAATATTCG     540

TAAAAGATGA AGATTACTGC GAATTTGTAA ACTATGACAA TAAAAAGCCA TTTATCTCAA     600

CGACATCGTG TAATTCTTCC ATGTTTTATG TATGTGTTTC AGATATTATG AGATTACTAT     660

AAACTTTTTG TATACTTATA TTCCGTAAAC TATATTAATC ATGAAGAAAA TGAAAAAGTA     720

TAGAAGCTGT TCACGAGCGG TTGTTGAAAA CAACAAAATT ATACATTCAA GATGGCTTAC     780

ATATACGTCT GTGAGGCTAT CATGGATAAT GACAATGCAT CTCTAAATAG GTTTTTGGAC     840

AATGGATTCG ACCCTAACAC GGAATATGGT ACTCTACAAT CTCCTCTTGA AATGGCTGTA     900

ATGTTCAAGA ATACCGAGGC TATAAAAATC TTGATGAGGT ATGGAGCTAA ACCTGTAGTT     960

ACTGAATGCA CAACTTCTTG TCTGCATGAT GCGGTGTTGA GAGACGACTA CAAAATAGTG    1020

AAAGATCTGT TGAAGAATAA CTATGTAAAC AATGTTCTTT ACAGCGGAGG CTTTACTCCT    1080

TTGTGTTTGG CAGCTTACCT TAACAAAGTT AATTTGGTTA AACTTCTATT GGCTCATTCG    1140

GCGGATGTAG ATATTTCAAA CACGGATCGG TTAACTCCTC TACATATAGC CGTATCAAAT    1200

AAAAATTTAA CAATGGTTAA ACTTCTATTG AACAAAGGTG CTGATACTGA CTTGCTGGAT    1260

AACATGGGAC GTACTCCTTT AATGATCGCT GTACAATCTG GAAATATTGA ATATGTAGC     1320

ACACTACTTA AAAAAAATAA AATGTCCAGA ACTGGGAAAA ATTGATCTTG CCAGCTGTAA    1380

TTCATGGTAG AAAAGAAGTG CTCAGGCTAC TTTTCAACAA AGGAGCAGAT GTAAACTACA    1440

TCTTTGAAAG AAATGGAAAA TCATATACTG TTTTGGAATT GATTAAAGAA AGTTACTCTG    1500

AGACACAAAA GAGGTAGCTG AAGTGGTACT CTCAAAATGC AGAACGATGA CTGCGAAGCA    1560

AGAAGTAGAG AAATAACACT TTATGACTTT CTTAGTTGTA GAAAAGATAG AGATATAATG    1620

ATGGTCATAA ATAACTCTGA TATTGCAAGT AAATGCAATA ATAAGTTAGA TTTATTTAAA    1680

AGGATAGTTA AAAATAGAAA AAAAGAGTTA ATTTGTAGGG TTAAAATAAT ACATAAGATC    1740

TTAAAATTTA TAAATACGCA TAATAATAAA AATAGATTAT ACTTATTACC TTCAGAGATA    1800

AAATTTAAGA TATTTACTTA TTTAACTTAT AAAGATCTAA AATGCATAAT TTCTAAATAA    1860

TGAAAAAAAA GTACATCATG AGCAACGCGT TAGTATATTT TACAATGGAG ATTAACGCTC    1920

TATACCGTTC TATGTTTATT GATTCAGATG ATGTTTTAGA AAAGAAAGTT ATTGAATATG    1980

AAAACTTTAA TGAAGATGAA GATGACGACG ATGATTATTG TTGTAAATCT GTTTTAGATG    2040

AAGAAGATGA CGCGCTAAAG TATACTATGG TTACAAAGTA TAAGTCTATA CTACTAATGG    2100

CGACTTGTGC AAGAAGGTAT AGTATAGTGA AAATGTTGTT AGATTATGAT TATGAAAAAC    2160

CAAATAAATC AGATCCATAT CTAAAGGTAT CTCCTTTGCA CATAATTTCA TCTATTCCTA    2220

GTTTAGAATA CTTTTCATTA TATTTGTTTA CAGCTGAAGA CGAAAAAAAT ATATCGATAA    2280

TAGAAGATTA TGTTAACTCT GCTAATAAGA TGAAATTGAA TGAGTCTGTG ATAATAGCTA    2340
```

-continued

```
TAATCAGAGA AGTTCTAAAA GGAAATAAAA ATCTAACTGA TCAGGATATA AAAACATTGG    2400

CTGATGAAAT CAACAAGGAG GAACTGAATA TAGCTAAACT ATTGTTAGAT AGAGGGGCCA    2460

AAGTAAATTA CAAGGATGTT TACGGTTCTT CAGCTCTCCA TAGAGCTGCT ATTGGTAGGA    2520

AACAGGATAT GATAAAGCTG TTAATCGATC ATGGAGCTGA TGTAAACTCT TTAACTATTG    2580

CTAAAGATAA TCTTATTAAA AAAAATAAT ATCACGTTTA GTAATATTAA AATATATTAA     2640

TAACTCTATT ACTAATAACT CCAGTGGATA TGAACATAAT ACGAAGTTTA TACATTCTCA    2700

TCAAAATCTT ATTGACATCA AGTTAGATTG TGAAAATGAG ATTATGAAAT TAAGGAATAC    2760

AAAAATAGGA TGTAAGAACT TACTAGAATG TTTTATCAAT AATGATATGA ATACAGTATC    2820

TAGGGCTATA AACAATGAAA CGATTAAAAA TTATAAAAAT CATTTCCCTA TATATAATAC    2880

GCTCATAGAA AAATTCATTT CTGAAAGTAT ACTAAGACAC GAATTATTGG ATGGAGTTAT    2940

AAATTCTTTT CAAGGATTCA ATAATAAATT GCCTTACGAG ATTCAGTACA TTATACTGGA    3000

GAATCTTAAT AACCATGAAC TAAAAAAAAT TTTAGATAAT ATACATTAAA AAGGTAAATA    3060

GATCATCTGT TATTATAAGC AAAGATGCTT GTTGCCAATA ATATACAACA GGTATTTGTT    3120

TTTATTTTTA ACTACATATT TGATGTTCAT TCTCTTTATA TAGTATACAC AGAAAATTCA    3180

TAATCCACTT AGAATTTCTA GTTATCTAG                                      3209
```

(2) INFORMATION FOR SEQ ID NO:63:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
GCTTCCCGGG AATTCTAGCT AGCTAGTTT                                        29
```

(2) INFORMATION FOR SEQ ID NO:64:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

```
ACTCTCAAAA GCTTCCCGGG AATTCTAGCT AGCTAGTTTT TATAAA                     46
```

(2) INFORMATION FOR SEQ ID NO:65:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

```
GATCTTTATA AAAACTAGCT AGCTAGAATT CCCGGGAAGC TTTTGAGAGT                 50
```

(2) INFORMATION FOR SEQ ID NO:66:

(i) SEQUENCE CHARACTERISTICS:

(A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

CTGAAATTAT TCATTATCG CGATATCCGT TAAGTTTGTA TCGTAATGGT TCCTCAGGCT       60

CTCCTGTTTG T                                                          71

(2) INFORMATION FOR SEQ ID NO:67:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

CATTACGATA CAAACTTAAC GGATATCGCG ATAATGAAAT AATTTCAG                   48

(2) INFORMATION FOR SEQ ID NO:68:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

ACCCCTTCTG GTTTTCCGT TGTGTTTTGG GAAATTCCCT ATTTACACGA TCCCAGACAA       60

GCTTAGATCT CAG                                                        73

(2) INFORMATION FOR SEQ ID NO:69:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

CTGAGATCTA AGCTTGTCTG GGATCGTGTA AATAGGGAAT TTCCCAAAAC A               51

(2) INFORMATION FOR SEQ ID NO:70:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

CAACGGAAAA ACCAGAAGGG GTACAAACAG GAGAGCCTGA GGAAC                      45

(2) INFORMATION FOR SEQ ID NO:71:

(i) SEQUENCE CHARACTERISTICS:
        (A) LENGTH: 11 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:71:

GGATCCCCGG G    11

(2) INFORMATION FOR SEQ ID NO:72:

(i) SEQUENCE CHARACTERISTICS:
(A) LENGTH: 3659 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:72:

```
GATATCTGTG GTCTATATAT ACTACACCCT ACCGATATTA ACCAACGAGT TTCTCACAAG      60
AAAACTTGTT TAGTAGATAG AGATTCTTTG ATTGTGTTTA AAAGAAGTAC CAGTAAAAAG     120
TGTGGCATAT GCATAGAAGA AATAAACAAA AAACATATTT CCGAACAGTA TTTTGGAATT     180
CTCCCAAGTT GTAAACATAT TTTTTGCCTA TCATGTATAA GACGTTGGGC AGATACTACC     240
AGAAATACAG ATACTGAAAA TACGTGTCCT GAATGTAGAA TAGTTTTTCC TTTCATAATA     300
CCCAGTAGGT ATTGGATAGA TAATAAATAT GATAAAAAAA TATTATATAA TAGATATAAG     360
AAAATGATTT TTACAAAAAT ACCTATAAGA ACAATAAAAA TATAATTACA TTTACGGAAA     420
ATAGCTGGTT TTAGTTTACC AACTTAGAGT AATTATCATA TTGAATCTAT ATTGTTTTTT     480
AGTTATATAA AAACATGATT AGCCCCCAAT CGGATGAAAA TATAAAGAT GTTGAGAATT      540
TCGAATACAA CAAAAGAGG AATCGTACGT TGTCCATATC CAAACATATA AATAAAAATT      600
CAAAAGTAGT ATTATACTGG ATGTTTAGAG ATCAACGTGT ACAAGATAAT TGGGCTTTAA     660
TTTACGCACA ACGATTAGCG TTAAAACTCA AAATACCTCT AAGAATATGC TTTTGTGTCG     720
TGCCAAAATT TCACACTACT ACTTCTAGAC ACTTTATGTT TTTAATATCC GGTCTTAAAG     780
AAGTCGCGGA AGAATGTAAA AGACTATGTA TAGGGTTTTC ATTGATATAT GGCGTACCAA     840
AAGTAATAAT TCCGTGTATA GTAAAAAAAT ACAGAGTCGG AGTAATCATA ACGGATTTCT     900
TTCCATTACG TGTTCCCGAA AGATTAATGA AACAGACTGT AATATCTCTT CCAGATAACA     960
TACCTTTTAT ACAAGTAGAC GCTCATAATA TAGTACCTTG TTGGGAAGCT TCTGATAAAG    1020
AAGAATACGG TGCACGAACT TTAAGAAAAA AGATATTTGA TAAATTATAT GAATATATGA    1080
CAGAATTTCC TGTTGTTCGT AAACATCCAT ACGGTCCATT TTCTATATCT ATTGCAAAAC    1140
CCAAAAAATAT ATCATTAGAC AAGACGGTAT TACCCGTAAA ATGGGCAACG CCTGGAACAA    1200
AAGCTGGAAT AATTGTTTTA AAAGAATTTA TAAAAAACAG ATTACCGTCA TACGACGCGG    1260
ATCATAACAA TCCTACGTGT GACGCTTTGA GTAACTTATC TCCGTGGCTA CATTTTGGTC    1320
ATGTATCCGC ACAACGTGTT GCCTTAGAAG TATTAAAATG TATACGAGAA AGCAAAAAAA    1380
ACGTTGAAAC GTTTATAGAT GAAATAATTG TAAGAAGAGA ACTATCGGAT AATTTTTGTT    1440
ACTATAACAA ACATTATGAT AGTATCCAGT CTACTCATTC ATGGGTTAGA AAAACATTAG    1500
AAGATCACAT TAATGATCCT AGAAAGTATA TATATTCCAT TAAACAACTC GAAAAAGCGG    1560
AAACTCATGA TCCTCTATGG AACGCGTCAC AAATGCAGAT GGTGAGAGAA GGAAAAATGC    1620
ATAGTTTTTT ACGAATGTAT TGGGCTAAGA AGATACTTGA ATGGACTAGA ACACCTGAAG    1680
ACGCTTTGAG TTATAGTATC TATTTGAACA ACAAGTACGA ACTAGACGGC ACGGATCCTA    1740
```

```
ACGGATACGT AGGTTGTATG TGGTCTATTT GCGGATTACA CGATAGAGCG TGGAAAGCAA      1800

GACCGATATT TGGAAAGATA AGATATATGA ATTATGAGAG TTCTAAGAAG AAATTTGATG      1860

TTGCTGTATT TATACAGAAA TACAATTAAG ATAAATAATA TACAGCATTG TAACCATCGT      1920

CATCCGTTAT ACGGGAATA ATATTACCAT ACAGTATTAT TAAATTTTCT TACGAAGAAT       1980

ATAGATCGGT ATTTATCGTT AGTTTATTTT ACATTTATTA ATTAAACATG TCTACTATTA      2040

CCTGTTATGG AAATGACAAA TTTAGTTATA TAATTTATGA TAAAATTAAG ATAATAATAA      2100

TGAAATCAAA TAATTATGTA AATGCTACTA GATTATGTGA ATTACGAGGA AGAAAGTTTA      2160

CGAACTGGAA AAAATTAAGT GAATCTAAAA TATTAGTCGA TAATGTAAAA AAAATAAATG      2220

ATAAAACTAA CCAGTTAAAA ACGGATATGA TTATATACGT TAAGGATATT GATCATAAAG      2280

GAAGAGATAC TTGCGGTTAC TATGTACACC AAGATCTGGT ATCTTCTATA TCAAATTGGA      2340

TATCTCCGTT ATTCGCCGTT AAGGTAAATA AAATTATTAA CTATTATATA TGTAATGAAT      2400

ATGATATACG ACTTAGCGAA ATGGAATCTG ATATGACAGA AGTAATAGAT GTAGTTGATA      2460

AATTAGTAGG AGGATACAAT GATGAAATAG CAGAAATAAT ATATTTGTTT AATAAATTTA      2520

TAGAAAAATA TATTGCTAAC ATATCGTTAT CAACTGAATT ATCTAGTATA TTAAATAATT      2580

TTATAAATTT TATAAATTTT AATAAAAAAT ACAATAACGA CATAAAGATA TTTAATCTTT      2640

AATTCTTGAT CTGAAAAACA CATCTATAAA ACTAGATAAA AAGTTATTCG ATAAAGATAA      2700

TAATGAATCG AACGATGAAA AATTGGAAAC AGAAGTTGAT AAGCTAATTT TTTTCATCTA      2760

AATAGTATTA TTTTATTGAA GTACGAAGTT TTACGTTAGA TAAATAATAA AGGTCGATTT      2820

TTACTTTGTT AAATATCAAA TATGTCATTA TCTGATAAAG ATACAAAAAC ACACGGTGAT      2880

TATCAACCAT CTAACGAACA GATATTACAA AAAATACGTC GGACTATGGA AAACGAAGCT      2940

GATAGCCTCA ATAGAAGAAG CATTAAAGAA ATTGTTGTAG ATGTTATGAA GAATTGGGAT      3000

CATCCTCAAC GAAGAAATAG ATAAAGTTCT AAACTGGAAA AATGATACAT TAAACGATTT      3060

AGATCATCTA AATACAGATG ATAATATTAA GGAAATCATA CAATGTCTGA TTAGAGAATT      3120

TGCGTTTAAA AAGATCAATT CTATTATGTA TAGTTATGCT ATGGTAAAAC TCAATTCAGA      3180

TAACGAACAT TGAAAGATAA AATTAAGGAT TATTTTATAG AAACTATTCT TAAAGACAAA      3240

CGTGGTTATA AACAAAAGCC ATTACCCGGA TTGGAAACTA AAATACTAGA TAGTATTATA      3300

AGATTTAAAA AACATAAAAT TAATAGGTTT TTATAGATTG ACTTATTATA TACAATATGG      3360

ATAAAAGATA TATATCAACT AGAAAGTTGA ATGACGGATT CTTAATTTTA TATTATGATT      3420

CAATAGAAAT TATTGTCATG TCGTGTAATC ATTTTATAAA TATATCAGCG TTACTAGCTA      3480

AGAAAAACAA GGACTTTAAT GAATGGCTAA AGATAGAATC ATTTAGAGAA ATAATAGATA      3540

CTTTAGATAA AATTAATTAC GATCTAGGAC AACGATATTG TGAAGAACTT ACGGCGCATC      3600

ACATTCCAGT GTAATTATTG AGGTCAAAGC TAGTAACTTA ATAGATGACA GGACAGCTG       3659
```

(2) INFORMATION FOR SEQ ID NO:73:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

```
TCATTATCGC GATATCCGTG TTAACTAGCT AGCTAATTTT TATTCCCGGG ATCCTTATCA        60
```

(2) INFORMATION FOR SEQ ID NO:74:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

```
GTATAAGGAT CCCGGGAATA AAAATTAGCT AGCTAGTTAA CACGGATATC GCGATAATGA      60
```

(2) INFORMATION FOR SEQ ID NO:75:

(i) SEQUENCE CHARACTERISTICS:
        (A) LENGTH: 2356 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:75:

```
TGTCTGGACT AACTGATTTC ATGGAACAAT TTTCATCAAA AATATCAGTT ATACCTAGTT      60
CTACAAAGAC AGAACTTTGA TGTTATGTTT GTGTTTGTAT AGAAAATTTT GGGATACTAA     120
CTGATATTTC TGAATATTTC TGAATATTTC ATGTTACTTA CTTACTCCTA TCTTAGACGA     180
TAATAAAATT CGAGGCGTAA TATGTTTTTC CAAATATTTG AAATTCTTAT ACGTATCGGC     240
GAAGAAAAGT AACATACTAT AAGTGTTATG CAAGTAAGGT ATGTTAATGA TATTGGATTT     300
AATTTCATTG ACAATACATA TGTCCAAACA TTCCACTCGT AATTATGTAC GGAACGACTT     360
TAGTTAAATA CTTAGTCACA AAAACTTAT GACTGTCATT ATCTGAAAAC GGTGATTCCC     420
ATAAATCAGA ATACTTAATA TTAAATAGAA TGCTCGCTTC TGGAGGTTTC CGGATACTAG     480
ATAACATATC TTCTGTATTA TAGTTTAATT CACTCATTTT ATTACATAAT ACAGTAACAT     540
CTCCCGAAAC CAATGATGTT ATATTAGATT TACTTACATA CTTCTTGTAA CTATCATGAA     600
TACGTTTGTT ATGATCTATA AGAAGATGG ATGTATATTC TGTTCTAGAT AGCAAGTTCT     660
TTAAGTTATT CTTTGTCTGT ATTACTATCA TCGTCTTCAT CATCGTCTAA AGGTAGCATT     720
ATATAATAAA TCTAATAGTT GATTTCTCGA TCTATCAGTA CTCGCTTTCA ATAACATTTT     780
TACTATAAGC ATAATAGAAG GCGGTGATAT CACTATATTT TTATCGGGTA TTCTTTTAGT     840
AATTAGTTAG TTCGTAGAAT TCGTAGAGA TAAAAGCCAA TTTGTTGTTG ATACTGCTTA     900
CGTTACTCAT GTTTCTTGTT TCTGTTAATT AACAGGTATA CCCTTACAAT AAGTTTAATT     960
AACTTTTAGG TTTTTGTGAA GAACTTTTAG CTTCTAGTTC CCTTATCCAT AATTGGGTCT    1020
TAGATCTAGA TTCTTCCCAT GTATAAAGGG GGACATACCC AAAATCTTTA AATGCTTTGT    1080
CCGTTTCTAT AGTAAATGTC GTACATTCCT TAATCAAAGT ATAAGGATTT AGTAAAGGCG    1140
TGTAAGAACA AATAGGTGAT AGTAATACTC TTAAACCTTT ATTAATATTA GCGATAAACC    1200
TTAAACACCA TAAAGGAAGA CATGTATTCC GTAGATCCAT CCCTAATTGA TTAAAGAAAT    1260
GCATGTTAAA ATCATGATAA TGTTCAGTAG GAGAGGTATC GTAACAGTAA TACACGTTAT    1320
TGCAGAGAGG ACTATGTTGA CCATTTTCTA TCATATTTCT TGCTGCTAAA ATATGCATCC    1380
AAGCTACGTT TCCTGCATAG ACTCTGCTAT GAAATACTTT ATCATCCGCA TATTTATACA    1440
TTTTCCTGCT TTTATACGAT CTTCTGTATA AAGTTTCTAG TACTGGACAG TATTCTCCGA    1500
AAACACCTAA TGGGCGTAGC GACAAGTGCA TAATCTAAGT CCTATATTAG ACATAGTACC    1560
```

```
GTTAGCTTCT AGTATATATT TCTCAGATAA CTTGTTTACT AAGAGGATAA GCCTCTTTAT      1620

GGTTAGATTG ATAATACGTA TTCTCGTTTC CTCTTATCAT CGCATCTCCG GAGAAAGTTA      1680

GGACCTACCG CAGAATAACT ACTCGTATAT ACTAAGACTC TTACGCCGTT ATACAGACAA      1740

GAATCTACTA CGTTCTTCGT TCCGTTGATA TTAACGTCCA TTATAGAGTC GTTAGTAAAC      1800

TTACCCGCTA CATCATTTAT CGAAGCAATA TGAATGACCA CATCTGCTGA TCTAAGCGCT      1860

TCGTCCAAAG TACTTTTATT TCTAACATCT CCAATCACGG GAACTATCTT TATTATATTA      1920

CATTTTTCTA CAAGATCTAG TAACCATTGG TCGATTCTAA TATCGTAAAC ACGAACTTCT      1980

TTTTAAAGAG GATTCGAACA AGATAAGATT ATTTATAATG TGTCTACCTA AAAATCCACA      2040

CCCTCCGGTT ACCACGTATA CTAGTGTACG CATTTTGAGT ATTAACTATA TAAGACCAAA      2100

ATTATATTTT CATTTTCTGT TATATTATAC TATATAATAA AAACAAATAA ATATACGAAT      2160

ATTATAAGAA ATTTAGAACA CGTTATTAAA GTATTGCCTT TTTTATTAAC GGCGTGTTCT      2220

TGTAATTGCC GTTTAGAATA GTCTTTATTT ACTTTAGATA ACTCTTCTAT CATAACCGTC      2280

TCCTTATTCC AATCTTCTTC AGAAGTACAT GAGTACTTAC CGAAGTTTAT CATCATAGAG      2340

ATTATATATG AAGAAA                                                     2356

(2) INFORMATION FOR SEQ ID NO:76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:76:

GACAATCTAA GTCCTATATT AGAC                                              24

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:77:

GGATTTTTAG GTAGACAC                                                     18

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

TCATCGTCTT CATCATCG                                                     18

(2) INFORMATION FOR SEQ ID NO:79:

(i) SEQUENCE CHARACTERISTICS:
        (A) LENGTH: 29 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO:79:

GTCTTAAACT TATTGTAAGG GTATACCTG                                                 29

(2) INFORMATION FOR SEQ ID NO:80:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

AACGATTAGT TAGTTACTAA AAGCTTGCTG CAGCCCGGGT TTTTTATTAG TTTAGTTAGT              60

C                                                                              61

(2) INFORMATION FOR SEQ ID NO:81:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

GACTAACTAA CTAATAAAAA ACCCGGGCTG CAGCAAGCTT TTTGTAACTA ACTAATCGTT              60

(2) INFORMATION FOR SEQ ID NO:82:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

GCACGGAACA AAGCTTATCG CGATATCCGT TAAGTTTGTA TCGTAATGCT ATCAATCACG              60

ATTCTGTTCC TGCTCATAGC AGAGGGCTCA TCTCAGAAT                                     99

(2) INFORMATION FOR SEQ ID NO:83:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

ATTCTGAGAT GAGCCCTCTG CTATGAGCAG GAACAGAATC GTGATTGATA GCATTACGAT              60

ACAAACTTAA CGGATATCGC GATAAGCTTT GTTCCGTGC                                     99

(2) INFORMATION FOR SEQ ID NO:84:

(i) SEQUENCE CHARACTERISTICS:
        (A) LENGTH: 66 base pairs
        (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:84:

GAAAAATTTA AAGTCGACCT GTTTTGTTGA GTTGTTTGCG TGGTAACCAA TGCAAATCTG      60

GTCACT                                                                66

(2) INFORMATION FOR SEQ ID NO:85:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:85:

TCTAGCAAGA CTGACTATTG CAAAAAGAAG CACTATTTCC TCCATTACGA TACAAACTTA      60

ACGGAT                                                                66

(2) INFORMATION FOR SEQ ID NO:86:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:86:

ATCCGTTAAG TTTGTATCGT AATGGAGGAA ATAGTGCTTC TTTTTGCAAT AGTCAGTCTT      60

GCTAGAAGTG ACCAGATTTG CATTGGT                                         87

(2) INFORMATION FOR SEQ ID NO:87:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:87:

TACCACGCAA ACAACTCAAC AAAACAGGTC GACTTTAAAT TTTTCTGCA                  49

(2) INFORMATION FOR SEQ ID NO:88:

(i) SEQUENCE CHARACTERISTICS:
            (A) LENGTH: 132 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:88:

GTACAGGTCG ACAAGCTTCC CGGGTATCGC GATATCCGTT AAGTTTGTAT CGTAATGAAT      60

ACTCAAATTC TAATACTCAC TCTTGTGGCA GCCATTCACA CAAATGCAGA CAAAATCTGC     120

CTTGGACATC AT                                                         132
```

(2) INFORMATION FOR SEQ ID NO:89:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

```
ATGATGTCCA AGGCAGATTT TGTCTGCATT TGTGTGAATG GCTGCCACAA GAGTGAGTAT      60

TAGAATTTGA GTATTCATTA CGATACAAAC TTAACGGATA TCGCGATACC CGGGAAGCTT     120

GTCGACCTGT AC                                                         132
```

(2) INFORMATION FOR SEQ ID NO:90:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

```
ATAACATGCG GTGCACCATT TGTATATAAG TTAACGAATT CCAAGTCAAG C               51
```

(2) INFORMATION FOR SEQ ID NO:91:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:91:

```
GCTTGACTTG GAATTCGTTA ACTTATATAC AAATGGTGCA CCGCATGTTA T               51
```

(2) INFORMATION FOR SEQ ID NO:92:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:92:

```
TAAGAATGGT AATTCT                                                     16
```

(2) INFORMATION FOR SEQ ID NO:93:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

```
TTCCCGGGTT AAACTTTACT TTCATTTTC                                       29
```

(2) INFORMATION FOR SEQ ID NO:94:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:94:

TTGTCGACTG AGATAAAGTG AAAATATATA TCATTATATT ACAAAGTACA ATTATTTAGG    60

TTTAATCATG TTTTCATTGT ATCTATAT    88

(2) INFORMATION FOR SEQ ID NO:95:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:95:

TTAGTACTTT CCGGTGTTGT TGGATCACAT ATTATTAAAG TATAAATAAT AAAGAA    56

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:96:

TGGAATGAAG TTATGAAACT    20

(2) INFORMATION FOR SEQ ID NO:97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:97:

TGCACTGATC ATTTCAATTT C    21

(2) INFORMATION FOR SEQ ID NO:98:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:98:

TGGAATTTTG AATGAAAACA CTAGAACC    28

(2) INFORMATION FOR SEQ ID NO:99:

(i) SEQUENCE CHARACTERISTICS:
        (A) LENGTH: 27 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:99:

TTCTAGTGTT TTCATTCAAA ATTCCAT                                          27

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:100:

CCTTCAAAGT TTAATACACC                                                  20

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:101:

TATGGCTTCA CGTTTGGCAC                                                  20

(2) INFORMATION FOR SEQ ID NO:102:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

CACCGGGGAT ATAATTCATA TGTCCCCTTT CTTTGGATTA CGAGATGGT                  49

(2) INFORMATION FOR SEQ ID NO:103:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:103:

CCATCTCGTA ATCCAAAGAA AGGGGACATA TGAAT                                 35

(2) INFORMATION FOR SEQ ID NO:104:

(i) SEQUENCE CHARACTERISTICS:
        (A) LENGTH: 2951 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:104:

```
AGTACAATAA AAAGTATTAA ATAAAAATAC TTACTTACGA AAAAATGACT AATTAGCTAT      60
AAAAACCCGG GAAAGGATCC TGATCCTTTT TCTGGGTAAG TAATACGTCA AGGAGAAAAC     120
GAAACGATCT GTAGTTAGCG GCCAAACTCG AGGTCGACTG AGATAAAGTG AAAATATATA     180
TCATTATATT ACAAAGTACA ATTATTTAGG TTTAATCATG TTTTCATTGT ATCTATATAT     240
TTTTTTTATT ATTTATACTT TAATAATATG TGATCCAACA ACACCGGAAA GTACTATTAA     300
TCCATTAAAT CATCACAATT TATCAACACC TAAACCTACT TCGGATGATA TTCGTGAAAT     360
TTTACGTGAA TCCCAAATTG AATCTGATGA TACATCAACA TTTTACATGT GCCCACCACC     420
ATCGGGATCA ACATTGGTGC GTTTGGAGCC ACCTAGAGCA TGTCCTAACT ATAAACTTGG     480
TAAAAATTTT ACAGAAGGAA TTGCTGTAAT ATTTAAGGAA AATATTTCTC CTTATAAATT     540
TAAAGCTAAT ATATACTACA AAAATATTAT TATCACCACT GTATGGTCTG GAAGCACATA     600
TGCAGTAATT ACTAATAGAT ATACAGATCG TGTACCTATA GGTGTTCCTG AAATTACAGA     660
GTTGATTGAT AGAAGAGGTA TGTGTTTATC AAAAGCTGAT TATATTCGTA ATAATTATGA     720
ATTTACCGCA TTTGATAAGG ATGAAGACCC CAGAGAAGTT CATTTAAAGC CTTCAAAGTT     780
TAATACACCA GGATCCCGTG GATGGCATAC AGTTAATGAT ACTTACACAA AAATTGGGGG     840
TTCTGGATTT TATCATTCTG GAACATCTGT AAATTGTATA GTTGAAGAAG TTGATGCCAG     900
ATCTGTTTAT CCATATGATT CATTTGCTAT CTCCACCGGG GATATAATTC ATATGTCCCC     960
TTTTTTTGGA TTACGAGATG GTGCTCATAC TGAATATATT AGTTATTCAA CTGATAGATT    1020
TCAACAAATA GAAGGTTATT ATCCTATCGA CTTAGATACT AGACTACAGC TTGGTGCACC    1080
AGTTTCTAGG AATTTTTTAA CAACACAACA CGTTACTGTT GCTTGGAATT GGGTTCCAAA    1140
AATTCGTGAA GTGTGTACTT TGGCTAAATG GCGTGAAATT GATGAAATTA TTCGTGATGA    1200
GTATAAGGGA TCTTACAGAT TTACAGCAAA ATCAATATCT GCAACATTTA TTTCTGATAC    1260
TACTCAATTT GATATTGATC GTGTAAAGTT AAGTGATTGT GCCAAACGTG AAGCCATAGA    1320
AGCTATTGAT AAGATCTACA AAAAAAAATA TAATAAAACT CATATTCAAA CAGGAGAATT    1380
GGAAACATAC TTGGCTAGAG GGGGATTTAT TATAGCATTT AGACCAATGA TTAGTAATGA    1440
GTTAGCAAAA TTGTATATAA ATGAGTTAGT AAGATCTAAT CGTACGGTTG ATTTGAAATC    1500
TCTTTTAAAT CCATCTGTAA GAGGGGGGGC TAGAAAGAGA AGATCAGTAG AGGAAAATAA    1560
AAGATCAAAA CGTAATATTG AAGGTGGTAT TGAAAATGTA ATAATTCAA CAATAATTAA    1620
GACAACTTCA TCTGTTCATT TTGCTATGCT TCAGTTTGCC TATGATCATA TTCAATCACA    1680
TGTTAATGAA ATGCTTAGTA GAATTGCAAC TGCATGGTGT AATCTTCAAA ATAAAGAGAG    1740
AACCCTTTGG AATGAAGTTA TGAAACTTAA TCCAACTAGT GTGGCTTCGG TTGCTATGGA    1800
TCAAAGAGTT TCAGCACGAA TGTTAGGGGA TGTTCTTGCA GTTACTCAAT GTGTTAATAT    1860
ATCAGGTTCT AGTGTTTTA TTCAAAATTC CATGCGTGTT TTAGGGTCAA CAACTACATG    1920
TTACAGTCGT CCTCTTATAT CATTTAAAGC ACTAGAAAAC TCAACTAACT ATATTGAAGG    1980
ACAACTTGGG GAAAATAATG AACTATTAGT AGAACGAAAG CTAATTGAAC CATGTACAGC    2040
TAACCATAAA AGATATTTTA AATTTGGTGC AGATTATGTA TATTTTGAAA ACTATGCATA    2100
TGTTCGAAAG GTACCTCTTA ATGAAATTGA AATGATCAGT GCATATGTAG ATCTTAATAT    2160
TACATTACTT GAGGATCGTG AATTTTTACC ACTAGAGGTA TATACTCGAG CAGAGTTAGA    2220
AGATACAGGA CTATTGGACT ATAGTGAGAT TCAACGTAGA AATCAACTAC ATGCACTTAA    2280
GTTTTATGAT ATTGACAGTG TTGTAAAAGT TGATAATAAT GTTGTAATTA TGAGGGGCAT    2340
```

```
TGCAAATTTT TTCCAAGGAC TTGGAGATGT TGGAGCGGGA TTTGGAAAAG TTGTTTTGGG    2400

TGCTGCAAAT GCTGTTATTG CAACTGTTTC TGGAGTGTCC TCGTTTCTTA ATAACCCATT    2460

TGGGGCGCTA GCCGTTGGAT TGCTGATTTT AGCTGGACTA TTTGCAGCGT TTTTGGCTTA    2520

TAGATATGTT TCTAAACTTA AGTCAAATCC AATGAAAGCA CTATACCCAG TAACTACAAA    2580

AAATTTAAAA GAAAGTGTTA AGAATGGTAA TTCTGGAAAT AATAGTGATG GAGAAGAAAA    2640

TGATGATAAT ATCGATGAAG AAAAGCTTCA ACAAGCTAAA GAAATGATTA AATATATGTC    2700

TCTAGTTTCT GCTATGGAAC AGCAGGAACA TAAAGCTATT AAAAAAAATA GTGGCCCTGC    2760

CCTTCTAGCA AGTCACATTA CAAACCTATC TCTTAAACAT CGTGGTCCAA AATACAAACG    2820

TTTGAAAAAT GTAAATGAAA ATGAAAGTAA AGTTTAACCC GGGTACCGAG CTCGAATTCT    2880

TTTTATTGAT TAACTAGTCA AATGAGTATA TATAATTGAA AAAGTAAAAT ATAAATCATA    2940

TAATAATGAA A                                                        2951

(2) INFORMATION FOR SEQ ID NO:105:

(i) SEQUENCE CHARACTERISTICS:
        (A) LENGTH: 2951 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

TCATGTTATT TTTCATAATT TATTTTTATG AATGAATGCT TTTTTACTGA TTAATCGATA      60

TTTTTGGGCC CTTTCCTAGG ACTAGGAAAA AGACCCATTC ATTATGCAGT TCCTCTTTTG     120

CTTTGCTAGA CATCAATCGC CGGTTTGAGC TCCAGCTGAC TCTATTTCAC TTTTATATAT     180

AGTAATATAA TGTTTCATGT TAATAAATCC AAATTAGTAC AAAAGTAACA TAGATATATA     240

AAAAAAATAA TAAATATGAA ATTATTATAC ACTAGGTTGT TGTGGCCTTT CATGATAATT     300

AGGTAATTTA GTAGTGTTAA ATAGTTGTGG ATTTGGATGA AGCCTACTAT AAGCACTTTA     360

AAATGCACTT AGGGTTTAAC TTAGACTACT ATGTAGTTGT AAAATGTACA CGGGTGGTGG     420

TAGCCCTAGT TGTAACCACG CAAACCTCGG TGGATCTCGT ACAGGATTGA TATTTGAACC     480

ATTTTTAAAA TGTCTTCCTT AACGACATTA TAAATTCCTT TTATAAAGAG GAATATTTAA     540

ATTTCGATTA TATATGATGT TTTTATAATA ATAGTGGTGA CATACCAGAC CTTCGTGTAT     600

ACGTCATTAA TGATTATCTA TATGTCTAGC ACATGGATAT CCACAAGGAC TTTAATGTCT     660

CAACTAACTA TCTTCTCCAT ACACAAATAG TTTTCGACTA ATATAAGCAT TATTAATACT     720

TAAATGGCGT AAACTATTCC TACTTCTGGG GTCTCTTCAA GTAAATTTCG GAAGTTTCAA     780

ATTATGTGGT CCTAGGGCAC CTACCGTATG TCAATTACTA TGAATGTGTT TTTAACCCCC     840

AAGACCTAAA ATAGTAAGAC CTTGTAGACA TTTAACATAT CAACTTCTTC AACTACGGTC     900

TAGACAAATA GGTATACTAA GTAAACGATA GAGGTGGCCC CTATATTAAG TATACAGGGG     960

AAAAAAACCT AATGCTCTAC CACGAGTATG ACTTATATAA TCAATAAGTT GACTATCTAA    1020

AGTTGTTTAT CTTCCAATAA TAGGATAGCT GAATCTATGA TCTGATGTCG AACCACGTGG    1080

TCAAAGATCC TTAAAAAATT GTTGTGTTGT GCAATGACAA CGAACCTTAA CCCAAGGTTT    1140

TTAAGCACTT CACACATGAA ACCGATTTAC CGCACTTTAA CTACTTTAAT AAGCACTACT    1200

CATATTCCCT AGAATGTCTA AATGTCGTTT TAGTTATAGA CGTTGTAAAT AAAGACTATG    1260

ATGAGTTAAA CTATAACTAG CACATTTCAA TTCACTAACA CGGTTTGCAC TTCGGTATCT    1320
```

```
TCGATAACTA TTCTAGATGT TTTTTTTTAT ATTATTTTGA GTATAAGTTT GTCCTCTTAA    1380

CCTTTGTATG AACCGATCTC CCCCTAAATA ATATCGTAAA TCTGGTTACT AATCATTACT    1440

CAATCGTTTT AACATATATT TACTCAATCA TTCTAGATTA GCATGCCAAC TAAACTTTAG    1500

AGAAAATTTA GGTAGACATT CTCCCCCCCG ATCTTTCTCT TCTAGTCATC TCCTTTTATT    1560

TTCTAGTTTT GCATTATAAC TTCCACCATA ACTTTTACAT TTATTAAGTT GTTATTAATT    1620

CTGTTGAAGT AGACAAGTAA AACGATACGA AGTCAAACGG ATACTAGTAT AAGTTAGTGT    1680

ACAATTACTT TACGAATCAT CTTAACGTTG ACGTACCACA TTAGAAGTTT TATTTCTCTC    1740

TTGGGAAACC TTACTTCAAT ACTTTGAATT AGGTTGATCA CACCGAAGCC AACGATACCT    1800

AGTTTCTCAA AGTCGTGCTT ACAATCCCCT ACAAGAACGT CAATGAGTTA CACAATTATA    1860

TAGTCCAAGA TCACAAAAAT AAGTTTTAAG GTACGCACAA AATCCCAGTT GTTGATGTAC    1920

AATGTCAGCA GGAGAATATA GTAAATTTCG TGATCTTTTG AGTTGATTGA TATAACTTCC    1980

TGTTGAACCC CTTTTATTAC TTGATAATCA TCTTGCTTTC GATTAACTTG GTACATGTCG    2040

ATTGGTATTT TCTATAAAAT TTAAACCACG TCTAATACAT ATAAAACTTT TGATACGTAT    2100

ACAAGCTTTC CATGGAGAAT TACTTTAACT TTACTAGTCA CGTATACATC TAGAATTATA    2160

ATGTAATGAA CTCCTAGCAC TTAAAAATGG TGATCTCCAT ATATGAGCTC GTCTCAATCT    2220

TCTATGTCCT GATAACCTGA TATCACTCTA AGTTGCATCT TTAGTTGATG TACGTGAATT    2280

CAAAATACTA TAACTGTCAC AACATTTTCA ACTATTATTA CAACATTAAT ACTCCCCGTA    2340

ACGTTTAAAA AAGGTTCCTG AACCTCTACA ACCTCGCCCT AAACCTTTTC AACAAAACCC    2400

ACGACGTTTA CGACAATAAC GTTGACAAAG ACCTCACAGG AGCAAAGAAT TATTGGGTAA    2460

ACCCCGCGAT CGGCAACCTA ACGACTAAAA TCGACCTGAT AAACGTCGCA AAAACCGAAT    2520

ATCTATACAA AGATTTGAAT TCAGTTTAGG TTACTTTCGT GATATGGGTC ATTGATGTTT    2580

TTTAAATTTT CTTTCACAAT TCTTACCATT AAGACCTTTA TTATCACTAC CTCTTCTTTT    2640

ACTACTATTA TAGCTACTTC TTTTCGAAGT TGTTCGATTT CTTTACTAAT TTATATACAG    2700

AGATCAAAGA CGATACCTTG TCGTCCTTGT ATTTCGAATA TTTTTTTTAT CACCGGGACG    2760

GGAAGATCGT TCAGTGTAAT GTTTGGATAG AGAATTTGTA GCACCAGGTT TTATGTTTGC    2820

AAACTTTTTA CATTTACTTT TACTTTCATT TCAAATTGGG CCCATGGCTC GAGCTTAAGA    2880

AAAATAACTA ATTGATCAGT TTACTCATAT ATATTAACTT TTTCATTTTA TATTTAGTAT    2940

ATTATTACTT T                                                         2951
```

(2) INFORMATION FOR SEQ ID NO:106:

(i) SEQUENCE CHARACTERISTICS:
        (A) LENGTH: 879 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:106:

```
Met Phe Ser Leu Tyr Leu Tyr Ile Phe Phe Ile Ile Tyr Thr Leu Ile
  1               5                  10                  15

Ile Cys Asp Pro Thr Thr Pro Glu Ser Thr Ile Asn Pro Leu Asn His
             20                  25                  30

His Asn Leu Ser Thr Pro Lys Pro Thr Ser Asp Asp Ile Arg Glu Ile
         35                  40                  45
```

```
Leu Arg Glu Ser Gln Ile Glu Ser Asp Asp Thr Ser Thr Phe Tyr Met
 50                  55                  60

Cys Pro Pro Ser Gly Ser Thr Leu Val Arg Leu Glu Pro Pro Arg
 65                  70                  75                  80

Ala Cys Pro Asn Tyr Lys Leu Gly Lys Asn Phe Thr Glu Gly Ile Ala
                     85                  90                  95

Val Ile Phe Lys Glu Asn Ile Ser Pro Tyr Lys Phe Lys Ala Asn Ile
                100                 105                 110

Tyr Tyr Lys Asn Ile Ile Ile Thr Thr Val Trp Ser Gly Ser Thr Tyr
                115                 120                 125

Ala Val Ile Thr Asn Arg Tyr Thr Asp Arg Val Pro Ile Gly Val Pro
                130                 135                 140

Glu Ile Thr Glu Leu Ile Asp Arg Arg Gly Met Cys Leu Ser Lys Ala
145                 150                 155                 160

Asp Tyr Ile Arg Asn Asn Tyr Glu Phe Thr Ala Phe Asp Lys Asp Glu
                165                 170                 175

Asp Pro Arg Glu Val His Leu Lys Pro Ser Lys Phe Asn Thr Pro Gly
                180                 185                 190

Ser Arg Gly Trp His Thr Val Asn Asp Thr Tyr Thr Lys Ile Gly Gly
                195                 200                 205

Ser Gly Phe Tyr His Ser Gly Thr Ser Val Asn Cys Ile Val Glu Glu
210                 215                 220

Val Asp Ala Arg Ser Val Tyr Pro Tyr Asp Ser Phe Ala Ile Ser Thr
225                 230                 235                 240

Gly Asp Ile Ile His Met Ser Pro Phe Phe Gly Leu Arg Asp Gly Ala
                245                 250                 255

His Thr Glu Tyr Ile Ser Tyr Ser Thr Asp Arg Phe Gln Gln Ile Glu
                260                 265                 270

Gly Tyr Tyr Pro Ile Asp Leu Asp Thr Arg Leu Gln Leu Gly Ala Pro
                275                 280                 285

Val Ser Arg Asn Phe Leu Thr Thr Gln His Val Thr Val Ala Trp Asn
290                 295                 300

Trp Val Pro Lys Ile Arg Glu Val Cys Thr Leu Ala Lys Trp Arg Glu
305                 310                 315                 320

Ile Asp Glu Ile Ile Arg Asp Glu Tyr Lys Gly Ser Tyr Arg Phe Thr
                325                 330                 335

Ala Lys Ser Ile Ser Ala Thr Phe Ile Ser Asp Thr Thr Gln Phe Asp
                340                 345                 350

Ile Asp Arg Val Lys Leu Ser Asp Cys Ala Lys Arg Glu Ala Ile Glu
                355                 360                 365

Ala Ile Asp Lys Ile Tyr Lys Lys Tyr Asn Lys Thr His Ile Gln
                370                 375                 380

Thr Gly Glu Leu Glu Thr Tyr Leu Ala Arg Gly Gly Phe Ile Ile Ala
385                 390                 395                 400

Phe Arg Pro Met Ile Ser Asn Glu Leu Ala Lys Leu Tyr Ile Asn Glu
                405                 410                 415

Leu Val Arg Ser Asn Arg Thr Val Asp Leu Lys Ser Leu Leu Asn Pro
                420                 425                 430

Ser Val Arg Gly Gly Ala Arg Lys Arg Ser Val Glu Glu Asn Lys
                435                 440                 445

Arg Ser Lys Arg Asn Ile Glu Gly Gly Ile Glu Asn Val Asn Asn Ser
                450                 455                 460

Thr Ile Ile Lys Thr Thr Ser Ser Val His Phe Ala Met Leu Gln Phe
465                 470                 475                 480
```

```
Ala Tyr Asp His Ile Gln Ser His Val Asn Glu Met Leu Ser Arg Ile
              485                 490                 495
Ala Thr Ala Trp Cys Asn Leu Gln Asn Lys Glu Arg Thr Leu Trp Asn
            500                 505                 510
Glu Val Met Lys Leu Asn Pro Thr Ser Val Ala Ser Val Ala Met Asp
            515                 520                 525
Gln Arg Val Ser Ala Arg Met Leu Gly Asp Val Leu Ala Val Thr Gln
530                 535                 540
Cys Val Asn Ile Ser Gly Ser Ser Val Phe Ile Gln Asn Ser Met Arg
545                 550                 555                 560
Val Leu Gly Ser Thr Thr Thr Cys Tyr Ser Arg Pro Leu Ile Ser Phe
                565                 570                 575
Lys Ala Leu Glu Asn Ser Thr Asn Tyr Ile Glu Gly Gln Leu Gly Glu
                580                 585                 590
Asn Asn Glu Leu Leu Val Glu Arg Lys Leu Ile Glu Pro Cys Thr Ala
            595                 600                 605
Asn His Lys Arg Tyr Phe Lys Phe Gly Ala Asp Tyr Val Tyr Phe Glu
        610                 615                 620
Asn Tyr Ala Tyr Val Arg Lys Val Pro Leu Asn Glu Ile Glu Met Ile
625                 630                 635                 640
Ser Ala Tyr Val Asp Leu Asn Ile Thr Leu Leu Glu Asp Arg Glu Phe
                645                 650                 655
Leu Pro Leu Glu Val Tyr Thr Arg Ala Glu Leu Glu Asp Thr Gly Leu
            660                 665                 670
Leu Asp Tyr Ser Glu Ile Gln Arg Arg Asn Gln Leu His Ala Leu Lys
            675                 680                 685
Phe Tyr Asp Ile Asp Ser Val Val Lys Val Asp Asn Val Val Ile
690                 695                 700
Met Arg Gly Ile Ala Asn Phe Phe Gln Gly Leu Gly Asp Val Gly Ala
705                 710                 715                 720
Gly Phe Gly Lys Val Val Leu Gly Ala Ala Asn Ala Val Ile Ala Thr
                725                 730                 735
Val Ser Gly Val Ser Ser Phe Leu Asn Asn Pro Phe Gly Ala Leu Ala
            740                 745                 750
Val Gly Leu Leu Ile Leu Ala Gly Leu Phe Ala Ala Phe Leu Ala Tyr
            755                 760                 765
Arg Tyr Val Ser Lys Leu Lys Ser Asn Pro Met Lys Ala Leu Tyr Pro
770                 775                 780
Val Thr Thr Lys Asn Leu Lys Glu Ser Val Lys Asn Gly Asn Ser Gly
785                 790                 795                 800
Asn Asn Ser Asp Gly Glu Glu Asn Asp Asp Asn Ile Asp Glu Glu Lys
                805                 810                 815
Leu Gln Gln Ala Lys Glu Met Ile Lys Tyr Met Ser Leu Val Ser Ala
            820                 825                 830
Met Glu Gln Gln Glu His Lys Ala Ile Lys Lys Asn Ser Gly Pro Ala
            835                 840                 845
Leu Leu Ala Ser His Ile Thr Asn Leu Ser Leu Lys His Arg Gly Pro
850                 855                 860
Lys Tyr Lys Arg Leu Lys Asn Val Asn Glu Asn Glu Ser Lys Val
865                 870                 875
```

(2) INFORMATION FOR SEQ ID NO:107:

(i) SEQUENCE CHARACTERISTICS:

(A) LENGTH: 1615 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:107:

GAGCTCGCGG CCGCCTATCA AAAGTCTTAA TGAGTTAGGT GTAGATAGTA TAGATATTAC      60

TACAAAGGTA TTCATATTTC CTATCAATTC TAAAGTAGAT GATATTAATA ACTCAAAGAT     120

GATGATAGTA GATAATAGAT ACGCTCATAT AATGACTGCA AATTTGGACG TTCACATTTT     180

TAATCATCAC GCGTTCATAA GTTTCAACTG CATAGATCAA AATCTCACTA AAAAGATAGC     240

CGATGTATTT GAGAGAGATT GGACATCTAA CTACGCTAAA GAAATTACAG TTATAAATAA     300

TACATAATGG ATTTTGTTAT CATCAGTTAT ATTAACATA AGTACAATAA AAAGTATTAA      360

ATAAAAATAC TTACTTACGA AAAAATGACT AATTAGCTAT AAAAACCCGG GCTGCAGCTC     420

GAGGAATTCT TTTTATTGAT TAACTAGTCA AATGAGTATA TATAATTGAA AAAGTAAAAT     480

ATAAATCATA TAATAATGAA ACGAAATATC AGTAATAGAC AGGAACTGGC AGATTCTTCT     540

TCTAATGAAG TAAGTACTGC TAAATCTCCA AAATTAGATA AAAATGATAC AGCAAATACA     600

GCTTCATTCA ACGAATTACC TTTTAATTTT TCAGACACA CCTTATTACA AACTAACTAA      660

GTCAGATGAT GAGAAAGTAA ATATAAATTT AACTTATGGG TATAATATAA TAAAGATTCA     720

TGATATTAAT AATTTACTTA ACGATGTTAA TAGACTTATT CCATCAACCC CTTCAAACCT     780

TTCTGGATAT TATAAAATAC CAGTTAATGA TATTAAAATA GATTGTTTAA GAGATGTAAA     840

TAATTATTTG GAGGTAAAGG ATATAAAATT AGTCTATCTT TCACATGGAA ATGAATTACC     900

TAATATTAAT AATTATGATA GGAATTTTTT AGGATTTACA GCTGTTATAT GTATCAACAA     960

TACAGGCAGA TCTATGGTTA TGGTAAAACA CTGTAACGGG AAGCAGCATT CTATGGTAAC    1020

TGGCCTATGT TTAATAGCCA GATCATTTTA CTCTATAAAC ATTTTACCAC AAATAATAGG    1080

ATCCTCTAGA TATTTAATAT TATATCTAAC AACAACAAAA AAATTTAACG ATGTATGGCC    1140

AGAAGTATTT TCTACTAATA AAGATAAAGA TAGTCTATCT TATCTACAAG ATATGAAAGA    1200

AGATAATCAT TTAGTAGTAG CTACTAATAT GGAAAGAAAT GTATACAAAA ACGTGGAAGC    1260

TTTTATATTA AATAGCATAT TACTAGAAGA TTTAAAATCT AGACTTAGTA TAACAAAACA    1320

GTTAAATGCC AATATCGATT CTATATTTCA TCATAACAGT AGTACATTAA TCAGTGATAT    1380

ACTGAAACGA TCTACAGACT CAACTATGCA AGGAATAAGC AATATGCCAA TTATGTCTAA    1440

TATTTTAACT TTAGAACTAA AACGTTCTAC CAATACTAAA AATAGGATAC GTGATAGGCT    1500

GTTAAAAGCT GCAATAAATA GTAAGGATGT AGAAGAAATA CTTTGTTCTA TACCTTCGGA    1560

GGAAAGAACT TTAGAACAAC TTAAGTTTAA TCAAACTTGT ATTTATGAAG GTACC        1615

(2) INFORMATION FOR SEQ ID NO:108:

(i) SEQUENCE CHARACTERISTICS:
        (A) LENGTH: 1615 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

CTCGAGCGCC GGCGGATAGT TTTCAGAATT ACTCAATCCA CATCTATCAT ATCTATAATG      60

ATGTTTCCAT AAGTATAAAG GATAGTTAAG ATTTCATCTA CTATAATTAT TGAGTTTCTA     120

```
CTACTATCAT CTATTATCTA TGCGAGTATA TTACTGACGT TTAAACCTGC CAAGTGTAAA      180

ATTAGTAGTG CGCAAGTATT CAAAGTTGAC GTATCTAGTT TTAGAGTGAT TTTTCTATCG      240

GCTACATAAA CTCTCTCTAA CCTGTAGATT GATGCGATTT CTTTAATGTC AATATTTATT      300

ATGTATTACC TAAAACAATA GTAGTCAATA TAAATTGTAT TCATGTTATT TTTCATAATT      360

TATTTTTATG AATGAATGCT TTTTTACTGA TTAATCGATA TTTTTGGGCC CGACGTCGAG      420

CTCCTTAAGA AAAATAACTA ATTGATCAGT TTACTCATAT ATATTAACTT TTTCATTTTA      480

TATTTAGTAT ATTATTACTT TGCTTTATAG TCATTATCTG TCCTTGACCG TCTAAGAAGA      540

AGATTACTTC ATTCATGACG ATTTAGAGGT TTTAATCTAT TTTTACTATG TCGTTTATGT      600

CGAAGTAAGT TGCTTAATGG AAAATTAAAA AAGTCTGTGT GGAATAATGT TTGATTGATT      660

CAGTCTACTA CTCTTTCATT TATATTTAAA TTGAATACCC ATATTATATT ATTTCTAAGT      720

ACTATAATTA TTAAATGAAT TGCTACAATT ATCTGAATAA GGTAGTTGGG GAAGTTTGGA      780

AAGACCTATA ATATTTTATG GTCAATTACT ATAATTTTAT CTAACAAATT CTCTACATTT      840

ATTAATAAAC CTCCATTTCC TATATTTTAA TCAGATAGAA AGTGTACCTT TACTTAATGG      900

ATTATAATTA TTAATACTAT CCTTAAAAAA TCCTAAATGT CGACAATATA CATAGTTGTT      960

ATGTCCGTCT AGATACCAAT ACCATTTTGT GACATTGCCC TTCGTCGTAA GATACCATTG     1020

ACCGGATACA AATTATCGGT CTAGTAAAAT GAGATATTTG TAAAATGGTG TTTATTATCC     1080

TAGGAGATCT ATAAATTATA ATATAGATTG TTGTTGTTTT TTTAAATTGC TACATACCGG     1140

TCTTCATAAA AGATGATTAT TTCTATTTCT ATCAGATAGA ATAGATGTTC TATACTTTCT     1200

TCTATTAGTA AATCATCATC GATGATTATA CCTTTCTTTA CATATGTTTT TGCACCTTCG     1260

AAAATATAAT TTATCGTATA ATGATCTTCT AAATTTTAGA TCTGAATCAT ATTGTTTTGT     1320

CAATTTACGG TTATAGCTAA GATATAAAGT AGTATTGTCA TCATGTAATT AGTCACTATA     1380

TGACTTTGCT AGATGTCTGA GTTGATACGT TCCTTATTCG TTATACGGTT AATACAGATT     1440

ATAAAATTGA AATCTTGATT TTGCAAGATG GTTATGATTT TTATCCTATG CACTATCCGA     1500

CAATTTTCGA CGTTATTTAT CATTCCTACA TCTTCTTTAT GAAACAAGAT ATGGAAGCCT     1560

CCTTTCTTGA AATCTTGTTG AATTCAAATT AGTTTGAACA TAAATACTTC CATGG          1615

(2) INFORMATION FOR SEQ ID NO:109:

(i) SEQUENCE CHARACTERISTICS:
         (A) LENGTH: 112 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:109:

CGATGTTAAT AAGTATTACC ACAATAATTG GTGGAGCCAT TTTCGTTATA GTATTGATTT       60

TCATAACAGC TTTATGTTTC TATTGTTCAA AAAATAATAA GATCTAACTG CA              112

(2) INFORMATION FOR SEQ ID NO:110:

(i) SEQUENCE CHARACTERISTICS:
         (A) LENGTH: 106 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:110:
```

```
GTTAGATCTT ATTATTTTTT GAACAATAGA AACATAAAGC TGTTATGAAA ATCAATACTA        60

TAACGAAAAT GGCTCCACCA ATTATTGTGG TAATACTTAT TAACAT                      106
```

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:111:

```
CGTAGATTCC AATGGAAAGT                                                   20
```

(2) INFORMATION FOR SEQ ID NO:112:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:112:

```
TTTTCGCGAT ATCCGTTAAG T                                                 21
```

(2) INFORMATION FOR SEQ ID NO:113:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:113:

```
TTTTCGCGAT ATCCGTTAAG TTTGTATCGT AATGAGTTTT AAAAATTTCT ATCTAATATA       60

TGTAATTATA ATTTTCATAA ACTCGATAAT AAC                                    93
```

(2) INFORMATION FOR SEQ ID NO:114:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:114:

```
TTTGTATACC TAATAAGAAA TCATTATAAA AGT                                    33
```

(2) INFORMATION FOR SEQ ID NO:115:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:115:

```
CTTTTATAAT GATTTCTTAT TAGGTATACA AAATC                                  35
```

(2) INFORMATION FOR SEQ ID NO:116:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:116:

```
AATTTGCA                                                                         8
```

(2) INFORMATION FOR SEQ ID NO:117:

(i) SEQUENCE CHARACTERISTICS:
        (A) LENGTH: 1760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:117:

```
AGTACAATAA AAAGTATTAA ATAAAAATAC TTACTTACGA AAAAATGACT AATTAGCTAT      60
AAAAACCCGG GAAAGGATCC TGATCCTTTT TCTGGGTAAG TAATACGTCA AGGAGAAAAC     120
GAAACGATCT GTAGTTAGCG GCCAAACTCG AGGTCGACGG TATCGATAAG CTTGATTCTT     180
TATTCTATAC TTAAAAAGTG AAAATAAATA CAAAGGTTCT TGAGGGTTGT GTTAAATTGA     240
AAGCGAGAAA TAATCATAAA TTATTTCATT ATCGCGATAT CCGTTAAGTT TGTATCGTAA     300
TGAGTTTTAA AAATTTTTAT CTAATATATG TAATTATAAT TTTTATAAAC TCGATAATAA     360
CTTCGGCATC TACATCCAAA CCTTCAACAC CTACCATAAT TCCAACTTCA GCAAATGAAT     420
CACCTGCTTC CATAGATACA ACTATAACAA AACCTATATC TACAGAGGCA ATAATTTAA     480
AATCAGTAAG TACCTCAATT AAACCACCTA AAAACTAAAA AAAAAAATTA CTTAAATCTA     540
AATGTAGAGA TAATGTTATT TATAGGCCAT ATTTTAGTCA ATTAGAAATT AACTGTACTA     600
TAACTAAAAA GCAAAATTTA AGTAATCCTT TAATTGAGTT ATGGTTTAAA GAACTTTCTA     660
CATATAATAA AACCAATGAA AATGTTGAAA GTTTAAAAAC AGATATATCA AAAAATATTT     720
TATTATTTTC GACAAAAAAT AATAGTGATA ACTTTTATAA TGATTTTTTA TTAGGTATAC     780
AAAATCAACC AGTAAATTAT AAACTTTACG GTTCCCAATT TTATGATAAT GGAAACATAT     840
TACTAAAATAT AAAGTCGGTT GACTTTAAAA CCTCTGGAAT ATATACTTGG AAACTATATA     900
ATTCAAATAA TGAAAGTATT TTTGAAACTT TTAAAATTCA AGTATATGCA TATCATTCCC     960
CAAATGTAAA CTTAAAATCA AACCCAAGTT TATATAATGA AAACTACAGC GCTATTTGTA    1020
CAATAGCAAA TTACTTTCCA TTGGAATCTA CGGAAATATT TTGGTTTAAC GATGGACAAC    1080
CTATTGATAA AAAATATATA GATGAAACTT ATAGTGTATG GATTGACGGT CTTATAACAC    1140
GCACTTCAAT ATTATCCCTT CCCTTTTCCG AAGCCATGGA AAGCCCCCCC AATTTGCGAT    1200
GTAATGTTGA ATGGTATAAA AATTCAAAGG CATCAAAAAA ATTTTCAAAT ACCGTTATTC    1260
CAAAAGTTTA CTATAAACCT TTATATCTA TAAAATTTGA TAATGGTTTA GCTATTTGTG    1320
ATGCTAAATG TGTTTCCCGT GAAAATAATA AATTACAATG GTTAGTTAAA GATATACCTA    1380
TAAATGGTGA TGATATTATA AGCGGCCCCT GTTTAAACCA CCCTGGTTTG GTCAATATTC    1440
AAAATAAAAT AGATATATCG GATTATGATG AACCTGTTAC CTATAAATGT TCAATTATTG    1500
GTTATCCAAT AATTTTTCCC AACTTTTATG ATGAAAAGGT GTTTGATGCA TCGGATGAAA    1560
```

```
ATGTTAGTAA ATCGATGTTA ATAAGTATTA CCACAATAAT TGGTGGAGCC ATTTTTGTTA    1620

TAGTATTGAT TTTTATAACA GCTTTATGTT TTTATTGTTC AAAAAATAAT AAGATCTAAC    1680

TGCAAATTCT TTTTATTGAT TAACTAGTCA AATGAGTATA TATAATTGAA AAAGTAAAAT    1740

ATAAATCATA TAATAATGAA                                                1760
```

(2) INFORMATION FOR SEQ ID NO:118:

(i) SEQUENCE CHARACTERISTICS:
        (A) LENGTH: 1760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:118:

```
TCATGTTATT TTTCATAATT TATTTTTATG AATGAATGCT TTTTTACTGA TTAATCGATA      60

TTTTTGGGCC CTTTCCTAGG ACTAGGAAAA AGACCCATTC ATTATGCAGT TCCTCTTTTG     120

CTTTGCTAGA CATCAATCGC CGGTTTGAGC TCCAGCTGCC ATAGCTATTC GAACTAAGAA     180

ATAAGATATG AATTTTTCAC TTTTATTTAT GTTTCCAAGA ACTCCCAACA CAATTTAACT     240

TTCGCTCTTT ATTAGTATTT AATAAAGTAA TAGCGCTATA GGCAATTCAA ACATAGCATT     300

ACTCAAAATT TTTAAAAATA GATTATATAC ATTAATATTA AAAATATTTG AGCTATTATT     360

GAAGCCGTAG ATGTAGGTTT GGAAGTTGTG GATGGTATTA AGGTTGAAGT CGTTTACTTA     420

GTGGACGAAG GTATCTATGT TGATATTGTT TTGGATATAG ATGTCTCCGT TTATTAAATT     480

TTAGTCATTC ATGGAGTTAA TTTGGTGGAT TTTTGAATTT TTTTTTTAAT GAATTAGAT      540

TTACATCTCT ATTACAATAA ATATCCGGTA TAAAATCAGT TAATCTTTAA TTGACATGAT     600

ATTGATTTTT CGTTTTAAAT TCATTAGGAA ATTAACTCAA TACCAAATTT CTTGAAAGAT     660

GTATATTATT TTGGTTACTT TTACAACTTT CAAATTTTTG TCTATATAGT TTTTTATAAA     720

ATAATAAAAG CTGTTTTTTA TTATCACTAT TGAAAATATT ACTAAAAAAT AATCCATATG     780

TTTTAGTTGG TCATTTAATA TTTGAAATGC CAAGGGTTAA AATACTATTA CCTTTGTATA     840

ATGATTTATA TTTCAGCCAA CTGAAATTTT GGAGACCTTA TATATGAACC TTTGATATAT     900

TAAGTTTATT ACTTTCATAA AAACTTTGAA AATTTTAAGT TCATATACGT ATAGTAAGGG     960

GTTTACATTT GAATTTTAGT TTGGGTTCAA ATATATTACT TTTGATGTCG CGATAAACAT    1020

GTTATCGTTT AATGAAAGGT AACCTTAGAT GCCTTTATAA AACCAAATTG CTACCTGTTG    1080

GATAACTATT TTTTATATAT CTACTTTGAA TATCACATAC CTAACTGCCA GAATATTGTG    1140

CGTGAAGTTA TAATAGGGAA GGGAAAAGGC TTCGGTACCT TTCGGGGGGG TTAAACGCTA    1200

CATTACAACT TACCATATTT TTAAGTTTCC GTAGTTTTTT TAAAAGTTTA TGGCAATAAG    1260

GTTTTCAAAT GATATTTGGA AAATATAGAT ATTTTAAACT ATTACCAAAT CGATAAACAC    1320

TACGATTTAC ACAAGGGCA CTTTTATTAT TTAATGTTAC CAATCAATTT CTATATGGAT     1380

ATTTACCACT ACTATAATAT TCGCCGGGGA CAAATTTGGT GGGACCAAAC CAGTTATAAG    1440

TTTTATTTTA TCTATATAGC CTAATACTAC TTGGACAATG GATATTTACA AGTTAATAAC    1500

CAATAGGTTA TTAAAAAGGG TTGAAAATAC TACTTTTCCA CAAACTACGT AGCCTACTTT    1560

TACAATCATT TAGCTACAAT TATTCATAAT GGTGTTATTA ACCACCTCGG TAAAAACAAT    1620

ATCATAACTA AAAATATTGT CGAAATACAA AAATAACAAG TTTTTTATTA TTCTAGATTG    1680

ACGTTTAAGA AAAATAACTA ATTGATCAGT TTACTCATAT ATATTAACTT TTTCATTTTA    1740
```

-continued

```
TATTTAGTAT ATTATTACTT                                              1760
```

(2) INFORMATION FOR SEQ ID NO:119:

(i) SEQUENCE CHARACTERISTICS:
        (A) LENGTH: 319 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:119:

```
Leu Leu Phe Ser Thr Lys Asn Asn Ser Asp Asn Phe Tyr Asn Asp Phe
1               5                   10                  15

Leu Leu Gly Ile Gln Asn Gln Pro Val Asn Tyr Lys Leu Tyr Gly Ser
            20                  25                  30

Gln Phe Tyr Asp Asn Gly Asn Ile Leu Leu Asn Ile Lys Ser Val Asp
                35                  40                  45

Phe Lys Thr Ser Gly Ile Tyr Thr Trp Lys Leu Tyr Asn Ser Asn Asn
50                  55                  60

Glu Ser Ile Phe Glu Thr Phe Lys Ile Gln Val Tyr Ala Tyr His Ser
65                  70                  75                  80

Pro Asn Val Asn Leu Lys Ser Asn Pro Ser Leu Tyr Asn Glu Asn Tyr
                85                  90                  95

Ser Ala Ile Cys Thr Ile Ala Asn Tyr Phe Pro Leu Glu Ser Thr Glu
                100                 105                 110

Ile Phe Trp Phe Asn Asp Gly Gln Pro Ile Asp Lys Lys Tyr Ile Asp
                115                 120                 125

Glu Thr Tyr Ser Val Trp Ile Asp Gly Leu Ile Thr Arg Thr Ser Ile
130                 135                 140

Leu Ser Leu Pro Phe Ser Glu Ala Met Glu Ser Pro Pro Asn Leu Arg
145                 150                 155                 160

Cys Asn Val Glu Trp Tyr Lys Asn Ser Lys Ala Ser Lys Lys Phe Ser
                165                 170                 175

Asn Thr Val Ile Pro Lys Val Tyr Tyr Lys Pro Phe Ile Ser Ile Lys
                180                 185                 190

Phe Asp Asn Gly Leu Ala Ile Cys Asp Ala Lys Cys Val Ser Arg Glu
                195                 200                 205

Asn Asn Lys Leu Gln Trp Leu Val Lys Asp Ile Pro Ile Asn Gly Asp
                210                 215                 220

Asp Ile Ile Ser Gly Pro Cys Leu Asn His Pro Gly Leu Val Asn Ile
225                 230                 235                 240

Gln Asn Lys Ile Asp Ile Ser Asp Tyr Asp Glu Pro Val Thr Tyr Lys
                245                 250                 255

Cys Ser Ile Ile Gly Tyr Pro Ile Ile Phe Pro Asn Phe Tyr Asp Glu
                260                 265                 270

Lys Val Phe Asp Ala Ser Asp Glu Asn Val Ser Lys Ser Met Leu Ile
                275                 280                 285

Ser Ile Thr Thr Ile Ile Gly Gly Ala Ile Phe Val Ile Val Leu Ile
                290                 295                 300

Phe Ile Thr Ala Leu Cys Phe Tyr Cys Ser Lys Asn Asn Lys Ile
305                 310                 315
```

(2) INFORMATION FOR SEQ ID NO:120:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:120:

CGATATCCGT TAAGTTTGTA TCGTAATGAT TAAACTTCTA TTTATCTTAT TTTATTTTAA        60

CCCAATAA                                                                68

(2) INFORMATION FOR SEQ ID NO:121:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:121:

TTGGGTTAAA ATAAAATAAG ATAAATAGAA GTTAATCAT TACGATACAA ACTTAACGGA         60

TATCG                                                                   65

(2) INFORMATION FOR SEQ ID NO:122:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:122:

TTGAATTCCT AAACATTTGT TGTTAATTTT TTATAATTAT TATATATTTT TTGTCTTTTA        60

TAAACAAAGA AT                                                           72

(2) INFORMATION FOR SEQ ID NO:123:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:123:

TTAGATCTGT AGGAGCATCA AAAGTTGACG ATGAACTTTT CTATCTAAAT AGAGCTGGTC        60

CCCAAACCCT GCTTAAATAT TATGTTATTA AAGATTTCTA T                          101

(2) INFORMATION FOR SEQ ID NO:124:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:124:

TTAGATCTAG ATTCCTTACA CCATTCCATA AAAGTTGGTT CAAATTTATC TTCTTTAGAG        60

AAATAACAAG TTTCTCGTGG TAATTGAACC ATAAAATCAG TATAGAAAAC　　　　　110

(2) INFORMATION FOR SEQ ID NO:125:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:125:

TATTTTGATT GTGATCC　　　　　17

(2) INFORMATION FOR SEQ ID NO:126:

(i) SEQUENCE CHARACTERISTICS:
        (A) LENGTH: 1415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:126:

AGTACAATAA AAAGTATTAA ATAAAAATAC TTACTTACGA AAAAATGACT AATTAGCTAT　　　　　60

AAAAACCCGG GAAAGGATCC TGATCCTTTT TCTGGGTAAG TAATACGTCA AGGAGAAAAC　　　　　120

GAAACGATCT GTAGTTAGCG GCCAAACTCG AGGTCGACGG TATCGATAAG CTTGATTCTT　　　　　180

TATTCTATAC TTAAAAAGTG AAAATAAATA CAAAGGTTCT TGAGGGTTGT GTTAAATTGA　　　　　240

AAGCGAGAAA TAATCATAAA TTATTTCATT ATCGCGATAT CCGTTAAGTT TGTATCGTAA　　　　　300

TGATTAAACT TCTATTTATC TTATTTTATT TTAACCCAAT AACTGGATAT AAATGGGTAG　　　　　360

ACCCTCCTCG TAGGTATAAT TACACCGTTT TAAGAATGAT TCCAGATATT CCAAATCCAA　　　　　420

TGGATCCTTC TAAAAACGCT GAAGTTCGGT ATGTAACTTC TACTGACCCA TGTGATATGG　　　　　480

TTGCTTTGAT TTCTAATCCA AATATAGAAT CTACAATTAA AACGATTCAA TTTGTGCAAA　　　　　540

AGAAAAAATT TTACAATGCA TCTCTTAGTT GGTTTAAAGT TGGAGATGAT TGTACATATC　　　　　600

CAATATATTT AATTCAATAT TTTGATTGTG ATCCTCAAAG AGAATTTGGC ATATGTTTAA　　　　　660

AAAGATCTCC AGATTTTTGG AAACCATCGT TAGTTGGTTA CACATTTTTA ACTGATGATG　　　　　720

AATTGGGATT AGTTTTAGCT GCCCCCGCTC CATTTAATCA AGGTCAATAT AGACGGGTTA　　　　　780

TTCAAATTGA AAATGAAGTT TTTTATACTG ATTTTATGGT TCAATTACCA CGAGAAACTT　　　　　840

GTTATTTTTC TAAAGAAGAT AAATTTGAAC CAACTTTTAT GGAATGGTGT AAGGAATCTA　　　　　900

GATCTGTAGG AGCATCAAAA GTTGACGATG AACTTTTTTA TCTAAATAGA GCTGGTCCCC　　　　　960

AAACCCTGCT TAAATATTAT GTTATTAAAG ATTTTTATAG ACTTAACGGT AGAGAACCTC　　　　　1020

CAATAAAATT TAAAGAAGCT CTTAGATACG ATATACCATA TAAAGTGAAT GATAAATTTG　　　　　1080

ATGATGAATT ACCATCGAGG CCACATATTA GTAATACTAT TAATAAAACT ATTAAAGAAA　　　　　1140

TTGTAAATCT TGAAGATTAT TTTAAAAATA CAAATGTTAT AGATACTACT ACCCCAACAC　　　　　1200

CAATAAATAA TACCCCAAAA AATATAACCG TGGGAATTGT TATAATTATA TTAATAATAC　　　　　1260

TATTTATAAT TGGATTTTTT GTTTATAAAA GACAAAAAAT ATATAATAAT TATAAAAAAT　　　　　1320

TAACAACAAA TGTTTAGGAA TTCTTTTTAT TGATTAACTA GTCAAATGAG TATATATAAT　　　　　1380

TGAAAAAGTA AATATAAAT CATATAATAA TGAAA　　　　　1415

(2) INFORMATION FOR SEQ ID NO:127:

(i) SEQUENCE CHARACTERISTICS:
        (A) LENGTH: 1415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:127:

| | | | | | |
|---|---|---|---|---|---|
| TCATGTTATT | TTTCATAATT | TATTTTTATG | AATGAATGCT | TTTTTACTGA | TTAATCGATA | 60 |
| TTTTTGGGCC | CTTTCCTAGG | ACTAGGAAAA | AGACCCATTC | ATTATGCAGT | TCCTCTTTTG | 120 |
| CTTTGCTAGA | CATCAATCGC | CGGTTTGAGC | TCCAGCTGCC | ATAGCTATTC | GAACTAAGAA | 180 |
| ATAAGATATG | AATTTTTCAC | TTTTATTTAT | GTTTCCAAGA | ACTCCCAACA | CAATTTAACT | 240 |
| TTCGCTCTTT | ATTAGTATTT | AATAAAGTAA | TAGCGCTATA | GGCAATTCAA | ACATAGCATT | 300 |
| ACTAATTTGA | AGATAAATAG | AATAAAATAA | AATTGGGTTA | TTGACCTATA | TTTACCCATC | 360 |
| TGGGAGGAGC | ATCCATATTA | ATGTGGCAAA | ATTCTTACTA | AGGTCTATAA | GGTTTAGGTT | 420 |
| ACCTAGGAAG | ATTTTTGCGA | CTTCAAGCCA | TACATTGAAG | ATGACTGGGT | ACACTATACC | 480 |
| AACGAAACTA | AGATTAGGT  | TTATATCTTA | GATGTTAATT | TTGCTAAGTT | AAACACGTTT | 540 |
| TCTTTTTTAA | AATGTTACGT | AGAGAATCAA | CCAAATTTCA | ACCTCTACTA | ACATGTATAG | 600 |
| GTTATATAAA | TTAAGTTATA | AAACTAACAC | TAGGAGTTTC | TCTTAAACCG | TATACAAATT | 660 |
| TTTCTAGAGG | TCTAAAAACC | TTTGGTAGCA | ATCAACCAAT | GTGTAAAAAT | TGACTACTAC | 720 |
| TTAACCCTAA | TCAAAATCGA | CGGGGGCGAG | GTAAATTAGT | TCCAGTTATA | TCTGCCCAAT | 780 |
| AAGTTTAACT | TTTACTTCAA | AAAATATGAC | TAAAATACCA | AGTTAATGGT | GCTCTTTGAA | 840 |
| CAATAAAAAG | ATTTCTTCTA | TTTAAACTTG | GTTGAAAATA | CCTTACCACA | TTCCTTAGAT | 900 |
| CTAGACATCC | TCGTAGTTTT | CAACTGCTAC | TTGAAAAAAT | AGATTATCT  | CGACCAGGGG | 960 |
| TTTGGGACGA | ATTTATAATA | CAATAATTTC | TAAAAATATC | TGAATTGCCA | TCTCTTGGAG | 1020 |
| GTTATTTTAA | ATTTCTTCGA | GAATCTATGC | TATATGGTAT | ATTTCACTTA | CTATTTAAAC | 1080 |
| TACTACTTAA | TGGTAGCTCC | GGTGTATAAT | CATTATGATA | ATTATTTTGA | TAATTTCTTT | 1140 |
| AACATTTAGA | ACTTCTAATA | AAATTTTTAT | GTTTACAATA | TCTATGATGA | TGGGGTTGTG | 1200 |
| GTTATTTATT | ATGGGGTTTT | TTATATTGGC | ACCCTTAACA | ATATTAATAT | AATTATTATG | 1260 |
| ATAAATATTA | ACCTAAAAAA | CAAATATTTT | CTGTTTTTTA | TATATTATTA | ATATTTTTA  | 1320 |
| ATTGTTGTTT | ACAAATCCTT | AAGAAAAATA | ACTAATTGAT | CAGTTTACTC | ATATATATTA | 1380 |
| ACTTTTTCAT | TTTATATTTA | GTATATTATT | ACTTT | | | 1415 |

(2) INFORMATION FOR SEQ ID NO:128:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:128:

Met Ile Lys Leu Leu Phe Ile Leu Phe Tyr Phe Asn Pro Ile Thr Gly
1               5                   10                  15

Tyr Lys Trp Val Asp Pro Pro Arg Arg Tyr Asn Tyr Thr Val Leu Arg
            20                  25                  30

```
Met Ile Pro Asp Ile Pro Asn Pro Met Asp Pro Ser Lys Asn Ala Glu
    35              40                  45
Val Arg Tyr Val Thr Ser Thr Asp Pro Cys Asp Met Val Ala Leu Ile
    50              55                  60
Ser Asn Pro Asn Ile Glu Ser Thr Ile Lys Thr Ile Gln Phe Val Gln
65              70                  75                      80
Lys Lys Lys Phe Tyr Asn Ala Ser Leu Ser Trp Phe Lys Val Gly Asp
                85                  90                  95
Asp Cys Thr Tyr Pro Ile Tyr Leu Ile Gln Tyr Phe Asp Cys Asp Pro
                100             105                 110
Gln Arg Glu Phe Gly Ile Cys Leu Lys Arg Ser Pro Asp Phe Trp Lys
            115             120                 125
Pro Ser Leu Val Gly Tyr Thr Phe Leu Thr Asp Asp Glu Leu Gly Leu
    130             135                 140
Val Leu Ala Ala Pro Ala Pro Phe Asn Gln Gly Gln Tyr Arg Arg Val
145             150                 155                 160
Ile Gln Ile Glu Asn Glu Val Phe Tyr Thr Asp Phe Met Val Gln Leu
                165                 170                 175
Pro Arg Glu Thr Cys Tyr Phe Ser Lys Glu Asp Lys Phe Glu Pro Thr
            180                 185                 190
Phe Met Glu Trp Cys Lys Glu Ser Arg Ser Val Gly Ala Ser Lys Val
            195                 200                 205
Asp Asp Glu Leu Phe Tyr Leu Asn Arg Ala Gly Pro Gln Thr Leu Leu
    210                 215                 220
Lys Tyr Tyr Val Ile Lys Asp Phe Tyr Arg Leu Asn Gly Arg Glu Pro
225                 230                 235                 240
Pro Ile Lys Phe Lys Glu Ala Leu Arg Tyr Asp Ile Pro Tyr Lys Val
                245                 250                 255
Asn Asp Lys Phe Asp Asp Glu Leu Pro Ser Arg Pro His Ile Ser Asn
                260                 265                 270
Thr Ile Asn Lys Thr Ile Lys Glu Ile Val Asn Leu Glu Asp Tyr Phe
        275                 280                 285
Lys Asn Thr Asn Val Ile Asp Thr Thr Thr Pro Thr Pro Ile Asn Asn
    290                 295                 300
Thr Pro Lys Asn Ile Thr Val Gly Ile Val Ile Ile Ile Leu Ile Ile
305             310                 315                 320
Leu Phe Ile Ile Gly Phe Phe Val Tyr Lys Arg Gln Lys Ile Tyr Asn
                325                 330                 335
Asn Tyr Lys Lys Leu Thr Thr Asn Val
            340                 345
```